US010793835B2

(12) United States Patent
Yan et al.

(10) Patent No.: US 10,793,835 B2
(45) Date of Patent: Oct. 6, 2020

(54) CHIMERIC ADENO-ASSOCIATED VIRUS/ BOCAVIRUS PARVOVIRUS VECTOR

(71) Applicants: University of Iowa Research Foundation, Iowa City, IA (US); University of Kansas, Lawrence, KS (US)

(72) Inventors: Ziying Yan, Iowa City, IA (US); John F. Engelhardt, Iowa City, IA (US); Jianming Qiu, Overland Park, KS (US)

(73) Assignees: University of Iowa Research Foundation, Iowa City, IA (US); University of Kansas, Lawrence, KS (US)

( * ) Notice: Subject to any disclaimer, the term of this patent is extended or adjusted under 35 U.S.C. 154(b) by 0 days.

(21) Appl. No.: 15/822,956

(22) Filed: Nov. 27, 2017

(65) Prior Publication Data

US 2018/0282702 A1 Oct. 4, 2018

Related U.S. Application Data

(63) Continuation of application No. 14/782,876, filed as application No. PCT/US2014/033343 on Apr. 8, 2014, now Pat. No. 9,828,587.

(60) Provisional application No. 61/809,702, filed on Apr. 8, 2013.

(51) Int. Cl.

| | |
|---|---|
| ***C12N 15/63*** | (2006.01) |
| ***C12N 15/79*** | (2006.01) |
| ***A61K 39/23*** | (2006.01) |
| ***C07H 21/04*** | (2006.01) |
| ***C12N 7/00*** | (2006.01) |
| ***A61K 39/00*** | (2006.01) |
| ***C12N 15/86*** | (2006.01) |
| *C12N 15/864* | (2006.01) |
| *C07K 14/435* | (2006.01) |

(52) U.S. Cl.

CPC ................ *C12N 7/00* (2013.01); *A61K 39/00* (2013.01); *A61K 39/23* (2013.01); *C12N 15/86* (2013.01); *A61K 2039/5256* (2013.01); *C07H 21/04* (2013.01); *C07K 14/435* (2013.01); *C12N 15/8645* (2013.01); *C12N 2750/14111* (2013.01); *C12N 2750/14121* (2013.01); *C12N 2750/14132* (2013.01); *C12N 2750/14143* (2013.01); *C12N 2750/14144* (2013.01); *C12N 2750/14145* (2013.01); *C12N 2750/14322* (2013.01); *C12N 2750/14333* (2013.01); *C12N 2810/6027* (2013.01)

(58) Field of Classification Search

CPC .. C12N 15/63; C12N 15/864; C12N 15/8645; C12N 2750/14143; C12N 2750/14144; C07H 21/02; C07H 21/04

USPC ........... 435/320.1, 455; 424/233.1; 536/23.1, 536/23.5

See application file for complete search history.

(56) References Cited

U.S. PATENT DOCUMENTS

| | | | |
|---|---|---|---|
| 6,491,907 | B1 | 12/2002 | Rabinowitz et al. |
| 8,110,350 | B2 | 2/2012 | Allander et al. |
| 9,828,587 | B2 | 11/2017 | Yan et al. |
| 2003/0053990 | A1 | 3/2003 | Rabinowitz et al. |
| 2008/0292654 | A1 | 11/2008 | Allander et al. |
| 2009/0297557 | A1 | 12/2009 | Delwart et al. |
| 2011/0014723 | A1 | 1/2011 | Erdman et al. |
| 2013/0012574 | A1 | 1/2013 | Monahan et al. |
| 2016/0068821 | A1 | 3/2016 | Yan et al. |
| 2019/0203229 | A1 | 7/2019 | Engelhardt et al. |
| 2019/0338312 | A1 | 11/2019 | Yan et al. |

FOREIGN PATENT DOCUMENTS

| | | | |
|---|---|---|---|
| AU | 2014251099 | B2 | 1/2019 |
| CN | 105431170 | A | 3/2016 |
| CN | 105431170 | B | 10/2019 |
| EP | 2983707 | B1 | 6/2019 |
| IN | 10078DELNP2015 | A | 4/2016 |
| JP | 2002538770 | A | 11/2002 |
| JP | 6516725 | B2 | 4/2019 |
| WO | WO-0028004 | A1 | 5/2000 |
| WO | WO-2014168953 | A1 | 10/2014 |
| WO | WO-2017139381 | A1 | 8/2017 |
| WO | WO-2017205739 | A1 | 11/2017 |
| WO | WO2018132747 | | 7/2018 |

OTHER PUBLICATIONS

Guido et al., 2016, World Journal of Gastroenterology, 22(39): 8684-8697.*

"Australian Application Serial No. 2014251099, First Examination Report dated May 30, 2018", 4 pgs.

"Chinese Application Serial No. 201480032420.6, Office Action dated Jul. 13, 2018", w/ English translation, 8 pgs.

(Continued)

*Primary Examiner* — Shin Lin Chen

(74) *Attorney, Agent, or Firm* — Schwegman Lundberg & Woessner, P.A.

(57) ABSTRACT

The invention provides an isolated chimeric virus comprising bocavirus capsid protein and a recombinant adeno-associated viral (AAV) genome, an isolated rBoV comprising human bocavirus capsid protein and a recombinant BoV genome, and uses therefor. For example, the chimeric virus may be employed to deliver transgenes, such as those encoding therapeutic or prophylactic gene products, to mammalian cells.

15 Claims, 39 Drawing Sheets

Specification includes a Sequence Listing.

(56) References Cited

OTHER PUBLICATIONS

"European Application Serial No. 14783418.8, Response filed May 30, 2018 to Communication Pursuant to Article 94(3) EPC dated Mar. 27, 2018", 271 pgs.
"Japanese Application Serial No. 2016-507610, Response filed Aug. 21, 2018 to Office Action dated Feb. 21, 2018", with English translation of claims, 27 pgs.
"U.S. Appl. No. 14/782,876, Non Final Office Action dated Feb. 16, 2017", 10 pgs.
"U.S. Appl. No. 14/782,876, Notice of Allowance dated Jul. 25, 2017", 8 pgs.
"U.S. Appl. No. 14/782,876, Preliminary Amendment filed Oct. 7, 2015", 9 pgs.
"U.S. Appl. No. 14/782,876, Response filed Jan. 11, 2017 to Restriction Requirement dated Oct. 14, 2016", 8 pgs.
"U.S. Appl. No. 14/782,876, Response filed Jun. 16, 2017 to Non Final Office Action dated Feb. 16, 2017", 8 pgs.
"U.S. Appl. No. 14/782,876, Restriction Requirement dated Oct. 14, 2016", 10 pgs.
"Chinese Application Serial No. 201480032420.6, Office Action dated May 3, 2017", w/English Translation of Claims, 20 pgs.
"Chinese Application Serial No. 201480032420.6, Office Action dated Dec. 14, 2017", (English Translation), 8 pgs.
"Chinese Application Serial No. 201480032420.6, Response filed Feb. 27, 2018 to Office Action dated Dec. 14, 2017", w/ Amended Claims, 73 pgs.
"Chinese Application Serial No. 201480032420.6, Response filed Sep. 18, 2017 to Office Action dated May 3, 2017", w/English Claims, 25 pgs.
"European Application Serial No. 14783418.8, Communication Pursuant to Article 94(3) EPC dated Mar. 27, 2018", 4 pgs.
"European Application Serial No. 14783418.8, Extended European Search Report dated Feb. 27, 2017", 15 pgs.
"European Application Serial No. 14783418.8, Response filed May 26, 2016", 13 pgs.
"European Application Serial No. 14783418.8, Response filed Sep. 22, 2017", 11 pgs.
"International Application Serial No. PCT/US2014/033343, International Preliminary Report on Patentability dated Oct. 13, 2015", 12 pgs.
"International Application Serial No. PCT/US2014/033343, International Search Report dated Sep. 2, 2014", 4 pgs.
"International Application Serial No. PCT/US2014/033343, Written Opinion dated Sep. 2, 2014", 10 pgs.
"Japanese Application Serial No. 2016-507610, Office Action dated Feb. 21, 2018", with English translation of claims, 16 pgs.
Brown, Kevin E., "The expanding range of parvoviruses which infect humans", Reviews in Medical Virology, GB, (2010), vol. 20, No. 4, (2010), 231-244.
Cheung, Andrew K., et al., "Identification and molecular cloning of a novel porcine parvovirus", Archives of Virology; Official Journal of the Virology Division of the International Union of Microbiological Societies, Springer-Verlag, VI, vol. 155, No. 5, (2010), 801-806.
Deng, Xuefeng, et al., "In vitro modeling of human bocavirus 1 infection of polarized primary human airway epithelia", J Virol. vol. 87, No. 7, 4097-4102, (Jan. 23, 2013), 7 pgs.
Gurda, Brittney L., et al., "Human Bocavirus Capsid Structure: Insights into the Structural Repertoire of the Parvoviridae", Journal of Virology, 84(12), (Jun. 2010), 5880-5889.
Haung, Qinfeng, et al., "Establishment of a Reverse Genetics System for Studying Human Bocavirus in Human Airway Epithelia", Journal PLOS Pathogens vol. 8(8), (2012), 1-14.
Ishiawata, Akira, et al., "Phenotype correction of hemophilia a mice with adeno-associated virus vectors carrying the B domain-deleted canine factor VIII gene", Thrombosis Research, Tarrytown, NY, US, vol. 118, No. 5, (2006), (2006), 627-635.
Kapoor, Amit, et al., "Bocavirus Episome in Infected Human Tissue Contains Non-Identical Termini", PLOS One, (2011), vol. 6, No. 6, e21362, (2011), 8 pgs.
Kapoor, Amit, et al., "Identification and Characterization of a New Bocavirus Species in Gorillas", PLOS One, (2010), vol, 5, No. 7, p. e11948, (Jul. 2010), 6 pgs.
Li, Wuping, et al., "Generation of Novel AAV Variants by Directed Evolution for Improved CFTR Delivery to Human Ciliated Airway Epithelium", Journal of Molecular Therapy vol. 17(12), (Dec. 2009), 2067-2077.
Ros, C, et al., "The ubiquitin-proteasome machinery is essential for nuclear translocation of incoming minute virus of mice", Virology 324, (2004), 350-360.
Sun, et al., "Molecular Characterization of Infectious Clones of the Minute Virus of Canines Reveals Unique Features of Bocaviruses", Journal of Virology, 83(8), (Apr. 2009), 3956-3967.
Yan, Z, et al., "A Novel Chimeric Adenoassociated Virus 2/ Human Bocavirus 1 Parvovirus Vector Effciently Transduces Human Airway Epithelia", Molecular Therapy, vol. 21 No. 12, (Dec. 2013), 2181-2194.
Yan, Z., et al., "A novel chimeric adenoassociated virus 2/human bocavirus 1 parvovirus vector efficiently transduces human airway epithelia", Mol Ther. vol. 21, No. 12, (Jul. 30, 2013), 2181-2194.
Yang, Wan-Zhu, et al., "Genome characterization of a novel porcine bocavirus", Archives of Virology; Official Journal of the Virology Divisionof the International Union of Microbiological Societies, Springer-Verlag, VI, (2012), vol. 157, No. 11,, (Jul. 21, 2012), 2125-2132.
"Australian Application Serial No. 2014251099, Response filed Dec. 19, 2018 to Examiner's Report dated May 30, 2018", 39 pgs.
"Chinese Application Serial No. 201480032420.6, Response filed Nov. 26, 2018 to Office Action dated Jul. 13, 2018", w/ English Claims, 73 pgs.
"International Application Serial No. PCT/US2017/034678, International Preliminary Report on Patentability dated Dec. 6, 2018", 9 pgs.
"International Application Serial No. PCT/US2017/034678, International Search Report dated Oct. 16, 2017", 7 pgs.
"International Application Serial No. PCT/US2017/034678, Written Opinion dated Oct. 16, 2017", 6 pgs.
"Israel Application Serial No. 241954, Office Action dated Oct. 9, 2018", W/English Translation, 10 pgs.
"Israel Application Serial No. 241954, Response filed Feb. 7, 2019 to Office Action dated Oct. 9, 2018", w/ English Translation, 14 pgs.
"Japanese Application Serial No. 2016-507610, Notification of Reasons for Refusal dated Jan. 24, 2019", w/ English translation, 6 pgs.
"Japanese Application Serial No. 2016-507610, Response filed Mar. 6, 2019 to Notification of Reasons for Refusal dated Jan. 24, 2019", w/o English Translation, 5 pgs.
Gao, Feng, et al., "DNA-guided genome editing using the Natronobacterium gregoryi Argonaute", In Journal of Nature Biotechnology Advance Online Publication, (May 2, 2016), 1-7.
Shen, Weiran, et al., "Analysis of cis and trans Requirements for DNA Replication at the Right-End Hairpin of the Human Bocavirus 1 Genome", Journal of Virology 90.17, (2016), 7761-7777.
Wei, Ran Shen, et al., "Identification and functional analysis of novel nonstructural proteins human bocavirus 1", Journal of Virology., vol. 89, No. 19, (Oct. 1, 2015), 10097-10109.
Y. Sun, et al., "Molecular Characterization of Infectious Clones of the Minute Virus of Canines Reveals Unique Features of Bocaviruse", Journal of Virology vol. 83 No. 8, (Feb. 11, 2009), 3956-3967.
Zou, Wei, et al., "Nonstructural Protein NP1 of Human Bocavirus 1 Plays Critical Role in the Expression of Viral Capsid Protein", Journal of Virology May 2016 vol. 90 No. 9, (Feb. 18, 2016), 4658-4669.
"U.S. Appl. No. 16/477,762, Preliminary Amendment filed Jul. 12, 2019", 8 pgs.
"International Application Serial No. PCT/US2017/017021, International Preliminary Report on Patentability dated Aug. 23, 2018", 12 pgs.
"International Application Serial No. PCT/US2017/017021, International Search Report dated May 23, 2017", 8 pgs.

(56) References Cited

OTHER PUBLICATIONS

"International Application Serial No. PCT/US2017/017021, Written Opinion dated May 23, 2017", 10 pgs.
"International Application Serial No. PCT/US2018/013634, International Search Report dated Jun. 18, 2018", 9 pgs.
"International Application Serial No. PCT/US2018/013634, Invitation to Pay Add'l Fees and Partial Search Report dated Apr. 17, 2018", 14 pgs.
"International Application Serial No. PCT/US2018/013634, Written Opinion dated Jun. 18, 2018", 12 pgs.
Ginn, S. L., et al., "Gene therapy clinical trials worldwide to 2012—an update.", J Gene Med, 15(2), (2013), 65-77.
Julia, Fakhiri, et al., "254. New Chimeric Gene Therapy Vectors Based on Four Different Mammalian Bocaviruses", Molecular Therapy, vol. 24, No. S1, (May 1, 2016), S100.
Kapoor, A., et al., "Human bocaviruses are highly diverse, dispersed, recombination prone, and prevalent enteric infections", J Infect Dis. 201(11), (Jun. 2010), 1633-1643.
Mihaylov, Ivailo, et al., "Complementation for an essential ancillary non-structural protein function across parvovirus genera", Virology, vols. 468-470, (2014), 226-237.
Olufemi, Fasina O, et al., "NP1 protein of the Bocaparvovirus Minute Virus of Canines controls acess to the viral capsid genes via its role in RNA processing", Journal of Virology., vol. 90, No. 4, (Dec. 4, 2015), 1718-1728.
Qinfeng, Huang, et al., "Internal polyadenylation of parvoviral precursor mRNA limits progeny virus production", Virology, Elsevier, Amsterdam, NL, vol. 426, No. 2, (Jan. 26, 2012), 167-177.
Qiu, Jianming, et al., "Characterization of the transcription profile of adeno-associated virus type 5 reveals a number of unique features compared to previously characterized adeno-associated viruses", Journal of Virol., 76, No. 24, (2002), 12435-12447.
Qiu, Jianming, et al., "The Transcription Pro?le of the Bocavirus Bovine Parvovirus Is Unlike Those of Previously Characterized Parvoviruses", Journal of Virology, vol. 81, No. 21, [Online]. Retrieved from the Internet: <URL: https://jvi.asm.org/>, (2007), 12080-12085.
Ricour, C., et al., "Human Bocavirus, a Newly Discovered Parvovirus of the Respiratory Tract", International Journal of Clinical and Laboratory Medicine, vol. 63, Issue 5, (2008), (Abstract only).
Sukhu, L, et al., "Characterization of the Nonstructural Proteins of the Bocavirus Minute Virus of Canines", Journal of Virology., vol. 87, No. 2, (Nov. 7, 2012), 1098-1104.
Wei, Zou, et al., "Nonstructural Protein NP1 of Human Bocavirus 1 Plays a Critical Role in the Expression of Viral Capsid Proteins", Journal of Virology., vol. 90, No. 9, (May 1, 2016), 4658-4669.
Xuefeng, Deng, et al., "DNA Damage Signaling Is Required for Replication of Human Bocavirus 1 DNA in Dividing HEK293 Cells", Journal of Virology, vol. 91 No. 1, (Jan. 1, 2017), 20 pgs.
Xuefeng, Deng, et al., "Replication of an Autonomous Human Parvovirus in Non-dividing Human Airway Epithelium Is Facilitated through the DNA Damage and Repair Pathways", PLOS Pathogens vol. 12 No. 1, (Jan. 14, 2016), 25 pgs.
"New Zealand Application Serial No. 713509, First Examiner Report dated Nov. 14, 2019", 7 pgs.
"Canadian Application Serial No. 2909085, Voluntary Amendment filed Sep. 6, 2019", 4 pgs.
"Israel Application Serial No. 241954, Office Action dated Dec. 5, 2019", w/ English Translation, 6 pgs.
Fakhiri, Julia, et al., "Novel Chimeric Gene Therapy Vectors Based on Adeno-Associated Virus and Four Different Mammalian Bocaviruses", Molecular Therapy: Methods & Clinical Development vol. 12, (Mar. 2019), 202-222.
Yan, Ziying, et al., "Human Bocavirus Type-1 Capsid Facilitates the Transduction of Ferret by Adeno-Associated Virus Genomes", Human Gene Therapy, vol. 28, No. 8, (2017), 612-625.
"Canadian Application Serial No. 2,909,085, Office Action dated Apr. 2, 2020", 5 pgs.
"Indian Application Serial No. 10078/DELNP/2015, First Examination Report dated Mar. 12, 2020", w/ English Translation, 8 pgs.

* cited by examiner a
P5
BspE1
PstI
HindIII
NS
NP1
polyA
VP
BglII
EcoRI PstI
polyA
pIHBoV1
BspE1Δ
CBA-Luciferase
EcoRIΔ/PstIΔ
prHBoV1-CBAluc
pHBoV1KUm630
b
1 2 3
DpnI Digested
c
Viral Genome copies (x10^7/μl)
CsCl Fraction
d
Density (g/ml)
e
Relative Luciferase Activity (X10^4)
HAE (ALI)
CuFi8 (ALI)
CuFi8 (UD)
IB3
HEK293
HAE ALI
Day3
Day7
Day11
Day Post-Infection a
Viral Genome Copies (X10⁹)
CsCl Fraction
Density (g/ml)
pAV2-F5tg83luc, pAd4.1 and pAVRC2.3
pAV2-F5tg83luc, pAd4.1, pHBoV1KUm630 and pAV-Rep2
pAV2-F5tg83luc, pAd4.1 and pHBoV1KUm630
Density
b
M
1
2
3
4
5.4k
4.8kb
c
15000 x
50000 x
100nm
50nm
d
AV2/2
AV2/HboV1
AV2/2
AV2/HboV1
AV2/2
AV2/HboV1
Anti-AAV
Anti-HBoV
Anti-AAV
Anti-HBoV1
AAV
VP3
VP2
VP1
HBoV1
VP2
VP1 a
AV2/2
AV2/HBc
rHBoV1
Viral DNA:
Plasmid DNA:
ds plasmid copies:
10⁷
10⁸
10⁹
10¹⁰
Probe for minus strand
Probe for plus strand
Viral Genome sense percentage (%)
Minus strand
Plus strand
b
AV2/2.F5tg83luc
AV2/HBc.F5tg83luc
AV2/HBc.CF5tg83luc
12kb
7kb
6kb
5kb
4kb
3kb
2kb
1.6kb
5.4kb
4.8kb
c
Luciferase copies:
10⁶
Probe for luciferase
HBoV1 copies:
Probe for HBoV1 NP1
Relative Copies (x10⁸)
Luciferase
HBoV1 NP1
17% a
HEK293
Relative Luciferase Activity(x10³)
200
160
120
80
40
0
AV2/2.F5tg83luc MOI=2.5K
AV2/HBc.F5tg83luc MOI=50K
b
HAE
Apical
Basal
Relative Luciferase Activity
10⁶
10⁵
10⁴
10³
10²
AV2/2. F5tg83luc
AV2/1. F5tg83luc
AV2/HBc. F5tg83luc
c
Cytoplasmic
Nuclear
Internalized Virions (x10⁸ vg)
10
8
6
4
2
0
AV2/1.CMVluc
AV2/2.CMVluc
AV2/2.F5tg83luc
AV2/HBc.F5tg83luc
d
Distribution (%)
Nuclear
Cytoplasmic
100
80
60
40
20
0
20
AV2/1.CMVluc
AV2/2.CMVluc
AV2/2.F5tg83luc
AV2/HBc.F5tg83luc a
Relative Luciferase Activity
Vehicle
PI (LLnL+Dox)
x2600
x1500
x1800
Day3
Day7
Day11
AV2/2.F5tg83luc
b
Relative Luciferase Activity
Vehicle
PI (LLnL+Dox)
x4500
x1400
x1300
Day3
Day7
Day11
AV2/HBc.F5tg83luc
c
Relative Luciferase Activity
Viral Genome Copies
CuFi-ALI(a)
CuFi-ALI(a) +PI
CuFi-ALI(b)
CuFi-ALI(b) +PI
CuFi-UD
CuFi-UD +PI
HEK293

Figure 8

Exemplary HBoV1 Sequences

Human bocavirus isolate Salvador1, complete genome

```
1 gtggttgtac agacgccatc ttggaatcca atatgtctgc cggctcagtc atgcctgcgc
      61 tgcgcgcagc gcgctgcgcg cgcgcatgat ctaatcgccg gcagacatat tggattccaa
     121 gatggcgtct gtacaaccac gtcacatata aaataataaa tattcacaag gaggagtggt
     181 tatatgatgt aatccataac cactcccagg aaatgacgta tgatagccaa tcagaattga
     241 gtattaaacc tatataagct gctgcacttc ctgattcaat cagactgcat ccggtctccg
     301 gcgagtgaac atctctggaa aaagctccac gcttgtggtg agtctactat ggctttcaat
     361 cctcctgtga ttagagcttt ttctcaacct gcttttactt atgtcttcaa atttccatat
     421 ccacaatgga aagaaaaaga atggctgctt catgcacttt tagctcatgg aactgaacaa
     481 tctatgatac aattaagaaa ctgcgctcct catccggatg aagacataat ccgtgatgac
     541 ttgcttattt ctttagaaga tcgccatttt ggggctgttc tctgcaaggc tgtttacatg
     601 gcaacaacta ctctcatgtc acacaaacaa aggaatatgt ttcctcgttg tgacatcata
     661 gttcagtctg agctaggaga gaaaaactta cactgccata ttatagttgg gggagaagga
     721 ctaagcaaga ggaatgctaa atcatcctgt gctcagttct atggtttaat actagctgaa
     781 ataattcaac gctgcaaatc tcttctggct acacgtcctt ttgaacctga agaggctgac
     841 atatttcaca ctttaaaaaa ggctgagcga gaggcatggg gtggagttac tggcggcaac
     901 atgcaaatcc ttcaatatag agatcgcaga ggagaccttc atgcacaaac agtggatcct
     961 cttcgcttct tcaaaaacta ccttttacct aaaaatagat gtatttcatc ttacagcaaa
    1021 cctgatgttt gtacttctcc tgacaactgg ttcattttag ctgaaaaaac ttactctcac
    1081 actcttatta acgggctgcc gcttccagaa cattacagaa aaaactacca cgcaacccta
    1141 gataacgaag tcattccagg gcctcaaaca atggcctatg gaggacgtgg tccgtgggaa
    1201 catcttcctg aggtaggaga tcagcgccta gctgcgtctt ctgttagcac tacttataaa
    1261 cctaacaaaa aagaaaaact tatgctaaac ttgctagaca aatgtaaaga gctaaatcta
    1321 ttagtttatg aagacttagt agctaattgt cctgaactac tccttatgct tgaaggtcaa
    1381 ccaggagggg cacgccttat agaacaagtc ttgggcatgc accatattaa tgtttgttct
    1441 aactttacag ctctcacata tctttttcat ctacatcctg ttacttcgct tgactcagac
    1501 aataaagctt tacagctttt gttgattcaa ggctataatc ctctagccgt tggtcacgcc
    1561 ctatgctgtg tcctgaacaa acaattcggg aaacaaaaca ctgtttgctt ttacgggcct
    1621 gcctcaacag gtaaaacaaa tatggccaag gcaatcgtcc aagggattag actttatggg
    1681 tgtgttaatc atttgaacaa aggatttgta tttaatgact gcagacaacg cctagttgtt
    1741 tggtgggagg agtgcttaat gcaccaggat tgggtggaac ctgcaaagtg tatcttgggc
    1801 gggacagaat gcagaattga cgtcaagcat agagacagtg tacttttaac tcaaacacct
    1861 gtaattatat ccactaacca cgatatctac gcggttgttg gtggcaattc tgtttctcat
    1921 gttcacgcgg ctccattaaa agaaagagtg attcagctaa attttatgaa acaacttcct
    1981 caaacatttg gagaaatcac tgctactgag attgcagctc ttctacagtg gtgtttcaat
    2041 gagtacgact gtactctgac aggatttaaa caaaaatgga atttagataa aattccaaac
    2101 tcatttcctc ttggggtcct ttgtcctact cattcacagg actttacact tcacgaaaac
    2161 ggatactgca ctgattgcgg tggttacctt cctcatagtg ctgacaattc tatgtacact
    2221 gatcgcgcaa gcgaaactag cacaggagac atcacaccaa gtaagtaaat acgcatgcgc
    2281 aagtaattct tttactttca cttcgctatt tttaccaatt tttactttta ggtgacttgg
```

Figure 8 (cont.)

```
2341 gggattcgga cggagaagac accaagcctg agacatcgca agtggactat tgtccaccca
2401 agaaacgtcg tctaactgct ccagcaagtc ctccaaactc acctgcgagc tctgtaagta
2461 ctattacttt ctttaacact tggcacgcac agccacgtga cgaagatgag ctcagggaat
2521 atgaaagaca agcatcgctc ctacaaaaga aaagggagtc cagaaagagg ggagaggaag
2581 agacactggc agacaactca tcacaggagc aggagccgca gcccgatccg acacagtggg
2641 gagagaggct cgggctcata tcatcaggaa caccccaatca gccacctatc gtcttgcact
2701 gcttcgaaga cctcagacca agtgatgaag acgagggaga gtacatcggg gaaaaaagac
2761 aatagaacaa atccatacac tgtattcagt caacacagag cttccaatcc tgaagctcca
2821 gggtggtgtg ggttctactg gcactctact cgcattgcta gagatggtac taattcaatc
2881 tttaatgaaa tgaaacaaca gtttcaacag ctacaaattg ataataaaat aggatgggat
2941 aacactagag aactattgtt taatcaaaag aaaacactag atcaaaaata cagaaatatg
3001 ttctggcact ttagaaataa ctctgattgt gaaagatgta attactggga tgatgtgtac
3061 cgtagacact tagctaatgt ttcctcacag acagaagcag acgagataac tgacgaggaa
3121 atgctttctg ctgctgaaag catggaagca gatgcctcca attaagagac agcctagagg
3181 gtgggtgctg cctggataca gatatcttgg gccatttaat ccacttgata acggtgaacc
3241 tgtaaataac gctgatcgcg ctgctcaatt acatgatcac gcctactctg aactaataaa
3301 gagtggtaaa aatccatacc tgtatttcaa taaagctgat gaaaaattca ttgatgatct
3361 aaaagacgat tggtcaattg gtggaattat tggatccagt ttttttaaaa taaagcgcgc
3421 cgtggctcct gctctgggaa ataaagagag agcccaaaaa agacactttt actttgctaa
3481 ctcaaataaa ggtgcaaaaa aaacaaaaaa aagtgaacct aaaccaggaa cctcaaaaat
3541 gtctgacact gacattcaag accaacaacc tgatactgta gacgcaccac agaacacctc
3601 aggggaggga acaggaagta ttggaggagg aaaaggatct ggtgtgggga tttccactgg
3661 agggtgggtc ggaggttctc acttttcaga caaatatgtg gttactaaaa acacaagaca
3721 atttataacc acaattcaga atggtcacct ctacaaaaca gaggccattg aaacaacaaa
3781 ccaaagtgga aaatcacagc gctgcgtcac aactccatgg acatacttta actttaatca
3841 atacagctgt cacttctcac cacaggattg gcagcgcctt acaaatgaat ataagcgctt
3901 cagacctaaa gcaatgcaag taaagattta caacttgcaa ataaaacaaa tactttcaaa
3961 tggtgctgac acaacataca acaatgacct cacagctggc gttcacatct tttgtgatgg
4021 agagcatgct tacccaaatg catctcatcc atgggatgag gacgtcatgc ctgatcttcc
4081 atacaagacc tggaaacttt ttcaatatgg atatattcct attgaaaatg aactcgcaga
4141 tcttgatgga aatgcagctg gaggcaatgc tacagaaaaa gcacttctgt atcagatgcc
4201 tttttttcta cttgaaaaca gtgaccacca agtacttaga actggtgaga gcactgaatt
4261 tacttttaac tttgactgtg aatgggttaa caatgaaaga gcatacattc ctcctggact
4321 aatgtttaat ccaaaagttc caacaagaag agttcagtac ataagacaaa acggaagcac
4381 agcagccagc acaggcagaa ttcagccata ctcaaaacca acaagctgga tgacaggacc
4441 tggcctgctc agtgcacaga gagtaggacc acagtcatca gacactgctc cattcatggt
4501 ttgcactaac ccagaaggaa cacacataaa cacaggtgct gcaggatttg gatctggctt
4561 tgatcctcca agcggatgtc tggcaccaac taacctagaa tacaaacttc agtggtacca
4621 gacaccagaa ggaacaggaa ataatggaaa cataattgca aacccatcac tctcaatgct
4681 tagagaccaa ctcctataca aaggaaacca gaccacatac aatctagtgg gggacatatg
4741 gatgtttcca aatcaagtct gggacagatt tcctatcacc agagaaaatc caatctggtg
4801 caaaaaacca agagctgaca aacacacaat catggatcca tttgatggat caattgcaat
4861 ggatcatcct ccaggcacta tttttataaa aatggcaaaa attccagttc caactgcctc
4921 aaatgcagac tcatacctaa acatatactg tactggacaa gtcagctgtg agattgtatg
```

Figure 8 (cont.)

```
4981 ggaagtaaaa agatacgcaa caaagaactg gcgtccagaa agaagacata ctgcactcgg
5041 gatgtcactg ggaggagaaa gcaactacac gcctacatac cacgtggatc caacaggagc
5101 atacatccag cccacgtcat atgatcaatg tatgccagta aaaacaaaca tcaataaagt
5161 gttgtaatct tataagcctc ttttttgctt ctgcttacaa gttcctcctc aatggacaag
5221 cggaaagtga agggtgactg tagtcctgag ctcatgggtt caagaccaca gcccgatggt
5281 agtggtgtta ccgtctcgaa cctagccgac agcccttgta cattgtgggg ggagctgttt
5341 tgtttgctta tgcaatcgcg aaactctata tcttttaatg tgttgttgtt gtacatgcgc
5401 catcttagtt ttatatcagc tggcgcctta gttatataac atgcatgtta tataactaag
5461 gcgccagctg atataaaact aagatggcgc atgtacaaca acaacacatt aaaagatata
5521 gagtttcgcg attgcataag caa (SEQ ID NO:9)
```

```
MAFNPPVIRAFSQPAFTYVFKFPYPQWKEKEWLLHALLAHGTEQ
SMIQLRNCAPHPDEDIIRDDLLISLEDRHFGAVLCKAVYMATTTLMSHKQRNMFPRCD
IIVQSELGEKNLHCHIIVGGEGLSKRNAKSSCAQFYGLILAEIIQRCKSLLATRPFEP
EEADIFHTLKKAEREAWGGVTGGNMQILQYRDRRGDLHAQTVDPLRFFKNYLLPKNRC
ISSYSKPDVCTSPDNWFILAEKTYSHTLINGLPLPEHYRKNYHATLDNEVIPGPQTMA
YGGRGPWEHLPEVGDQRLAASSVSTTYKPNKKEKLMLNLLDKCKELNLLVYEDLVANC
PELLLMLEGQPGGARLIEQVLGMHHINVCSNFTALTYLFHLHPVTSLDSDNKALQLLL
IQGYNPLAVGHALCCVLNKQFGKQNTVCFYGPASTGKTNMAKAIVQGIRLYGCVNHLN
KGFVFNDCRQRLVVWWEECLMHQDWVEPAKCILGGTECRIDVKHRDSVLLTQTPVIIS
TNHDIYAVVGGNSVSHVHAAPLKERVIQLNFMKQLPQTFGEITATEIAALLQWCFNEY
DCTLTGFKQKWNLDKIPNSFPLGVLCPTHSQDFTLHENGYCTDCGGYLPHSADNSMYT
DRASETSTGDITPSDLGDSDGEDTKPETSQVDYCPPKKRRLTAPASPPNSPASSVSTI
TFFNTWHAQPRDEDELREYERQASLLQKKRESRKRGEEETLADNSSQEQEPQPDPTQW
GERLGLISSGTPNQPPIVLHCFEDLRPSDEDEGEYIGEKRQ (SEQ ID NO:10)
```

```
MAFNPPVIRAFSQPAFTYVFKFPYPQWKEKEWLLHALLAHGTEQ
SMIQLRNCAPHPDEDIIRDDLLISLEDRHFGAVLCKAVYMATTTLMSHKQRNMFPRCD
IIVQSELGEKNLHCHIIVGGEGLSKRNAKSSCAQFYGLILAEIIQRCKSLLATRPFEP
EEADIFHTLKKAEREAWGGVTGGNMQILQYRDRRGDLHAQTVDPLRFFKNYLLPKNRC
ISSYSKPDVCTSPDNWFILAEKTYSHTLINGLPLPEHYRKNYHATLDNEVIPGPQTMA
YGGRGPWEHLPEVGDQRLAASSVSTTYKPNKKEKLMLNLLDKCKELNLLVYEDLVANC
PELLLMLEGQPGGARLIEQVLGMHHINVCSNFTALTYLFHLHPVTSLDSDNKALQLLL
IQGYNPLAVGHALCCVLNKQFGKQNTVCFYGPASTGKTNMAKAIVQGIRLYGCVNHLN
KGFVFNDCRQRLVVWWEECLMHQDWVEPAKCILGGTECRIDVKHRDSVLLTQTPVIIS
TNHDIYAVVGGNSVSHVHAAPLKERVIQLNFMKQLPQTFGEITATEIAALLQWCFNEY
DCTLTGFKQKWNLDKIPNSFPLGVLCPTHSQDFTLHENGYCTDCGGYLPHSADNSMYT
DRASETSTGDITPSK (SEQ ID NO:11)
```

```
MYTDRASETSTGDITPSDLGDSDGEDTKPETSQVDYCPPKKRRL
TAPASPPNSPASSVSTITFFNTWHAQPRDEDELREYERQASLLQKKRESRKRGEEETL
ADNSSQEQEPQPDPTQWGERLGLISSGTPNQPPIVLHCFEDLRPSDEDEGEYIGEKRQ (SEQ ID NO:12)
```

Figure 8 (cont.)

MSSGNMKDKHRSYKRKGSPERGERKRHWQTTHHRSRSRSPIRHS
GERGSGSYHQEHPISHLSSCTASKTSDQVMKTRESTSGKKDNRTNPYTVFSQHRASNP
EAPGWCGFYWHSTRIARDGTNSIFNEMKQQFQQLQIDNKIGWDNTRELLFNQKKTLDQ
KYRNMFWHFRNNSDCERCNYWDDVYRRHLANVSSQTEADETTDEEMLSAAESMEADAS
N (SEQ ID NO:13)

MPPIKRQPRGWVLPGYRYLGPFNPLDNGEPVNNADRAAQLHDHA
YSELIKSGKNPYLYFNKADEKFIDDLKDDWSIGGIIGSSFFKIKRAVAPALGNKERAQ
KRHFYFANSNKGAKKTKKSEPKPGTSKMSDTDIQDQQPDTVDAPQNTSGGGTGSIGGG
KGSGVGISTGGWVGGSHFSDKYVVTKNTRQFITTIQNGHLYKTEAIETTNQSGKSQRC
VTTPWTYFNFNQYSCHFSPQDWQRLTNEYKRFRPKAMQVKIYNLQIKQILSNGADTTY
NNDLTAGVHIFCDGEHAYPNASHPWDEDVMPDLPYKTWKLFQYGYIPIENELADLDGN
AAGGNATEKALLYQMPFFLLENSDHQVLRTGESTEFTFNFDCEWVNNERAYIPPGLMF
NPKVPTRRVQYIRQNGSTAASTGRIQPYSKPTSWMTGPGLLSAQRVGPQSSDTAPFMV
CTNPEGTHINTGAAGFGSGFDPPSGCLAPTNLEYKLQWYQTPEGTGNNGNIIANPSLS
MLRDQLLYKGNQTTYNLVGDIWMFPNQVWDRFPITRENPIWCKKPRADKHTIMDPFDG
SIAMDHPPGTIFIKMAKIPVPTASNADSYLNIYCTGQVSCEIVWEVKRYATKNWRPER
RHTALGMSLGGESNYTPTYHVDPTGAYIQPTSYDQCMPVKTNINKVL (SEQ ID NO:14)

MSDTDIQDQQPDTVDAPQNTSGGGTGSIGGGKGSGVGISTGGWV
GGSHFSDKYVVTKNTRQFITTIQNGHLYKTEAIETTNQSGKSQRCVTTPWTYFNFNQY
SCHFSPQDWQRLTNEYKRFRPKAMQVKIYNLQIKQILSNGADTTYNNDLTAGVHIFCD
GEHAYPNASHPWDEDVMPDLPYKTWKLFQYGYIPIENELADLDGNAAGGNATEKALLY
QMPFFLLENSDHQVLRTGESTEFTFNFDCEWVNNERAYIPPGLMFNPKVPTRRVQYIR
QNGSTAASTGRIQPYSKPTSWMTGPGLLSAQRVGPQSSDTAPFMVCTNPEGTHINTGA
AGFGSGFDPPSGCLAPTNLEYKLQWYQTPEGTGNNGNIIANPSLSMLRDQLLYKGNQT
TYNLVGDIWMFPNQVWDRFPITRENPIWCKKPRADKHTIMDPFDGSIAMDHPPGTIFI
KMAKIPVPTASNADSYLNIYCTGQVSCEIVWEVKRYATKNWRPERRHTALGMSLGGES
NYTPTYHVDPTGAYIQPTSYDQCMPVKTNINKVL (SEQ ID NO: 15)

MVLTQHTTMTSQLAFTSFVMESMLTQMHLIHGMRTSCLIFHTRP
GNFFNMDIFLLKMNSQILMEMQLEAMLQKKHFCIRCLFFYLKTVTTKYLELVRALNLL
LTLTVNGLTMKEHTFLLD (SEQ ID NO: 16)

HBoV ST1 genomic DNA 1 caaggaggag tggttatatg atgtaatcca taaccactcc caggaaatga cgtatgatag 61 ccaatcagaa ttgagtattg aacctatata agctgctgca cttcctgatt caatcagact 121 gcatccggtc tccggcgagt gaacatctct ggaaaaagct ccacgcttgt ggtgagtcta 181 ctatggcttt caatcctcct gtgattagag ctttttctca acctgctttt acttatgtct 241 tcaaatttcc atatccacaa tggaaagaaa aagaatggct gcttcatgca cttttagctc 301 atggaactga acaatctatg atacaattaa gaaactgcgc tcctcatccg gatgaagaca

Figure 8 (cont.)

361 taatccgtga tgacttgctt atttctttag aagatcgcca ttttggggct gttctctgca 421 aggctgttta catggcaaca actactctca tgtcacacaa acaaaggaat atgtttcctc 481 gttgtgacat catagttcag tctgagctag gagagaaaaa cttacactgc catattatag 541 ttggggggaga aggactaagc aagaggaatg ctaaatcatc ctgtgctcag ttctatggtt 601 taatactagc tgaaataatt caacgctgca aatctcttct ggctacacgt cctttgaac 661 ctgaagaggc tgacatattt cacactttaa aaaaggctga gcgagaggca tggggtggag 721 ttactggcgg caacatgcaa atccttcaat atagagatcg cagaggagac cttcatgcac 781 aaacagtgga tcctcttcgc ttcttcaaaa actacctttt acctaaaaat agatgtattt 841 catcttacag caaacctgat gtttgtactt ctcctgacaa ctggttcatt ttagctgaaa 901 aaacttactc tcacactctt attaacgggc tgccgcttcc agaacattac agaaaaaact 961 accacgcaac cctagataac gaagtcattc cagggcctca aacaatggcc tatggaggac 1021 gtggtccgtg ggaacatctt cctgaggtag gagatcagcg cctagctgcg tcttctgtta 1081 gcactactta taaacctaac aaaaaagaaa aacttatgct aaacttgcta gacaaatgta 1141 aagagctaaa tctattagtt tatgaagact tagtagctaa ttgtcctgaa ctactcctta 1201 tgcttgaagg tcaaccagga ggggcacgcc ttatagaaca agtcttgggc atgcaccata 1261 ttaatgtttg ttctaacttt acagctctca catatctttt tcatctacat cctgttactt 1321 cgcttgactc agacaataaa gctttacagc ttttgttgat tcaaggctat aatcctctag 1381 ccgttggtca cgccctgtgc tgtgtcctga acaaacaatt cgggaaacaa aacactgttt 1441 gcttttacgg gcctgcctca acaggtaaaa caaatatggc caaggcaatc gtccaaggga 1501 ttagacttta tgggtgtgtt aatcatttga acaaaggatt tgtatttaat gactgcagac 1561 aacgcttagt tgtttggtgg gaggagtgct taatgcacca ggattgggtg gaacctgcaa 1621 agtgtatctt gggcgggaca gaatgcagaa ttgacgtcaa gcatagagac agtgtacttt 1681 taactcaaac acctgtaatt atatccacta accacgatat ctacgcggtt gttggtggca 1741 attctgtttc tcatgttcac gcggctccat taaaagaaag agtgattcag ctaaatttta 1801 tgaaacaact tcctcaaaca tttggagaaa tcactgctac tgagattgca gctcttctac 1861 agtggtgttt caatgagtac gactgtactc tgacaggatt taaacaaaaa tggaatttag 1921 ataaaattcc aaactcattt cctcttgggg tcctttgtcc tactcattca caggacttta 1981 cacttcacga aaacggatac tgcactgatt gcggtggtta ccttcctcat agtgctgaca 2041 attctatgta cactgatcgc gcaagcgaaa ctagcacagg agacatcaca ccaagtaagt 2101 aaatacgcat gcgcaagtaa ttcttttact ttcacttcgc tatttttacc aatttttact

Figure 8 (cont.)

2161 tttaggtgac ttggggggatt cggacggaga agacaccgag cctgagacat cgcaagtgga 2221 ctattgtcca cccaagaaac gtcgtctaac tgctccagca agtcctccaa actcacctgc 2281 gagctctgta agtactatta ctttctttaa cacttggcac gcacagccac gtgacgaaga 2341 tgagctcagg gaatatgaaa gacaagcatc gctcctacaa aagaaaaggg agtccagaaa 2401 gaggggagag gaagagacac tggcagacaa ctcatcacag gagcaggagc cgcagcccga 2461 tccgacacag tggggagaga ggctcgggct catatcatca ggaacaccca atcagccacc 2521 tatcgtcttg cactgcttcg aagacctcag accaagtgat gaagacgagg gagagtacat 2581 cggggaaaaa agacaataga acaaatccat acactgtatt cagtcaacac agagcttcca 2641 atcctgaagc tccagggtgg tgtgggttct actggcactc tactcgcatt gctagagatg 2701 gtactaattc aatctttaat gaaatgaaac aacagtttca acagctacaa attgataata 2761 aaataggatg ggataacact agagaactat tgtttaatca aaagaaaaca ctagatcaaa 2821 aatacagaaa tatgttctgg cactttagaa ataactctga ttgtgaaaga tgtaattact 2881 gggatgatgt gtaccgtagg cacttagcta atgtttcctc acagacagaa gcagacgaga 2941 taactgacga ggaaatgctt tctgctgctg aaagcatgga agcagatgcc tccaattaag 3001 agacagccta gagggtgggt gctgcctgga tacagatatc ttgggccatt taatccactt 3061 gataacggtg aacctgtaaa taacgctgat cgcgctgctc aattacatga tcacgcctac 3121 tctgaactaa taaagagtgg taaaaatcca tacctgtatt tcaataaagc tgatgaaaaa 3181 ttcattgatg atctaaaaga cgattggtca attggtggaa ttattggatc cagttttttt 3241 aaaataaagc gcgccgtggc tcctgctctg ggaaataaag agagagccca aaaaagacac 3301 ttttactttg ctaactcaaa taaaggtgca aaaaaaacaa aaaaaagtga acctaaacca 3361 ggaacctcaa aaatgtctga cactgacatt caagaccaac aacctgatac tgtggacgca 3421 ccacagaacg cctcaggggg aggaacagga agtattggag gaggaaaagg atctggtgtg 3481 gggatttcca ctggagggtg ggtcggaggt tctcactttt cagacaaata tgtggttact 3541 aaaaacacaa gacaatttat aaccacaatt cagaatggtc acctctacaa aacagaggcc 3601 attgaaacaa caaaccaaag tggaaaatca cagcgctgcg tcacaactcc atggacatac 3661 tttaacttta atcaatacag ctgtcacttc tcaccacaag attggcagcg ccttacaaat 3721 gaatataagc gcttcagacc taaagcaatg caagtaaaga tttacaactt gcaaataaaa 3781 caaatacttt caaatggtgc tgacacaaca tacaacaatg acctcacagc tggcgttcac 3841 atcttttgtg atggagagca tgcttaccca aatgcatctc atccatggga tgaggacgtc

Figure 8 (cont.)

3901 atgcctgatc ttccatacaa gacctggaaa cttttcaat atggatatat tcctattgaa 3961 aatgaactag cagatcttga tggaaatgca gctggaggca atgctacaga aaaagcactt 4021 ctgtatcaga tgcctttttt tctacttgaa aacagtgacc accaagtact tagaactggt 4081 gagagcactg aatttacttt taactttgac tgtgaatggg ttaataatga aagagcatac 4141 attcctcctg gattgatgtt caatccaaaa gttccaacaa gaagagttca gtacataaga 4201 caaaacggaa gcacagcagc cagcacaggc agaattcagc catactcaaa accaacaagc 4261 tggatgacag gacctggcct gctcagtgca cagagagtag gaccacagtc atcagacact 4321 gctccattca tggtttgcac taacccagaa ggaacacaca taaacacagg tgctgcagga 4381 tttggatctg gctttgatcc tccaagcgga tgtctggcac caactaacct agaatacaaa 4441 cttcagtggt accagacacc agaaggaaca ggaaataatg gaaacataat tgcaaaccca 4501 tcactctcaa tgcttagaga ccaactccta tacaaaggaa accagaccac atacaatcta 4561 gtgggggaca tatggatgtt tccaaatcaa gtctgggaca gatttcctat caccagagaa 4621 aatccaatct ggtgcaaaaa accaagggct gacaaacaca caatcatgga tccatttgat 4681 ggatccattg caatggatca tcctccaggc actattttta taaaaatggc aaaaattcca 4741 gtaccaactg caacaaatgc agactcatat ctaaacatat actgtactgg acaagtcagc 4801 tgtgaaattg tatgggaagt agaaagatac gcaacaaaga actggcgtcc agaaagaaga 4861 catactgcac tcgggatgtc actgggagga gagagcaact acacgcctac ataccacgtg 4921 gatccaacag gagcatacat ccagcccacg tcatatgatc agtgtatgcc agtaaaaaca 4981 aacatcaata aagtgttgta atcttataag cctctttttt gcttctgctt acaagttcct 5041 cctcaatgga caagcggaaa gtgaagggtg actgtagtcc tgagctcatg ggttcaagac 5101 cacagcccga tggtagtggt gttaccgtct cgaacctagc cgacagccct tgtacattgt 5161 gggggagct gttttgtttg cttatgcaat cgcgaaactc tatatctttt aatgtgt (SEQ ID NO: 17)

HBoV ST2 genomic DNA 1 gccggcagac atattggatt ccaagatggc gtctgtacaa ccacgtcaca tataaaataa 61 taaatattca caaggaggag tggttatatg atgtaatcca taaccactcc caggaaatga 121 cgtatgatag ccaatcagaa ttgagtatta aacctatata agctgctgca cttcctgatt 181 caatcagact gcatccggtc tccggcgagt gaacatctct ggaaaaagct ccacgcttgt 241 ggtgagtcta ctatggcttt caatcctcct gtgattagag ctttttctca acctgctttt 301 acttatgtct tcaaatttcc atatccacaa tggaaagaaa aagaatggct gcttcatgca 361 cttttagctc atggaactga acaatctatg atacaattaa gaaactgcgc tcctcatccg

Figure 8 (cont.)

421 gatgaagaca taatccgtga tgacttgctt atttctttag aagatcgcca tttgggggct 481 gtctctgcca aggctgttta catggcaaca actactctca tgtcacacaa acaaaggaat 541 atgtttcctc gttgtgacat catagttcag tctgagctag gagagaaaaa cttacactgc 601 catattatag ttgggggaga aggactaagc aagaggaatg ctaaatcatc ctgtgctcag 661 ttctatggtt taatactagc tgagataatt caacgctgca aatctcttct ggctacacgt 721 ccttttgaac ctgaggaggc tgacatattt cacactctaa aaaaggctga gcgagaggca 781 tggggtggag ttactggcgg caacatgcag atccttcaat atagagatcg cagaggagac 841 cttcatgcac aaacagtgga tcctcttcgc ttcttcaaaa actacctttt acctaaaaat 901 agatgtattt catcttacag caaacctgat gtttgtactt ctcctgacaa ctggttcatt 961 ttagctgaaa aaacttactc tcacactctt attaacgggc tgccgcttcc agaacattac 1021 agaaaaaact accacgcaac cctagataac gaagtcattc cagggcctca aacaatggcc 1081 tatggaggac gtggtccgtg ggaacatctt cctgaggtag gagatcagcg cctagctgcg 1141 tcttctgtta gcactactta taaacctaac aaaaaagaaa aacttatgct aaacttgcta 1201 gacaaatgta aagagctaaa tctattagtt tatgaagact tagtagctaa ttgtcctgaa 1261 ctactcctta tgcttgaagg tcaaccagga ggggcacgcc ttatagaaca agtcttgggc 1321 atgcaccata ttaatgtttg ttctaacttt acagctctca catatctttt tcatctacat 1381 cctgttactt cgcttgactc agacaataaa gctttacagc ttttgttgat tcaaggctat 1441 aatcctctag ccgttggtca cgccctgtgc tgtgtcctga acaaacaatt cgggaaacaa 1501 aacactgttt gcttttacgg gcctgcctca acaggtaaaa caaatatggc caaggcaatc 1561 gtccaaggga ttagacttta tgggtgtgtt aatcatttga acaaaggatt tgtatttaat 1621 gactgcagac aacgcctagt tgtttggtgg gaggagtgct taatgcacca ggattgggtg 1681 gaacctgcaa agtgtatctt gggcgggaca gaatgcagaa ttgacgtcaa gcatagagac 1741 agtgtacttt taactcaaac acctgtaatt atatccacta accacgatat ctacgcggtt 1801 gttggtggca attctgtttc tcatgttcac gcggctccat taaaagaaag agtgattcag 1861 ctaaatttta tgaaacaact tcctcaaaca tttggagaaa tcactgctac tgagattgca 1921 gctcttctac agtggtgttt caatgagtac gactgtactc tgacaggatt taaacaaaaa 1981 tggaatttag ataaaattcc aaactcattt cctcttgggg tcctttgtcc tactcattca 2041 caggacttta cacttcacga aaacggatac tgcactgatt gcggtggtta ccttcctcat 2101 agtgctgaca attctatgta cactgatcgc gcaagcgaaa ctagcacagg agacatcaca 2161 ccaagtaagt aaatacgcat gcgcaagtaa ttcttttact ttcacttcgc tatttttacc

Figure 8 (cont.)

2221 aatttttact tttaggtgac ttgggggatt cggacggaga agacaccgag cctgagacat
2281 cgcaagtgga ctattgtcca cccaagaaac gtcgtctaac tgctccagca agtcctccaa
2341 actcacctgc gagctctgta agtactatta ctttctttaa cacttggcac gcacagccac
2401 gtgacgaaga tgagctcagg gaatatgaaa gacaagcatc gctcctacaa aagaaaaggg
2461 agtccagaaa gaggggagag gaagagacac tggcagacaa ctcatcacag gagcaggagc
2521 cgcagcccga tccgacacag tggggagaga ggctcgggct catatcatca ggaacaccca
2581 atcagccacc tatcgtcttg cactgcttcg aagacctcag accaagtgat gaagacgagg
2641 gagagtacat cggggaaaaa agacaataga acaaatccat acactgtatt cagtcaacac
2701 agagcttcca atcctgaagc tccagggtgg tgtgggttct actggcactc tactcgcatt
2761 gctagagatg gtactaattc aatctttaat gaaatgaaac aacagtttca acaactacaa
2821 attgataata aaataggatg ggataacact agagaactat tgtttaatca aaagaaaaca
2881 ctagatcaaa aatacagaaa tatgttctgg cactttagaa ataactctga ttgtgaaaga
2941 tgtaattact gggatgatgt gtaccgtaga cacttagcta atgtttcctc acagacagaa
3001 gcagacgaga taactgacga ggaaatgctt tctgctgctg aaagcatgga agcagatgcc
3061 tccaattaag agacagccta gagggtgggt gctgcctgga tacagatatc ttgggccatt
3121 taatccactt gataacggtg aacctgtaaa taacgctgat cgcgctgctc aattacatga
3181 tcacgcctac tctgaactaa taaagagtgg taaaaatcca tacctgtatt tcaataaagc
3241 tgatgaaaaa ttcattgatg atctaaaaga cgattggtca attggtggaa ttattggatc
3301 cagttttttt aaaataaagc gcgccgtggc tcctgctctg ggaaataaag agagagccca
3361 aaaaagacac ttttactttg ctaactcaaa taaaggtgca aaaaaaacaa aaaaaagtga
3421 acctaaacca ggaacctcaa aaatgtctga cactgacatt caagaccaac aacctgatac
3481 tgtggacgca ccacaaaaca cctcaggggg aggaacagga agtattggag gaggaaaagg
3541 atctggtgtg gggatttcca ctggagggtg ggtcggaggt tctcactttt cagacaaata
3601 tgtggttact aaaaacacaa gacaatttat aaccacaatt cagaatggtc acctctacaa
3661 aacagaggcc attgaaacaa caaaccaaag tggaaaatca cagcgctgcg tcacaactcc
3721 atggacatac tttaacttta atcaatacag ctgtcacttc tcaccacagg attggcagcg
3781 ccttacaaat gaatataagc gcttcagacc taaagcaatg caagtaaaga tttacaactt
3841 gcaaataaaa caaatacttt caaatggtgc tgacacaaca tacaacaatg acctcacagc
3901 tggcgttcac atcttttgtg atggagagca tgcttaccca aatgcatctc atccatggga
3961 tgaggacgtc atgcctgatc ttccatacaa gacctggaaa ctttttcaat atggatatat

Figure 8 (cont.)

```
4021 tcctattgaa aatgaactcg cagatcttga tggaaatgca gctggaggca atgctacaga
4081 aaaagcactt ctgtatcaga tgcctttttt tctacttgaa aacagtgacc accaagtact
4141 tagaactggt gagagcactg aatttacttt taactttgac tgtgaatggg ttaacaatga
4201 aagagcatac attcctcctg gactaatgtt taatccaaaa gtcccaacaa gaagagttca
4261 gtacataaga caaaacggaa gcacagcagc cagcacaggc agaattcagc catactcaaa
4321 accaacaagc tggatgacag gacctggcct gctcagtgca caaagagtag gaccacagtc
4381 atcagacact gctccattca tggtttgcac taacccagaa ggaacacaca taaacacagg
4441 tgctgcagga tttggatctg gctttgatcc tccaaacgga tgtctggcac caactaacct
4501 agaatacaaa cttcagtggt accagacacc agaaggaaca ggaaataatg gaaacataat
4561 tgcaaaccca tcactctcaa tgcttagaga ccaactccta tacaaaggaa accaaaccac
4621 atacaatcta gtgggggaca tatggatgtt tccaaatcaa gtctgggaca gatttcctat
4681 caccagagaa aatccaatct ggtgcaaaaa accaagggct gacaaacaca caatcatgga
4741 tccatttgat ggatcaattg caatggatca tcctccaggc actattttta taaaaatggc
4801 aaaaattcca gttccaactg cctcaaatgc agactcatac ctaaacatat actgtactgg
4861 acaagtcagc tgtgaaattg tatgggaggt agaaagatac gcaacaaaga actggcgtcc
4921 agaaagaaga catactgcac tcgggatgtc actgggagga gagagcaact acacgcctac
4981 ataccacgtg gatccaacag gagcatacat ccagcccacg tcatatgatc agtgtatgcc
5041 agtaaaaaca aacatcaata aagtgttgta atcttataag cctctttttt gcttctgctt
5101 acaagttcct cctcaatgga caagcggaaa gtgaagggtg actgtagtcc tgagctcatg
5161 ggttcaagac cacagcccga tggtagtggt gttaccgtct cgaacctagc cgacagcccc
5221 tgtacattgt gggggagct gttttgtttg cttatgcaat cgcgaaactc tatatctttt
5281 aatgtgttgt tgttgtaca (SEQ ID NO: 18)
```

NS1

Met Ala Phe Asn Pro Pro Val Ile Arg Ala Phe Ser Gln Pro Ala Phe Thr Tyr Val Phe Lys Phe Pro Tyr Pro Gln Trp Lys Glu Lys Glu Trp Leu Leu His Ala Leu Leu Ala His Gly Thr Glu Gln Ser Met Ile GlnLeu Arg Asn Cys Ala Pro His Pro Asp Glu Asp Ile Ile Arg Asp Asp Leu Leu Ile Ser Leu Glu Asp Arg His Phe Gly Ala Val Leu Cys Lys Ala Val Tyr Met Ala Thr Thr Thr Leu Met Ser His Lys Gln Arg Asn Met Phe Pro Arq Cys Asp Ile Ile Val Gln Ser Glu Leu Gly Glu Lys Asn Leu His Cys His Ile Ile Val Gly Gly Glu Gly Leu Ser Lys Arg Asn Ala Lys Ser Ser Cys Ala Gln Phe Tyr Gly Leu Ile Leu Ala Glu Ile Ile Gln Arg Cys Lys Ser Leu Leu Ala Thr Arg Pro Phe Glu Pro Glu Glu Ala Asp Ile Phe His Thr Leu Lys Lys Ala Glu Arg Glu Ala Trp Gly Gly Val Thr Gly Gly Asn Met Gln Ile Leu Gln Tyr Arg Asp Arg Arg Gly Asp Leu His Ala Gln Thr Val Asp Pro Leu Arg Phe Phe Lys Asn Tyr Leu Leu Pro Lys Asn Arg Cys Ile Ser Ser Tyr Ser Lys Pro Asp Val Cys Thr Ser Pro Asp Asn Trp Phe Ile Leu Ala Glu Lys Thr Tyr Ser His Thr Leu Ile Asn Gly Leu Pro Leu Pro Glu His TyrArg

Figure 8 (cont.)

Lys Asn Tyr His Ala Thr Leu Asp Asn Glu Val Ile Pro Gly ProGln Thr Met Ala Tyr Gly Gly Arg Gly Pro Trp Glu His Leu Pro GluVal Gly Asp Gln Arg Leu Ala Ala Ser Ser Val Ser Thr Thr Tyr LysPro Asn Lys Lys Glu Lys Leu Met Leu Asn Leu Leu Asp Lys Cys LysGlu Leu Asn Leu Leu Val Tyr Glu Asp Leu Val Ala Asn Cys Pro GluLeu Leu Leu Met Leu Glu Gly Gln Pro Gly Gly Ala Arg Leu Ile GluGln Val Leu Gly Met His His Ile Asn Val Cys Ser Asn Phe Thr AlaLeu Thr Tyr Leu Phe His Leu His Pro Val Thr Ser Leu Asp Ser AspAsn Lys Ala Leu Gln Leu Leu Leu Ile Gln Gly Tyr Asn Pro Leu AlaVal Gly His Ala Leu Cys Cys Val Leu Asn Lys Gln Phe Gly Lys GlnAsn Thr Val Cys Phe Tyr Gly Pro Ala Ser Thr Gly Lys Thr Asn MetAla Lys Ala Ile Val Gln Gly Ile Arg Leu Tyr Gly Cys Val Asn HisLeu Asn Lys Gly Phe Val Phe Asn Asp Cys Arg Gln Arg Leu Val ValTrp Trp Glu Glu Cys Leu Met His Gln Asp Trp Val Glu Pro Ala LysCys Ile Leu Gly Gly Thr Glu Cys Arg Ile Asp Val Lys His Arg AspSer Val Leu Leu Thr Gln Thr Pro Val Ile Ile Ser Thr Asn His AspIle Tyr Ala Val Val Gly Gly Asn Ser Val Ser His Val His Ala AlaPro Leu Lys Glu Arg Val Ile Gln Leu Asn Phe Met Lys Gln Leu ProGln Thr Phe Gly Glu Ile Thr Ala Thr Glu Ile Ala Ala Leu Leu GlnTrp Cys Phe Asn Glu Tyr Asp Cys Thr Leu Thr Gly Phe Lys Gln LysTrp Asn Leu Asp Lys Ile Pro Asn Ser Phe Pro Leu Gly Val Leu CysPro Thr His Ser Gln Asp Phe Thr Leu His Glu Asn Gly Tyr Cys ThrAsp Cys Gly Gly Tyr Leu Pro His Ser Ala Asp Asn Ser Met Tyr ThrAsp Arg Ala Ser Glu Thr Ser Thr Gly Asp Ile Thr Pro Ser Lys (SEQ ID NO: 19)

NP1

Met Ser Ser Gly Asn Met Lys Asp Lys His Arg Ser Tyr Lys Arg Lys Gly Ser Pro Glu Arg Gly Glu Arg Lys Arg His Trp Gln Thr Thr His His Arg Ser Arg Ser Arg Ser Pro Ile Arg His Ser Gly Glu Arg Gly Ser Gly Ser Tyr His Gln Glu His Pro Ile Ser His Leu Ser Ser Cys Thr Ala Ser Lys Thr Ser Asp Gln Val Met Lys Thr Arg Glu Ser Thr Ser Gly Lys Lys Asp Asn Arg Thr Asn Pro Tyr Thr Val Phe Ser Gln His Arg Ala Ser Asn Pro Glu Ala Pro Gly Trp Cys Gly Phe Tyr Trp His Ser Thr Arg Ile Ala Arg Asp Gly Thr Asn Ser Ile Phe Asn Glu Met Lys Gln Gln Phe Gln Gln Leu Gln Ile Asp Asn Lys Ile Gly Trp Asp Asn Thr Arg Glu Leu Leu Phe Asn Gln Lys Lys Thr Leu Asp Gln Lys Tyr Arg Asn Met Phe Trp His Phe Arg Asn Asn Ser Asp Cys Glu Arg Cys Asn Tyr Trp Asp Asp Val Tyr Arg Arg His Leu Ala Asn Val Ser Ser Gln Thr Glu Ala Asp Glu Ile Thr Asp Glu Glu Met Leu Ser Ala Ala Glu Ser Met Glu Ala Asp Ala Ser Asn (SEQ ID NO: 20)

VP1

Met Pro Pro Ile Lys Arg Gln Pro Arg Gly Trp Val Leu Pro Gly Tyr Arg Tyr Leu Gly Pro Phe Asn Pro Leu Asp Asn Gly Glu Pro Val Asn Asn Ala Asp Arg Ala Ala Gln Leu His Asp His Ala Tyr Ser Glu Leu Ile Lys Ser Gly Lys Asn Pro Tyr Leu Tyr Phe Asn Lys Ala Asp Glu Lys Phe Ile Asp Asp Leu Lys Asp Asp Trp Ser Ile Gly Gly Ile Ile Gly Ser Ser Phe Phe Lys Ile Lys Arg Ala Val Ala Pro Ala Leu Gly Asn Lys Glu Arg Ala Gln Lys Arg His Phe Tyr Phe Ala Asn Ser Asn Lys Gly Ala Lys Lys Thr Lys Lys Ser Glu Pro Lys Pro Gly Thr Ser Lys Met Ser Asp Thr Asp Ile Gln Asp Gln Gln Pro Asp Thr Val Asp Ala Pro Gln Asn Ala Ser Gly Gly Gly Thr Gly Ser Ile Gly Gly Gly Lys Gly Ser Gly Val Gly Ile Ser Thr Gly Gly Trp Val Gly Gly Ser His Phe Ser Asp Lys Tyr Val Val Thr Lys Asn Thr Arg Gln Phe Ile Thr Thr Ile Gln Asn Gly His Leu Tyr Lys Thr Glu Ala Ile Glu Thr Thr Asn Gln Ser Gly Lys Ser Gln Arg Cys Val Thr Thr Pro Trp Thr Tyr Phe Asn Phe Asn Gln Tyr Ser Cys His Phe Ser Pro Gln Asp Trp Gln Arg Leu Thr Asn Glu Tyr Lys Arg Phe Arg Pro Lys Ala Met Gln Val Lys Ile Tyr Asn Leu Gln Ile Lys Gln Ile Leu Ser Asn Gly Ala Asp Thr Thr Tyr Asn Asn Asp Leu Thr Ala Gly Val His Ile Phe Cys Asp Gly Glu His Ala Tyr Pro Asn Ala Ser His Pro Trp Asp Glu Asp Val Met Pro Asp Leu Pro Tyr Lys Thr Trp Lys Leu Phe Gln Tyr Gly Tyr Ile Pro Ile Glu Asn Glu Leu Ala Asp Leu Asp Gly Asn Ala Ala Gly Gly Asn Ala Thr Glu Lys Ala Leu Leu Tyr Gln Met Pro Phe Phe Leu Leu Glu Asn Ser Asp His Gln Val Leu Arg Thr Gly Glu Ser Thr Glu Phe Thr Phe Asn Phe Asp Cys Glu Trp Val Asn Asn Glu Arg Ala Tyr Ile Pro Pro Gly Leu Met Phe Asn Pro Lys Val Pro Thr Arg Arg Val Gln Tyr Ile Arg Gln Asn Gly Ser

Figure 8 (cont.)

Thr Ala Ala Ser Thr Gly Arg Ile Gln Pro Tyr Ser Lys Pro Thr Ser Trp Met Thr Gly Pro Gly Leu Leu Ser Ala Gln Arg Val Gly Pro Gln Ser Ser Asp Thr Ala Pro Phe Met Val Cys Thr Asn Pro Glu Gly Thr His Ile Asn Thr Gly Ala Ala Gly Phe Gly Ser Gly Phe Asp Pro Pro Ser Gly Cys Leu Ala Pro Thr Asn Leu Glu Tyr Lys Leu Gln Trp Tyr Gln Thr Pro Glu Gly Thr Gly Asn Asn Gly Asn Ile Ile Ala Asn Pro Ser Leu Ser Met Leu Arg Asp Gln Leu Leu Tyr Lys Gly Asn Gln Thr Thr Tyr Asn Leu Val Gly Asp (SEQ ID NO: 21)

VP2

Met Ser Asp Thr Asp Ile Gln Asp Gln Gln Pro Asp Thr Val Asp Ala Pro Gln Asn Ala Ser Gly Gly Gly Thr Gly Ser Ile Gly Gly Gly Lys Gly Ser Gly Val Gly Ile Ser Thr Gly Gly Trp Val Gly Gly Ser His Phe Ser Asp Lys Tyr Val Val Thr Lys Asn Thr Arg Gln Phe Ile Thr Thr Ile Gln Asn Gly His Leu Tyr Lys Thr Glu Ala Ile Glu Thr Thr Asn Gln Ser Gly Lys Ser Gln Arg Cys Val Thr Thr Pro Trp Thr Tyr Phe Asn Phe Asn Gln Tyr Ser Cys His Phe Ser Pro Gln Asp Trp Gln Arg Leu Thr Asn Glu Tyr Lys Arg Phe Arg Pro Lys Ala Met Gln Val Lys Ile Tyr Asn Leu Gln Ile Lys Gln Ile Leu Ser Asn Gly Ala Asp Thr Thr Tyr Asn Asn Asp Leu Thr Ala Gly Val His Ile Phe Cys Asp Gly Glu His Ala Tyr Pro Asn Ala Ser His Pro Trp Asp Glu Asp Val Met Pro Asp Leu Pro Tyr Lys Thr Trp Lys Leu Phe Gln Tyr Gly Tyr Ile Pro Ile Glu Asn Glu Leu Ala Asp Leu Asp Gly Asn Ala Ala Gly Gly Asn Ala Thr Glu Lys Ala Leu Leu Tyr Gln Met Pro Phe Phe Leu Leu Glu Asn Ser Asp His Gln Val Leu Arg Thr Gly Glu Ser Thr Glu Phe Thr Phe Asn Phe Asp Cys Glu Trp Val Asn Asn Glu Arg Ala Tyr Ile Pro Pro Gly Leu Met Phe Asn Pro Lys Val Pro Thr Arg Arg Val Gln Tyr Ile Arg Gln Asn Gly Ser Thr Ala Ala Ser Thr Gly Arg Ile Gln Pro Tyr Ser Lys Pro Thr Ser Trp Met Thr Gly Pro Gly Leu Leu Ser Ala Gln Arg Val Gly Pro Gln Ser Ser Asp Thr Ala Pro Phe Met Val Cys Thr Asn Pro Glu Gly Thr His Ile Asn Thr Gly Ala Ala Gly Phe Gly Ser Gly Phe Asp Pro Pro Ser Gly Cys Leu Ala Pro Thr Asn Leu Glu Tyr Lys Leu Gln Trp Tyr Gln Thr Pro Glu Gly Thr Gly Asn Asn Gly Asn Ile Ile Ala Asn Pro Ser Leu Ser Met Leu Arg Asp Gln Leu Leu Tyr Lys Gly Asn Gln Thr Thr Tyr Asn Leu Val Gly Asp Ile Trp Met Phe Pro Asn Gln Val Trp Asp Arg Phe Pro Ile Thr Arg Glu Asn Pro Ile Trp Cys Lys Lys Pro Arg Ala Asp Lys His Thr Ile Met Asp Pro Phe Asp Gly Ser Ile Ala Met Asp His Pro Pro Gly Thr Ile Phe Ile Lys Met Ala Lys Ile Pro Val Pro Thr Ala Thr Asn Ala Asp Ser Tyr Leu Asn Ile Tyr Cys Thr Gly Gln Val Ser Cys Glu Ile Val Trp Glu Val Glu Arg Tyr Ala Thr Lys Asn Trp Arg Pro Glu Arg Arg His Thr Ala Leu Gly Met Ser Leu Gly Gly Glu Ser Asn Tyr Thr Pro Thr Tyr His Val Asp Pro Thr Gly Ala Tyr Ile Gln Pro Thr Ser Tyr Asp Gln Cys Met Pro Val Lys Thr Asn Ile Asn Lys Val Leu (SEQ ID NO: 22)

VP1

Met Pro Pro Ile Lys Arg Gln Pro Arg Gly Trp Val Leu Pro Gly Tyr Arg Tyr Leu Gly Pro Phe Asn Pro Leu Asp Asn Gly Glu Pro Val Asn Asn Ala Asp Arg Ala Ala Gln Leu His Asp His Ala Tyr Ser Glu Leu Ile Lys Ser Gly Lys Asn Pro Tyr Leu Tyr Phe Asn Lys Ala Asp Glu Lys Phe Ile Asp Asp Leu Lys Asp Asp Trp Ser Ile Gly Gly Ile Ile Gly Ser Ser Phe Phe Lys Ile Lys Arg Ala Val Ala Pro Ala Leu Gly Asn Lys Glu Arg Ala Gln Lys Arg His Phe Tyr Phe Ala Asn Ser Asn Lys Gly Ala Lys Lys Thr Lys Lys Ser Glu Pro Lys Pro Gly Thr Ser Lys Met Ser Asp Thr Asp Ile Gln Asp Gln Gln Pro Asp Thr Val Asp Ala Pro Gln Asn Thr Ser Gly Gly Gly Thr Gly Ser Ile Gly Gly Gly Lys Gly Ser Gly Val Gly Ile Ser Thr Gly Gly Trp Val Gly Gly Ser His Phe Ser Asp Lys Tyr Val Val Thr Lys Asn Thr Arg Gln Phe Ile Thr Thr Ile Gln Asn Gly His Leu Tyr Lys Thr Glu Ala Ile Glu Thr Thr Asn Gln Ser Gly Lys Ser Gln Arg Cys Val Thr Thr Pro Trp Thr Tyr Phe Asn Phe Asn Gln Tyr Ser Cys His Phe Ser Pro Gln Asp Trp Gln Arg Leu Thr Asn Glu Tyr Lys Arg Phe Arg Pro Lys Ala Met Gln Val Lys Ile Tyr Asn Leu Gln Ile Lys Gln Ile Leu Ser Asn Gly Ala Asp Thr Thr Tyr Asn Asn Asp Leu Thr Ala Gly Val His Ile Phe Cys Asp Gly Glu His Ala Tyr Pro Asn Ala Ser His Pro Trp Asp Glu Asp Val Met Pro Asp Leu Pro Tyr Lys Thr Trp Lys Leu Phe Gln Tyr Gly Tyr Ile Pro Ile Glu Asn Glu Leu Ala Asp Leu Asp Gly

Figure 8 (cont.)

Asn Ala Ala Gly Gly Asn Ala Thr Glu Lys Ala Leu Leu Tyr Gln Met Pro Phe Phe Leu Leu Glu Asn Ser Asp His Gln Val Leu Arg Thr Gly Glu Ser Thr Glu Phe Thr Phe Asn Phe Asp Cys Glu Trp Val Asn Asn Glu Arg Ala Tyr Ile Pro Pro Gly Leu Met Phe Asn Pro Lys Val Pro Thr Arg Arg Val Gln Tyr Ile Arg Gln Asn Gly Ser Thr Ala Ala Ser Thr Gly Arg Ile Gln Pro Tyr Ser Lys Pro Thr Ser Trp Met Thr Gly Pro Gly Leu Leu Ser Ala Gln Arg Val Gly Pro Gln Ser Ser Asp Thr Ala Pro Phe Met Val Cys Thr Asn Pro Glu Gly Thr His Ile Asn Thr Gly Ala Ala Gly Phe Gly Ser Gly Phe Asp Pro Pro Asn Gly Cys Leu Ala Pro Thr Asn Leu Glu Tyr Lys Leu Gln Trp Tyr Gln Thr Pro Glu Gly Thr Gly Asn Asn Gly Asn Ile Ile Ala Asn Pro Ser Leu Ser Met Leu Arg Asp Gln Leu Leu Tyr Lys Gly Asn Gln Thr Thr Tyr Asn Leu Val Gly Asp Ile Trp Met Phe Pro Asn Gln Val Trp Asp Arg Phe Pro Ile Thr Arg Glu Asn Pro Ile Trp Cys Lys Lys Pro Arg Ala Asp Lys His Thr Ile Met Asp Pro Phe Asp Gly Ser Ile Ala Met Asp His Pro Pro Gly Thr Ile Phe Ile Lys Met Ala Lys Ile Pro Val Pro Thr Ala Ser Asn AlaAsp Ser Tyr Leu Asn Ile Tyr Cys Thr Gly Gln Val Ser Cys Glu Ile Val Trp Glu Val Glu Arg Tyr Ala Thr Lys Asn Trp Arg Pro Glu Arg Arg His Thr Ala Leu Gly Met Ser Leu Gly Gly Glu Ser Asn Tyr Thr Pro Thr Tyr His Val Asp Pro Thr Gly Ala Tyr Ile Gln Pro Thr Ser Tyr Asp Gln Cys Met Pro Val Lys Thr Asn Ile Asn Lys Val Leu (SEQ ID NO: 23)

VP2

Met Ser Asp Thr Asp Ile Gln Asp Gln Gln Pro Asp Thr Val Asp Ala Pro Gln Asn Thr Ser Gly Gly Gly Thr Gly Ser Ile Gly Gly Gly Lys Gly Ser Gly Val Gly Ile Ser Thr Gly Gly Trp Val Gly Gly Ser His Phe Ser Asp Lys Tyr Val Val Thr Lys Asn Thr Arg Gln Phe Ile Thr Thr Ile Gln Asn Gly His Leu Tyr Lys Thr Glu Ala Ile Glu Thr Thr Asn Gln Ser Gly Lys Ser Gln Arg Cys Val Thr Thr Pro Trp Thr Tyr Phe Asn Phe Asn Gln Tyr Ser Cys His Phe Ser Pro Gln Asp Trp Gln Arg Leu Thr Asn Glu Tyr Lys Arg Phe Arg Pro Lys Ala Met Gln Val Lys Ile Tyr Asn Leu Gln Ile Lys Gln Ile Leu Ser Asn Gly Ala Asp Thr Thr Tyr Asn Asn Asp Leu Thr Ala Gly Val His Ile Phe Cys Asp Gly Glu His Ala Tyr Pro Asn Ala Ser His Pro Trp Asp Glu Asp Val Met Pro Asp Leu Pro Tyr Lys Thr Trp Lys Leu Phe Gln Tyr Gly Tyr Ile Pro Ile Glu Asn Glu Leu Ala Asp Leu Asp Gly Asn Ala Ala Gly Gly Asn Ala Thr Glu Lys Ala Leu Leu Tyr Gln Met Pro Phe Phe Leu Leu Glu Asn Ser Asp His Gln Val Leu Arg Thr Gly Glu Ser Thr Glu Phe Thr Phe Asn Phe Asp Cys Glu Trp Val Asn Asn Glu Arg Ala Tyr Ile Pro Pro Gly Leu Met Phe Asn Pro Lys Val Pro Thr Arg Arg Val Gln Tyr Ile Arg Gln Asn Gly Ser Thr Ala Ala Ser Thr Gly Arg Ile Gln Pro Tyr Ser Lys Pro Thr Ser Trp Met Thr Gly Pro Gly Leu Leu Ser Ala Gln Arg Val Gly Pro Gln Ser Ser Asp Thr Ala Pro Phe Met Val Cys Thr Asn Pro Glu Gly Thr His Ile Asn Thr Gly Ala Ala Gly Phe Gly Ser Gly Phe Asp Pro Pro Asn Gly Cys Leu Ala Pro Thr Asn Leu Glu Tyr Lys Leu Gln Trp Tyr Gln Thr Pro Glu Gly Thr Gly Asn Asn Gly Asn Ile Ile Ala Asn Pro Ser Leu Ser Met Leu Arg Asp Gln Leu Leu Tyr Lys Gly Asn Gln Thr Thr Tyr Asn Leu Val Gly Asp Ile Trp Met Phe Pro Asn Gln Val Trp Asp Arg Phe Pro Ile Thr Arg Glu Asn Pro Ile Trp Cys Lys Lys Pro Arg Ala Asp Lys His Thr Ile Met Asp Pro Phe Asp Gly Ser Ile Ala Met Asp His Pro Pro Gly Thr Ile Phe Ile Lys Met Ala Lys Ile Pro Val Pro Thr Ala Ser Asn Ala Asp Ser Tyr Leu Asn Ile Tyr Cys Thr Gly Gln Val Ser Cys Glu Ile Val Trp Glu Val Glu Arg Tyr Ala Thr Lys Asn Trp Arg Pro Glu Arg Arg His Thr Ala Leu Gly Met Ser Leu Gly Gly Glu Ser Asn Tyr Thr Pro Thr Tyr His Val Asp Pro Thr Gly Ala Tyr Ile Gln Pro Thr Ser Tyr Asp Gln Cys Met Pro Val Lys Thr Asn Ile Asn Lys Val Leu (SEQ ID NO: 24)

<u>Large non-structural protein</u>

MAFNPPVIRAFSQPAFTYVFKFPYPQWKEKEWLLHALLAHGTEQ
SMIQLRNCAPHPDEDIIRDDLLISLEDRHFGAVLCKAVYMATTTLMSHKQRNMFPRCD
IIVQSELGEKNLHCHIIVGGEGLSKRNAKSSCAQFYGLILAEIIQRCKSLLATRPFEP
EEADIFHTLKKAEREAWGGVTGGNMQILQYRDRRGDLHAQTVDPLRFFKNYLLPKNRC
ISSYSKPDVCTSPDNWFILAEKTYSHTLINGLPLPEHYRKNYHATLDNEVIPGPQTMA

Figure 8 (cont.)

YGGRGPWEHLPEVGDQRLAASSVSTTYKPNKKEKLMLNLLDKCKELNLLVYEDLVANC
PELLLMLEGQPGGARLIEQVLGMHHINVCSNFTALTYLFHLHPVTSLDSDNKALQLLL
IQGYNPLAVGHALCCVLNKQFGKQNTVCFYGPASTGKTNMAKAIVQGIRLYGCVNHLN
KGFVFNDCRQRLVVWWEECLMHQDWVEPAKCILGGTECRIDVKHRDSVLLTQTPVIIS
TNHDIYAVVGGNSVSHVHAAPLKERVIQLNFMKQLPQTFGEITATEIAALLQWCFNEY
DCTLTGFKQKWNLDKIPNSFPLGVLCPTHSQDFTLHENGYCTDCGGYLPHSADNSMYT
DRASETSTGDITPSDLGDSDGEDTKPETSQVDYCPPKKRRLTAPASPPNSPASSVSTI
TFFNTWHAQPRDEDELREYERQASLLQKKRESRKRGEEETLADNSSQEQEPQPDPTQW
GERLGLISSGTPNQPPIVLHCFEDLRPSDEDEGEYIGEKRQ (SEQ ID NO: 25)

Large non-structural protein 1-70K

MAFNPPVIRAFSQPAFTYVFKFPYPQWKEKEWLLHALLAHGTEQ
SMIQLRNCAPHPDEDIIRDDLLISLEDRHFGAVLCKAVYMATTTLMSHKQRNMFPRCD
IIVQSELGEKNLHCHIIVGGEGLSKRNAKSSCAQFYGLILAEIIQRCKSLLATRPFEP
EEADIFHTLKKAEREAWGGVTGGNMQILQYRDRRGDLHAQTVDPLRFFKNYLLPKNRC
ISSYSKPDVCTSPDNWFILAEKTYSHTLINGLPLPEHYRKNYHATLDNEVIPGPQTMA
YGGRGPWEHLPEVGDQRLAASSVSTTYKPNKKEKLMLNLLDKCKELNLLVYEDLVANC
PELLLMLEGQPGGARLIEQVLGMHHINVCSNFTALTYLFHLHPVTSLDSDNKALQLLL
IQGYNPLAVGHALCCVLNKQFGKQNTVCFYGPASTGKTNMAKAIVQGIRLYGCVNHLN
KGFVFNDCRQRLVVWWEECLMHQDWVEPAKCILGGTECRIDVKHRDSVLLTQTPVIIS
TNHDIYAVVGGNSVSHVHAAPLKERVIQLNFMKQLPQTFGEITATEIAALLQWCFNEY
DCTLTGFKQKWNLDKIPNSFPLGVLCPTHSQDFTLHENGYCTDCGGYLPHSADNSMYT
DRASETSTGDITPSK(SEQ ID NO: 26)

middle-ORF non-structural protein 1

MSSGNMKDKHRSYKRKGSPERGERKRHWQTTHHRSRSRSPIRHS
GERGSGSYHQEHPISHLSSCTASKTSDQVMKTRESTSGKKDNRTNPYTVFSQHRASNP
EAPGWCGFYWHSTRIARDGTNSIFNEMKQQFQQLQIDNKIGWDNTRELLFNQKKTLDQ
KYRNMFWHFRNNSDCERCNYWDDVYRRHLANVSSQTEADEITDEEMLSAAESMEADAS
N (SEQ ID NO: 27)

large structural protein

MPPIKRQPRGWVLPGYRYLGPFNPLDNGEPVNNADRAAQLHDHA
YSELIKSGKNPYLYFNKADEKFIDDLKDDWSIGGIIGSSFFKIKRAVAPALGNKERAQ
KRHFYFANSNKGAKKTKKSEPKPGTSKMSDTDIQDQQPDTVDAPQNTSGGGTGSIGGG
KGSGVGISTGGWVGGSHFSDKYVVTKNTRQFITTIQNGHLYKTEAIETTNQSGKSQRC
VTTPWTYFNFNQYSCHFSPQDWQRLTNEYKRFRPKAMQVKIYNLQIKQILSNGADTTY
NNDLTAGVHIFCDGEHAYPNASHPWDEDVMPDLPYKTWKLFQYGYIPIENELADLDGN
AAGGNATEKALLYQMPFFLLENSDHQVLRTGESTEFTFNFDCEWVNNERAYIPPGLMF
NPKVPTRRVQYIRQNGSTAASTGRIQPYSKPTSWMTGPGLLSAQRVGPQSSDTAPFMV
CTNPEGTHINTGAAGFGSGFDPPSGCLAPTNLEYKLQWYQTPEGTGNNGNIIANPSLS
MLRDQLLYKGNQTTYNLVGDIWMFPNQVWDRFPITRENPIWCKKPRADKHTIMDPFDG
SIAMDHPPGTIFIKMAKIPVPTASNADSYLNIYCTGQVSCEIVWEVKRYATKNWRPER
RHTALGMSLGGESNYTPTYHVDPTGAYIQPTSYDQCMPVKTNINKVL (SEQ ID NO: 28)

small structural protein

MSDTDIQDQQPDTVDAPQNTSGGGTGSIGGGKGSGVGISTGGWV
GGSHFSDKYVVTKNTRQFITTIQNGHLYKTEAIETTNQSGKSQRCVTTPWTYFNFNQY

Figure 8 (cont.)

SCHFSPQDWQRLTNEYKRFRPKAMQVKIYNLQIKQILSNGADTTYNNDLTAGVHIFCD
GEHAYPNASHPWDEDVMPDLPYKTWKLFQYGYIPIENELADLDGNAAGGNATEKALLY
QMPFFLLENSDHQVLRTGESTEFTFNFDCEWVNNERAYIPPGLMFNPKVPTRRVQYIR
QNGSTAASTGRIQPYSKPTSWMTGPGLLSAQRVGPQSSDTAPFMVCTNPEGTHTNTGA
AGFGSGFDPPSGCLAPTNLEYKLQWYQTPEGTGNNGNIIANPSLSMLRDQLLYKGNQT
TYNLVGDIWMFPNQVWDRFPITRENPIWCKKPRADKHTIMDPFDGSIAMDHPPGTIFI
KMAKIPVPTASNADSYLNIYCTGQVSCEIVWEVKRYATKNWRPERRHTALGMSLGGES
NYTPTYHVDPTGAYIQPTSYDQCMPVKTNINKVL (SEQ ID NO: 29)

large non-structural protein

MAFNPPVIRAFSQPAFTYVFKFPYPQWKEKEWLLHALLAHGTEQ
SMIQLRNCAPHPDEDIIRDDLLISLEDRHFGAVLCKAVYMATTTLMSHKQRNMFPRCD
IIVQSELGEKNLHCHIIVGGEGLSKRNAKSSCAQFYGLILAEIIQRCKSLLATRPFEP
EEADIFHTLKKAEREAWGGVTGGNMQILQYRDRRGDLHAQTVDPLRFFKNYLLPKNRC
ISSYSKPDVCTSPDNWFILAEKTYSHTLINGLPLPEHYRKNYHATLDNEVIPGPQTMA
YGGRGPWEHLPEVGDQRLAASSVSTTYKPNKKEKLMLNLLDKCKELNLLVYEDLVANC
PELLLMLEGQPGGARLIEQVLGMHHINVCSNFTALTYLFHLHPVTSLDSDNKALQLLL
IQGYNPLAVGHALCCVLNKQFGKQNTVCFYGPASTGKTNMAKAIVQGIRLYGCVNHLN
KGFVFNDCRQRLVVWWEECLMHQDWVEPAKCILGGTECRIDVKHRDSVLLTQTPVIIS
TNHDIYAVVGGNSVSHVHAAPLKERVIQLNFMKQLPQTFGEITATEIAALLQWCFNEY
DCTLTGFKQKWNLDKIPNSFPLGVLCPTHSQDFTLHENGYCTDCGGYLPHSADNSMYT
DRASETSTGDITPSDLGDSDGEDTKPETSQVDYCPPKKRRLTAPASPPNSPASSVSTI
TFFNTWHAQPRDEDELREYERQASLLQKKRESRKRGEEETLADNSSQEQEPQPDPTQW
GERLGLISSGTPNQPPIVLHCFEDLRPSDEDEGEYIGEKRQ (SEQ ID NO: 30)

large non-structural protein

MAFNPPVIRAFSQPAFTYVFKFPYPQWKEKEWLLHALLAHGTEQ
SMIQLRNCAPHPDEDIIRDDLLISLEDRHFGAVLCKAVYMATTTLMSHKQRNMFPRCD
IIVQSELGEKNLHCHIIVGGEGLSKRNAKSSCAQFYGLILAEIIQRCKSLLATRPFEP
EEADIFHTLKKAEREAWGGVTGGNMQILQYRDRRGDLHAQTVDPLRFFKNYLLPKNRC
ISSYSKPDVCTSPDNWFILAEKTYSHTLINGLPLPEHYRKNYHATLDNEVIPGPQTMA
YGGRGPWEHLPEVGDQRLAASSVSTTYKPNKKEKLMLNLLDKCKELNLLVYEDLVANC
PELLLMLEGQPGGARLIEQVLGMHHINVCSNFTALTYLFHLHPVTSLDSDNKALQLLL
IQGYNPLAVGHALCCVLNKQFGKQNTVCFYGPASTGKTNMAKAIVQGIRLYGCVNHLN
KGFVFNDCRQRLVVWWEECLMHQDWVEPAKCILGGTECRIDVKHRDSVLLTQTPVIIS
TNHDIYAVVGGNSVSHVHAAPLKERVIQLNFMKQLPQTFGEITATEIAALLQWCFNEY
DCTLTGFKQKWNLDKIPNSFPLGVLCPTHSQDFTLHENGYCTDCGGYLPHSADNSMYT
DRASETSTGDITPSK (SEQ ID NO: 31)

small non-structural protein

MYTDRASETSTGDITPSDLGDSDGEDTKPETSQVDYCPPKKRRL
TAPASPPNSPASSVSTITFFNTWHAQPRDEDELREYERQASLLQKKRESRKRGEEETL
ADNSSQEQEPQPDPTQWGERLGLISSGTPNQPPIVLHCFEDLRPSDEDEGEYIGEKRQ (SEQ ID NO: 32)

small non-structural protein

Figure 8 (cont.)

MSSGNMKDKHRSYKRKGSPERGERKRHWQTTHHRSRSRSPIRHS
GERGSGSYHQEHPISHLSSCTASKTSDQVMKTRESTSGKKDNRTNPYTVFSQHRASNP
EAPGWCGFYWHSTRIARDGTNSIFNEMKQQFQQLQIDNKIGWDNTRELLFNQKKTLDQ
KYRNMFWHFRNNSDCERCNYWDDVYRRHLANVSSQTEADETTDEEMLSAAESMEADASN (SEQ ID NO: 33)

large structural protein

MPPIKRQPRGWVLPGYRYLGPFNPLDNGEPVNNADRAAQLHDHA
YSELIKSGKNPYLYFNKADEKFIDDLKDDWSIGGIIGSSFFKIKRAVAPALGNKERAQ
KRHFYFANSNKGAKKTKKSEPKPGTSKMSDTDIQDQQPDTVDAPQNTSGGGTGSIGGG
KGSGVGISTGGWVGGSHFSDKYVVTKNTRQFITTIQNGHLYKTEAIETTNQSGKSQRC
VTTPWTYFNFNQYSCHFSPQDWQRLTNEYKRFRPKAMQVKIYNLQIKQILSNGADTTY
NNDLTAGVHIFCDGEHAYPNASHPWDEDVMPDLPYKTWKLFQYGYIPIENELADLDGN
AAGGNATEKALLYQMPFFLLENSDHQVLRTGESTEFTFNFDCEWVNNERAYIPPGLMF
NPKVPTRRVQYIRQNGSTAASTGRIQPYSKPTSWMTGPGLLSAQRVGPQSSDTAPFMV
CTNPEGTHINTGAAGFGSGFDPPSGCLAPTNLEYKLQWYQTPEGTGNNGNIIANPSLS
MLRDQLLYKGNQTTYNLVGDIWMFPNQVWDRFPITRENPIWCKKPRADKHTIMDPFDG
SIAMDHPPGTIFIKMAKIPVPTASNADSYLNIYCTGQVSCEIVWEVKRYATKNWRPER
RHTALGMSLGGESNYTPTYHVDPTGAYIQPTSYDQCMPVKTNINKVL (SEQ ID NO: 34)

small structural protein

MSDTDIQDQQPDTVDAPQNTSGGGTGSIGGGKGSGVGISTGGWV
GGSHFSDKYVVTKNTRQFITTIQNGHLYKTEAIETTNQSGKSQRCVTTPWTYFNFNQY
SCHFSPQDWQRLTNEYKRFRPKAMQVKIYNLQIKQILSNGADTTYNNDLTAGVHIFCD
GEHAYPNASHPWDEDVMPDLPYKTWKLFQYGYIPIENELADLDGNAAGGNATEKALLY
QMPFFLLENSDHQVLRTGESTEFTFNFDCEWVNNERAYIPPGLMFNPKVPTRRVQYIR
QNGSTAASTGRIQPYSKPTSWMTGPGLLSAQRVGPQSSDTAPFMVCTNPEGTHINTGA
AGFGSGFDPPSGCLAPTNLEYKLQWYQTPEGTGNNGNIIANPSLSMLRDQLLYKGNQT
TYNLVGDIWMFPNQVWDRFPITRENPIWCKKPRADKHTIMDPFDGSIAMDHPPGTIFI
KMAKIPVPTASNADSYLNIYCTGQVSCEIVWEVKRYATKNWRPERRHTALGMSLGGES
NYTPTYHVDPTGAYIQPTSYDQCMPVKTNINKVL (SEQ ID NO: 35)

small non-structural protein

MVLTQHTTMTSQLAFTSFVMESMLTQMHLIHGMRTSCLIFHTRP
GNFFNMDIFLLKMNSQILMEMQLEAMLQKKHFCIRCLFFYLKTVTTKYLELVRALNLL
LTLTVNGLTMKEHTFLLD (SEQ ID NO: 36)

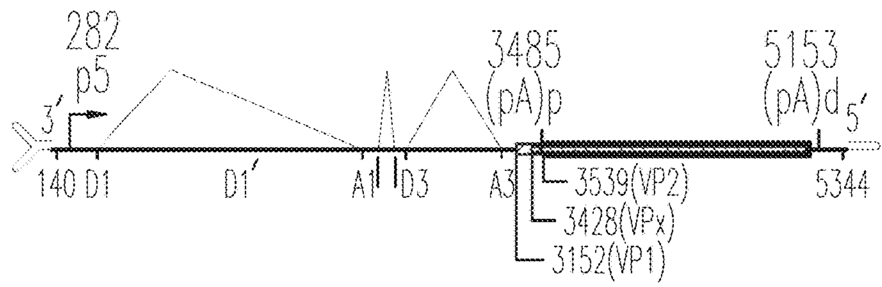
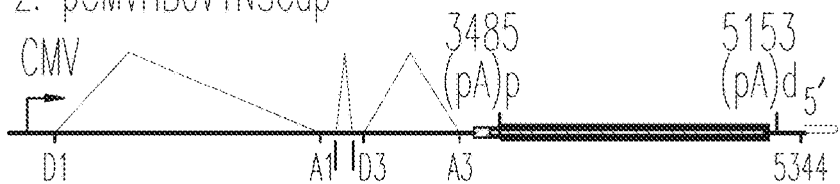
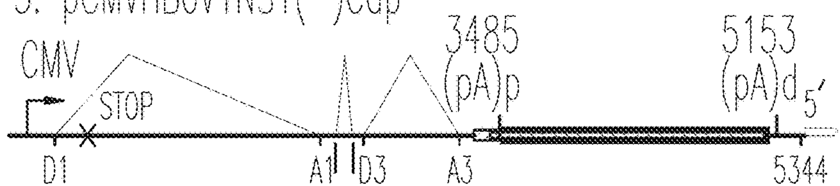
*Fig.9A*
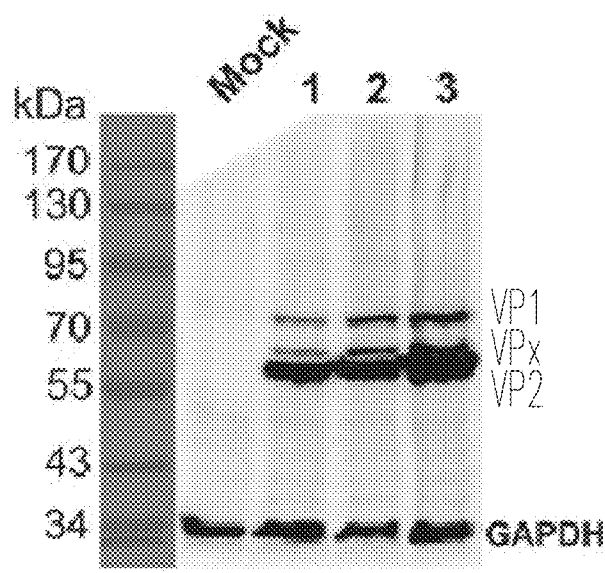
*Fig.9B*
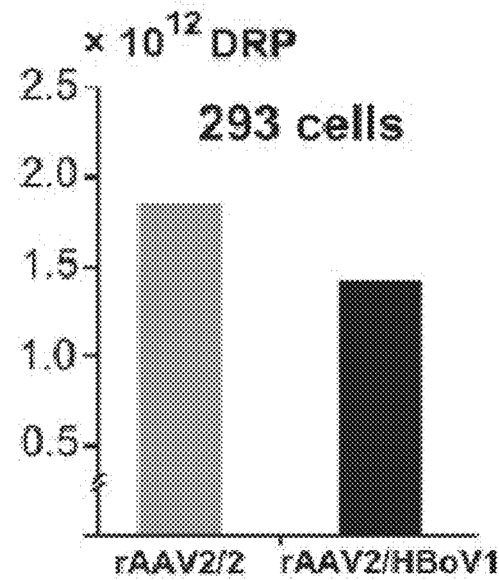
*Fig.9C*

WEB-PAGE

AV2.CMV.PTM24CF
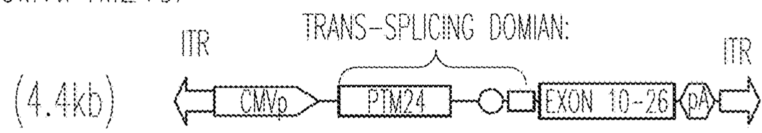
*Fig. 14A*
TRANS-SPLICING DOMIAN:
5'.TCACOCTCACCATTCACTTOCCTCCAATTATCATCCTAAOCACAAOTOTATATTCTTATTTOTAAAOAT
TCTATTAACTCATTTOATTCAAAATATTTAAAATACTTCCTOTTTCAOOTACTCTOCTATOCACCCCCCCAA
CATTATTATAACCTTOCTCCAATACTAACTCCTACCTCTTCTTTTTTTTTTCATATCCTCCAC-3'
*Fig. 14B*
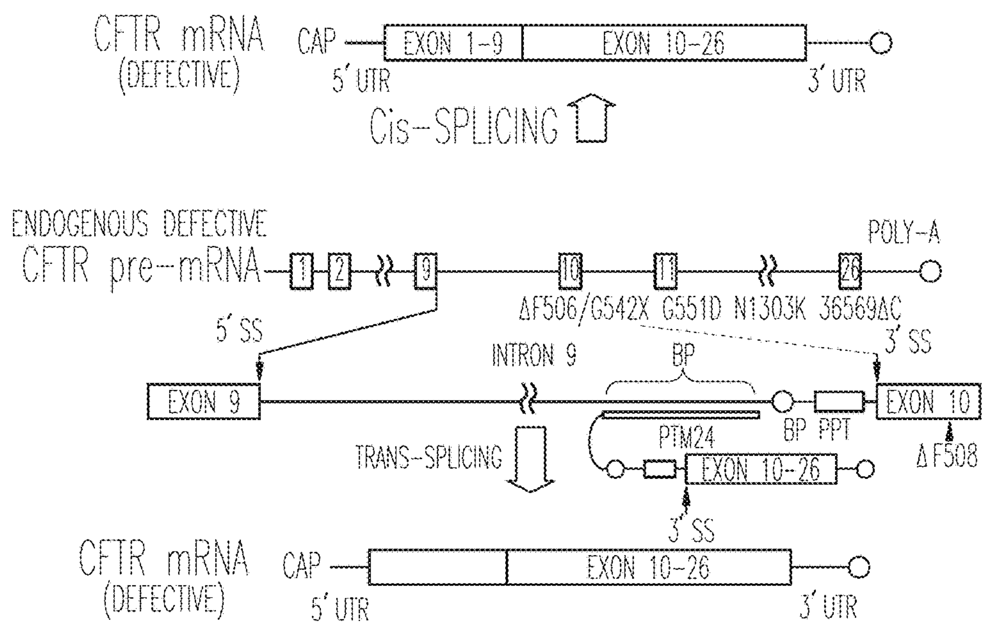
*Fig. 14C*
AV2.CBA.PTM24CF-3UTR
(5.55kb)
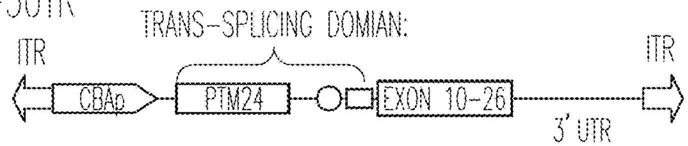
*Fig. 14D*

1 aaccagacat tgggagagca gatgtttttc tcgtcaagag tgtgtaatct ggaggatatt
61 cttgcagaac aaggatacag gcagtgtttt atgatcggat cggatgtgac attcggcgga
121 cgaaaagctt attttaacag ccatggaaat tgtgagatct gggactatta taccgctgtc
181 gaagaaggaa gaattccgga agattattac agatggtggg gatatgagga cgagaagctc
241 tttacatatg ccagggaaaa actgacagag ctgagttcag gatcagaacc attcaatctt
301 acacttctta cagtagacac acattttgaa gacggatatg tctgtgattt gtgtcaggat
361 gaattcggag atgaccagta cgcgaatgtt atggcatgct caagtagaca gattgcagca
421 tttattgaat ggatacagca gcaggatttc tatgagaata cgacgatcat actttgtggt
481 gagtaaccat gcctctgaac aactttcaag ccgcatttga aagcttcggg ggaattgcat
541 atacttatat tctgagactt cctaaatttc ctacgaataa ttatcataat atgctgcagc
601 gatgtttggg ggatagcgag catatctact tgcatgaaag agaggaatgc ggaaagcact
661 atccagactt tccaaatggt tgctccgact tagcagatta ccagaaaaaa tcatacgaac
721 acaacattgc tatatttgct gaaaccgccg taaaaaaggt gtttgaaaat cagcaaatga
781 caagaacacc atcttatgct tgctttgttc aagttgagca cggaaaaaat ctccatgttc
841 atttagtatt atcaggagac ggactcacaa aatatacagc aaaaaacttt agatcaaaat
901 tagctgtata tttttacgca caacttgaac aaaaacaaaa agaagaatta caagagctgt
961 atggaaaccc aaattgggaa gcatatacaa aaccaatttc agaagctcta actaaatcac
1021 aagatggaag cacagaattc tgcacagtac tacagtacaa aagcagaaac ggagaaatgt
1081 actcttgccg cgtggacgca agaagcttca tagctaatta tatgctacca aagaacttag
1141 aaatcaacga taaaatatgg tcaaatacct acaagattcc gggaccacta gcagacacgt
1201 ttcttttaaa tgggaaaact tatacataca gcagcatcaa ctcaatgcaa atcttaccgc
1261 acattagaag agatctaaaa gagtggctgg aagatttgca tggaataaac actgacgaac
1321 caattttttc tggagatccg ctttctgatc tgcctaaggt aagaaaggca caatgggaaa
1381 aaacaactca gccgggagga aaaatgtcta aaagagaagg acttgtacta gactgtatga
1441 atagagccat tgaatctgac tgtttaacgt atgaacaact agtagacaaa catccagaaa
1501 taataataat gatggaaagc caagcaggag gaagcaaatt aatagagcag actttgaaca
1561 tggtgcatat aaaacttacg caaaagtata cagccatgtc atatatgatg aaacggtttc
1621 caacctttaa cctgcaatca aacaataaag caataagact gttaaattat caaggatata
1681 attactggca ggttggacat tggctatgca ctgttttaga taagaagagc ggaaagcaga
1741 acacaataag tttttatggt cctgccagta caggaaagac aaaccttgcc aaggccatag
1801 tgaattgtgt taatctattt ggcaatgtta atcatttaaa caagaacttt gtattcaatg
1861 attgctcaaa caaacttgtt gtatggtggg aagaagcact gatgcatacg gactgggtag
1921 aacctgctaa atgtgttttg ggaggaacaa ccgtacgaat tgacagaaaa cacaaagact
1981 cacaattact gccacagaca ccatgcatca tatccacaaa taacaatata tacgagtgtg
2041 ttggtggtaa tcatgtgtct catgtacatt gcaaaccgct aaaagacaga gtggttcaac
2101 taaattttat gaagacactg ccgcaacact ttggtgaaat ttcaacagaa gaggtggcag
2161 catggctcct aacttgcaag aacaaatttc agtgcacatt agaaggttac tgcaatcaat
2221 ggaaagtgaa gcacgtaata aacgacatgc cgcttgccaa agtgtgtgcc tctcattcac
2281 aggattttac cttacatgaa caaggaacgt gcacccattg tggtgcttac ctgcctctta
2341 ctattgatat tgaatcttgc ggcggtgata atcctgggga cgacggacgt aagtaacatt
2401 ttttacaaaa gggacaggga aataaatctt taaaagatac taaatatcta tttcttcata
2461 ggtgtccctg attcagcaat catcggaact aatagctcga gtgctcgagg tcaaggcgga
2521 gaacctgaca gaaagaaggt gaaataccag gtacttacta aagaacagga agaattccta
2581 gatgagtggg catcacaacc acaggatgaa tcagagatcg agctatacaa ccgaagaaga
2641 gagcagctct tcgaatcgcc gctctcctct ggcagcaagg acatctccga aacagagccg
2701 acatcggagt tggagtcgga gtcggagtcg gagtccaaga agaaaaaggg aggagagccc
2761 atacaggggg aggaaagaga tgagcagatc tccccagaaa caggggaaag agaggattga
2821 gcagcctaga aaacaattta aagaaaaaaa gaatagcatt gttgatgctt ttgtaaaata
2881 taaagctaag cataatactg atcaatcttt ttgcgggttt cactggcatt catggagatt

*Fig. 16A*

2941 agctaaaaag ggcacagaca gggtatttga tgaaatgaaa gctgaatttc aaattcgctg
3001 cagggatggg aaaattgagt ggcctgatgc aagagaaatg ttgtttaaat ttaaaaaagc
3061 tatagataaa gattacagaa gcatgctgtg gcacttcaga tttactgaat gtactaaatg
3121 tgatttttgg gatgatgtgt acaaaaaaca tatggctaat gtgcatcatg aacctccaca
3181 ggaattaaca gacgaagagc tacttgcagc attgcaagaa gctgaagctg gaaaataaaa
3241 ctgatgatca ttgtgctcat gtttattata agcttaataa aatttgacat atgaatcaat
3301 tgtttcctgt ggtacgctcc aaaaaaaacg acggcaaaag aggacacggg aaaaaagctg
3361 aaaaacgacc aagtgaacta aaagatcctg aaaaacctac aggtgaactc gaactagttg
3421 gagaaagatc caactgttcc aaaactcaaa gacattttta ctttgcgcgc caaaaccaag
3481 gtgcaaaaag agcaaaaatg tccgcacagg ggggcgagaa cattgaagag gttgaagtgg
3541 atacaggtgc gggaagtggg cggtcaggcg gtggcggagg aggtggagga ggaggaggct
3601 ctacaaatgg aggaattgga atggcaacag gaggttgggt tggaggaaca tactttggaa
3661 aaaacaaaat agtaacaaac ataacacgtc aatggtacgt gccgatatat aacggccaca
3721 aatacacaaa acagacagaa acagataata ctaacttttg gaacggaata agaacaccat
3781 ggggctacat taacatgaac tcatacagct gtcatttttc tccaaatgac tggcaaagac
3841 ttttaaacaa ctacaaaagg tggaaaccaa aaaaaatgag gctgcagtta tacaacttac
3901 aaataaagca agtagtccaa ctaggcacag atacactata caacaatgat ctgacagcag
3961 gggtgcacat tatgtatgac gggtcacacc aatacccata ctcacaaagt ggatgggaca
4021 gtgagctaat ccctgaactg ccagggatga tttataaact accaaactat tgctacttcc
4081 aggaactagg tgacataggt gatacaggct cagacttaag agaatcatgg ctagggacag
4141 catgtccctt attctttctt gaaagctcct cacatgaggt actaagaaca ggagaagaaa
4201 caggatttga atttgatttt gattgtggat gggtacataa tgacagagca ttttgtccac
4261 cacaatgcga ctttaatccc ctaatcaaaa ccaggcgaag cagaataata atgggttctt
4321 caggaaacac atcagaacca tactatgact acaaaaaacc tagcaattgg atgccaggac
4381 caggaactcg actaaacgga caccaatcag gaagcaatct aaaaacatct tctggcccct
4441 ttaacacatc atgggcacca ccaggggtaa cacagggaag tgacacaacc tacctaaact
4501 caccagcaat gaatcaatca caatgggcct caaaatcaat gccaacagca ccagcaaatg
4561 ctgcatgcag tcaagtagac ccaaactcac tagcattcaa cgaaccaaca caattaggac
4621 agcaaggtga cactaacata agatacaaca acataagcaa tgatctaact agatggggaa
4681 cagtatggag tcagtcacaa caagtataca catcacaacc aacacgaact cgactagaca
4741 cagtatggca atacccaatg caagcatgga acggacagga agtaacacgc tacgctccaa
4801 tttgggacaa acaaccaaac acagattacc atacaacatt atcatcatca gacggaacac
4861 ttccaatgaa acatcctcca ggaaacatat tcattaaagt agcaaaaatt ccaataccaa
4921 cggaaacaaa cacagattca tatctaaaca tatactgcac aggacaaatt tccattgaaa
4981 ttgaatggga cgctgaagaa tatgaaacaa agaactggag accagaacta agaataacat
5041 cctcaaacat tggcagaggg gtgtacaaca taaatgccgc aggagaatac aacacaacag
5101 gaagccaact cagcaacatg ccaacaagat ttggaatgaa cagaatcaac taaacaagga
5161 tttgatattt ctttacaaga ccaccaccag gacgccatat ttgttttggg aaattatttt
5221 tcccaaaact aactttgtga tctatcctcc tgtttcttct cctgttc (SEQ ID NO: 37)

1 MNQLFPVVRS KKNDGKRGHG KKAEKRPSEL KDPEKPTGEL ELVGERSNCS KTQRHFYFAR
61 QNQGAKRAKM SAQGGENIEE VEVDTGAGSG RSGGGGGGGG GGGSTNGGIG MATGGWVGGT
121 YFGKNKIVTN ITRQWYVPIY NGHKYTKQTE TDNTNFWNGI RTPWGYINMN SYSCHFSPND
181 WQRLLNNYKR WKPKKMRLQL YNLQIKQVVQ LGTDTLYNND LTAGVHIMYD GSHQYPYSQS
241 GWDSELIPEL PGMIYKLPNY CYFQELGDIG DTGSDLRESW LGTACPLFFL ESSSHEVLRT
301 GEETGFEFDF DCGWVHNDRA FCPPQCDFNP LIKTRRSRII MGSSGNTSEP YYDYKKPSNW
361 MPGPGTRLNG HQSGSNLKTS SGPFNTSWAP PGVTQGSDTT YLNSPAMNQS QWASKSMPTA
421 PANAACSQVD PNSLAFNEPT QLGQQGDTNI RYNNISNDLT RWGTVWSQSQ QVYTSQPTRT
481 RLDTVWQYPM QAWNGQEVTR YAPIWDKQPN TDYHTTLSSS DGTLPMKHPP GNIFIKVAKI
541 PIPTETNTDS YLNIYCTGQI SIEIEWDAEE YETKNWRPEL RITSSNIGRG VYNINAAGEY
601 NTTGSQLSNM PTRFGMNRIN (SEQ ID NO: 38)

Fig. 16B

1 MSAQGGENIE EVEVDTGAGS GRSGGGGGGG GGGGSTNGGI GMATGGWVGG TYFGKNKIVT
61 NITRQWYVPI YNGHKYTKQT ETDNTNFWNG IRTPWGYINM NSYSCHFSPN DWQRLLNNYK
121 RWKPKKMRLQ LYNLQIKQVV QLGTDTLYNN DLTAGVHIMY DGSHQYPYSQ SGWDSELIPE
181 LPGMIYKLPN YCYFQELGDI GDTGSDLRES WLGTACPLFF LESSSHEVLR TGEETGFEFD
241 FDCGWVHNDR AFCPPQCDFN PLIKTRRSRI IMGSSGNTSE PYYDYKKPSN WMPGPGTRLN
301 GHQSGSNLKT SSGPFNTSWA PPGVTQGSDT TYLNSPAMNQ SQWASKSMPT APANAACSQV
361 DPNSLAFNEP TQLGQQGDTN IRYNNISNDL TRWGTVWSQS QQVYTSQPTR TRLDTVWQYP
421 MQAWNGQEVT RYAPIWDKQP NTDYHTTLSS SDGTLPMKHP PGNIFIKVAK IPIPTETNTD
481 SYLNIYCTGQ ISIEIEWDAE EYETKNWRPE LRITSSNIGR GVYNINAAGE YNTTGSQLSN
541 MPTRFGMNRI N (SEQ ID NO: 39)

1 MAPTNRKPGG WVLPGHRYLG PFNPIENGEP VNAADAAARR HDLKYDQYLK EGKNPYLYFN
61 KADSDFLEDL ESDRSFGGWI GKGVFGLKRA IAPTLDESSG KQNTGGPSAA KKPRVDPQRA
121 QKRKLYFARQ AKEAKKQKMS SGGDPSEDTG AGDGEQGGES SAMTGRSGGG AGGGGGGGSV
181 GFSTGGWEGG TYFSDHTVTT TNTRQWYTGI LNGHRYSKLA QTTGSNLQAA KPWVGIQTPW
241 AYLNLNCYHC LFSPQDWQRL LNEYKAWRPK RMHVRIYNLQ IKQITTVGAD TLYQNDLTAG
301 VHIFCDGSHQ YPYAQHPWDE GASPELPNEI WKLPQYAYFQ YQGDLTDHAT ANTPQNVESM
361 LKSNIPLFLL ENSNHEVLRT GEMTEFSFTF QSGWVTNDRA YCCPQSDFNP LVQTRRYYPT
421 WNGSSNSYSY NRYGPYKKPS NWMPGPGLAY KGATHTNQNP DDARGPIITT IAPRGTISVG
481 STPSNEAPND GDNTISSDGV KQGGWQTAPV NGACSRTDYP TLAFDPSDRS SNQNIPTRNL
541 DIDMTRWYRV HEAVRGASGS TYYNVDDIWM YPNQAWNSTP ICRDNPIWDK VPRTDKHTLL
601 DSSDGTLPMK HPPGNIFIKC AKIPVPTSNN TDSYLNIYVT GQVTYTVEWE VQRYQTKNWR
661 PELRTSAGSY NQHEIYNIGE NGVYNRANTF NECMPTKCGI NRVLKNWR (SEQ ID NO: 40)

1 MSSGGDPSED TGAGDGEQGG ESSAMTGRSG GGAGGGGGGG SVGFSTGGWE GGTYFSDHTV
61 TTTNTRQWYT GILNGHRYSK LAQTTGSNLQ AAKPWVGIQT PWAYLNLNCY HCLFSPQDWQ
121 RLLNEYKAWR PKRMHVRIYN LQIKQITTVG ADTLYQNDLT AGVHIFCDGS HQYPYAQHPW
181 DEGASPELPN EIWKLPQYAY FQYQGDLTDH ATANTPQNVE SMLKSNIPLF LLENSNHEVL
241 RTGEMTEFSF TFQSGWVTND RAYCCPQSDF NPLVQTRRYY PTWNGSSNSY SYNRYGPYKK
301 PSNWMPGPGL AYKGATHTNQ NPDDARGPII TTIAPRGTIS VGSTPSNEAP NDGDNTISSD
361 GVKQGGWQTA PVNGACSRTD YPTLAFDPSD RSSNQNIPTR NLDIDMTRWY RVHEAVRGAS
421 GSTYYNVDDI WMYPNQAWNS TPICRDNPIW DKVPRTDKHT LLDSSDGTLP MKHPPGNIFI
481 KCAKIPVPTS NNTDSYLNIY VTGQVTYTVE WEVQRYQTKN WRPELRTSAG SYNQHEIYNI
541 GENGVYNRAN TFNECMPTKC GINRVL (SEQ ID NO: 41)

Feline bocavirus 1 cctggcgcga tgacgtgtca gtgagggtgt tgtctaaaga ctatagggat caatgatagg
61 ttcagccatg taatgattaa ctgaccttta acgtgattgg ttgggagtta atgattaaca
121 tgtgaccttt acagtgattg gttctctgaa cctataaaaa gagctgcatt tccgtgtctg
181 tgtcattctg cttccggcgc tcgacgagat cggacctgga gaagaacaag ttccgtcaat
241 tggtgagtcg ccatcaatgg ctgaattcga tacagcaagt ctcgacgact tcatccaatt
301 tgcagaccca gcatatacat acgtgctgcg tcttccatta cctacagggg aaaattatga
361 gagccagcta cagaatgtat tatgcgctcg ataccccgat ttattatccg atccggcatt
421 gttcgcaaca atgcctggac ctgaatctcc aggcgctcag actgattttt tggagcgttt
481 tggtcctagc cgctgctttg ggctgaagt ctgctatgcg gcgcatatgg cagcctttaa
541 ctwctttagt aggaaacagg gaaargcgcc rcctatygcc agcatctaca cacaatgcga
601 attaggccag agaaacattc awtgtcatct agtcatggcc ggcgacggtc tgtctcgttt
661 ctcggctaar agcgctgcct acatactagg ccaaaaattt gcagacaatc tgatttctat
721 catcgaaaat aatctaagaa arggcgacgt magyaatcca gcttttgcta ccgcttttat
781 caragaaata caagargctc aaagaaaatg cgaaccaggc aacgctggcg acctttgtac
841 tgtgwtgcaa tataaagta gaggaggcgg catgtacgcg tgccgaatcg atggccgcga

Fig. 16C 901 gtacatctgt aactacctat tatgcaagaa cctgaaatgg gtatcttgcg tggaaccaga
961 caaggcgact cctcttaaag ccttctttcc aatcgcttca aaaacatatg catttactct
1021 aattaatgga aagattgttc cgtatcacgt acgtcgtgaa tggtggaatc aactacgaga
1081 caaggtccta gtcagggacg aaccaatctt taagggagac gtgtttggag atcttccaaa
1141 ggtaaatgct gcgtcatgga aattaactgg taatatgggt caaggtacat ctcagccgca
1201 tgtgaatgcc agaatgagta aaaaagaatc attaatacta gactgtctta aacgttgcga
1261 ggataatcta tggctaacct atgaagatct ggtcggtggt tgtgccgatt taattttaat
1321 gttggaatcg atgccaggtg gaagtaaatt aattgagtct gtacttaaca tgttgcatgt
1381 tagaatcact caaactcata gtgcgttgtc ctatttgcat gtgagatatg acatgaaaga
1441 actggcgact cacgcagact cgctccacgc taataaagca tggagattac tactaaaaca
1501 aggatataat cctctacaag tgggacattg gatctgctgt gtcctacata aaaaagcagg
1561 aaaacaaaat acattaaatt tctttggacc ggctagcacc ggtaaaacaa atctggcaaa
1621 agcaatcgtg aatgcaatca agctctatgg ttgcgtcaat caccaaaaca aaaattttat
1681 ctttaacgat tgtgccgcaa aactagttgt ctggtgggaa gaatgtctca tgcattcaga
1741 ctgggtcgag caagctaaat gtatcttggg cggcacggag tttagaattg acagaaaaca
1801 cagagaatcg catctattgc cacaaactcc tgtaatcatc tcaacgaata acaatatata
1861 tcaaacactg ggtggcaact cggtctcaca tgtacatgaa gctcctctaa gagaaagagt
1921 cgtccagttt aatttcatga cacgtctaga aagcaccttt ggagagattg aaccaagaga
1981 agtagccgaa tggctatcca tctgtctctc tcggtttgac atctctctgg ttggctttca
2041 tactcaatgg aagctaaata aaactccaaa tgactttcca ttggctaaat tctgcggtgg
2101 tcactcacag gatctcgtgt tacatgagac cggaacgtgt atgagctgtg gcggatacta
2161 tcctctagaa ctacacgatc gaggcgacat cgaggacgct acaccaggta cgagctactc
2221 aactctatta caattaacac ctaaatctga aaaatacata caagaattta acttggatct
2281 cttgaaatct ccaatagcgg ccacgagcac tcctgtgact cgacaggatc cacctgagct
2341 tcctccaaaa aagaaggtac gcaaagaaaa acactgcgca cgcgctctct ttactgacga
2401 ctggtgctct caacctcgag acgatgtcga gtggcgcgtc gtccaagaac gagcagaagc
2461 ggcggcggcc gaggtctctg gatcgagatc cgagtccgat tccggacaag cgagctcgat
2521 ggagctcgac ctctcaccag aacaatgggg agagatgctc ggactcatct ccggggacat
2581 cgaagcggga gaaccgccga tcacactcca ctgctttgaa tccatcaccg aagctgactt
2641 actttgtcaa acggactcag aaaccgaata aacaaacacc tcttgatgtc tttatgaaac
2701 atagagccaa agaggggga gatgtacctc cattttgtgg gttttactgg catagtacta
2761 gattagcaag atttggaaca gatgcaatct ttaatttgta taaacctaaa tttcaagaaa
2821 tgtcaaaaaa caatgtaatt acgtgggatc aatgtcgtga tttgttgttt gattttaaaa
2881 agaacctaga ctataaatac agatctatga tgtggcattt tagcatgggt gaacaatgtc
2941 ataaatgtaa ttactgggat aaaatgtacg ctgggcatct ggctaatgta tctctatcta
3001 cacaggaaga ggactctgac cctgtaactg acgctgaaat gctggcggtt gccatggagg
3061 ttgatggcac cgaccaatag gcgtcctggc ggttggactc tgcccggttt cagatatctt
3121 ggtccattta atccattgaa taacggtaaa ccagtaaacg aagtagataa agttgctcaa
3181 aagcacgata aagcttacga ttcttatatc aaggctggcg tcaatccata tttgcacttt
3241 aataaagctg actctgattt cattgattcg ctgtctactg attcgtctgt tgccgggtgg
3301 ctgggaaaat cggcgtttaa actcaagaga cttttggcgc cacatctttc aaaagaaaaa
3361 gaagcagcgg gtaataaagg aggaactggt ggaaaacgcg ccaagcttga tccggtacgg
3421 gctcaaaaaa gaaaatatta ttttgcccgt caaaaccagg gaaaaaatcc taaacaacaa
3481 aaaatggaaa atgaagttga gacggctggg gatggacaag agggggcgcc agctggcact
3541 gctcgtgctg gtggtggtgg taacggtgct ggtatgggtg gtggtggcca tggtgtcggt
3601 gtaagcacgg gagggtggag agctggaact atcttttctg ataatgttat aattacaaca
3661 tcaactagac aatggtatgt tccaatatat aatggtcatc tgtacaaaga aatattcgca
3721 aatgggagcg taagagaatg ggtaggaata agtacccctt ggggatactt taatttcaat
3781 gaatacgatg ctcactttac accaaacgat tggcaacgac tcacaaacga gtatgccaaa
3841 tggagaccaa aaagaatgca tgtcaagata tacaatctcc aaattaaaca aaaggtgaca
3901 ctgggggtgg acaccctata taacaacgac cttacggcgg gtgtacacat tttttgtgac
3961 ggttctcatc aattcccata ctcacaaaaa ccttgggatt ttggaacaat gccagaattg
4021 ccatatgatg tatggaagct tccacaatac gggtattttc aatttcaaaa tgatctctca

Fig. 16D 4081 gatcaatcat caaactcgct tgcagcagat aatgtagaaa aaaatattgt gagaaatgct
4141 ccatttttg tattagaatc tgcatctcac gaggtcctca gaacaggaga agaaacagaa
4201 ttcaactttg aatttgaatg tgggtgggtc acaaatacac gtgcatatgc tccgcctcag
4261 gcagacttca atccattagt tgaaactaga cgttattatc caacatacga caactcatct
4321 agcactaaat ttgtatacgc tagatattca ccatataaca aacctagtaa ctggatgccc
4381 ggtccgagta ttggatatat aggaaacaca acaaccggct caaactacca aacaagaggg
4441 ccaatcacag tatgcccaca tccatatttt actacacctg gaaatttaga aacagacagg
4501 gcatatgacc cacaaagtgg aacaaataca ttaaccgaag ctggcatgag aaaatcggga
4561 tacgatgtaa cacctgtaaa tggtgcctgc tcccgactgg actctgttga cttggcatat
4621 gattcgtctg aatatagctt aaatcaaaca aaattaattt caagaaacat agatagtgac
4681 atggctagat ggggttcagt gtgggcacag gatggattga ataaagaaat aggagacaat
4741 ggacaaccaa acaacacaga cagaaaaaat atcagccagc taaaaaacat atggatgtat
4801 ccaaaccagg catgggacac aacaccaata gcaagaaaca cacccatatg ggacaaagtt
4861 ccagacacag acagaaacac tatgctagat tcggctgatg gcacactacc gatgccacat
4921 ccacctggta ctatctttgt aaaagttgca aaaataccaa taccaaccga aaacaatgca
4981 gatgcatatt tagatctata tgtaacagga caagtaacat gtacaataga atgggaagta
5041 gcaagattca agaccaaaaa ctggagaccg gaaatcagaa catctgcaac aatgttttca
5101 gacccaaaaa tatactctgt caatgccagt ggtgtataca atacaccaga aaccttcaca
5161 gaatctatgc caacaaaatg gggaatcaac aaagttctgt aaaaataaaa ttacatcatt
5221 catcaaactg tacgtgtcac gtgagttttc ttttgcgcgc caaaaaatct ttcgttgatc
5281 tctatactct tatacaacac cctccacact gctacgtcag tgtgtatgag a (SEQ ID NO: 42)

Canine bocavirus 1 tacaccgagc ggcttcgccg ctgcgccctg cgggcgcgct gtatatgttc ctcggcgaac
61 gtgacgtaat gtagtagtgg tgtctataaa gattatatca attgcgctgt cttgtggttg
121 gttaatgagt gactcgctgt gtcagctgtt tgcgattggc tgttgtttta tggccttgtt
181 atgttattgg ttactgattg atgaattttg ggcgggccga gtgactatat atataagtgt
241 gcttcctgct tcgtgtcatt ctgcttccgg ctttcgtcgc gttgagatct ctctgagggt
301 gagtgatggc tcttgctctg gccggggtcg acgatattat tcactttgct cgtcctgcct
361 atacctatgt tctcaagttt ccttacgctg agtggcggcg ggatgaggct cgtcttcaga
421 gcgctctggg gtacccgcat catgatttac tcaaggactc gactccgttc cttactatgc
481 cggggcaaga ttctccggcc gagcaggctt cctttctgga gtctaagggt cctcagtacg
541 gatatgcctt attactggca cgcacggctc acgctgctgc atattctata ttctcgcaga
601 agcagggcaa atatcctcct gctgctagca tatatgttca gtgcgagctt ggccttaagt
661 atcttcacgt acacgtcgtg atgggcggtg acggcttgaa ccggtacaac gccaaggcca
721 cttgctctaa cctggcctat aagtggctgg acaacattca gtctcagctc gagattaacg
781 tcaagaccgg tcacaacacc gaccttgaca tgtgcaattc tctcatcggc tgcgtctacc
841 aggccaagag agagtgcttt gacatgagga ccgagatttg taccatcctg cagtacaagt
901 gccggaacgg cgagatgtac gcctgccggg tcgatcctat agagtttatc tgtaactacc
961 tgttgtgcaa aaacttgaaa ttctttacta tggtcgaccc tgacagagca actccgtttg
1021 tctctcactt tgcctgttct ggtaaaacgt acgcggctac atttgtcaat gggaagtggg
1081 tcttgcctca ggttaggaag cagtggctaa attatcttcg agactctgtc tgtcagaagg
1141 ccgatccagt cttttccggc gacatgtttg aaaacttacc caaggtacct cgcgcgacct
1201 ggtcggtcga agtttcctcc aataaatcta aaatcactaa aaaggaaact ctgatgattg
1261 actgtatcga tcgctgcgaa aagaatcact tgcttaccta tgaagatttg gtcaatgagt
1321 gttctgatct tgtaatcatg ctcggctcac agccgggcgg aactaaattg attgagacct
1381 tgcttcagat ggttcacatt aagatttgtc agaaatatac ggccttgtct tatgtcttgt
1441 cgcggtactc ggcgattgag ctgctgcctg agaacaaggc tatacagctc ttgatctttc
1501 agggatacaa tccctggcag gtcggccact ggctgtgctg cgtgctgcac aagacggccg
1561 gtaaacagaa taccgtgtgc tttttcggtc cggccagcac cggcaagacc aactttgcca
1621 aggctatagt gaatgccgtt aagctgtacg gatgtgtgaa ccatcagaat aagaattttg

Fig. 16E 1681 tgtttaacga ctgcgcgtcc aagctggtca attggtggga agagtgcctc atgcacaatg
1741 attgggtaga gcaggccaag tgcctgctgg gaggaacgga gtttagaatc gaccgtaagc
1801 ataaagactc tcagctgctg ccgcagactc ctgttgtgat cagtaccaat cacgacgtgt
1861 acaccgtggt cggtggaaac accactacta tggttcacgc taagccgctt cgggaaagga
1921 tcgttcagtt taatttcatg aaacagctgt cttccacctt tggggagatt gatcctatgg
1981 atgtggtggc tctgttgcaa gcctgctctt ctcgattcga tgcgtcgctc gactcgtttt
2041 atgctcagtg gcagcttcag tgcactccta acgattttcc tctcgcttcg ttctgtgacg
2101 ggcattcgca ggactttgtc cttcacgagg tcggcttctg cgacacgtgc ggtggctacg
2161 ctcctctgga gactacggac cgcagtcagc cgctgccggc tcgacctgct tcgtccggtg
2221 agtctttgat ttttgcctgt acgctgcctt gactgtttta ttttctgtat gctatactca
2281 gctttgtgct ctttttcag cgtcgggtgt gaagcgtcgc ctggactttg acccggatcc
2341 tgctccttcc acgtcgacgg ctcctccggc gaagcgccac tccaaggtga ggcgtcccgt
2401 gttccacgac gactggtgta gtcagccggt agatcgccta gaccgcatcc gctatgaaaa
2461 gttcgtcgag agcgtcgtcg gcgcgtcaga cgagtcacca tcggagccgg agtcggagtc
2521 cacgggactc acgccttcag agtggggaga gatgctcgga gtcgtctgca agtcgctgga
2581 ggaggaaccg atcgtcttac actgcttcga agacatcacc tctctctcgg aaaccgaaga
2641 cgactccgat ggaggtcttc aatcaacacc gcgccaagac aaagactgac atttcaatgt
2701 gtggctttta ctggcacagt actcgcctcg cgcggtcggg taccgactgg atctttaaca
2761 gtggaaagcc tctgtttcaa tctaaatgtt ctaataatct tgtatcttgg gatgtggttc
2821 gtgagattct gtttgaattt aaaaaaacta tagatcagaa atatagaaat atgctgtggc
2881 actttggtcg ggtgggtac tgcaataaat gtgaatactg ggataatgtg taccttgaac
2941 acctagctaa tgtagattcc tctaatgatg ttgttatgca ggagataagt gacgctgaga
3001 tgttggaggc tgccatggag attgatggcg ccagcgaata gaaagcccgg tggttgggtc
3061 gtgcctggct atagatattt gggtcccttt aaccctgctg acaacgggga acctgtaaat
3121 tctgctgacg aggccgctcg gtctcatgat ctcgcctatc agtcctatct cgatgctggt
3181 gtaaacccgt actttagcta caataaagct gattctgatt tcattgagtc attggctcac
3241 gactcttcat tcggcggctg gctggggcgc tcggcctttg gcctcaagaa attgcttgcg
3301 ccgcatctcg cggatacaaa gggcaatcct gacgctccgt ccacctcgcg gggaggttcc
3361 tctgtatcca agtcagagag agcacaaaag agaaaactct attttgccag atcaaacaaa
3421 caggccaaac aacaaaagat gtcagctcca gaagctccga ccgaagatgt ggcagaaccg
3481 ggtccatctg gctccgatcc gcgggcggga ggaaatggag gtggtggagg catgggagga
3541 ggtggaggac atggagtggg agtgagcacc ggcggatgga aggccgggac cgtgtttggg
3601 aatgactttg tcatcaccac aaacaccaga cagtggttcg ctcccatctt taacggccac
3661 gagtacaaac gcatggcgcc gaacgagaac agcgaaccgg ccaccaacag acactgggtg
3721 ggaatcagta ctccgtgggg atactttaac tttaacgagt acagttcaca tttctcacca
3781 caagactggc agcgcctcac caacgaatat aaaagatgga gacccaaggc catgagggtc
3841 aaagtataca acctgcaaat aaaacaggtg gtcactctgg ggtcagacac tttatacaac
3901 aatgacctga cggccggcgt tcacatcttt tgtgacggga gccatcagtt tccgtactct
3961 cagcatccgt gggacaccgg gaccatgccc gagctgcctc atcgcatctg gaggatctcg
4021 cagtacgggt actttcagct acaggctgac ctgacgaacg gggcgtatc atccgagacg
4081 cccgacgtcg ggaaccaaga aaagcagctg ctaaagagtg cgccgctata catgctcgag
4141 acggcgtcgc accaagtgtt gaggacgggg gaggaatcca gcttctcttt ctcgtttgac
4201 agcgggtggg ttatcaacga caaggcatac gccattccac aggcagattt taaccctctg
4261 attcacacca gacgatactt tcctacacga aacaataaca ccacatcaac aggggggctc
4321 atgttttacc atagatataa tccatacaac aaaccgagca actggatgcc ggggccgagc
4381 ttgggctacc tgggggcgac acagacatca accaatccac agtacgcgcg tggtccggtt
4441 actgttgtca cgcagccgcc gggaacgacg gcagatagcg ccaatataga cgagcaatca
4501 accacacacg tcccgtcaaa ggcgaccatg caaaattcag ggtacgacgt gaaccctgtc
4561 aactgcggta gcagcagatt agacgcgcac tcgcttgcat atgattcagg gccagagagt
4621 cgaggacaga acatcattac cgtaaggggg atagacttag acatggcctt gggtctccat
4681 caaatggtgc aggacggaac agaaacagaa gttggtaccc aaactcccag aactaatttt
4741 actgaactca aaaacgtatg gatgtaccca aatcaggcgt gggacaccac tccggtatcc
4801 agggacactc ctatttgggt caagattcca aaaacagaca ggcacaccat gcaagacacc

Fig. 16F 4861 tcggacggaa cgctgccgat ggcgcatccg ccgggaacca tctttgtcag ggtcgcaaag
4921 gtgcccattc cgggggagtc agactcttac ctaaacctat acgtgacagg acagataacg
4981 tgtgaaatac tctgggaaac agagaggttc cagaccaaaa attggagacc ggaaatcaaa
5041 aacgatccat ccgtattcag cgacccttta ctatacactt tcgacagaca gggggtctac
5101 aatacaccgg aaacattcat agagggcatg cccacaaaac ggggaataaa cagggtcctg
5161 taactttaag aacaaataaa gccataaaac gaaaagtttt gcgcatttgt tatttcttta
5221 aaaggaccat cagtactgta cgtcactata gatcatctga tacggtcagg tattgcttaa
5281 ttatatggcg cagcttagtt atatatcagg tatatgctcg tcacataact aagctaccat
5341 ataattaagc aatacctgac gtatcagatg atctatagtg acgtacagta ctgatggtcc
5401 ttttaaagaa tac (SEQ ID NO: 43)

1 MAPANRKPGG WVVPGYRYLG PFNPADNGEP VNSADEAARS HDLAYQSYLD AGVNPYFSYN
61 KADSDFIESL AHDSSFGGWL GRSAFGLKKL LAPHLADTKG NPDAPSTSRG GSSVSKSERA
121 QKRKLYFARS NKQAKQQKMS APEAPTEDVA EPGPSGSDPR AGGNGGGGM GGGGGHGVGV
181 STGGWKAGTV FGNDFVITTN TRQWFAPIFN GHEYKRMAPN ENSEPATNRH WVGISTPWGY
241 FNFNEYSSHF SPQDWQRLTN EYKRWRPKAM RVKVYNLQIK QVVTLGSDTL YNNDLTAGVH
301 IFCDGSHQFP YSQHPWDTGT MPELPHRIWR ISQYGYFQLQ ADLTNGGVSS ETPDVGNQEK
361 QLLKSAPLYM LETASHQVLR TGEESSFSFS FDSGWVINDK AYAIPQADFN PLIHTRRYFP
421 TRNNNTTSTG GLMFYHRYNP YNKPSNWMPG PSLGYLGATQ TSTNPQYARG PVTVVTQPPG
481 TTADSANIDE QSTTHVPSKA TMQNSGYDVN PVNCGSSRLD AHSLAYDSGP ESRGQNIITV
541 RGIDLDMALG LHQMVQDGTE TEVGTQTPRT NFTELKNVWM YPNQAWDTTP VSRDTPIWVK
601 IPKTDRHTMQ DTSDGTLPMA HPPGTIFVRV AKVPIPGESD SYLNLYVTGQ ITCEILWETE
661 RFQTKNWRPE IKNDPSVFSD PLLYTFDRQG VYNTPETFIE GMPTKRGINR VL (SEQ ID NO: 44)

1 MSAPEAPTED VAEPGPSGSD PRAGGNGGGG GMGGGGGHGV GVSTGGWKAG TVFGNDFVIT
61 TNTRQWFAPI FNGHEYKRMA PNENSEPATN RHWVGISTPW GYFNFNEYSS HFSPQDWQRL
121 TNEYKRWRPK AMRVKVYNLQ IKQVVTLGSD TLYNNDLTAG VHIFCDGSHQ FPYSQHPWDT
181 GTMPELPHRI WRISQYGYFQ LQADLTNGGV SSETPDVGNQ EKQLLKSAPL YMLETASHQV
241 LRTGEESSFS FSFDSGWVIN DKAYAIPQAD FNPLIHTRRY FPTRNNNTTS TGGLMFYHRY
301 NPYNKPSNWM PGPSLGYLGA TQTSTNPQYA RGPVTVVTQP PGTTADSANI DEQSTTHVPS
361 KATMQNSGYD VNPVNCGSSR LDAHSLAYDS GPESRGQNII TVRGIDLDMA LGLHQMVQDG
421 TETEVGTQTP RTNFTELKNV WMYPNQAWDT TPVSRDTPIW VKIPKTDRHT MQDTSDGTLP
481 MAHPPGTIFV RVAKVPIPGE SDSYLNLYVT GQITCEILWE TERFQTKNWR PEIKNDPSVF
541 SDPLLYTFDR QGVYNTPETF IEGMPTKRGI (SEQ ID NO: 45)

*Fig. 16G*

CHIMERIC ADENO-ASSOCIATED VIRUS/ BOCAVIRUS PARVOVIRUS VECTOR

CROSS-REFERENCE TO RELATED APPLICATIONS

This application is a continuation of U.S. application Ser. No. 14/782,876, filed Oct. 7, 2015, which application is a U.S. National Stage Application under 35 U.S.C. 371 from International Application No. PCT/US2014/033343, filed Apr. 8, 2014, which application claims the benefit of the filing date of U.S. application Ser. No. 61/809,702 filed on Apr. 8, 2013, the disclosures of which are incorporated herein.

STATEMENT OF GOVERNMENT RIGHTS

This invention was made with government support under HL108902 awarded by National Institutes of Health. The Government has certain rights in the invention.

BACKGROUND

Gene therapy has been widely used in clinical trials since 1990s with many successful cases reported using viral or non-viral vectors to deliver therapeutic genes. The lung is an important organ for the gene therapy treatment to patients with inherent gene defects such as cystic fibrosis (CF), alpha 1-antitrypsin (AAT) deficiency, or with other chronic acquired respiratory disorders such as asthma and lung cancers. Of these lung diseases, CF, caused by single gene defect in coding a protein cystic fibrosis transmembrane conductance regulator (CFTR), is the most common life-threatening gene defect inherent disease with about $450 million spent annually on patient care in the U.S. alone. Although clinical treatments have improved CF patients' quality of life and lifespan in the recent decades, for this single gene defect inherent disease, gene therapy appears the best cure to permanently correct the disorder by replacing the defective CFTR gene (Mueller et al., 2008; Driskell et al., 2003; Griesenbach et al., 2010).

CF is an autosomal recessive genetic disorder caused by mutations in the CFTR gene coding (Rommens et al., 1989). It is a multi-organ disease, but CF pulmonary disease is the most life-threatening (Rowe et al., 2005). Recombinant adeno-associated viral vectors (rAAV) are currently one gene therapy agent that is being pursued for CF lung gene therapy (Griesenbach et al., 2010; Flotte, 2007; Carter, 2005).

rAAV vectors for CF lung gene therapy have been under development for nearly two decades, and most serotypes appear to be effectively endocytosed from the apical surface of airway epithelia despite varying degrees of transduction (i.e., expression of an encoded transgene). Although these vectors have demonstrated good safety profiles in CF clinical trails (Aitken et al., 2001; Moss et al., 2007; Wagner et al., 2002), they have failed to achieve complementation in vivo for two significant reasons. First, post-entry barriers in virion processing following infection appear to limit nuclear translocation, and thus transgene expression, in a proteasome-dependent manner (Duan et al., 2000; Ding et al., 2005; Yan et al., 2002; Zhong et al., 2008; Zhong et al., 2007). This feature of rAAV2 is reflected in CF clinical trials where viral genomes persisted in the airway epithelia of test subjects without detection of transgene-derived CFTR mRNA or clinical improvement in lung function (Aitken et al., 2001; Moss et al., 2007; Wagner et al., 2002). Identifying an appropriate rAAV serotype that bypassed these limitations has proved challenging due to species-specific differences between animal models and humans (Flotte et al., 2010; Liu et al., 2007a; Liu et al., 2007b). rAAV1 proves to be the most efficient serotype for apical infection of human airway (Flotte et al., 2010; Yan et al., 2012; Yan et al., 2006), while others have found success using directed capsid evolution to enhanced the tropism of rAAV for apical human epithelium (HAE) transduction (Li et al., 2009; Excoffon et al., 2009). However, effective CFTR complementation in CF HAE still requires the use of proteasome inhibitors to enhance transduction (Li et al., 2009; Zhang et al., 2004).

A second major barrier to efficient CFTR expression from rAAV vectors is their limited packaging capacity (about 4.9 kb) that necessitates the use of small, weak promoters and/or the use of CFTR minigenes (Zhang et al., 1998). The first generation rAAV-CFTR tested in a clinical trial utilized the cryptic promoter within the AAV2 ITR to drive the expression of a full-length CFTR cDNA (Aitken et al., 2001), and this was later improved by the incorporation of a short 83 bp synthetic promoter (Zhang et al., 2004). Other efforts to circumvent the small packing capacity of rAAV vectors have included trimming down size of the CFTR cDNA by deletion of non-critical sequences (such as partial deletion at the R-domain) to expand room for core promoter elements such as a shortened CMV promoter (Li et al., 2009; Zhang et al., 1998; Ostedgaard et al., 2005; Ostedgaard et al., 2002). Although these strategies have improved expression of CFTR, it is clear that pushing the packaging limits of rAAV can lead to inconsistent deletions at the 5' end of rAAV genome (Kapranov et al., 2012), thus further jeopardizing genome stability and expression.

SUMMARY OF THE INVENTION

As described herein, a recombinant human bocavirus virus-1 (HBoV-1) was generated from an ORF-disrupted rHBoV1 genome that efficiently transduces human airway epithelium (HAE) from the apical surface. The larger genome and high airway tropism of HBoV1 is ideal for creating a viral vector for gene transfer, e.g., airway gene transfer, including gene therapy for genetic and acquired diseases such as genetic and acquired pulmonary diseases, cancer, as well as vaccines, for instance, against respiratory disease. As further described herein, a rAAV2/HBoV1 chimeric virus (e.g., about 5.5-kb genome) was created, where HBoV1 capsids packaged oversized rAAV2 genomes. Clinical trials have supported the safety of applying the rAAV2 genome in the context of gene therapy for cystic fibrosis (CF) lung disease. The chimeric vector retains the high safety profile of the rAAV2 genome while also providing the airway apical tropism of the HBoV1 capsid. rAAV2/HBoV1 was shown to be capable of apically transducing HAE at 5.6- and 70-fold greater efficiency than rAAV1 or rAAV2 (4.7-kb genomes), respectively. Molecular studies demonstrated that polarization of airway epithelial cells was required for HBoV1 capsid-mediated gene transfer. Further, rAAV2/HBoV1-CFTR virus containing the full-length CFTR coding sequence and the strong CBA promoter efficiently corrected CFTR-dependent chloride transport in cystic fibrosis HAE. Thus, the chimeric AAV/HBoV viral vector is useful for gene therapy of cystic fibrosis and other pulmonary diseases, and the development of vaccines against HBoV1 infections and other respiratory viruses such as influenza virus. Co-administration of proteasome inhibitors during the infection period also significantly enhanced the AAV/HBoV1 chimeric vector transduction by a thousand fold.

The invention thus provides a gene transfer vector. e.g., for human pulmonary disease gene therapy and vaccines. The vector is highly tropic for the human airway, has spacious package capacity of the HBoV capsid, and efficiently encapsidates the rAAV genome. As a highly efficient airway transduction vector, the vector may be employed for CF gene therapy strategies, as well as gene therapy for other pulmonary diseases such as AAT deficiency, chronic obstructive pulmonary disease (COPD), asthma, lung cancers, as well as vaccination against wild-type HBoV infections and other respiratory infections (such as influenza virus and respiratory syncytial virus (RSV) infections), e.g., in infants, toddlers, juveniles or adults.

The invention also provides a platform for the development of bocavirus (BoV)-based gene transfer vaccines with rAAV genomes for use in humans, pets, and livestock, including but not limited to pulmonary diseases. The bocavirus capsid for the gene transfer vectors, e.g. recombinant bocavirus vector (rBoV) and chimeric adeno-associated/bocavirus parvoviral vector (rAAV/BoV), can be from different stains of human bocaviruses and non-human bocaviruses. Human bocavirus 1 (HBoV1) is a respiratory virus of tropism to infect the airway tract and human bocavirus 2 to 4 (HBoV2, HBoV3 and HBoV4) are enteric viruses of tropism to infect the gastrointestinal tract. Non-human bocaviruses, such as swine bocavirus, canine bocavirus and feline bocavirus, are isolated from non-human mammals.

In one embodiment, the invention provides an isolated chimeric virus comprising a bocavirus capsid protein, e.g., a human bocavirus capsid protein, and a recombinant heterologous parvovirus genome, e.g., a recombinant adeno-associated viral (AAV) genome. For example, the rAAV genome may include an expression cassette encoding a heterologous gene product, e.g., which is a therapeutic protein such as cystic fibrosis transmembrane conductance regulator, α-antitrypsin, β-globin, γ-globin, tyrosine hydroxylase, glucocerebrosidase, aryl sulfatase A, factor VIII, dystrophin or erythropoietines an antigen such as viral, bacterial, tumor or fungal antigen, or a neutralizing antibody or a fragment thereof that targets an epitope of an antigen such as one from a human respiratory virus, e.g., influenza virus or RSV. In one embodiment, the gene product is a therapeutic gene product. In one embodiment, the gene product is a prophylactic gene product. In one embodiment, the gene product is a catalytic RNA. In one embodiment the gene product is a polypeptide or peptide. In one embodiment, the capsid protein is HBoV1, HBoV2, HBoV3 or HBoV4 capsid protein. In one embodiment the bocavirus capsid protein is from a bocavirus isolated from a non-human species that imparts a unique tropism for infection of lung or other organs, for example, porcine bocavirus. In one embodiment, the rAAV/HBoV or rAAV/BoV vector used for vaccination is used in animals to protect lifestock or pets. In one embodiment, the AAV genome is an AAV-1, AAV-2 or AAV-5 genome. In one embodiment, the MV genome is a AAV-1, AAV-3, AAV-4, AAV-5, AAV-6, AAV-7, AAV-8 or AAV-9 genome.

BoV sequences within the scope of the invention include but are not limited to nucleic acid sequences having at least 80%, 85%, 90%, 95%, 98%, 99% or 100% nucleic acid sequence identity to contiguous sequences having, for example, one of SEQ ID Nos. 9, 17-18, 39, or 42-43, or the complement thereof. BoV capsid sequences within the scope of the invention include but are not limited to amino acid sequences having at least 80%, 85%, 90%, 95%, 98%, 99% or 100% identity to sequences having, for example, one of SEQ ID Nos. 21-24, 39-41, or 44-45.

The invention provides a method of preparing a chimeric virus comprising a bocavirus (BoV) capsid protein and a recombinant heterologous parvovirus genome, such as a recombinant AAV (rAAV) genome. The method includes providing a first vector comprising a nucleic acid sequence for a recombinant MV genome; a second vector comprising a nucleic acid sequence for one or more adenovirus genes for MV replication, for instance, one or more of the E4orf6 gene, the E2A protein gene, and the VA RNA genes; a third vector comprising a nucleic acid sequence encoding one or more Rep proteins, e.g., Rep40, Rep52, Rep68 or Rep78; and a fourth vector comprising a terminal sequence that is a deleted bocavirus genome that encodes BoV1 capsid and gene product(s) for encapsidation. Cells, e.g., mammalian or insect cells, are transfected with the vectors in an amount effective to yield the chimeric virus. In one embodiment, the vectors for introduction to insect cells include a AAV2 Rep helper baculovirus (Bac-AAV2Rep), which expresses AAV2 Rep78/Rep52, a HBoV1 Cap helper virus (Bac-HBoVCap), which expresses HBoV1 capsid proteins VP1, VPx, and VP2; and a transfer vector (Bac-rAAV), which contains an rAAV2 genome carrying gene of interest (GOI). The insect cells are infected with these baculovirus vectors in an amount effective to yield the chimeric virus.

In one embodiment, the chimeric virus may not include a transgene, but has ITRs and a non-coding sequence ("stuffer" sequence). Such a virus has a capsid (e.g., a HBoV capsid) that induces a humoral response and so is useful as a vaccine. In one embodiment, the chimeric virus is delivered to the lungs. In one embodiment, the chimeric virus is delivered to the nose, tracheobronchial airways and/or lungs. In one embodiment, the chimeric virus is generated with BoV strains that infect other organs, such as the gastrointestinal tract. In one embodiment, the chimeric virus is used to infect humans. In one embodiment, the chimeric virus is used to infect animals such as livestock or pets.

In one embodiment, the chimeric virus includes a transgene, the gene product of which enhances humoral or cellular response to BoV and has ITRs. Such a virus is useful as a vaccine as a result of the humoral response to the BoV capsid and the immune response (humoral and/or cellular) that is enhanced by expression of the transgene. In one embodiment, the chimeric virus is delivered to the lungs. In one embodiment, the chimeric virus is delivered to the nose, tracheobronchial airways and/or lungs. In one embodiment, the chimeric virus is generated with BoV strains that infect other organs. In one embodiment, the chimeric virus is used to infect humans. In one embodiment, the chimeric virus is used to infect animals such as livestock or pets.

In one embodiment, the chimeric AAV/BoV virus includes a transgene and has ITRs. The transgene may encode any antigen, e.g., a tumor antigen, BoV proteins (but not proteins that allow for BoV replication), influenza virus protein, e.g., H1 or N1 protein, or SARS viral genes such as capsid genes), or an immune response modulator, e.g., cytokines including but not limited to IFN-alpha, IFN-gamma, TNF, IL-1, IL-17, or IL-6, or other gene products that enhance the cellular or humoral immune response. In one embodiment, the chimeric virus is delivered to the lungs. In one embodiment, the chimeric virus is delivered to the nose, tracheobronchial airways and/or lungs. In one embodiment, the chimeric virus is generated with BoV strains that infect other organs. In one embodiment, the chimeric virus is used to infect humans. In one embodiment, the chimeric virus is used to infect animals such as livestock or pets.

In one embodiment, the transgene may encode an antibody for passive immunization, for instance, against respiratory virus infections, e.g. a broadly neutralizing antibody targeted the epitopes conserved among diverse influenza virus strains, or against other respiratory viruses such as respiratory syncytial virus (RSV) and SARS virus. In one embodiment, the chimeric virus is generated with BoV strains that infect organs other than the respiratory tract. In one embodiment, the chimeric virus is used to infect humans. In one embodiment, the chimeric virus is used to infect animals such as livestock or pets Further provided is a method to enhance chimeric virus transduction of a mammalian cell. The method includes contacting a mammalian cell, e.g., a human cell, with an isolated chimeric virus comprising bocavirus capsid protein and a rAAV genome encoding a heterologous gene product and at least one agent in an amount effective to additively or synergistically enhance rAAV transduction. In one embodiment, the mammalian cell is a mammalian lung cell. In one embodiment, the agent is a chemotherapeutic, a lipid lowering agent, a mucolytic agent, an antibiotic or a food additive. In one embodiment, the mammalian cell is a mammalian cell other than the lung for which alternative strains of bocavirus (isolated from human or other animals) allow for efficient infection. In one embodiment, the agent is a proteasome modulator, e.g., a proteasome inhibitor.

The invention includes a method to enhance virus transduction of a mammalian cell, e.g., a mammalian lung cell. For example, a mammalian lung cell is contacted with a chimeric virus comprising a bocavirus capsid protein and a rAAV genome and an agent in an amount effective to enhance transduction of the virus relative to a mammalian cell that is not contacted with the agent, wherein the agent is a proteasome inhibitor.

In one embodiment, the invention provides a method to enhance the expression of a transgene in a mammalian cell, such as a mammalian lung cell. The method includes contacting the mammalian cell with an amount of an agent that is a proteasome inhibitor and a chimeric virus comprising a human bocavirus capsid protein and a rAAV genome comprising the transgene, wherein the amount enhances transduction of the rAAV, thereby enhancing expression of the transgene, relative to a mammalian cell that is not contacted with the agent.

In one embodiment, the invention provides a method to immunize a mammal. The method includes contacting a mammal with a chimeric virus comprising a bocavirus capsid protein and a recombinant heterologous parvovirus genome, e.g., rAAV genome, comprising a transgene useful to induce a protective immune response to an antigen, e.g., a microbial antigen such as a virus, bacteria, parasite, or fungus, or a tumor antigen, or a neutralizing antibody or fragment thereof useful to prevent infections by a pathogen including but not limited to a virus, bacterium, fungus or parasite. In one embodiment, the mammal is also contacted with a proteasome inhibitor. In one embodiment, the transgene encodes a neutralizing antibody or an antigen binding fragment thereof. Thus, the chimeric virus may be employed as a vaccine, e.g., a passive vaccine.

Also provided is a method to inhibit or treat a condition associated with aberrant expression of an endogenous gene product. The method includes contacting a mammal at risk of or having the condition, with an effective amount of at least one proteasome inhibitor, a chemotherapeutic, a lipid lowering agent, a mucolytic agent, an antibiotic or a food additive that enhances transduction and an effective amount of an isolated chimeric virus comprising bocavirus capsid protein and a rAAV genome, wherein the genome comprises a transgene encoding at least a portion of a functional gene product, the expression of which in the mammal inhibits or treats at least one symptom of the condition. In one embodiment, the transgene encodes cystic fibrosis transmembrane conductance regulator, alpha-1 antitrypsin, β-globin, γ-globin, tyrosine hydroxylase, glucocerebrosidase, aryl sulfatase A, factor VIII, dystrophin or erythropoietin.

In one embodiment, a mammal subjected to viral gene therapy with an isolated chimeric virus comprising bocavirus capsid proteins and a rAAV genome is administered an agent that is a proteasome inhibitor in an amount effective to enhance expression of a transgene in the rAAV in the cells of the mammal relative to cells in a mammal that are not contacted with the agent.

Further provided is a rHBoV virus. In one embodiment, the rHBoV virus may not include a transgene, but has terminal palindromic sequences (TPSs) that are not identical and a non-coding sequence ("stuffer" sequence), i.e., it is not replication competent. Such a virus has a capsid (BoV) that induces a humoral response and so is useful as a vaccine. In one embodiment, the chimeric virus is delivered to the lungs. In one embodiment, the chimeric virus is delivered to other non-lung cell types for which BoV capsid sequences are tropic for infection.

To produce rBoV, in one embodiment, two or more vectors are employed. One vector has cis elements for replication and packaging, which include the TPSs, and optionally a heterologous sequence (transgene). The other vector has sequences for trans acting factors but lacks the cis elements (they are deleted). The two vectors may be on one plasmid or two different plasmids. Moreover, the trans acting factors may be on different plasmids. For example, sequences for the non-structural proteins, e.g., NS and NP1, may be on one plasmid and another plasmid may have sequences for the capsid proteins. Structural proteins required for packaging rBoV may also be split into multiple vectors to avoid generation of wild-type BoV.

In one embodiment the AAV/BoV virus is produced in cultured insect cells. This method includes the utility of recombinant baculovirus vectors (BEV): a MV Rep helper baculovirus (Bac-AAVRep), which expresses AAV Rep78/Rep52, a BoV1 Cap helper virus (Bac-BoVCap), which expresses BoV1 capsid proteins VP1, VPx, and VP2; and a transfer vector (Bac-rAAV), which contains an rAAV genome carrying gene of interest (GOI). The insect cells are infected with these baculovirus vectors in an amount effective to yield the chimeric virus.

In one embodiment, the rBoV virus includes a transgene, the gene product of which enhances humoral or cellular response to BoV and has TPSs, e.g., it is not by itself replication competent or can produce infectious BoV. Such a virus is useful as a vaccine as a result of the humoral response to the BoV capsid and the immune response (humoral and/or cellular) that is enhanced by expression of the transgene. In one embodiment, the rHBoV is delivered to the lungs. Structural proteins required for packaging rBoV may also be split into multiple vectors to avoid generation of wild-type BoV. In one embodiment, the chimeric virus is delivered to other non-lung cell types for which BoV capsid sequences are tropic for infection In one embodiment the AAV/BoV virus is produced in cultured insect cells. This method includes the utility of recombinant baculovirus vectors (BEV): a AAV Rep helper baculovirus (Bac-AAVRep), which expresses AAV Rep78/Rep52, a BoV1 Cap helper virus (Bac-BoVCap), which expresses BoV1 capsid proteins VP1, VPx, and VP2; and a transfer vector (Bac-rAAV), which contains an rAAV genome carrying gene of interest (GOI). The insect cells are infected with these baculovirus vectors in an amount effective to yield the chimeric virus.

In one embodiment, the rHBoV virus includes a transgene and has HBoV TPSs. The transgene may encode any antigen, e.g., a tumor antigen, HBoV proteins (but not proteins that allow for HBoV replication), influenza virus protein, e.g., H1 or N1 protein, or SARS viral genes such as capsid genes)), or an immune response modulator, e.g., a cytokine including but not limited to IFN-alpha, IFN-gamma, TNF, IL-1, IL-17, or IL-6 or other gene products that enhance the cellular or humoral immune response. In one embodiment, the rBoV is delivered to the nose, tracheobronchial airways and/or lungs. In one embodiment, the vector for virus production includes the TPSs and NS sequences, and replaces the capsid sequences with the transgene, which allows for replication in cells but without other sequences provided in trans, does not generate progeny. In one embodiment, the vector for virus production includes the TPSs and NS sequences, and replaces the capsid sequences with a transgene for a prodrug for tumor cells or a cytokine, e.g., IFN-alpha, IFN-gamma, IL-1, TNF, or IL-17, to enhance the immune response to BoV.

Further provided is a method to enhance rBoV transduction of a mammalian cell. The method includes contacting a mammalian cell, e.g., a human cell, with an isolated rHBoV comprising bocavirus capsid protein and a rBoV genome encoding a heterologous gene product and in one embodiment includes at least one agent in an amount effective to additively or synergistically enhance transduction. In one embodiment, the mammalian cell is a mammalian lung cell. In one embodiment, the agent is a proteasome modulator, e.g., a proteasome inhibitor. In one embodiment, the agent is a chemotherapeutic, a lipid lowering agent, an antibiotic, a mucolytic agent, or a food additive.

The invention includes a method to enhance virus transduction of a mammalian cell, e.g., a mammalian lung cell. For example, a mammalian lung cell is contacted with a rBoV comprising a bocavirus capsid protein and a rBoV genome and optionally an agent in an amount effective to enhance transduction of the virus relative to a mammalian cell that is not contacted with the agent, wherein the agent is a proteasome inhibitor.

In one embodiment, the invention provides a method to enhance the expression of a transgene in a mammalian cell, such as a mammalian lung cell. The method includes contacting the mammalian cell with an amount of an agent that is a proteasome inhibitor and a rBoV comprising a bocavirus capsid protein and a rBoV genome comprising the transgene, wherein the amount enhances transduction of the rBoV, thereby enhancing expression of the transgene, relative to a mammalian cell that is not contacted with the agent.

In one embodiment, the invention provides a method to immunize a mammal. The method includes contacting a mammal with a rBoV comprising a bocavirus capsid protein, e.g., a human bocavirus capsid protein, and a rBoV genome comprising a transgene useful to induce a protective immune response to an antigen, e.g., a microbial antigen such as a virus, bacteria, parasite, or fungus, or a tumor antigen, or a neutralizing antibody or an antigen binding fragment thereof. In one embodiment, the mammal is also contacted with a proteasome inhibitor. Thus, the rBoV may be employed as a vaccine, e.g., a passive vaccine.

Also provided is a method to inhibit or treat a condition associated with aberrant expression of an endogenous gene product. The method includes contacting a mammal at risk of or having the condition, with an effective amount of at least one proteasome inhibitor, a chemotherapeutic, a lipid lowering agent, an antibiotic, a mucolytic agent, or a food additive that enhances transduction and an effective amount of an isolated rBoV comprising human bocavirus capsid protein and a rBoV genome, wherein the genome comprises a transgene encoding at least a portion of a functional gene product, the expression of which in the mammal inhibits or treats at least one symptom of the condition. In one embodiment, the transgene encodes cystic fibrosis transmembrane conductance regulator, alpha1-antitrypsin, β globin, γ-globin, tyrosine hydroxylase, glucocerebrosidase, aryl sulfatase A, factor VIII, dystrophin or erythropoietin.

In one embodiment, a mammal subjected to viral gene therapy with an isolated rHBoV comprising human bocavirus capsid proteins and a rHBoV genome is administered an agent that is a proteasome inhibitor in an amount effective to enhance expression of a transgene in the rHBoV genome the cells of the mammal relative to cells in a mammal that are not contacted with the agent.

Figure 1:
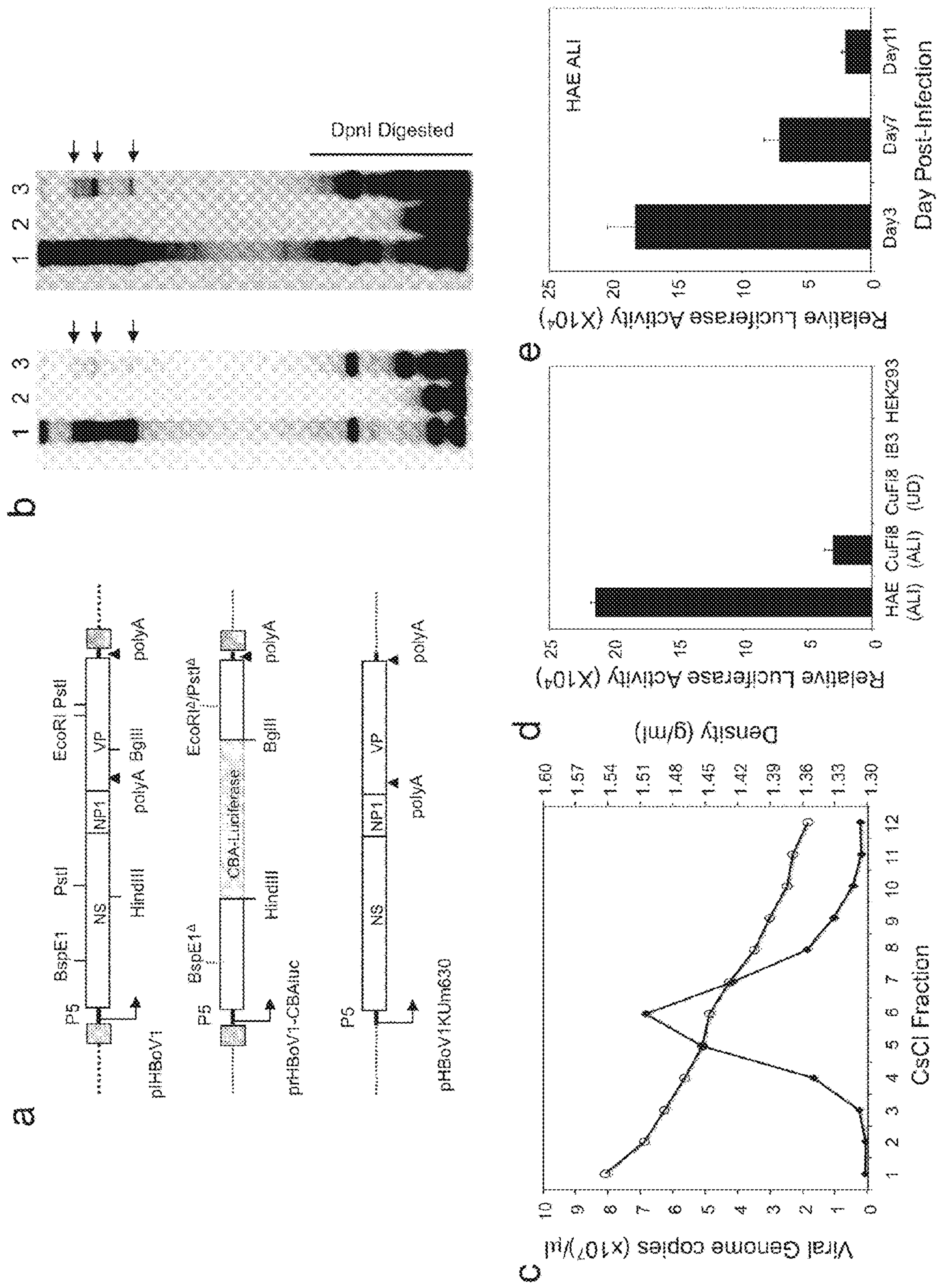
FIGS. 1A-E. rHBoV1 vector production and infection of primary polarized HAE. (A) Schematic structure of the HBoV1 genome and the proviral plasmids used in this study. pHBoV1KUm630 is the helper plasmid for trans-complementation of HBoV1 viral proteins, pIHBoV1 is the infectious clone of the HBoV1 complete genome, and prHBoV1-CBAluc is the rHBoV1 cis transfer proviral plasmid. Critical restriction enzyme cutting sites used for cloning are also indicated and small deletions within NS and VP genes are marked (Δ). (B) Replication complementation assay of the rHBoV1 proviral plasmid in HEK293 cells. pIHBoV1 (lane 1), prHBoV1-CBAluc (lane 2), or prHBoV1-CBAluc+prHBoV1KUm630 (lane 3) plasmids were transfected to HEK293 cells. Hirt DNA was extracted at 48 hours post-transfection and digested by DpnI before resolving on an agarose gel. HBoV1 replication intermediates (indicated by arrows) were visualized by Southern blotting with a $^{32}$P-labeled HBoV1 probe. Hirt DNA from cells transfected with the HBoV1 infectious clone (pIHBoV1, lane 1) was used as positive control. Short and long exposures are shown on the left and right of the panel, respectively. (C) DNase I-digested cell lysates from HEK293 co-transfected with rHBoV1-CBAluc and prHBoV1KUm630 were fractionated by CsCl equilibrium ultracentrifugation. The plot shows the distribution of rHBoV1.CBAluc (solid dots) genomes against the observed density of the gradient (open dots). The genome copies in each fraction (about 750 μL) were determined by TaqMan PCR. (D) Transduction assay following rHBoV1.CBAluc infection of HEK293 cells, IB3 cells, undifferentiated (UD) CuFi8 cell monolayers, polarized CuFi8 cells in ALI cultures, and primary HAE ALI cultures. Data represents the mean (+/−SEM) relative luciferase activity per well at 2-day post-infection (n=4). (E) Transgene expression from rHBoV1.CBAluc infected HAE ALI cultures at different time points post-infection. Data represents the mean (+/−SEM) relative luciferase activity per well (n=3).

lane 1: pAV2-F5tg83luc+pAV-Rep2; lane 2: pAV2-F5tg83luc+pAVRC2.3; lane 3: pAV2-CF5tg83luc+pAV-Rep2; land 4: pAV2-CF5tg83+pAV-Rep2+pHBoV1KUm630) together with the Ad helper pAd4.1. Low molecular weight (Hirt) DNA was extracted from transfected cells after 48 hours and digested with DpnI, followed by Southern blotting using a $^{32}$P-labeled luciferase probe. The 4.8 kb and 5.4 kb replicative form (RF) DNA of the rAV2.F5tg83Luc and rAV2.CF5tg83Luc genomes are indicated by arrows. (C) Negatively stained transmission electron micrographs of the chimeric vector rAV2/HBc.F5tg83luc (bar=100 nm in the 15000× image and 50 nm for the 50000× image). The virus-like particle with incompletely packaged viral DNA (<1% of total virions) is marked by a white arrow in the inset. (D) A two-color Western blot (Red: AAV; Green: HBoV1) was performed on the indicated viral preparations using an Infrared Image System. Converted single channel images are also shown with dark arrows pointing to the AAV2 and HBoV1 VP proteins (VP1 and VP2) in the left and right panels, respectively. Grey arrows and white arrows mark protein from HBoV1 VPx proteins.

Figure 3:
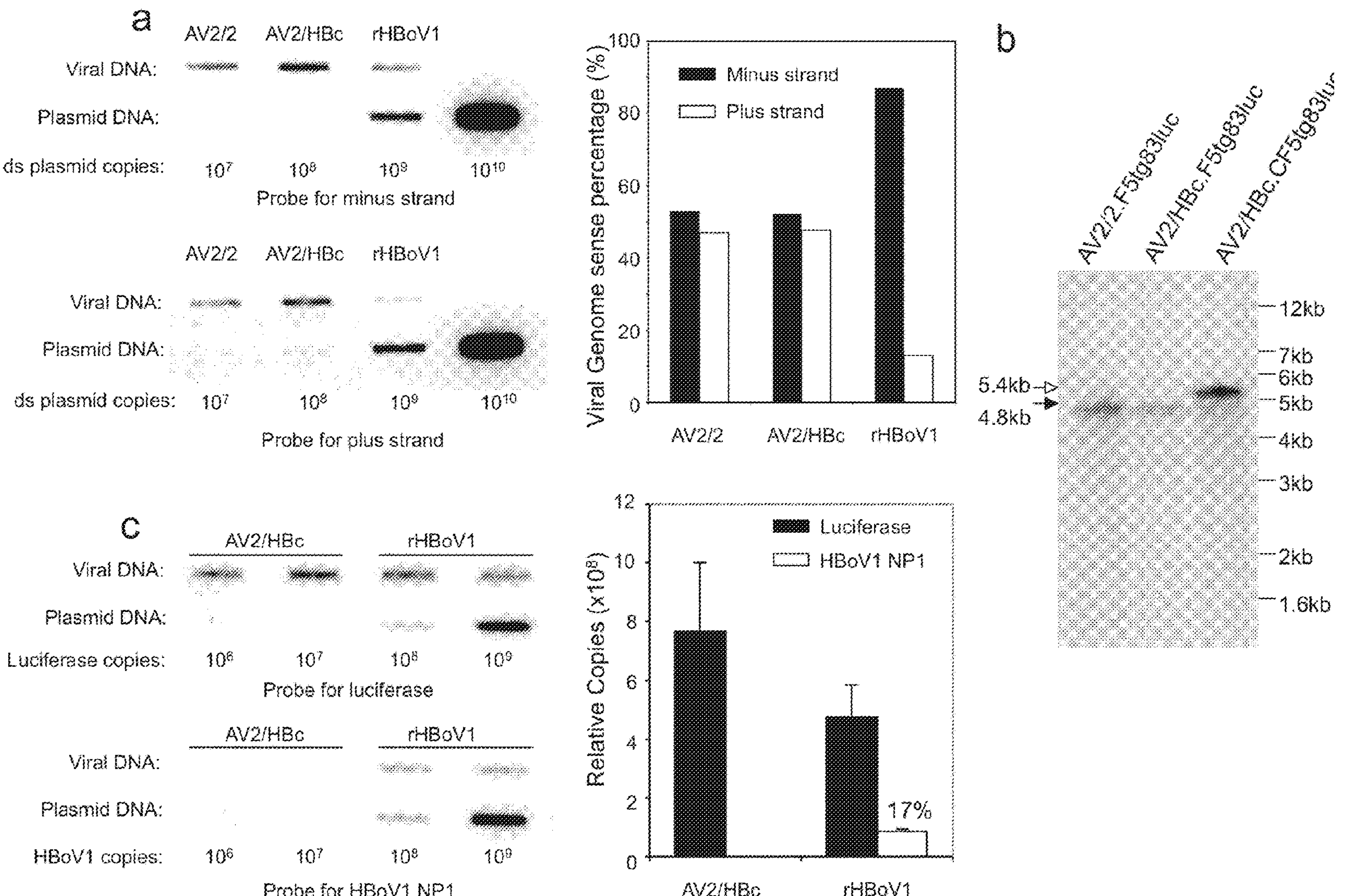

FIGS. 3A-C. Package polarity and capacity of rHBoV1 and rAAV2/HBoV1 vectors. (A) Viruses AV2/2.F5tg83luc, AV2/HBc.F5tg83luc, and rHBoV1.CBAluc were loaded on nylon membrane by slot blotting and visualized with $^{32}$P-labeled 32-mer oligonucleotide probes against the minus and plus strand of the Luciferase gene (left panels). The percentages of the minus and plus strands in each viral preparation was calculated based on the signal density quantitated with NIH ImageJ software (right panel). (B) $2\times10^8$ DRP of rAAV vector AV2/2.F5tg83luc, chimeric viruses AV2/HBc.F5tg83luc, and AV2/HBc.CF5tg83luc were heated in alkaline gel loading buffer at 95° C. for 10 minutes and then resolved in a 0.9% alkaline agarose gel. Following transferred to Nylon membrane, Southern blotting was performed with $^{32}$P-labeled Luciferase probe. Black and white arrows mark the shorter rAV2.F5tg83luc (4.8 kb) and longer rAV2.CF5tg83luc (5.4 kb) genomes, respectively. (C) Left panels depict slot blots of AV2/HBc.F5tg83luc and rHBoV1.CBAluc viral preparations (about $10^9$ DRP based on TaqMan PCR for the luciferase transgene) probed with $^{32}$P-labeled fragments recognizing the luciferase gene (1.7 kb) or the HBoV1 genome region unique to the helper plasmid (a 2.64 kb HindIII/BglII fragment covering the NP1 coding region). Right panel depicts the relative copies of luciferase or NP1 gene fragments based on the signal intensity relative to the plasmid standards. NIH ImageJ software was used to quantify the mean (+/−range) signal density for rAAV2/HBoV1 and rHBoV1 viral preparations shown.

FIGS. 4A-D. Transduction comparisons between rAAV2/HBoV1 and rAAV vectors. (A) Luciferase expression at 2 days following infection of HEK293 cells with AV2/2.F5tg83luc (MOI=2,500 DRP/cell) or AV2/HBc.F5tg83luc (MOI=50,000 DRP/cell). Results show the mean (+/−SEM, N=4) relative luciferase activities per well of a 24-well plate. (B) Primary HAE ALI cultures were infected with AV2/2.F5tg83luc, AV2/1.F5tg83luc, or AV2/HBc.F5tg83luc from the apical or basolateral surface. The vector amount in the inoculum was $10^{10}$ DRP for each Millicell insert, roughly 5,000 to 10,000 DRP/cell. Data represent the mean (+/−SEM) relative luciferase activities measured at 7 days post-infection (RLU/well) for N=6 independent infections of HAE ALI cultures derived from three donors. (C, D) Virion internalization and subcellular distribution analyses were performed at 18 hours after primary HAE ALI cultures were apically infected with rAAV2/1, rAAV2/2 and rAAV2/HBoV1 vectors of $10^{10}$ DRP per Millicell insert. Viral genomes in the cytoplasmic and nuclear fractions were quantified by TaqMan PCR. The total viral genomes detected in each culture is presented in (C) with the black bars representing the nuclear fraction and while bars representing the cytoplasmic fraction. The percentage of viral genomes in each fraction is presented in (D). Data represent the mean (+/−SEM) viral genome copies (per well) for N=3 independent infections.

Figure 5:
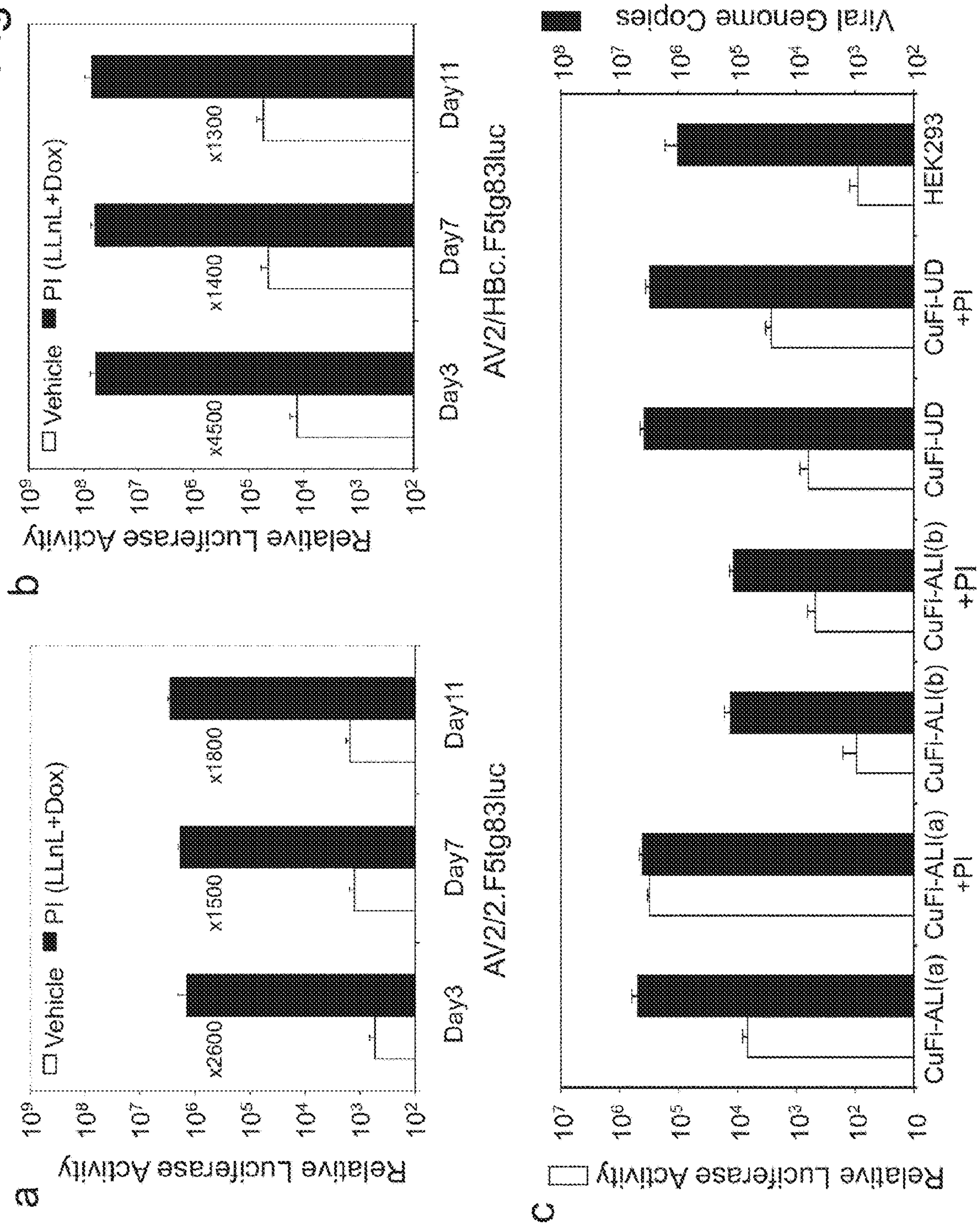

FIGS. 5A-C. Effect of proteasome inhibitors on rAAV2/HBoV1 transduction in polarized and nonpolarized cultures of human airway epithelial cells. (A, B) Primary HAE ALI cultures were apically infected with $10^{10}$ DRP per Millicell insert with (A) AV2/2.F5tg83luc or (B) AV2/HBc.F5tg83luc for a period of 16 hours. When indicated, proteasome inhibitors (PI) LLnL (40 nM) and doxorubicin (5 μM) were applied only during the infection period. Luciferase expression was monitored over 11 days by biophotonic imaging of live cells using the Xenogen 200 IVIS. Data represent the mean (+/−SEM, n=6) relative luciferase activity per well at three time points of 3, 7 and 11 day post-infection. (C) CuFi8 cells cultured as a polarized epithelium at an ALI (CuFi-ALI; a: apical infection, b: basolateral infection) or non-polarized undifferentiated monolayers on plastic (CuFi-UD), and HEK293 cells, were incubated with $1.5\times10^9$ DRP of AV2/HBc.F5tg83luc at 37° C. for 4 hours. All cultures contained about $5\times10^5$ cells at the time of infection. Following infection, unbound virus was washed off and cells were either detached from the culture supports with trypsin and lysed for TaqMan PCR quantification of viral genomes, or returned to the incubator for luciferase expression assays at 24 hours post-infection using cell lysates. When indicated (+PI). CuFi8 cells were treated with proteasome inhibitors doxorubicin (1 μM) and LLnL (8 nM) during the 4 hour infection period. Data represent the mean (+/−SEM) total vector genomes (n=4) at 4 hours post-infection and relative luciferase activity (n=3) at 24 hours post-infection.

Figure 6:
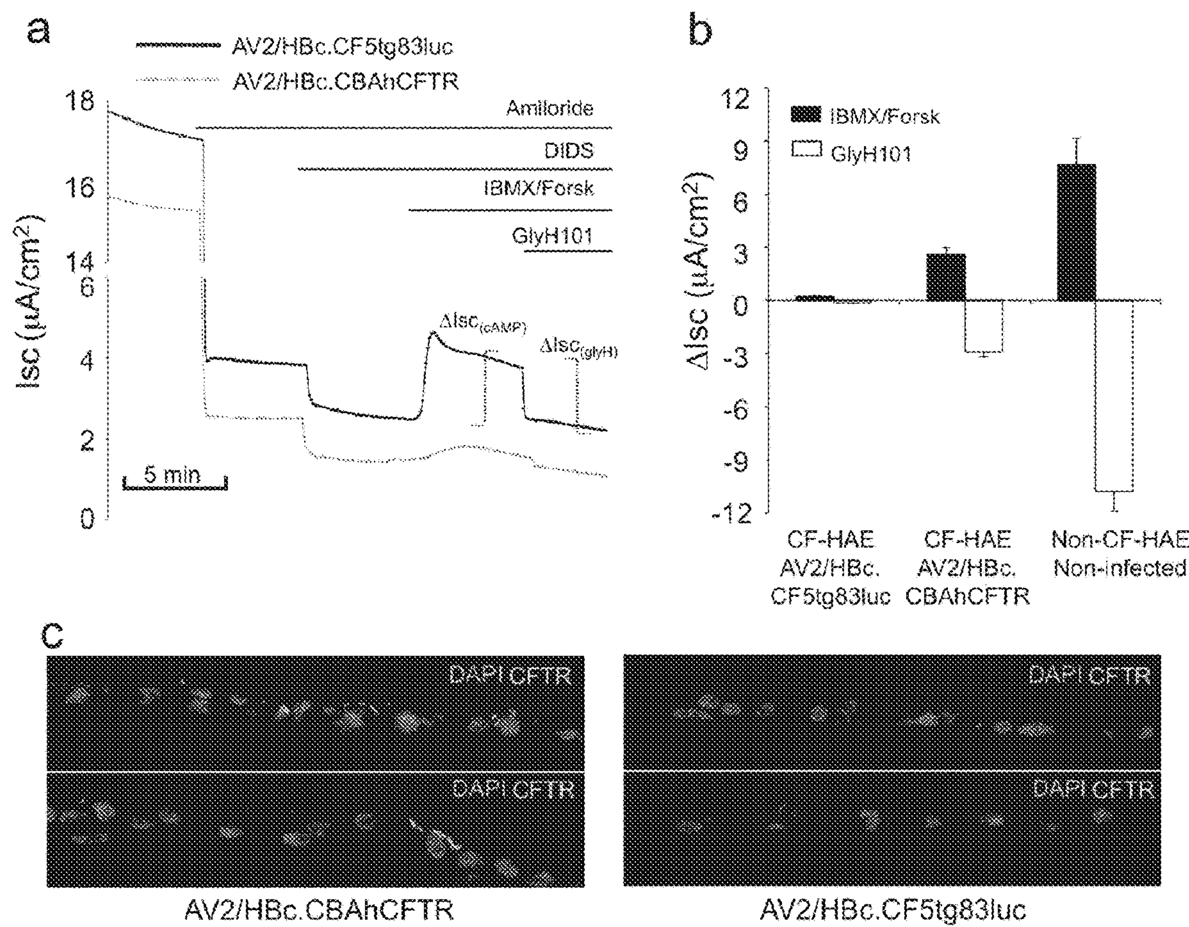

FIGS. 6A-C. Partial correction of CFTR-dependent chloride transport by primary CF HAE ALI cultures following infection with AV2/HBc.CBAhCFTR. CF HAE ALI cultures derived from two CF patient donors (genotypes: ΔF508/ΔF508 homozygous) were infected with AV2/HBc.CF5tg83luc or AV2/HBc.CBAhCFTR at $10^{10}$ DRP per Millicell insert (MOI of 5000 to 10000 DRP/cell) in the presence of proteasome inhibitors LLnL (40 nM) and doxorubicin (5 μM). Uninfected non-CF HAE were also cultured for electrophysiologic comparisons and experimental cultures were evaluated at 10 days postinfection. (A) Representative traces of transepithelial short-circuit current (Isc) of CF HAE following the sequential addition of various inhibitors and agonists as indicated. Amiloride and DIDS were used to block ENaC-mediated sodium currents and non-CFTR chloride channels prior to cAMP agonists (forskolin and IBMX) induction and GlyH101 inhibition of CFTR currents. $\Delta Isc_{(cAMP)}$ reflects the activation of CFTR-mediated chloride currents following cAMP agonist induction and $\Delta Isc_{(glyH)}$ reflects the inhibition of CFTR-mediated chloride currents following addition of GlyH101. (B) Summary data of the $\Delta Isc_{(cAMP)}$ and $\Delta Isc_{(glyH)}$ (mean+/−SEM, n=6 independent transwells) for both CF infected cultures and non-CF controls. (C) Immunofluorescent detection of CFTR expression (green) in CF HAE following infection with AV2/HBc.CBAhCFTR (left panels) or AV2/HBc.CF5tg83luc (right panels).

FIGS. 7A-B. One potential model for how polarization of human airway epithelia cells influences HBoV1 virion infection and transduction. (A) Polarized HAE may contain multiple binding and/or coreceptors for HBoV1. In this illustrated scenario, a single binding receptor exists on the apical membrane and is significantly reduced or absent on the basolateral membrane. Two different coreceptors exist including an efficient co-receptor-1 on the apical membrane and a more abundant inefficient co-receptor-2 on the basolateral membrane. Endocytosis through co-receptor-1 leads to functionally efficient (from a transduction standpoint) virion processing that is highly influences by activity of the proteasome, whereas internalization through co-receptor-2 is ineffective at processing the virion and not influenced by proteasome function. This model is consistent with significantly less viral uptake and transduction from the basolateral surface, as compared to the apical membrane. Other models not shown might include a second type of binding receptor on the basolateral surface that is inefficiently endocytosed with co-receptor-1 or co-receptor-2. (B) In non-polarized human airway cells, the primary binding receptor, co-receptor-1, and co-receptor-2 exist in the same membrane. Both coreceptors can interact with the same binding receptor, however, co-receptor-2 is in greater abundance than co-receptor-1. Thus, endocytosis of HBoV1 virions through co-receptor-2 predominates, and since this pathway inefficiently processes HBoV1 virions for productive transduction, transgene expression is low. These findings are consistent with high-level HBoV1 virion endocytosis, but poor transduction and weak proteasome inhibitor responsiveness, in non-polarized human airway cells.

FIG. 8. Exemplary HoBV sequences including a full length nucleotide sequence (JQ923422, with left 5' hairpin at nts 1-140 and right 3' hairpin at nts 5344-5543, which are the cis elements for HBoV1 replication and packaging), nucleotide sequences (e.g., GQ925675) without terminal hairpins at both ends and proteins encoded thereby. Proteins useful in the viruses of the invention include proteins having at least 80%, 85%, 90%, 95%, 96%, 97%, 98%, or at least 99% amino acid sequence identity to the sequence of the HBoV proteins in FIG. 8. SEQ ID NOs: 9-36.

FIGS. 9A-9C. Optimization of rAAV2/HBoV1 vector production in 293 cells. (A) HBoV1 Cap helper plasmids. (1) pHBoV1NSCap is the prototype HBoV1 helper; (2) pCMVHBoV1NSCap was derived from the prototype helper, a CMV promoter in front of the P5 promoter; and (3) pCMVHBoV1NS1(−)Cap was derived from pCMVHBoV1NSCap, with the NS1 ORF terminated early. (B) Western blot analysis of HBoV1 VP1, VPx and VP2 in the 4-plasmid transfected 293 cell production system (transfected with pAV2.CMVGFP(5.4 kb), pAd4.1, pAV2-Rep, and one of the Cap helper independent transwells) for both CF infected cultures and non-CF controls. (C) The yield of rAAV2/HBoV1 from the improved rAAV2/HBoV1 production system (transfected with pAV2.CMVGFP(5.4 kb), pAd4.1, pAV2-Rep and pCMVHBoV1NS1(−)Cap helper) was comparable to that of rAAV2/2 production system (transfected with pAV2.CMVGFP(5.4 kb), pAd4.1, pAV2-RepCap helper) in 293 cells. Comparison was plotted from side-by-side preparations at the scale of 20 145-mm plates.

FIGS. 10A-10E. rAAV2/HBoV1 production in Sf9 cells. (A) Construction of the BEV for rAAV2/HBoV1 production. The three BEV shown were generated using the Bac-to-Bac method (Invitrogen). Bac-Cap was designed according to the Kotin method, but the a silent point mutation was introduced at nt 273 (G to A) of the VP1-coding sequence to ensure an appropriate ratio of VP1:VPx:VP2. Bac-Rep was also constructed according to the Kotin method; Ph: polyhedrin promoter. (B) Analysis of virus protein expression and rAAV2 DNA replication. At 72 hours p.i., the Sf9 cells infected with the 3 BEV were analyzed for the expression of HBoV1 Cap and AAV2 Rep by Western blotting, and for replication of the rAAV2 genome by Southern blotting. HBoV1 Cap proteins (VP1, VPx, and, VP2) were produced efficiently, at a ratio similar to that in pHBoV1 NSCap-transfected 293 cells, and their expression did not interfere with the expression of AAV2 Rep78/52 or with the rescue of rAAV2 genome replication in the co-infected Sf9 cells. The replicative form (RF) and double RF of the rAAV2 DNA are indicated. (C) Vector purification. Infected Sf9 cells from 200 mL culture were used to purify the vector on a CsCl gradient. Fractions were collected and quantified for DRP. Purified vector was visualized under an electron microscope using negative staining. The pictograph reveals fully-packaged virions of about 25 nm in diameter. (D) Side-by-side comparison of rAAV2/HBoV1 and rAAV2/2 vector production in Sf9 cells (from 200 mL of Sf9-cell culture). The BEV used to generate rAAV2 were Bac-(ITR)GFP and Bac-Rep/(AAV2)Cap (kindly provided by the Kotin laboratory). Vectors were purified using a CsCl gradient, and quantified as DRP/prep using a GFP probe. (E) Functionality of the rAAV2/HBoV1 vectors produced in Sf9 cells was as active as that produced from 293 cells. Data represent the RLU in CuFi-ALI cultures apically infected with vector produced in Sf9 or 293 cells. MOI of 10K were applied and cells were lysed for luciferase assays at 48 hours p.i.

Figure 11:
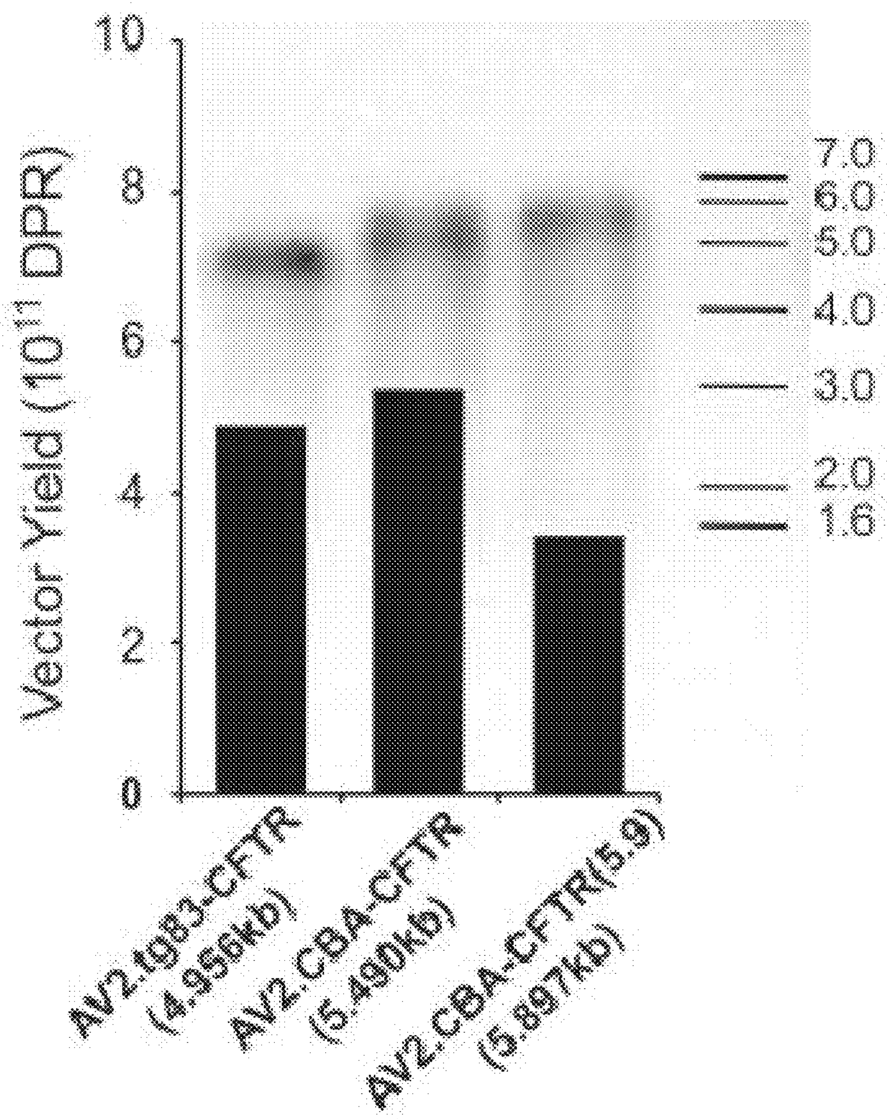

FIG. 11. HBoV1 can encapsidate a recombinant parvoviral genome larger than 5.5 Kb-packaging of a 5.9-kb AAV2 genome into the HBoV1 capsid. rAAV2/HBoV1 vectors were produced from three transfer plasmids, each with a genome of a different size, as indicated. The vector yield represents production from transfected 293 cells in eight 150-mm plates, following CsCl-gradient ultracentrifugation. Viral DNA was extracted, resolved on a 0.9% alkaline gel, and visualized using a $^{32}$P-labeled CFTR probe.

Figures 12A, 12B:
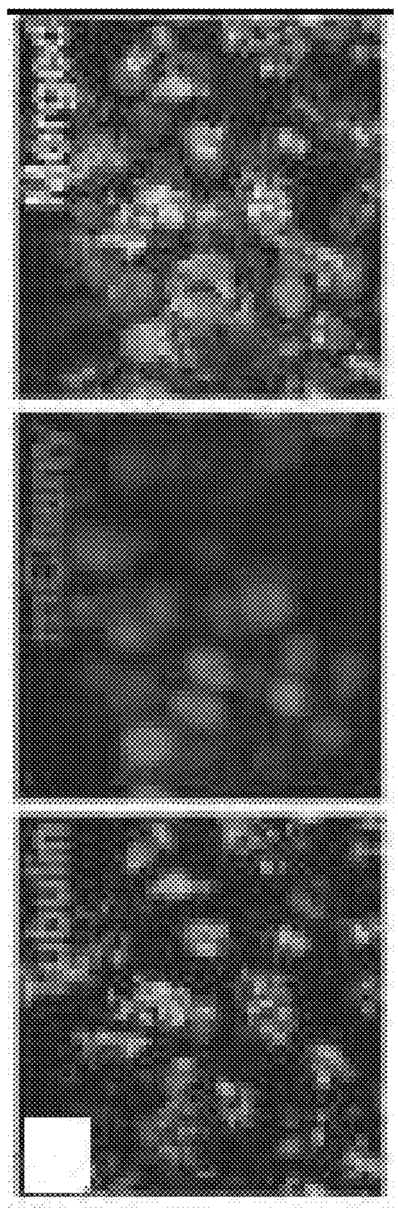

FIGS. 12A-12B. The rAAV2/HBoV1 vector efficiently transduces ciliated and K18-positive epithelial cells in HAE-ALI cultures. The indicated vector was applied apically at an MOI of 10 k; expression of the mCherry reporter protein (Red) identifies the transduced airway cells. At 10 days p.i., the HAE was (A) fixed and stained with anti-β-tubulin IV (Green), a marker of ciliated cells, and (B) trypsinized, cytospun onto a slide, fixed, and stained with anti-K18 (Green), for both ciliated and non-ciliated columnar cells. Confocal images were taken at ×100. DAPI: nucleus.

Figure 13A:
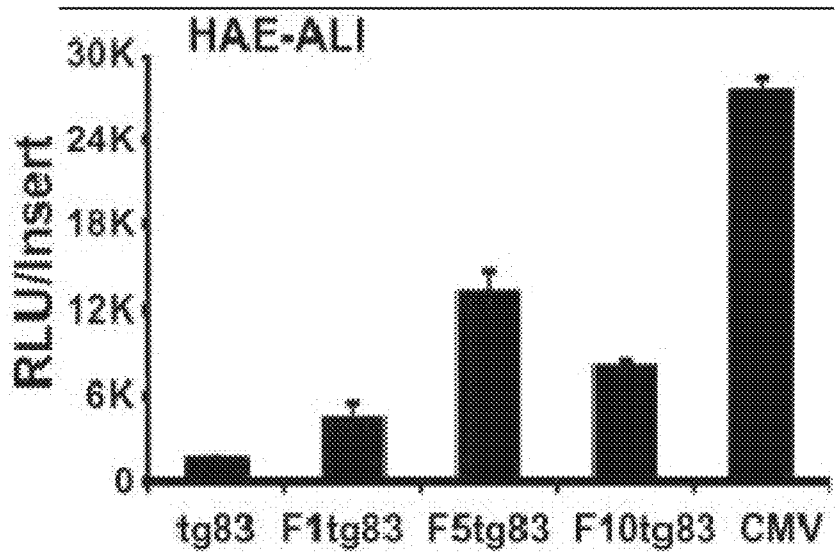
Figure 13B:
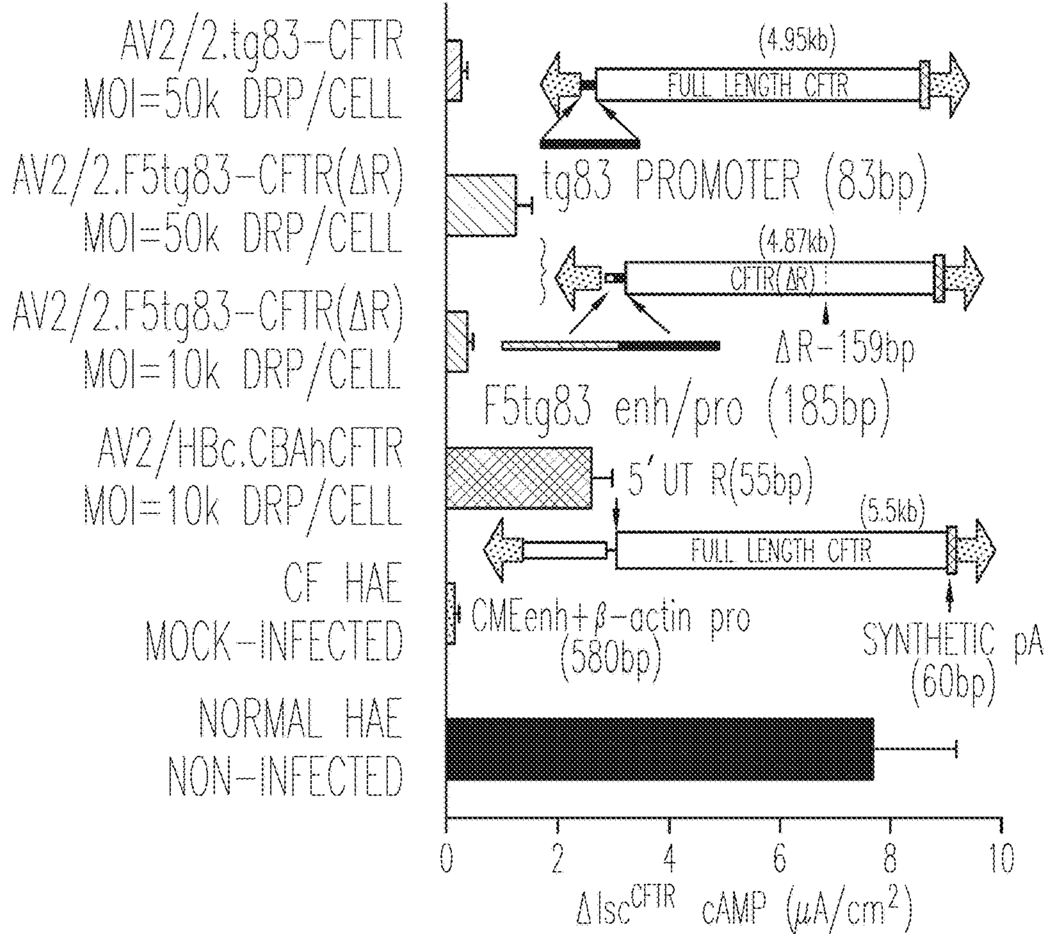
Figure 13C:
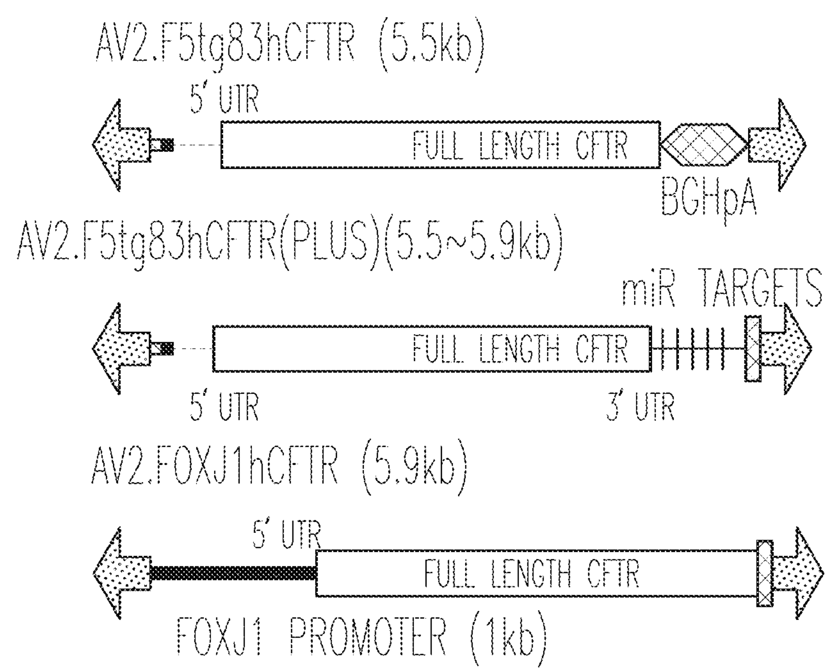

FIGS. 13A-13C. rAAV2 genome constructs for CFTR gene delivery. (A) Screening for short synthetic enhancers for the tg83 synthetic promoter. HAE-ALI were infected with rAAV2/2 vectors carrying a tg83-driven luciferase cassette and various enhancers. At 3 days p.i., the infected HAE were analyzed for luciferase activity (RLU). (B) Correction (30%) of $Cl^-$ transport in CF HAE-ALI by the rAAV2/HBoV1 vector is more effective than that achieved with rAAV2/2. CF HAE-ALI cultures were mock infected or infected with the vector depicted (n=6 for each condition), from the apical side and at the indicated MOI. At 10 days p.i., the infected CF HAE were evaluated for correction of the CF phenotype, based on changes in transepithelial short circuit current (isc), using an epithelial voltage clamp and a self-contained Ussing chamber system. At an MOI of 10 k, rAAV2/HBoV1 (AV2/HBc) restored about 30% of CFTR-mediated transepithelial $Cl^-$ transport as that of the normal HAE (n=13). rAAV2/2-CFTR vectors were inefficient at correcting the CF phenotype, even at an MOI of 50 k. (C) rAAV2 genome constructs for rAAV2/HBoV1 vector. rAAV2-CFTR genome constructs that include a ciliated cell-specific promoter (FOXJ1) or synthetic promoter/enhancer (F5tg83), or incorporate post-transcriptional elements (miR) are shown, and will be packaged into the HBoV1 capsid.

FIGS. 14A-14D. Schematic approach for correcting a defective CFTR mRNA using a SMaRT vector. (A) The rAAV2 genome AV2.CMV-PTM24CF, which is pseudotyped in the HBoV1 capsid, and the effectiveness of SMaRT will be tested by apical infection of the CF HAE. (B) Sequence of the trans-splicing domain of AV2.CMV-PTM24CF, which consists of: the 133-nt PTM24 binding sequence (in blue, complementary to a 133-nt BD RNA sequence at intron 9) following with endogenous branch point (BP in red), polypyrimidine tract (PPT in green) and the 3'SS (CAG) (SEQ ID NO: 46). (C) Schematic representation of structure of the CFTR pre-mRNA and targeting mechanism. Some critical mutations that cause defects in, or the lack of, CFTR protein, lie in and downstream of exon 10, as indicated. (D) The proposed new rAAV2 genome AV2.CBA-PTM24CF-3UTR.

Figure 15:
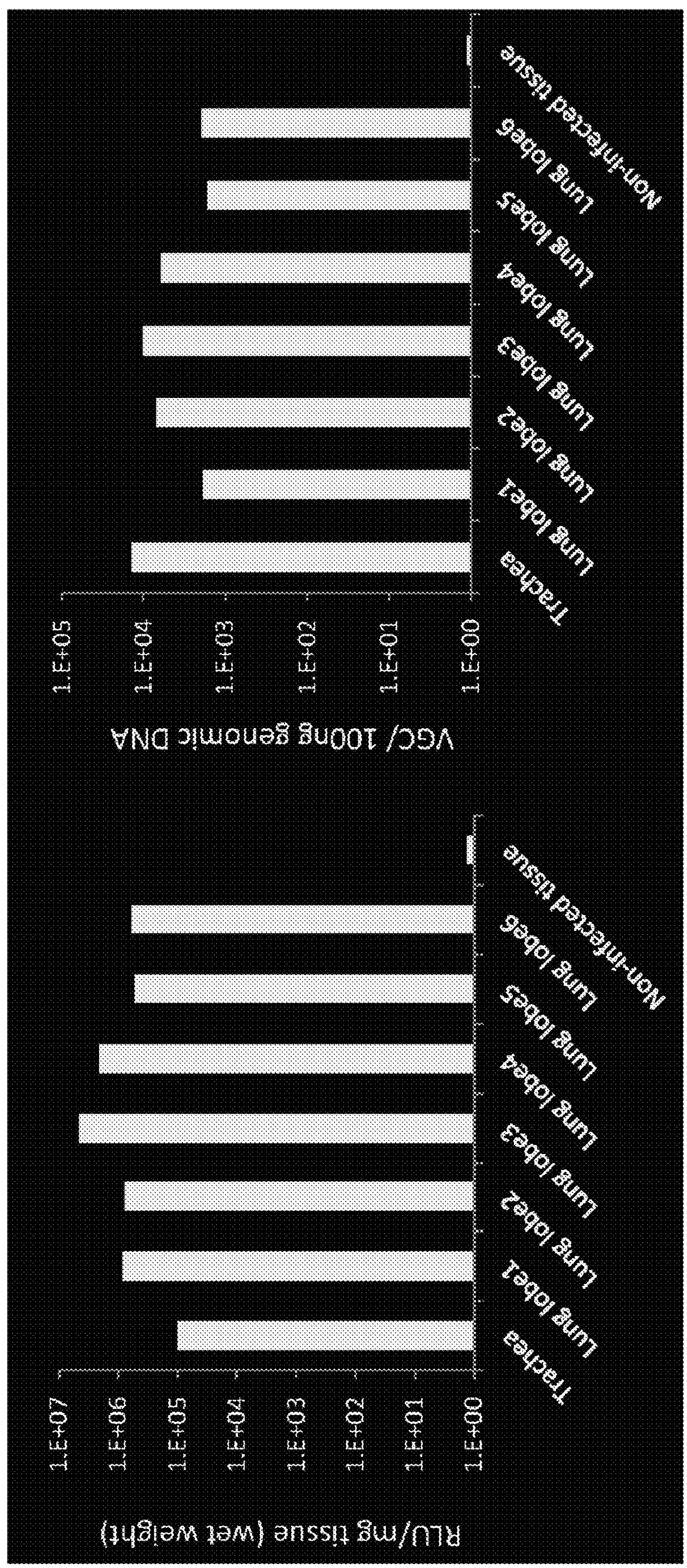

FIG. 15. rAAV2/HBoV1 Transduction in New Born Ferret. 3-day old ferret pup was infected with $4\times10^{10}$ DRP of AAV2/HBoV1.F5tg83luc through intratracheal injection. The volume of the inoculum is 300 μL with doxorubicin at the final concentration of 250 μM. The animal was sacrificed 1 week post-infection, the airway cassette was harvested and dissected. 200 μL reporter lysis buffer (for each piece of tissue) was used to extracted the protein from the trachea and the lobes of the lung (six lobes varied in size and weight). Luciferase activity (RLU) was measured from the protein extraction and normalized to per mg of the tissue (wet weight). 100 ng genome DNA of each tissue sample was used for probing the amount of vector genome copies (VGC) by TaqMan PCR. Uninfected lungs from a ferret pup are shown as a negative control.

FIGS. 16A-16G. Exemplary swine, feline and canine bocavirus genome and VP sequences (SEQ ID NOs: 37-45).

DETAILED DESCRIPTION

Definitions

A "vector" as used herein refers to a macromolecule or association of macromolecules that comprises or associates with a polynucleotide and which can be used to mediate delivery of the polynucleotide to a cell, either in vitro or in vivo. Illustrative vectors include, for example, plasmids, viral vectors, liposomes and other gene delivery vehicles. The polynucleotide to be delivered, sometimes referred to as a "target polynucleotide" or "transgene," may comprise a coding sequence of interest in gene therapy (such as a gene encoding a protein of therapeutic or interest), a coding sequence of interest in vaccine development (such as a polynucleotide expressing a protein, polypeptide or peptide suitable for eliciting an immune response in a mammal), and/or a selectable or detectable marker.

"AAV" is adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight serotypes of primate AAVs, AAV-1 to MV-8. For example, serotype AAV2 is used to refer to an MV which contains capsid proteins encoded from the cap gene of MV 2 and a genome containing 5' and 3' ITR sequences from the same AAV2 serotype. For each example illustrated herein the description of the vector design and production describes the serotype of the capsid and 5'-3' ITR sequences. The abbreviation "rAAV" refers to recombinant adeno-associated virus, also referred to as a recombinant AAV vector (or "rAAV vector").

BoV is bocavirus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to a BoV, which is identified by and distinguished from other BoVs based on capsid protein reactivity with defined antisera, e.g., there are four known serotypes of human bocavirus (HBoV), HBoV1, HBoV2, HBoV3, and HBoV4. However, included in BoV are serotypes derived from other non-human mammals such as swine BoV. Like for MV, different serotypes of HBoV and BoV can have different tropisms that infect different cell types and organs.

rAAV/HBoV is a chimeric vector which is composed of HBoV capsids and a rAAV genome. In such a chimeric virus there is no genetic information from HBoV within the genome. The rAAV genome may be from any serotype of MV.

rAAV/BoV is a chimeric vector which is composed of a non-human BoV capsids and a rAAV genome. In such a chimeric virus there is no genetic information from BoV within the genome. The rAAV genome may be from any serotype of AAV.

Tropism as used herein, is a term referring to the ability of a particular viral serotype to productively infect cells of differing phenotypes or organs to deliver their genomic information to the nucleus.

"Transduction" or "transducing" as used herein, are terms referring to a process for the introduction of an exogenous polynucleotide, e.g., a transgene in rAAV vector, into a host cell leading to expression of the polynucleotide, e.g., the transgene in the cell. The process includes one or more of 1) endocytosis of the chimeric virus, 2) escape from endosomes or other intracellular compartments in the cytosol of a cell, 3) trafficking of the viral particle or viral genome to the nucleus, 4) uncoating of the virus particles, and generation of expressible double stranded MV genome forms, including circular intermediates. The rAAV expressible double stranded form may persist as a nuclear episome or optionally may integrate into the host genome. The alteration of any or a combination of endocytosis of the chimeric virus after it has bound to a cell surface receptor, escape from endosomes or other intracellular compartments to the cytosol of a cell, trafficking of the viral particle or viral genome to the nucleus, or uncoating of the virus particles, and generation of expressive double stranded AAV genome forms, including circular intermediates, by an agent of the invention, e.g., a proteasome inhibitor, may result in altered expression levels or persistence of expression, or altered trafficking to the nucleus, or altered types or relative numbers of host cells or a population of cells expressing the introduced polynucleotide. Altered expression or persistence of a polynucleotide introduced via the chimeric virus can be determined by methods well known to the art including, but not limited to, protein expression, e.g., by ELISA, flow cytometry and Western blot, measurement of and DNA and RNA production by hybridization assays, e.g., Northern blots, Southern blots and gel shift mobility assays. The agents of the invention may alter, enhance or increase viral endocytosis, escape from endosomes or other intracellular cytosolic compartments, and trafficking into or to the nucleus, uncoating of the viral particles in the nucleus, and/or increasing concatamerization or generation of double stranded expressible forms of the rAAV genome in the nucleus, so as to alter expression of the introduced polynucleotide, e.g., a transgene in a rAAV vector, in vitro or in vivo. Methods used for the introduction of the exogenous polynucleotide include well-known techniques such as transfection, lipofection, viral infection, transformation, and electroporation, as well as non-viral gene delivery techniques. The introduced polynucleotide may be stably or transiently maintained in the host cell.

"Increased transduction or transduction frequency", "altered transduction or transduction frequency", or "enhanced transduction or transduction frequency" refers to an increase in one or more of the activities described above in a treated cell relative to an untreated cell. Agents of the invention which increase transduction efficiency may be determined by measuring the effect on one or more transduction activities, which may include measuring the expression of the transgene, measuring the function of the transgene, or determining the number of particles necessary to yield the same transgene effect compared to host cells not treated with the agents.

"Proteasome modulator" refers to an agent or class of agents which alter or enhance rAAV including chimeric virus transduction or transduction frequencies by interacting with, binding to, or altering the function of, and/or trafficking or location of the proteasome. Proteasome modulators may have other cellular functions as described in the art, e.g., such as doxyrubicin, an antibiotic. Proteasome modulators include proteasome inhibitors, e.g., such as tripeptidyl aldehydes (MG132, i.e., Z-LLL or MG101, i.e., LLnL), bortezomib (Velcade), agents that inhibit calpains, cathepsins, cysteine proteases, and/or chymotrypsin-like protease activity of proteasomes (Wagner et al., 2002; Young et al., 2000; Seisenberger et al., 2001).

"Gene delivery" refers to the introduction of an exogenous polynucleotide into a cell for gene transfer, and may encompass targeting, binding, uptake, transport, localization, replicon integration and expression.

"Gene transfer" refers to the introduction of an exogenous polynucleotide into a cell which may encompass targeting, binding, uptake, transport, localization and replicon integration, but is distinct from and does not imply subsequent expression of the gene.

"Gene expression" or "expression" refers to the process of gene transcription, translation, and post-translational modification.

A "detectable marker gene" is a gene that allows cells carrying the gene to be specifically detected (e.g., distinguished from cells which do not carry the marker gene). A large variety of such marker genes are known in the art.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. A variety of positive and negative selectable markers are known in the art, some of which are described below.

An "rAAV vector" as used herein refers to an AAV vector comprising a polynucleotide sequence not of AAV origin (i.e., a polynucleotide heterologous to AAV), typically a sequence of interest for the genetic transformation of a cell. In preferred vector constructs of this invention, the heterologous polynucleotide is flanked by one or two MV inverted terminal repeat sequences (ITRs). The term rAAV vector encompasses both rAAV vector particles and rAAV vector plasmids.

A "Chimeric virus" or "Chimeric viral particle" refers to a viral particle composed of at least one capsid protein and an encapsidated polynucleotide, which is from a different virus.

A "helper virus" for MV refers to a virus that allows AAV (e.g., wild-type AAV) to be replicated and packaged by a mammalian cell. A variety of such helper viruses for AAV are known in the art, including adenoviruses, herpes viruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC.

An "infectious" virus or viral particle is one that comprises a polynucleotide component, which it is capable of delivering into a cell for which the viral species is trophic. The term does not necessarily imply any replication capacity of the virus.

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "transcriptional regulatory sequence" or "TRS," as used herein, refers to a genomic region that controls the transcription of a gene or coding sequence to which it is operably linked. Transcriptional regulatory sequences of use in the present invention generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from that of the rest of the entity to which it is compared. For example, a polynucleotide introduced by genetic engineering techniques into a different cell type is a heterologous polynucleotide (and, when expressed, can encode a heterologous polypeptide). Similarly, a TRS or promoter that is removed from its native coding sequence and operably linked to a different coding sequence is a heterologous TRS or promoter.

"Packaging" as used herein refers to a series of subcellular events that results in the assembly and encapsidation of a viral vector. Thus, when a suitable vector is introduced into a packaging cell line under appropriate conditions, it can be assembled into a viral particle. Functions associated with packaging of viral vectors are described herein and in the art.

A "terminator" refers to a polynucleotide sequence that tends to diminish or prevent read-through transcription (i.e., it diminishes or prevent transcription originating on one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences," are specific sequences that tend to disrupt read-through transcription by RNA polymerase, presumably by causing the RNA polymerase molecule to stop and/or disengage from the DNA being transcribed. Typical examples of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("unidirectional" terminators) or from both directions ("bi-directional" terminators), and may be comprised of sequence-specific termination sequences or sequence-non-specific terminators or both. A variety of such terminator sequences are known in the art; and illustrative uses of such sequences within the context of the present invention are provided below.

"Host cells," "cell lines," "cell cultures," "packaging cell line" and other such terms denote higher eukaryotic cells, e.g., mammalian cells, such human cells, useful in the present invention. These cells can be used as recipients for recombinant vectors, viruses or other transfer polynucleotides, and include the progeny of the original cell that was transduced. It is understood that the progeny of a single cell may not necessarily be completely identical (in morphology or in genomic complement) to the original parent cell.

A "therapeutic gene," "prophylactic gene," "target polynucleotide," "transgene," "gene of interest" and the like generally refer to a gene or genes to be transferred using a vector. Typically, in the context of the present invention, such genes are located within the rAAV vector (which vector is flanked by inverted terminal repeat (ITR) regions and thus can be replicated and encapsidated into rAAV particles). Target polynucleotides can be used in this invention to generate rAAV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into antisense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as E1A tumor suppressor genes or p53 tumor suppressor genes for the treatment of various cancers. To effect expression of the transgene in a recipient host cell, it is operably linked to a promoter, either its own or a heterologous promoter. A large number of suitable promoters are known in the art, the choice of which depends on the desired level of expression of the target polynucleotide; whether one wants constitutive expression, inducible expression, cell-specific or tissue-specific expression, etc. The rAAV vector may also contain a selectable marker.

A "gene" refers to a polynucleotide containing at least one open reading frame that is capable of encoding a particular protein after being transcribed and translated.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAV ITR promoters, as well as heterologous promoters.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Genetic alteration" refers to a process wherein a genetic element is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. The genetic element may be introduced into a chromosome or mini-chromosome in the cell; but any alteration that changes the phenotype and/or genotype of the cell and its progeny is included in this term.

A cell is said to be "stably" altered, transduced or transformed with a genetic sequence if the sequence is available to perform its function during extended culture of the cell in vitro. In some examples, such a cell is "inheritably" altered in that a genetic alteration is introduced which is also inheritable by progeny of the altered cell.

The terms "polypeptide" and "protein" are used interchangeably herein to refer to polymers of amino acids of any length. The terms also encompass an amino acid polymer that has been modified; for example, disulfide bond formation, glycosylation, acetylation, phosphorylation, lipidation, or conjugation with a labeling component. Polypeptides such as "CFTR" and the like, when discussed in the context of gene therapy and compositions therefor, refer to the respective intact polypeptide, or any fragment or genetically engineered derivative thereof, that retains the desired biochemical function of the intact protein. Similarly, references to CFTR, and other such genes for use in gene therapy (typically referred to as "transgenes" to be delivered to a recipient cell), include polynucleotides encoding the intact polypeptide or any fragment or genetically engineered derivative possessing the desired biochemical function.

An "isolated" plasmid, virus, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture.

A preparation of AAV is said to be "substantially free" of helper virus if the ratio of infectious AAV particles to infectious helper virus particles is at least about $10^2$:1; e.g., at least about $10^4$:1, including at least about $10^6$:1 or at least about $10^8$:1. Preparations may also be free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the AAV capsid proteins VP1, VP2 and VP3).

"Efficiency" when used in describing viral production, replication or packaging refers to useful properties of the method: in particular, the growth rate and the number of virus particles produced per cell. "High efficiency" production indicates production of at least 100 viral particles per cell; e.g., at least about 10,000 or at least about 100,000 particles per cell, over the course of the culture period specified.

An "individual" or "subject" treated in accordance with this invention refers to vertebrates, particularly members of a mammalian species, and includes but is not limited to domestic animals, sports animals, and primates, including humans.

"Treatment" of an individual or a cell is any type of intervention in an attempt to alter the natural course of the individual or cell at the time the treatment is initiated, e.g., eliciting a prophylactic, curative or other beneficial effect in the individual. For example, treatment of an individual may be undertaken to decrease or limit the pathology caused by any pathological condition, including (but not limited to) an inherited or induced genetic deficiency, infection by a viral, bacterial, or parasitic organism, a neoplastic or aplastic condition, or an immune system dysfunction such as autoimmunity or immunosuppression. Treatment includes (but is not limited to) administration of a composition, such as a pharmaceutical composition, and administration of compatible cells that have been treated with a composition. Treatment may be performed either prophylactically or therapeutically; that is, either prior or subsequent to the initiation of a pathologic event or contact with an etiologic agent.

The practice of the present invention will employ, unless otherwise indicated, conventional techniques of molecular biology, virology, microbiology, recombinant DNA, and immunology, which are within the skill of the art. Such techniques are explained fully in the literature. See e.g., Sambrook et al., 1989; Gait, 1984; Freshney, 1987; the series *Methods in Enzymology* (Academic Press, Inc.); Miller et al., 1987; Weir et al., 1996; Ausubel et al., 1998; Coligan et al., 1991; Coligan et al., 1995; and Scopes 1994.

I. Chimeric Viruses

Human airway epithelial cells are highly resistant to infection by most viral vectors included the adeno-associated virus (rAAV), the most widely used gene therapy vector in clinical trials. Human Bocavirus 1 (HBoV1), an autonomous human parvovirus which is likely an etiological agent of acute respiratory tract infections (ARTI) associated with wheezing in infants and young children (Allander et al., 2007; Christensen et al., 2010; Deng et al., 2012; Don et al., 2010), efficiently infects HAE from the apical membrane, resulting in replication of progeny viruses and cytopathology (Huang et al., 2012a). Impressively, HBoV1 infection of HAE at extremely low multiplicities of infection (MOI) of $10^{-3}$ DNase-resistant particles (DRP) per cell results in a productive infection (see Example 2). Recently, the full-length 5543-nt HBoV1 complete genome (including terminal palindromic sequences at both ends) was cloned, and cell culture systems for HBoV1 production have been established (Example 1). Given the high efficiency of HBoV1 infection from the apical surface of HAE, HoBV1 was hypothesized to be suitable for engineering recombinant vectors for human airway gene therapy.

HBoV1 is a relative of AAV and other Parvoviridae family members. HBoV1 belongs to the genus Bocavirus, while AAV is in the genus *Dependovirus* (Tijssen et al., 2011). HBoV1 and AAV are both small single-stranded DNA viruses, but 90% of encapsidated HBoV1 genomes are of the minus strand, while for AAV, an equal ratio of plus and minus strands are encapsidated (Schildgen et al., 2012). These two viruses differ greatly in their lytic phase life cycle; MV requires co-infection with a helper virus, while HBoV1 autonomously replicates progeny in permissive cells (Huang et al., 2012a; Dijkman et al., 2009). The HBoV1 genome size is 5543 nt, 18.5% (863 nt) larger than that of AAV2 (4679-nt), and its structural features include asymmetrical hairpins with unique palindromic sequences at 5' (140 nt) and 3' (200 nt) termini, which are involved in replication and encapsidation, and a single P5 promoter that transcribes all viral structural and non-structural proteins (Huang et al., 2012; Chen et al., 2010). This is in contrast to the inverted terminal repeats and multiple internal promoters found in AAV genomes. The HBoV1 genome encodes three major open reading frames (ORF). Two of them code for nonstructural proteins, NS1/NS2 and NP1, which are essential for virus replication. The third ORF encodes two structural capsid proteins VP1 and VP2. By contrast, the MV cap ORF encodes three capsid proteins, VP1, VP2, and VP3 (Schidgen et al., 2012). HBoV1 capsid surface topology possesses common features with other parvoviruses (icoshedral capsid), and is most closely similar to human parvovirus B19 (Gurda et al., 2010). Like the cloned AAV genome, a plasmid that encodes the HBoV1 proviral genome is infectious and can be used to produce infectious particles through transfection into HEK 293 cells without the need for helper virus co-infection (Example 1).

Cross-genera pseudopackaging between Parvoviridae was first established when a rAAV genome was encapsidated into a human parvovirus B19 capsid (Ponnazhagan et al., 1998). This resultant cross-genera chimera was able to deliver the rAAV genome into human bone marrow cells that are resistant to rAAV infection (Ponnazhagan et al., 1998). Thus, it was hypothesized that pseudotyping the rAAV genome into HBoV1 capsid might create a novel chimeric vector with unique properties for gene therapy of CF and other pulmonary diseases.

The production of rHBoV1 vectors and chimeric rAAV2/HBoV1 vectors is described herein below. The first virus was a conventional recombinant vector (a rHBoV1 vector). An open reading frame disrupted or gutted HBoV genome carrying a foreign gene is packaged inside the HBoV1 capsid. rHBoV1 vector is produced in HEK293 cells by trans-complementation from the co-transfection of rHBoV1 proviral plasmid and HBoV1 helper plasmid. The rHBoV1 proviral plasmid harbors a foreign gene (of about 5.2 kb in length or more, which can accommodate a heterologous promoter, e.g., a strong promoter, operably linked to an open reading frame for the foreign gene) and all the cis-elements for replication and package, the helper plasmid encodes only the expression cassette for HBoV viral proteins. One important feature of the HBoV1 virus is that its genome autonomously replicates in permissive cells, in contrast to rAAV, which is a dependent parvovirus and needs helper virus coinfection for replication.

With the success in trans-complementation for rHBoV1 vector production, a so-called replicative rHBoV1 vector was developed by retaining the coding sequences for HBoV1 rep genes but replacing the structural gene by a transgene. This type of vector can deliver a high level of therapeutic gene expression in the airway cells for the therapy such as CF, AAT deficiency, COPD, or lung cancers. Such a replicating HBoV1 vector could have high utility as a vaccine against WT HBoV1 infections.

Another vector developed was an AAV2-HBoV1 chimeric virus, which packages a rAAV genome into a HBoV1 capsid particle. The vector was also produced in HEK293 cells with a procedure similar for rAAV vector, but the capsid genes are substituted by HBoV1 capsids. This AAV/HBoV1 vector combines both the advantages of MV and HBoV1 transduction biology, with less safety concerns than the rHBoV1 vector since rAAV vector genomes have been extensively studied in many pre-clinical research and clinical trials, but higher airway cell tropism than rAAV. More importantly, the large HBoV1 package capacity makes it possible to encapsidate an oversized rAAV genome up to about 5.5 kb or about 6.0 kb. The 20% greater capacity than rAAV is enough to house a strong expression cassette for effective gene expression. A rAAV genome provides advantages of persistent gene expression by the stable circular transduction intermediates and double stranded genome concatemers. Indeed, AAV/HBoV1 vectors featured more persistent transgene expression than the rHBoV1 vector. Furthermore, the rescue and replication of rAAV genomes in HEK293 cells was very efficient, so that the production yield of the AAV/HBoV1 vector was also better than an rHBoV1 vector.

Utilizing the larger packaging capacity of HBoV1, a rAAV2/1-1BoV1-CFTR vector was prepared that harbors a 5.5 kb oversized rAAV genome with a 5.2 kb CFTR expression cassette having a strong chimeric promoter that included the human CMV immediate gene enhancer and the chicken β-actin promoter (CBA promoter). That vector demonstrated about 30% restoration of CFTR-mediate chloride currents in CF HAE following apical infection. Therefore, the vector can efficiently deliver normal CFTR protein expression on the surface of the airway epithelial cells and correct the defective CFTR specific chloride transport in the CF HAE. In addition, the HBoV1 genome can encapsidate the self-complementary double stranded form of a rAAV genome of about 2.7 kb to about 2.8 kb in length, which vector can bypass genome conversion and allow for enhanced or more rapid transgene expression. The AAV/HBoV chimeric vectors could also be expanded to other therapies for other lung diseases such as alpha-antitrypsin deficiency, asthma, and lung cancer, as well as vaccination against wild-type HBoV infections in infants.

The capsids and/or genomes of the viruses of the invention may be chimeric, e.g., as a result of directed evolution (see, e.g., Li et al., 2009).

II. rAAV Vectors

Besides prophylactic or therapeutic gene products, recombinant AAV vectors and/or viruses can also comprise polynucleotides that do not encode proteins, including, e.g., polynucleotides encoding for antisense mRNA (the complement of mRNA) which can be used to block the translation of normal mRNA by forming a duplex with it, and polynucleotides that encode ribozymes (RNA catalysts). In addition selected pairs of rAAV vectors having portions of open reading frames flanked by appropriately placed splice acceptor sites and/or splice donor sites, or having transcription regulatory sequences such as a heterologous enhancer, a heterologous promoter, or a heterologous enhancer and a promoter, may be employed. See, e.g., U.S. Pat. No. 6,436,392, the disclosure of which is incorporated by reference herein. For example, a first MV vector may include a first DNA segment comprising a 5'-inverted terminal repeat of MV: a second DNA segment comprising a promoter operably linked to a DNA fragment comprising an exon of a gene and a splice donor site, wherein the second DNA segment does not encode a full-length polypeptide; and a third DNA segment comprising a 3'-inverted terminal repeat of MV: and a second AAV vector comprising linked: a first DNA segment comprising a 5'-inverted terminal repeat of AAV; a second DNA segment comprising a splice acceptor site and a DNA fragment with at least one other exon which together with the DNA segment of the first MV vector encodes a full-length polypeptide; and a third DNA segment comprising a 3'-inverted terminal repeat of AAV. In one example, a first MV vector includes the following: a first nucleic acid segment comprising a 5'-inverted terminal repeat of MV; a second nucleic acid segment comprising a portion of a gene which includes a transcriptional regulatory region; a third nucleic acid segment comprising a splice donor site; and a fourth nucleic acid segment comprising a 3'-inverted terminal repeat of MV; and a second AAV vector comprising linked: a first nucleic acid segment comprising a 5'-inverted terminal repeat of MV; a second nucleic acid segment comprising a splice acceptor site; a third nucleic acid segment comprising a portion of a gene which together with the nucleic acid segment of the first MV vector comprises a gene comprising an open reading frame which encodes a functional polypeptide; and a fourth nucleic acid segment comprising a 3'-inverted terminal repeat of MV. In a further example, a first AAV vector includes the following: a first nucleic acid segment comprising a 5'-inverted terminal repeat of AAV; a second nucleic acid segment comprising a splice acceptor site; a third nucleic acid segment comprising a portion of a gene; and a fourth nucleic acid segment comprising a 3'-inverted terminal repeat of MV; and a second composition comprising a second AAV vector comprising: a first nucleic acid segment comprising a 5'-inverted terminal repeat of AAV; a second nucleic acid segment comprising a portion of a gene which together with the nucleic acid segment above having the portion comprises a gene comprising an open reading frame which encodes a functional polypeptide, wherein the portion of the gene includes a transcriptional regulatory region; a third nucleic acid segment comprising a splice donor site; a fourth nucleic acid segment comprising a 3'-inverted terminal repeat of MV; which vectors in a host cell yield a RNA transcript which comprises sequences from the first MV vector linked to sequences from the second AAV vector, which sequences are positioned so that the splice donor site is 5' to the splice acceptor site, and which transcript is spliced to a mRNA which encodes the functional protein.

Adeno-associated viruses of any serotype are suitable to prepare rAAV, since the various serotypes are functionally and structurally related, even at the genetic level (see, e.g., Blacklow, 1988; and Rose, 1974). All AAV serotypes apparently exhibit similar replication properties mediated by homologous rep genes; and all generally bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to ITRs. The similar infectivity patterns also suggest that the replication functions in each serotype are under similar regulatory control. Among the various MV serotypes, AAV2 is most commonly employed.

An AAV vector of the invention typically comprises a polynucleotide that is heterologous to MV. The polynucleotide is typically of interest because of a capacity to provide a function to a target cell in the context of gene therapy, such as up- or down-regulation of the expression of a certain phenotype. Such a heterologous polynucleotide or "transgene," generally is of sufficient length to provide the desired function or encoding sequence.

Where transcription of the heterologous polynucleotide is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and may be preferred when it is desired that the therapeutic or prophylactic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific: that is, they exhibit their activity only in certain cell types, presumably due to gene regulatory elements found uniquely in those cells.

Illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences of many such promoters are available in sequence databases such as the GenBank database.

Where translation is also desired in the intended target cell, the heterologous polynucleotide will preferably also comprise control elements that facilitate translation (such as a ribosome binding site or "RBS" and a polyadenylation signal). Accordingly, the heterologous polynucleotide generally comprises at least one coding region operatively linked to a suitable promoter, and may also comprise, for example, an operatively linked enhancer, ribosome binding site and poly-A signal. The heterologous polynucleotide may comprise one encoding region, or more than one encoding regions under the control of the same or different promoters. The entire unit, containing a combination of control elements and encoding region, is often referred to as an expression cassette.

The heterologous polynucleotide is integrated by recombinant techniques into or in place of the AAV genomic coding region (i.e., in place of the AAV rep and cap genes), but is generally flanked on either side by AAV inverted terminal repeat (ITR) regions. This means that an ITR appears both upstream and downstream from the coding sequence, either in direct juxtaposition, e.g., (although not necessarily) without any intervening sequence of AAV origin in order to reduce the likelihood of recombination that might regenerate a replication-competent AAV genome. However, a single ITR may be sufficient to carry out the functions normally associated with configurations comprising two ITRs (see, for example, WO 94/13788), and vector constructs with only one ITR can thus be employed in conjunction with the packaging and production methods of the present invention.

The native promoters for rep are self-regulating, and can limit the amount of AAV particles produced. The rep gene can also be operably linked to a heterologous promoter, whether rep is provided as part of the vector construct, or separately. Any heterologous promoter that is not strongly down-regulated by rep gene expression is suitable; but inducible promoters may be preferred because constitutive expression of the rep gene can have a negative impact on the host cell. A large variety of inducible promoters are known in the art; including, by way of illustration, heavy metal ion inducible promoters (such as metallothionein promoters); steroid hormone inducible promoters (such as the MMTV promoter or growth hormone promoters); and promoters such as those from 17 phage which are active in the presence of T7 RNA polymerase. One sub-class of inducible promoters are those that are induced by the helper virus that is used to complement the replication and packaging of the rAAV vector. A number of helper-virus-inducible promoters have also been described, including the adenovirus early gene promoter which is inducible by adenovirus EIA protein; the adenovirus major late promoter; the herpesvirus promoter which is inducible by herpesvirus proteins such as VP16 or 1CP4; as well as vaccinia or poxvirus inducible promoters.

Methods for identifying and testing helper-virus-inducible promoters have been described (see, e.g., WO 96/17947). Thus, methods are known in the art to determine whether or not candidate promoters are helper-virus-inducible, and whether or not they will be useful in the generation of high efficiency packaging cells. Briefly, one such method involves replacing the p5 promoter of the MV rep gene with the putative helper-virus-inducible promoter (either known in the art or identified using well-known techniques such as linkage to promoter-less "reporter" genes). The AAV rep-cap genes (with p5 replaced), e.g., linked to a positive selectable marker such as an antibiotic resistance gene, are then stably integrated into a suitable host cell (such as the HeLa or A549 cells exemplified below). Cells that are able to grow relatively well under selection conditions (e.g., in the presence of the antibiotic) are then tested for their ability to express the rep and cap genes upon addition of a helper virus. As an initial test for rep and/or cap expression, cells can be readily screened using immunofluorescence to detect Rep and/or Cap proteins. Confirmation of packaging capabilities and efficiencies can then be determined by functional tests for replication and packaging of incoming rAAV vectors. Using this methodology, a helper-virus-inducible promoter derived from the mouse metallothionein gene has been identified as a suitable replacement for the p5 promoter, and used for producing high titers of rAAV particles (as described in WO 96/17947).

Removal of one or more MV genes is in any case desirable, to reduce the likelihood of generating replication-competent AAV ("RCA"). Accordingly, encoding or promoter sequences for rep, cap, or both, may be removed, since the functions provided by these genes can be provided in trans.

The resultant vector is referred to as being "defective" in these functions. In order to replicate and package the vector, the missing functions are complemented with a packaging gene, or a plurality thereof, which together encode the necessary functions for the various missing rep and/or cap gene products. The packaging genes or gene cassettes are in one embodiment not flanked by AAV ITRs and in one embodiment do not share any substantial homology with the rAAV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of homologous sequences and with their level of shared identity. The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCA. Even further reductions in the frequency of generating RCA (e.g., by nonhomologous recombination) can be obtained by "splitting" the replication and encapsidation functions of MV, as described by Allen et al., WO 98/27204).

The rAAV vector construct, and the complementary packaging gene constructs can be implemented in this invention in a number of different forms. Viral particles, plasmids, and stably transformed host cells can all be used to introduce such constructs into the packaging cell, either transiently or stably.

In certain embodiments of this invention, the MV vector and complementary packaging gene(s), if any, are provided in the form of bacterial plasmids, AAV particles, or any combination thereof. In other embodiments, either the MV vector sequence, the packaging gene(s), or both, are provided in the form of genetically altered (preferably inheritably altered) eukaryotic cells. The development of host cells inheritably altered to express the AAV vector sequence, AAV packaging genes, or both, provides an established source of the material that is expressed at a reliable level.

A variety of different genetically altered cells can thus be used in the context of this invention. By way of illustration, a mammalian host cell may be used with at least one intact copy of a stably integrated rAAV vector. An AAV packaging plasmid comprising at least an AAV rep gene operably linked to a promoter can be used to supply replication functions (as described in U.S. Pat. No. 5,658,776). Alternatively, a stable mammalian cell line with an AAV rep gene operably linked to a promoter can be used to supply replication functions (see, e.g., Trempe et al., WO 95/13392); Burstein et al. (WO 98/23018); and Johnson et al. (U.S. Pat. No. 5,656,785). The AAV cap gene, providing the encapsidation proteins as described above, can be provided together with an AAV rep gene or separately (see, e.g., the above-referenced applications and patents as well as Allen et al. (WO 98/27204). Other combinations are possible and included within the scope of this invention.

III. Uses of Chimeric Virus or rBoV

The chimeric virus or rBoV can be used for administration to an individual for purposes of gene therapy or vaccination. Suitable diseases for therapy include but are not limited to those induced by viral, bacterial, or parasitic infections, various malignancies and hyperproliferative conditions, autoimmune conditions, and congenital deficiencies.

Gene therapy can be conducted to enhance the level of expression of a particular protein either within or secreted by the cell. Vectors of this invention may be used to genetically alter cells either for gene marking, replacement of a missing or defective gene, or insertion of a therapeutic gene. Alternatively, a polynucleotide may be provided to the cell that decreases the level of expression. This may be used for the suppression of an undesirable phenotype, such as the product of a gene amplified or overexpressed during the course of a malignancy, or a gene introduced or overexpressed during the course of a microbial infection. Expression levels may be decreased by supplying a therapeutic or prophylactic polynucleotide comprising a sequence capable, for example, of forming a stable hybrid with either the target gene or RNA transcript (antisense therapy), capable of acting as a ribozyme to cleave the relevant mRNA or capable of acting as a decoy for a product of the target gene.

Vaccination can be conducted to protect cells from infection by infectious pathogens. As the traditional vaccine methods, vectors of this invention may be used to deliver transgenes encoding viral, bacterial, tumor or fungal antigen and their subsequent expression in host cells. The antigens, which expose to the immune system to evoke an immune response, can be in the form of virus-like particle vaccines or subunit vaccines of virus-coding proteins. Alternatively, as the method of passive immunolization, vectors of this invention might be used to deliver genes encoding neutralizing antibodies and their subsequent expression in host non-hematopoietic tissues. The vaccine-like protection against pathogen infection can be conducted through direct provision of neutralizing antibody from vector-mediated transgene expression, bypassing the reliance on the natural immune system for mounting desired humoral immune responses.

The introduction of the chimeric or rBoV vectors by the methods of the present invention may involve use of any number of delivery techniques (both surgical and non-surgical) which are available and well known in the art. Such delivery techniques, for example, include vascular catheterization, cannulization, injection, inhalation, endotracheal, subcutaneous, inunction, topical, oral, percutaneous, intra-arterial, intravenous, and/or intraperitoneal administrations. Vectors can also be introduced by way of bioprostheses, including, by way of illustration, vascular grafts (PTFE and dacron), heart valves, intravascular stents, intravascular paving as well as other non-vascular prostheses. General techniques regarding delivery, frequency, composition and dosage ranges of vector solutions are within the skill of the art.

In particular, for delivery of a vector of the invention to a tissue, any physical or biological method that will introduce the vector to a host animal can be employed. Vector means both a bare recombinant vector and vector DNA packaged into viral coat proteins, as is well known for administration. Simply dissolving a chimeric or rHBoV vector in phosphate buffered saline has been demonstrated to be sufficient to provide a vehicle useful for muscle tissue expression, and there are no known restrictions on the carriers or other components that can be coadministered with the vector (although compositions that degrade DNA should be avoided in the normal manner with vectors). Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The vectors can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the chimeric or rHBoV vector as a free acid (DNA contains acidic phosphate groups) or a pharmacologically acceptable salt can be prepared in water suitably mixed with a surfactant such as hydroxypropylcellulose. A dispersion of viral particles can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the chimeric or rHBoV vector in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the methods of preparation include but are not limited to vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration), otherwise similar to the above parenteral solutions, are prepared in containers suitable for incorporation into a transdermal patch, and can include known carriers, such as pharmaceutical grade di methylsulfoxide (DMSO).

Of interest is the correction of the genetic defect of cystic fibrosis, by supplying a properly functioning cystic fibrosis transmembrane conductance regulator (CFTR) to the airway epithelium. Thus, the use of chimeric or rHBoV vectors encoding native CFTR protein, and mutants and fragments thereof, is envisioned.

Compositions of this invention may be used in vivo as well as ex vivo. In vivo gene therapy comprises administering the vectors of this invention directly to a subject. Pharmaceutical compositions can be supplied as liquid solutions or suspensions, as emulsions, or as solid forms suitable for dissolution or suspension in liquid prior to use. For administration into the respiratory tract, one mode of administration is by aerosol, using a composition that provides either a solid or liquid aerosol when used with an appropriate aerosolubilizer device. Another mode of administration into the respiratory tract is using a flexible fiberoptic bronchoscope to instill the vectors. Typically, the viral vectors are in a pharmaceutically suitable pyrogen-free buffer such as Ringer's balanced salt solution (pH 7.4). Although not required, pharmaceutical compositions may optionally be supplied in unit dosage form suitable for administration of a precise amount.

An effective amount of virus is administered, depending on the objectives of treatment. An effective amount may be given in single or divided doses. Where a low percentage of transduction can cure a genetic deficiency, then the objective of treatment is generally to meet or exceed this level of transduction. In some instances, this level of transduction can be achieved by transduction of only about 1 to 5% of the target cells, but is more typically 20% of the cells of the desired tissue type, usually at least about 50%, at least about 80%, at least about 95%, or at least about 99% of the cells of the desired tissue type. As a guide, the number of vector particles present in a single dose given by bronchoscopy will generally be at least about $1\times10^{12}$, e.g., about $1\times10^{13}$, $1\times10^{14}$, $1\times10^{15}$ or $1\times10^{16}$ particles, including both DNAse-resistant and DNAse-susceptible particles. In terms of DNAse-resistant particles, the dose will generally be between $1\times10^{12}$ and $1\times10^{16}$ particles, more generally between about $1\times10^{12}$ and $1\times10^{15}$ particles. The treatment can be repeated as often as every two or three weeks, as required, although treatment once in 180 days may be sufficient.

To confirm the presence of the desired DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence of a polypeptide expressed from a gene present in the vector, e.g., by immunological means (immunoprecipitation, immunoaffinity columns, ELISAs and Western blots) or by any other assay useful to identify the presence and/or expression of a particular nucleic acid molecule falling within the scope of the invention.

To detect and quantitate RNA produced from introduced DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the DNA segment in question, they do not provide information as to whether the DNA segment is being expressed. Expression may be evaluated by specifically identifying the polypeptide products of the introduced DNA sequences or evaluating the phenotypic changes brought about by the expression of the introduced DNA segment in the host cell.

Thus, the effectiveness of the genetic alteration can be monitored by several criteria, including analysis of physiological fluid samples, e.g., urine, plasma, serum, blood, cerebrospinal fluid or nasal or lung washes. Samples removed by biopsy or surgical excision may be analyzed by in situ hybridization, PCR amplification using vector-specific probes, RNAse protection, immunohistology, or immunofluorescent cell counting. When the vector is administered by bronchoscopy, lung function tests may be performed, and bronchial lavage may be assessed for the presence of inflammatory cytokines. The treated subject may also be monitored for clinical features, and to determine whether the cells express the function intended to be conveyed by the therapeutic or prophylactic polynucleotide.

The decision of whether to use in vivo or ex vivo therapy, and the selection of a particular composition, dose, and route of administration will depend on a number of different factors, including but not limited to features of the condition and the subject being treated. The assessment of such features and the design of an appropriate therapeutic or prophylactic regimen is ultimately the responsibility of the prescribing physician.

The foregoing description provides, inter alia, methods for generating high titer preparations of recombinant chimeric viruses or rHBoV that are substantially free of helper virus (e.g., adenovirus) and cellular proteins. It is understood that variations may be applied to these methods by those of skill in this art without departing from the spirit of this invention.

IV. Agents Useful in the Practice of the Invention

Classes of agents useful in the invention include but are not limited to antibiotics, chemotherapeutics, e.g., anthracyclines, proteasome modulators, lipid lowering agents, mucolytic agents, and food additives. Exemplary agents include proteasome inhibitors (Wagner et al., 2002; Young et al., 2000; Seisenberger et al., 2001), as well as agents that modulate the proteosome and ubiquitin pathways, e.g., bind to proteosomes and/or modulate the activity of proteosomes, ubiquitin, ubiquitin carrier protein, or ubiquitin ligase. Examples of these agents include without limitation antibiotics, e.g., epoxomicin, lipid lowering drugs, e.g., simvastatin, food additives, e.g., tannic acid, and chemotherapeutics, e.g., cisplatin, anthracyclines such as doxorubicin, and camptothecin. In one embodiment, the agent is LLnL (MG101), Z-LLL (MG132), bortezomib (Velcade), epoxomicin, doxorubicin, doxil, daunorubicin, idarubicin, epirubicin, aclarubicin, simvastatin, tannic acid, camptothecin, or cisplatin.

In one embodiment, the agent is a compound of formula (I): $R_1$-A-$(B)_n$—C wherein $R_1$ is an N-terminal amino acid blocking group; each A and B is independently an amino acid; C is an amino acid wherein the terminal carboxy group has been replaced by a formyl (CHO) group; and n is 0, 1, 2, or 3; or a pharmaceutically acceptable salt thereof. In one embodiment, $R_1$ is $(C_1\text{-}C_{10})$alkanoyl. In one embodiment, $R_1$ is acetyl or benzyloxycarbonyl. In one embodiment, each A and B is independently alanine, arginine, glycine, isoleucine, leucine, valine, nor-leucine or nor-valine. In one embodiment, each A and B is isoleucine. In one embodiment, C is alanine, arginine, glycine, isoleucine, leucine, valine, nor-leucine or nor-valine, wherein the terminal carboxy group has been replaced by a formyl (CHO) group. In one embodiment, C is nor-leucine or nor-valine, wherein the terminal carboxy group has been replaced by a formyl (CHO) group. In one embodiment, $R_1$ is $(C_1\text{-}C_{10})$alkanoyl or benzyloxycarbonyl; A and B are each isoleucine; C is nor-leucine or nor-valine, wherein the terminal carboxy group has been replaced by a formyl (CHO) group; and N is 1.

Another example of an agent is a compound of formula (II):

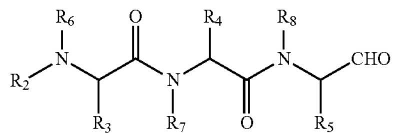

wherein $R_2$ is an N-terminal amino acid blocking group;

$R_3$, $R_4$, and $R_5$ are each independently hydrogen, $(C_1\text{-}C_{10})$alkyl, aryl or aryl$(C_1\text{-}C_{10})$alkyl; and $R_6$, $R_7$, and $R_8$ are each independently hydrogen, $(C_1\text{-}C_{10})$alkyl, aryl or aryl$(C_1\text{-}C_{10})$alkyl; or a pharmaceutically acceptable salt thereof.

In yet another example, an agent useful in the methods is a compound of formula (III): R-A-$A_1$-$R_1$ wherein R is hydrogen, an amino acid, or a peptide, wherein the N-terminus amino acid can optionally be protected at the amino group with acetyl, acyl, trifluoroacetyl, or benzyloxycarbonyl; A is an amino acid or a direct bond; $A_1$ is an amino acid; and $R_1$ is hydroxy or an amino acid, wherein the C-terminus amino acid can optionally be protected at the carboxy group with $(C_1-C_6)$alkyl, phenyl, benzyl ester or amide (e.g., $C(=O)NR_2$, wherein each R is independently hydrogen or $(C_1-C_6)$alkyl);

or a pharmaceutically acceptable salt thereof.

In one embodiment, the agent is H-Leu-Ala-OH, H—His-Ala-OH, or a combination thereof.

V. Dosages, Formulations and Routes of Administration of the Agents of the Invention Administration of the agents identified in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. When the agents of the invention are employed for prophylactic purposes, agents of the invention are amenable to chronic use, e.g., by systemic administration.

One or more suitable unit dosage forms comprising the agents of the invention, which, as discussed below, may optionally be formulated for sustained release, can be administered by a variety of routes including oral, or parenteral, including by rectal, transdermal, subcutaneous, intravenous, intramuscular, intraperitoneal, intrathoracic, intrapulmonary and intranasal routes. For example, for administration to the liver, intravenous administration may be preferred. For administration to the lung, airway administration may be preferred. The formulations may, where appropriate, be conveniently presented in discrete unit dosage forms and may be prepared by any of the methods well known to pharmacy. Such methods may include the step of bringing into association the agent with liquid carriers, solid matrices, semi-solid carriers, finely divided solid carriers or combinations thereof, and then, if necessary, introducing or shaping the product into the desired delivery system.

When the agents of the invention are prepared for oral administration, they may be combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the agents of the invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The agents of the invention can also be formulated as elixirs or solutions for convenient oral administration or as solutions appropriate for parenteral administration, for instance by intramuscular, subcutaneous or intravenous routes.

The pharmaceutical formulations of the agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$-$C_4$ alkyl esters of short-chain acids, e.g., ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and $\alpha$-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or for instance in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The agents of the invention can be delivered via patches for transdermal administration. See U.S. Pat. No. 5,560,922 for examples of patches suitable for transdermal delivery of an agent. Patches for transdermal delivery can comprise a backing layer and a polymer matrix which has dispersed or dissolved therein an agent, along with one or more skin permeation enhancers. The backing layer can be made of any suitable material which is impermeable to the agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. The materials used for the backing layer may be laminates of such polymer films with a metal foil such as aluminum foil. In such laminates, a polymer film of the laminate will usually be in contact with the adhesive polymer matrix.

The backing layer can be any appropriate thickness, which will provide the desired protective and support functions. A suitable thickness will be from about 10 to about 200 microns.

Generally, those polymers used to form the biologically acceptable adhesive polymer layer are those capable of forming shaped bodies, thin walls or coatings through which agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel), polyvinylidene chloride, poly(ethylene terephthalate), butyl rubber, epichlorohydrin rubbers, ethylene vinyl alcohol copolymers, ethylene-vinyloxyethanol copolymers; silicone copolymers, for example, polysiloxane-polycarbonate copolymers, polysiloxane-polyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

A biologically acceptable adhesive polymer matrix may be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

A plasticizer and/or humectant may be dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Agents released from a transdermal delivery system must be capable of penetrating each layer of skin. In order to increase the rate of permeation of an agent, a transdermal drug delivery system must be able in particular to increase the permeability of the outermost layer of skin, the stratum corneum, which provides the most resistance to the penetration of molecules. The fabrication of patches for transdermal delivery of agents is well known to the art.

For administration to the upper (nasal) or lower respiratory tract by inhalation, the agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the agent may be administered via nose drops, a liquid spray, such as via a plastic bottle atomizer or metered-dose inhaler. Typical of atomizers are the Mistometer (Wintrop) and the Medihaler (Riker).

The local delivery of the agents of the invention can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the agents may be formulated as is known in the art for direct application to a target area. Conventional forms for this purpose include wound dressings, coated bandages or other polymer coverings, ointments, creams, lotions, pastes, jellies, sprays, and aerosols. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of an agent of the invention present in a topical formulation will depend on various factors, but generally will be from 0.01% to 95% of the total weight of the formulation, and typically 0.1-25% by weight.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The formulations and compositions described herein may also contain other ingredients such as antimicrobial agents, or preservatives. Furthermore, the active ingredients may also be used in combination with other agents, for example, bronchodilators.

The agents of this invention may be administered to a mammal alone or in combination with pharmaceutically acceptable carriers. As noted above, the relative proportions of active ingredient and carrier are determined by the solubility and chemical nature of the compound, chosen route of administration and standard pharmaceutical practice.

The dosage of the present agents will vary with the form of administration, the particular compound chosen and the physiological characteristics of the particular patient under treatment. Generally, small dosages will be used initially and, if necessary, will be increased by small increments until the optimum effect under the circumstances is reached.

VI. Exemplary Embodiments

In one embodiment, the invention provides an isolated chimeric virus comprising bocavirus capsid protein and a rAAV genome. In one embodiment, the bocavirus capsid is a HBoV capsid. In one embodiment, the HBoV capsid is HBoV1, HBoV2, HBoV3 or HBoV4capsid. In one embodiment, the genome comprises an expression cassette encoding a heterologous gene product, e.g., a therapeutic protein. In one embodiment, the rAAV genome is a rAAV-2 genome. In one embodiment, the rAAV genome is a rAAV-1, rAAV-3, rAAV-4, rAAV-5, rAAV-6, rAAV-7, rAAV-8 or rAAV-9 genome. In one embodiment, the rAAV genome is derived from a non-human species of AAV. In one embodiment, the expression cassette includes a promoter that is expressed in ciliated airway epithelial cells, e.g., a FOXJ1 promoter. In one embodiment, the genome includes a trans-splicing domain. The gene product encoded by the viral genome may be a viral, bacterial, tumor or fungal antigen. In one embodiment, the transgene encodes a neutralizing antibody or an antigen binding fragment thereof. In one embodiment, the gene product is cystic fibrosis transmembrane conductance regulator, β-globin, γ-globin, tyrosine hydroxylase, glucocerebrosidase, aryl sulfatase A, factor VIII, dystrophin, alpha 1-antitrypsin, surfactant protein SP-D, SP-A or SP-C, erythropoietin, RSV protein, HBoV protein, influenza virus protein, SARS protein, a cytokine, e.g., IFN-alpha, IFN-gamma, TNF, IL-1, IL-17, or IL-6. Also provided is a method to express a heterologous gene product in mammalian cells which employs the isolated chimeric virus to infect cells in an amount effective to express a heterologous gene product, e.g., a therapeutic gene product, a catalytic RNA, a prophylactic gene product, a polypeptide or peptide. In one embodiment, the virus is isolated from insect cells or mammalian cells. Further provided is a method to enhance chimeric virus transduction of a mammalian cell. The method includes contacting a mammalian cell with an isolated chimeric virus comprising human bocavirus capsid protein and a rAAV genome comprising a transgene encoding a heterologous gene product and at least one agent in an amount effective to additively or synergistically enhance rAAV transduction. In one embodiment, the mammalian cell is a mammalian lung cell. In one embodiment, the agent is a proteasome inhibitor, chemotherapeutic, a lipid lowering agent, a mucolytic agent, an antibiotic or a food additive.

The isolated chimeric virus may be employed in a method to inhibit or treat a condition associated with aberrant expression of an endogenous gene product. The method includes contacting a mammal at risk of or having the condition, with an effective amount of the isolated chimeric virus comprising human bocavirus capsid proteins and a rAAV genome, wherein the rAAV genome comprises a transgene encoding at least a portion of a functional gene product, the expression of which in the mammal inhibits or treats at least one symptom of the condition. In one embodiment, the gene product is cystic fibrosis transmembrane conductance regulator, β-globin, γ-globin, tyrosine hydroxylase, glucocerebrosidase, aryl sulfatase A, factor VIII, dystrophin, alpha 1-antitrypsin, surfactant protein SP-D, SP-A or SP-C, erythropoietin, RSV protein, HBoV protein, influenza virus protein, SARS protein, a cytokine, e.g., IFN-alpha, IFN-gamma, TNF, IL-1, IL-17, or IL-6. In one embodiment, the mammal is further contacted with at least one proteasome inhibitor, a chemotherapeutic, a lipid lowering agent, an antibiotic or a food additive in an amount that enhances transduction. In one embodiment, the at least one agent is LLnL (MG101), Z-LLL (MG132), bortezomib (Velcade), epoxomicin, doxorubicin, doxil, daunorubicin, idarubicin, epirubicin, aclarubicin, simvastatin, tannic acid, camptothecin, or cisplatin. An agent may be employed in a method to enhance virus transduction of a mammalian cell. A mammalian cell is contacted with a chimeric virus comprising a human bocavirus capsid protein and a rAAV genome and an agent in an amount effective to enhance transduction of the virus relative to a mammalian cell that is not contacted with the agent. In one embodiment, the agent is a proteasome inhibitor. Further provided is a method to enhance the expression of a transgene in a mammalian cell, where a mammalian cell is contacted with an amount of an agent that is a proteasome inhibitor and a chimeric virus comprising a human bocavirus capsid protein and a rAAV genome comprising the transgene. The amount of the agent enhances transduction of the rAAV, thereby enhancing expression of the transgene, relative to a mammalian cell that is not contacted with the agent.

Also provided is a method in which a mammal subjected to viral gene therapy with an isolated chimeric virus comprising human bocavirus capsid proteins and a rAAV genome, wherein the genome comprises a transgene the expression of which in the mammal is therapeutic, is administered an agent that is a proteasome inhibitor in an amount effective to enhance expression of the transgene in the cells of the mammal relative to cells in a mammal that are not contacted with the agent. In one embodiment, the rAAV encodes a therapeutic peptide or a therapeutic polypeptide. In one embodiment, the cell or mammal is contacted with the agent before the cell or mammal is contacted with the virus. In one embodiment, the cell or mammal is contacted with the virus before the cell or mammal is contacted with the agent. In one embodiment, the cell or mammal is contacted with the virus and agent concurrently. In one embodiment, the agent and the virus are administered to the lung. In one embodiment, the virus is orally administered. In one embodiment, the virus is nasally administered. In one embodiment, the virus is administered to a blood vessel.

Further provided is a method to immunize a mammal. The method includes administering to a mammal an isolated chimeric virus comprising human bocavirus capsid proteins and a rAAV genome encoding a prophylactic gene product in an amount effective to prevent or inhibit microbial infection or replication. In one embodiment, the gene product is an antigen of a virus, bacteria, fungus or parasite. In one embodiment, the gene product is a neutralizing antibody against a virus, bacteria, fungus or parasite.

The invention provides an isolated rHBoV comprising human bocavirus capsid protein and a recombinant HBoV genome. In one embodiment, the genome comprises an expression cassette encoding a heterologous gene product. In one embodiment, the gene product encodes a therapeutic protein. In one embodiment, the gene product is a viral, bacterial, tumor or fungal antigen. In one embodiment, the gene product is cystic fibrosis transmembrane conductance regulator, β-globin, γ-globin, tyrosine hydroxylase, glucocerebrosidase, aryl sulfatase A, factor VIII, dystrophin, alpha 1-antitrypsin, surfactant protein SP-D, SP-A or SP-C, erythropoietin, HBoV protein, influenza virus protein, RSV protein, SARS protein, or a cytokine, e.g., IFN-alpha, IFNγ, TNF, IL-1, IL-17, or IL-6. The isolated rHBoV may be employed to express a heterologous gene product in mammalian cells. The cells are infected with the virus in an amount effective to express the heterologous gene product, e.g., a therapeutic gene product, a catalytic RNA, a prophylactic gene product, a polypeptide or peptide. Also provided is a method to enhance chimeric virus transduction of a mammalian cell. The method includes contacting a mammalian cell with an isolated rHBoV comprising human bocavirus capsid protein and a rHBoV genome comprising a transgene encoding a heterologous gene product and at least one agent in an amount effective to additively or synergistically enhance transduction. In one embodiment, the mammalian cell is a mammalian lung cell. In one embodiment, the agent is a proteasome inhibitor, chemotherapeutic, a lipid lowering agent, an antibiotic or a food additive.

Further provided is a method to inhibit or treat a condition associated with aberrant expression of an endogenous gene product. The method includes contacting a mammal at risk of or having the condition, with an effective amount of an isolated rHBoV comprising human bocavirus capsid proteins and a rHBoV genome, wherein the rHBoV genome comprises a transgene encoding at least a portion of a functional gene product, the expression of which in the mammal inhibits or treats at least one symptom of the condition. In one embodiment, the gene product is cystic fibrosis transmembrane conductance regulator, β-globin, γ-globin, tyrosine hydroxylase, glucocerebrosidase, aryl sulfatase A, factor VIII, dystrophin, alpha 1-antitrypsin, surfactant protein SP-D, SP-A or SP-C, erythropoietin, HBoV protein, influenza virus protein, RSV protein, SARS protein, IFN-alpha, TNF, IL-1, IL-17, or IL-6. In one embodiment, further comprising contacting the mammal with at least one proteasome inhibitor, a chemotherapeutic, a lipid lowering agent, a mucolytic agent, an antibiotic or a food additive in a an amount that enhances transduction. In one embodiment, the at agent is LLnL (MG101), Z-LLL (MG132), bortezomib (Velcade), epoxomicin, doxorubicin, doxil, daunorubicin, idarubicin, epirubicin, aclarubicin, simvastatin, tannic acid, camptothecin, or cisplatin.

In addition the invention provides a method to enhance virus transduction of a mammalian cell, where a mammalian cell is contacted with a rHBoV comprising a human bocavirus capsid protein and a rHBoV genome and an agent in an amount effective to enhance transduction of the virus relative to a mammalian cell that is not contacted with the agent, e.g., the agent is a proteasome inhibitor. The agent and rHBoV may be employed to a method to enhance the expression of a transgene in a mammalian cell. The method includes contacting the mammalian cell with an amount of an agent that is a proteasome inhibitor and a rHBoV comprising a human bocavirus capsid protein and a rHBoV genome comprising the transgene, wherein the amount enhances transduction, thereby enhancing expression of the transgene, relative to a mammalian cell that is not contacted with the agent. An agent may be administered to a mammal subjected to viral gene therapy with an isolated rHBoV comprising human bocavirus capsid proteins and a rHBoV genome, wherein the genome comprises a transgene the expression of which in the mammal is therapeutic. The agent may be a proteasome inhibitor and is administered in an amount effective to enhance expression of the transgene in the cells of the mammal relative to cells in a mammal that are not contacted with the agent. In one embodiment, the rHBoV encodes a therapeutic peptide or a therapeutic polypeptide. In one embodiment, the cell or mammal is contacted with the agent before the cell is contacted with the virus. In one embodiment, the cell or mammal is contacted with the virus before the cell is contacted with the agent. In one embodiment, the cell or mammal is contacted with the virus and agent concurrently. In one embodiment, the agent and the virus are administered to the lung. In one embodiment, the virus is orally administered. In one embodiment, the virus is nasally administered. In one embodiment, the virus is administered to a blood vessel.

An isolated rHBoV comprising human bocavirus capsid proteins and a rHBoV genome encoding a prophylactic gene product may be employed in a method to immunize a mammal. The virus is administered to a mammal in an amount effective to prevent or inhibit microbial infection or replication.

Further provided is a method to immunize a mammal, including administering to a mammal an isolated chimeric virus comprising human bocavirus capsid proteins and a rAAV genome in an amount effective to prevent or inhibit HBoV infection or replication. In one embodiment, the chimeric virus is administered to the lung. Also provided is a vaccine comprising the chimeric virus.

Further provided is a method to immunize a mammal, comprising: administering to a mammal an isolated rHBoV comprising human bocavirus capsid proteins and a rHBoV genome in an amount effective to prevent or inhibit HBoV infection or replication. In one embodiment, the chimeric virus is administered to the lung. Also provided is a vaccine comprising the virus.

The invention will be further described by the following non-limiting examples.

Example 1

Materials and Methods

Cell Culture

Cell lines and primary cells. Human embryonic kidney 293 (HEK293) cells (CRL-1573), HeLa (CCL-2), MDCK (CCL-34), MRC-5 (CCL-171), LLC-MK2 (CCL-7), and Vero-E6 (CRL-1586) were obtained from American Type Culture Collection (ATCC, Manassas, Va.), and were cultured in Dulbecco's Modified Eagle Medium (DMEM) with 10% fetal calf serum (FCS). The cell lines originating from human airway epithelial cells are A549 (ATCC CCL-185). BEAS-2B (ATCC CRL-9609), 16HBE14o- (obtained from Dr. Dieter Gruenert), as well as NuLi-1 and CuFi-8 (Tissue and Cell Culture Core, Center for Gene Therapy, University of Iowa). NuLi-1 and CuFi-8 were immortalized from normal and cystic fibrosis human primary airway cells, respectively, by expressing hTERT and HPV E6/E7 genes (Zabner et al., 2003). Primary Clonetics normal human bronchial/tracheal epithelial cells (NHBE) were purchased from Lonza (Walkersville, Md.). Cells were cultured in media following instructions provided by the supplier.

Human airway epithelium cultures. Polarized primary HAE, termed as primary B-HAE, was generated by growing isolated human airway (tracheobronchial) epithelial cells (three HAE cultures were generated from different donors) on collagen coated, semipermeable membrane inserts (0.6 cm2, Millicell-PCF; Millipore, Billerica, Mass.), and then allowing them to differentiate at an air-liquid interface (ALI); this was carried out at the Tissue and Cell Culture Core of the Center for Gene Therapy, University of Iowa (Zabner et al., 2003; Karp et al., 2002; Yan et al., 2004; Yan et al., 2006). After 3-4 weeks of culture at an ALI, the polarity of the HAE was determined based on the transepithelial electrical resistance (TEER) using an epithelial Volt-Ohm Meter (Millipore) and the relationship to infectibility was assessed; a value of over 1,000 V·cm2 was required for HBoV1 infection. CuFi- and NuLi-HAE were generated following the same method as above, but using the immortalized airway epithelial cell lines, CuFi-8 and NuLi-1, respectively. The primary B-, CuFi-, and NuLi-HAE were cultured, differentiated and maintained in (50%:50%) DMEM:F12 medium containing 2% Ultroser G (Pall BioSepra, Cergy-Staint-Christophe, France).

Isolation of Virus and Extraction of Viral DNA

A nasopharyngeal aspirate was obtained from a child with community-acquired pneumonia in Salvador, Brazil, who had an acute HBoV1 infection (seroconversion, viraemia, and over 104 gc of HBoV1 per ml of aspirate) (Nascimento-Carvalho et al., 2012). Viral DNA was extracted according to a method described in Kantola et al. (2010).

Primers Used and Sequence Amplification by the Polymerase Chain Reaction (PCR)

The sequence of the head-to-tail junction of the HBoV1 episome suggests that HBoV LEH and REH share similarities both in structure and sequence with that of the BPV LEH and MVC REH, respectively (Sun et al., 2009; Lusebrink et al., 2011). The Phusion high fidelity PCR kit (NEB, Ipswich, Mass.) was used following the manufactures' instructions, to amplify the left-end hairpin (LEH) and the right-end hairpin (REH) of HBoV1. Briefly, the DNA denaturation at 98° C. for 30 seconds was followed by 35 cycles of: denaturing at 98° C. for 10 seconds; annealing at 55° C. for 15 seconds; and extension at 72° C. for 30 seconds. Following the final cycle, extension was continued at 72° C. for 10 minutes. The PCR products were analyzed by electrophoresis in a 2% agarose gel. DNA bands were extracted using the QIAquick gel extraction kit (Qiagen, Valencia, Calif.), and the extracted DNA was directly sequenced at MCLAB (South San Francisco, Calif.), using primers complementary to the extended sequences on the forward and reverse amplification primers. PCR-generated DNA was cloned in pGEM-T vector (Promega, Madison, Wis.), and DNAs isolated from cultures of individual clones were subsequently sequenced.

Construction of a Full-Length HBoV1 Clone and its Mutants

Construction of the pBB Vector.

A pBBSmaI vector was constructed by inserting a linker of 59-SalI-SacII-KpnI-SmaIApaI-SphI-KpnI-HindIII-XhoI-39 into a vector backbone (pProEX HTb vector; Invitrogen) generated from the B19V infectious clone pM20 (Zhi et al., 2004) by removing all of the B19V sequence (SalI-digestion). All cloning work was carried out in the *Escherichia coli* strain of Sure 2 (Agilent, La Jolla, Calif.). All the nucleotide numbers of HBoV1 refer to the HBoV1 full-length genome (GenBank accession no.: JQ923422).

Cloning of the Left-End Hairpin.

The DNA fragment SalI-BglII-nt93-518(BspEI)-576-XhoI-HindIII (containing the HBoV1 sequence nt 93-576), was amplified from the viral DNA and inserted into SalI/HindIII-digested pBBSmaI, to produce pBB2.1. Another DNA, SalI-nt1-86-BclI (containing HBoV1 nt 1-86 sequence), was synthesized according to the LEH sequence obtained, and placed between the SalI and BglII sites in pBB2.1, with ligation of the BclI and BglII sites reproducing the HBoV1 sequence nt 87-92. The resultant plasmid harboring the 59 HBoV1 nt 1-576 sequence with an intact LEH is designated pBB-LEH.

Cloning of the Right-End Hairpin.

The DNA fragment SalI-nt4097-4139(BglII)-5427(KasI)-ApaI (containing the HBoV1 nt 4097-5427 sequence) was amplified from viral DNA and inserted into Sail/ApaI-digested pBBSmaI, resulting in pBB2.2. Another DNA fragment, ApaI-nt5460(KasI)-5543-XhoI (containing HBoV1 nt 5460-5543 sequence) was synthesized based on the REH sequence and placed between the ApaI and HindIII sequences in pBB2.2, resulting in pBBREH (D5428-5459). The missing short fragment between the two KasI sites encompassing nt 5428-5459 was recovered by a synthesized KasI linker based on the REH sequence and inserted into KasI-digested pBB-REH(D5428-5459). The resultant plasmid harboring the 39 HBoV1 nt 4097-5543 sequence with an intact REH is designated pBB-REH.

Cloning of the pIHBoV1.

The HBoV1 DNA fragment SalI-nt1-518(BspEI)-576-XhoI, which was obtained from SalI/XhoI-digestion of pBB-LEH, was ligated into SalI-digested pBB-REH, resulting in pBB-LEH(BspEI/BglII)REH. The larger fragment produced by digestion of this plasmid with BspEI/BglII was ligated to the HBoV1 DNA fragment nt 518(BspEI)-4139 (BglII), which was amplified from the viral DNA. The final construct containing the full-length HBoV1 (nt 1-5543) was designated pIHBoV1.

Construction of pIHBoV1 Mutants.

pIHBoV1NS1(2) and pi HBoV1NP1(2) were constructed by mutating HBoV1 nt 542 from T to A, and nt 2588 from G to A, resulting in stop codons that lead to early termination of the NS1 and NP1 ORFs, respectively. Similarly, pIHBoV1VP1(2) and pIHBoV1 VP2(2) were generated by mutating HBoV1 nt 3205 from T to A, and nt 3540 from T to G, disrupting VP1 and VP2 ORFs, respectively.

Transfection

Cells grown in 60-mm dishes were transfected with 2 mg of plasmid; the Lipofectamine and Plus reagents (Invitrogen/Life Technologies, Carlsbad, Calif.) were used as described in Qiu et al. (2002). For some of the transfection experiments, HEK293 cells were cotransfected with 2 mg of pHelper plasmid (Agilent), which contains the adenovirus 5 (Ad5) Eta, E4orf6, and VA genes, or infected with adenovirus type 5 (Ad) at an MOI of 5 as described in Qiu et al. (2002).

Southern Blot Analysis

Low molecular weight (Hirt) DNA was extracted from transfected cells, digested with DpnI (or left undigested) and analyzed by Southern blotting as described in Qiu et al. (2006).

Western Blot Analysis

Cells were lysed, separated by SDS-8% polyacrylamide gel electrophoresis (PAGE), and blotted with antibodies as indicated as described in Liu et al. (2004).

Production and Purification of HBoV1

HEK293 cells were cultured on fifteen 150-mm plates in DMEM-10% FCS, and transfected with 15 mg of pIHBoV1 per dish using LipoD293 (SignaGen, Gaithersburg, Md.). After being maintained for 48 hours at 5% $CO_2$ and 37° C., the cells were collected, resuspended in 10 mL of phosphate buffered saline, pH7.4 (PBS), and lysed by subjecting them to four freezing (−196° C.) and thawing (37° C.) cycles. The cell lysate was then spun at 10,000 rpm for 30 minutes. The supernatant was collected and assessed on a continuous CsCl gradient. In brief, the density was adjusted to 1.40 g/mL by adding CsCl, and the sample was loaded into an 11-ml centrifuge tube and spun in a Sorvall TH641 rotor at 36,000 rpm, for 36 hours at 20° C.

Fractions of 550 mL (20 fractions) were collected with a Piston Gradient Fractionator (BioComp, Fredericton, NB, Canada), and the density of each was determined by an Abbe's Refractometer. Viral DNA was extracted from each fraction and quantified with respect to the number of HBoV1 gc, using HBoV1-specific qPCR as described below. Those fractions containing the highest numbers of HBoV1 gc were dialyzed against PBS, and then viewed by electron microscope and used to infect HAE cultures.

Observation by Electron Microscopy (EM)

The final purified virus preparation was concentrated by about 5-fold, and adsorbed for 1 minute on a 300-mesh copper EM grid coated with a carbon film, followed by washing with deionized water for 5 seconds and staining with 1% uranyl acetate for 1 minute. The grid was air dried, and was inspected on a 200 kV Tecnai F20 G2 transmission electron microscope equipped with a field emission gun.

Virus Infection

Fully differentiated primary B- (each of the three distinct subtypes), CuFi- and NuLi-HAE were cultured in Millicell inserts (0.6 $cm^2$; Millipore) and inoculated with 150 μL of purified HBoV1 ($1\times10^7$ gc/mL in phosphate buffered saline, pH7.4; PBS) from the apical surface (at a multiplicity of infection, MOI, of about 750 gc/cell; an average of $2\times10^6$ cells per insert). For each of the HAE, a 2 hour incubation was followed by aspiration of the virus from the apical chamber and by three washes of the cells with 200 mL of PBS to remove unbound virus. The HAEs were then further cultured at an ALI.

For conventional monolayer cells, cells cultured in chamber slides (Lab-Tek II; Nalge Nunc) were infected with purified HBoV1 at an MOI of 1,000 gc/cell.

Immunofluorescence Analysis

After HBoV1 infection, ALI membranes were fixed with 3.7% paraformaldehyde in PBS at room temperature for 15 min. The fixed membranes were cut into several small pieces, washed in PBS three times for 5 minutes, and permeabilized with 0.2% Triton X-100 for 15 minutes at room temperature. The membranes were then incubated with primary antibody at a dilution of 1:100 in PBS with 2% FCS for 1 hour at 37° C. This was followed by incubation with a fluorescein isothiocyanate- or rhodamine-conjugated secondary antibody. Confocal images were taken with an Eclipse C1 Plus confocal microscope (Nikon, Melville, N.Y.) controlled by Nikon EZ-C1 software. Primary antibodies used were anti-(HBoV1) NS1, NP1 and VP1/2 antibodies, as reported in Chen et al. (2010).

For infected cells cultured in chamber slides, IF analysis was carried out as previously described in Chen et al. (2010).

Quantitative PCR (qPCR) Analysis

Virus samples were collected from both the apical and basolateral surfaces at multiple time points. Apical washing and harvesting was performed by adding 200 mL of PBS to the apical chamber, incubating the samples for 10 minutes at 37° C. and 5% $CO_2$, and removing and storing the 200 mL of PBS from the apical chamber. Thereafter, 50 mL of medium were collected from each basolateral chamber.

Aliquots (100 mL apical or 50 mL basolateral) of the samples were incubated with 25 units of Benzonase (Sigma, St Louis, Mo.) for 2 hours at 37° C., and then digested with 20 mL of proteinase K (15 mg/mL) at 56° C. for 10 minutes. Viral DNA was extracted using QIAamp blood mini kit (Qiagen), and eluted in 100 mL or 50 mL of deionized $H_2O$. The extracted DNA was quantified with respect to the number of HBoV1 gc, by a qPCR method that has been used previously (see Lin et al., 2007). Briefly, the pskHBoV1 plasmid (Chen et al., 2010), which contains the HBoV1 sequence (nt 1-5299), was used as a control (1 gc=5.4610212 mg) to establish a standard curve for absolute quantification with an Applied Biosystems 7500 Fast system (Foster City, Calif.). The amplicon primers and the PrimeTime dual-labeled probe were designed by Primer Express (version 2.0.0; Applied Biosystems/Life Technologies) and synthesized at IDT Inc. (Coralville, Iowa). Their sequences are as follows (GenBank: JQ411251): forward primers, 5'-GCA CAG CCA CGT GAG GAA-3' (SEQ ID NO:1; nt 2391 to 2408); reverse primer, 5'-TGG ACT CCC TTT TCT TTT GTA GGA-3' (SEQ ID NO:2; nt 2466 to 2443); and PrimeTime probe, 5' 6FAM-TGA GCT CAG GGA ATA TGA AAG ACA AGC ATC G-3' Iowa Black FQ (SEQ ID NO:3; nt 2411 to 2441). Premix Ex Taq (Takara Bio USA, Madison, Wis.) was used for qPCR following a standard protocol. 2.5 mL of extracted DNA was used in a reaction volume of 25 mL.

Histology Analysis

On the last day of infection, the HAE on the Millicell inserts were washed with PBS and fixed in 4% paraformaldehyde for about 30 minutes. The fixed membranes were cut into several small pieces, and washed with PBS three times. Each membrane fragment was transferred to 20% sucrose in a 15-mL conical tube and allowed to drop to the bottom; it was then embedded vertically in cryoprotectant OCT in an orientation that enabled sectioning of the membrane perpendicular to the blade. Cryostat sections were cut at a thickness of 10 mm, placed onto slides, and stained with hematoxylin and eosin (H&E). Images were taken with a Nikon 80i fluorescence microscope at a magnification of ×60.

Results

The terminal hairpins of the HBoV1 genome are typical of those of the genus Bocavirus A head-to-tail junction of an HBoV1 episome identified in an HBoV1-infected HAE (Schildgren et al., 2012; Lasebrink et al., 2011) was found to possess two sequences (3'-CGCGCGTA-5' and 3'-GATTAG-5') identical to parts of the BPV1 left-end hairpin (LEH) (Sun et al., 2009; Chen et al., 1986). This finding suggested that the head sequence is part of the HBoV1 LEH. The head sequence was used as the 39 end of a reverse primer (RHBoV1_LEH). Together with a forward primer (FHBoV1_nt1), which anchors the 39 end of the HBoV1 genome predicted from the BPV1 LEH, the hairpin of the LEH was amplified from a viral DNA extract (1.26108 gc/mL) prepared from a nasopharyngeal aspirate taken from an HBoV1-infected patient (HBoV1 Salvador1 isolate) (Nascimento-Carvalho et al., 2012). Only one specific DNA band was detected at approximately 150-bp.

Sequencing of this DNA revealed a novel sequence of the HBoV1 LEH. Because the LEHs of the prototype bocaviruses BPV1 and MVC are asymmetric (Sun et al., 2009; Chen et al., 1986), another PCR reaction was set up with a forward primer located in the hairpin (FHBoV1_LEH) and a reverse primer targeting a sequence downstream of the LEH at nt 576 (RHBoV1_nt576). Sequencing of a DNA fragment, detected as expected as an about 600-bp band, confirmed the presence of the novel joint sequence and the LEH.

The tail of the HBoV1 head-to-tail junction was found to contain a sequence (5'-GCG CCT TAG TTA TAT ATA ACA T-3'; SEQ ID NO:4) identical to that of the right-end hairpin (REH) of the other prototypic bocavirus MVC (Sun et al., 2009). Thus it was speculated that the entire HBoV1 REH is similar in structure to its MVC counterpart. Using a reverse primer targeted to this sequence (RHBoV1_nt5464) and a forward primer located upstream of the REH (FHBoV1_nt5201), a specific about 300-bp-long DNA fragment was amplified. Sequencing confirmed the presence of the palindromic hairpin of the predicted REH, and revealed two novel nucleotides at the end of the hairpin.

These results indicate that the HBoV1 genome structure is typical of the genus Bocavirus.

A Full-Length HBoV1 Clone (pIHBoV1) is Capable of Replicating and Producing Progeny Virus in HEK293 Cells The non-structural (NS) and capsid (VP) protein-coding (NSVP) genes of the HBoV1 Salvador1 isolate was cloned and sequenced from the patient-extracted viral DNA. Then the LEH, NSVP genes and REH were ligated into pBBSmaI. This sequence of the full-length genome of the isolate is deposited in GenBank (JQ923422), which is incorporated by reference herein.

It was investigated whether the adenovirus helper function is necessary for pIHBoV1 replication in HEK293 cells. Specifically, pIHBoV1 was transfected into HEK293 cells (untreated or infected with adenovirus), alone or with pHelper. Interestingly, it was found that pIHBoV1 replicated well in the absence of helper virus. Indeed, all the three representative forms of replicated bocavirus DNA (Sun et al., 2009; Luo et al., 2011) (DpnI digestion-resistant dRF DNA, mRF DNA and ssDNA) were detected in each test case, and at similar levels. DpnI digestion-resistant DNA bands are newly replicated DNA in cells as DpnI digestion only cleaves plasmid DNA prepared from prokaryotic cells, which is methylated at the dam site (Wohbe et al., 1985). In contrast, these DNA forms of the viral genome were absent in pIHBoV1-transfected primary airway epithelial cells (NHBE) and present at very low levels (over 20 times lower than in pIHBoV1-transfected HEK293 cells) in pIHBoV1-transfected human airway epithelial cell lines BEAS-2B, A549 and 16HBE14o-, even in the presence of adenovirus. Thus, replication in these cells appears to be non-existent or poor in these contexts.

To confirm the specificity of DNA replication and the identity of the DpnI-resistant DNA bands, the ORFs encoding viral proteins NS1, NP1, VP1 and VP2 in pIHBoV1 were disrupted; knockout of expression of the corresponding viral protein was confirmed by Western blot analysis. When the NS1 ORF was disrupted, no DpnI digestion-resistant DNA was detected, confirming that replication of this DNA requires NS1. Notably, when the NP1 ORF was disrupted, an RF DNA band was detected but it was very weak, suggesting that NP1 is also involved. When the VP2 ORF was knocked out, the ssDNA band disappeared, but this was not the case when VP1 was disrupted (VP2 was still expressed), these findings are consistent with a role for the capsid formation in packaging of the parvoviral ssDNA genome (Cotmore et al., 2005; Cheng et al., 2009; Plevka et al., 2011).

The presence of the ssDNA band in pIHBoV1-transfected HEK293 cells suggested that progeny virions were produced. Large-scale pIHBoV1 transfection and CsCl equilibrium centrifugation was carried out to purify the virus that was produced. The CsCl gradient was fractionated, and the highest HBoV1 gc (1-5×10$^8$ gc/mL) was found at a density of 1.40 mg/mL, which is typical of the parvovirus virion. Electron microscopy analysis revealed that purified virus displayed a typical icosahedral structure, with a diameter of about 26 nm.

Collectively, these findings confirm that a full-length clone of HBoV1 capable of replicating and producing progeny virus in transfected HEK293 cells was obtained.

HBoV1 Progeny Virus Produced from pIHBoV1-Transfected Cells is Infectious

The infectivity of the HBoV1 virions purified from pi HBoV1-transfected HEK293 cells was examined in polarized primary HAE, the in vitro culture model known to be permissive to HBoV1 infection (Dijkman et al., 2009). Three sets (different donors, culture lots # B29-11, B31-11 and B33-11) of B-HAE were generated, and these were infected with HBoV1 from the apical side. Initially the B-HAE cultures were infected with various amounts of virus, and when a multiplicity of infection (MOI) of about 750 gc/cell was used, most of the cells (about 80%) were positive for anti-NS1 staining (indicating that the viral genome had replicated and that genes encoded by it had been expressed) at 5 days post-infection (p.i.). This MOI was subsequently used for apical infection. Notably, B29-11, B31-11 and B33-11 HAE each supported productive HBoV1 infection. Immunofluorescence (IF) analysis of infected B31-11 HAE at 12 days p.i. showed that virtually all the cells expressed NS1 and NP1, and that a good portion of the infected cells expressed capsid proteins (VP1/2).

The production of progeny virus following HBoV1 infection was monitored daily by collecting samples from both the apical and basolateral chambers of the HAE culture and carrying out HBoV1-specific quantitative PCR (qPCR). In the case of B33-11 B-HAE, apical release was obviously initiated at 3 days p.i., then continued to increase to a peak of about $10^8$ gc/mL at 5-7 days p.i., then decreased slightly through day 10 p.i. and was maintained at a level of about $10^7$ gc/mL through day 22 p.i. The total virus yield from one Millicell insert of 0.6 $cm^2$ over a 24 hour interval was greater than $2\times10^1$a gc. This result suggested that productive HBoV1 infection of primary B-HAE is persistent. Notably, in the B-HAE cultures from both donors, virus was also continuously released from the basolateral side, keeping pace with apical secretion throughout, though at levels about one log lower than the release from the apical surface. The genomes of the progeny virions released from infected B-HAE were amplified and sequenced. The result showed an identical sequence with that of the HBoV1 Salvador isolate (Genbank JQ923422). Additionally, no virus was detected in mock-infected B-HAE.

Taken together, these results demonstrate that the HBoV1 virions produced by pIHBoV1 transfection is capable of infecting polarized primary HAE cultures from cells derived from various donors and releasing identical progeny virions from infected primary HAE. More importantly, we found that productive HBoV1 infection was persistent.

HBoV1 Infection of Primary B-HAE Features Characteristics of Respiratory-Tract Injury Although no gross cytopathic effects were observed in HBoV1-infected B-HAE, histology analysis of mock- vs. HBoV1-infected epithelia (B33-11) revealed morphological differences: infected BHAE did not feature obvious cilia at 7 days p.i., and was significantly thinner than the mock-infected one on average at 22 days p.i. The transepithelial electrical resistance (TEER) was monitored during infection of B-HAE, and found that at 6 days it was reduced from a value of about 1,200 to about 400 $\Omega\cdot cm^2$, while the mock-infected B-HAE maintained the initial TEER. Notably, the decrease in TEER in the infected B-HAE was accompanied by an increase in HBoV1 secretion.

To confirm a role for HBoV1 infection in disruption of the barrier function of the epithelium, the distribution of the tight junction protein Zona occludens-1 (ZO-1) was examined (Gonzalez-Mariscal et al., 2003). Infected B-HAE showed dissociation of ZO-1 from the periphery of cells started from 7 days p.i., compared with mock-infected B-HAE, which likely plays a role in reducing TEER. Cumulatively, these results demonstrate that HBoV1 infection disrupts the integrity of HAE and that this may involve breakdown of polarity and redistribution of the tight junction protein ZO-1. To confirm a role for HBoV1 infection in the loss of cilia, we examined expression of the b-tubulin IV, which is a marker of cilia (Matrosovich et al., 2004; Villenave et al., 2012). In HBoV1-infected B-HAE, expression of β-tubulin IV was drastically decreased at 7 days p.i., and was not detected at 22 days p.i., in contrast to that in mock-infected B-HAE. These results confirmed that HBoV1 infection caused the loss of cilia in infected B-HAE. Notably, infected B-HAE showed changes of nuclear enlargement, which became obvious at 22 days p.i., indicating airway epithelial cell hypertrophy.

Collectively, it was found that productive HBoV1 infection disrupted the tight junction barrier, lead to the loss of cilia and airway epithelial cell hypertrophy. These are hallmarks of respiratory tract injury when a loss of epithelial cell polarity occurs.

An Immortalized Human Airway Epithelial Cell Line Supports HBoV1 Infection when the Cells are Polarized Although primary HAE cultures support HBoV1 infection, their usefulness is limited by the variability between donors, tissue availability and high cost. Alternative cell culture models were explored for their abilities to support HBoV1 infection. Using the purified HBoV1, other cells were examined including HEK293 cells, other common epithelial cell lines permissive to common respiratory viruses (Reins et al., 2001), including HeLa, MDCK, MRC-5, LLC-MK2 and Vero-E6, and several transformed or immortalized human airway epithelial cell lines (A549, BEAS-2B, 16HBE14o- (Cozens et al., 1994), NuLi-1 and CuFi-8 (Zabner et al., 2013), as well as primary NHBE cells for the ability to support infection in conventional monolayer culture. All were negative for HBoV1 infection as determined by IF analysis. It was speculated that since some respiratory viruses infect polarized HAE but not undifferentiated cells (Pyrc et al., 2010), some characteristics of the polarized epithelia may be critical for HBoV1 infection. Thus immortalized cells (NuLi-1 and CuFi-8) were polarized at an air-liquid interface (ALI) for one month. Once polarization was confirmed by detection of a TEER of >500 $\Omega\cdot cm^2$, the cultures were infected with HBoV1, under the same conditions as used for primary B-HAE cultures. Notably, IF analysis revealed that at 10 days p.i., HBoV1-infected CuFi-HAE (differentiated from CuFi-8 cells) was uniformly positive for NS1, whereas the HBoV1-infected NuLi-HAE (differentiated from NuLi-1 cells) was not. Moreover, the CuFi-HAE did express HBoV1 NS1, NP1 and VP1NP2 proteins. The kinetics of virus release from the apical surface was similar to that of a primary B-HAE infected with virus at a similar titer (maximally 26107 gc/mL), although virus release from the basolateral surface was undetectable. HBoV1 infection also resulted in a decrease in the thickness of the epithelium, and dissociation of the tight junction protein ZO-1 from the epithelial cell peripheries.

Collectively, these findings demonstrate that the immortalized cell line CuFi-8 (Zabner et al., 2003), when cultured and polarized at an ALI, supports HBoV1 infection, and recapitulates the infection phenotypes observed in primary HAE, including destruction of the airway epithelial structure.

Discussion

A full-length HBoV1 genome was cloned and its terminal hairpins identified. Virions produced from transfection of this clone into HEK293 cells are capable of infecting polarized HAE cultures. Thus, a reverse genetics system was established that overcomes the critical barriers to studying the molecular biology and pathogenesis of HBoV1, using an in vitro culture model system of HAE.

It is notable that the HBoV1 terminal hairpins appear to be hybrid relicts of the prototype bocavirus BPV1 at the LEH, but of MVC at the REH (Schildgren et al., 2012).

Replication of HBoV1 DNA in HEK293 cells revealed typical replicative intermediates of parvoviral DNA Although the head-tail junctions are unexpected in the replication of autonomous parvoviruses, they were likely generated during the cycle of rolling hairpin-dependent DNA replication (Cotmore et al., 1987). Therefore, it is believed that the replication of HBoV1 DNA basically follows the model of rolling hairpin-dependent DNA replication of autonomous parvoviruses, with terminal and junction resolutions at the REH and LEH, respectively (Cotmore et al., 1987). The replication of parvoviral DNA depends on entry into S phase of the cell cycle or the presence of helper viruses (Cotmore et al., 1987; Berns et al., 1990). In this regard, it is puzzling that mature, uninjured airway epithelia are mitotically quiescent (<1% of cells dividing) (Wang et al., 1999; Leigh et al., 1995; Axers et al., 1988), as are the majority of the cells in polarized HAE (in the GO phase of the cell cycle). However, recombinant adeno-associated virus (AAV; in genus Dependovirus of the family of Parvoviridae) infects HAE apically and expresses reporter genes. Gene expression by recombinant AAV requires a conversion of the ssDNA viral genome to a double-stranded DNA form that is capable to be transcribed. This conversion involves DNA synthesis. Hence, it was hypothesized that HBoV1 employs a similar approach to synthesize its replicative form DNA Notably, wild type AAV infected primary HAE apically and replicated when adenovirus was co-infected. The exact mechanism of how HBoV1 replicates in normal HAE will be an interesting topic for further investigation.

The airway epithelium, a ciliated pseudo-stratified columnar epithelium, represents the first barrier against inhaled microbes and actively prevents the entry of respiratory pathogens. It consists of ciliated cells, basal cells and secretory goblet cells that together with the mucosal immune system, provide local defense mechanisms for the mucociliary clearance of inhaled microorganisms. The polarized ciliated primary HAE, which is generated by growing isolated tracheobronchial epithelial cells at an ALI for on average one month, forms a pseudo-stratified, mucociliary epithelium and displays morphologic and phenotypic characteristics resembling those of the in vivo human cartilaginous airway epithelium of the lung. Recent studies have revealed that this model system recapitulates important characteristics of interactions between respiratory viruses and their host cells.

In the current study, primary B-HAE cultures obtained from three different donors were examined. HBoV1 infection of primary B-HAE was persistent and caused morphological changes of the epithelia, i.e., disruption of the tight barrier junctions, loss of cilia and epithelial cell hypertrophy. The loss of the former, plasma membrane structures that seal the perimeters of the polarized epithelial cells of the monolayer, is known to damage the cell barrier necessary to maintain vectorial secretion, absorption and transport. ZO-1, which were monitored here, is specifically associated with the tight junctions and remains the standard marker for these structures. Similarly, cilia play important roles in airway epithelia, in that they drive inhaled particles that adhere to mucus secreted by goblet cells outward. HBoV1 infection compromises barrier function, and thus potentially increases permeability of the airway epithelia to allergens and susceptibility to secondary infections by microbes. The observed shedding of virus from the basolateral surface of infected primary HAE, albeit at a lower level (about 1 log lower than that from the apical surface), is consistent with the facts that HBoV1 infection disrupted the polarity of the pseudo-stratified epithelial barrier and resulted in the leakage to the basolateral chamber. This explanation is also supported by HBoV1 infection of CuFi-HAE, where disruption of the tight junction structure was less severe and virus was released only from the apical membrane. The induction of leakage by HBoV1 also suggests a mechanism that accounts for the viraemia observed in HBoV1-infected patients. Further disease pathology could be accounted for by infection-induced loss of cilia of the airway epithelia; a lack of cilia is often responsible for bronchiolitis. Therefore, the data provide direct evidence that HBoV1 is pathogenic to polarized HAE, which serves as in vitro model of the lung. Since HBoV1 is frequently detected with other respiratory viruses in infants hospitalized for acute wheezing, the apparent pathological changes observed in HBoV1-infected HAE suggest that prior-infection of HBoV1 likely facilitates the progression of co-infection-driven pathogenesis in the patient.

The kinetics of virus release from the apical chamber of HAE infected with the progeny virus of pIHBoV1 (cloned from the clinical Salvador1 isolate) was similar to that following infection with the HBoV1 Bonn1 isolate, a clinical specimen (Dijkman et al., 2009). It is believed that the present study of HBoV1 infection of primary HAE reproduces infection of the virus from clinical specimens. In addition, virus was generated from a pIHBoV1-b clone, which contains the NSVP genes from the prototype HBoV1 st2 isolate (Allander et al., 2005). Infection of primary B-HAE with this st2 virus resulted in a level of virus production similar to that observed here using the Salvador1 isolate. It is believed that the study with the laboratory-produced HBoV1 Salvador1 represents infection of HBoV1 of clinical specimens in HAE. The MOI used for infection in the current study was high. However, it should be noted that this titer is based on the physical numbers of virion particles as there are no practical methods for determining the infectious titer of HBoV1 preparations. It should also be taken into consideration that extensive parvovirus inactivation occurs during the purification process, i.e., during CsCl equilibrium ultracentrifugation (McClare et al., 2011). Virus infection of HAE most likely reflects HBoV1 infection of the lung airways in patients with a high virus load in respiratory secretions (Jartii et al., 2011).

The fact that pIHBoV1 did not replicate well in undifferentiated human airway epithelial cells indicates that polarization and differentiation of the HAE is critical for HBoV1 DNA replication. Nevertheless, polarized NuLi-HAE, which is derived from normal human airway epithelial cells, did not support HBoV1 infection, but the CuFi-HAE derived from airway epithelial cells isolated from a cystic fibrosis patient did. The CuFi-HAE is unique relative to the others in that it retains the capacity to develop epithelia that actively transport in Na+ but not Cl2 because of the mutation in the cystic fibrosis gene (Zabner et al., 2003). Given the high complexity of the airway epithelium, we speculate that the permissiveness of HBoV1 infection is dependent on various steps of virus infection, e.g. attachment, entry, intracellular trafficking, and DNA replication of the virus. Nevertheless, a polarized CuFi-HAE model derived from the CuFi-8 cell line represents a novel stable cell culture model that is providing unexpected insights into the infection characteristics of HBoV1. Although HBoV1 infection of CuFi-HAE reproduced disruption of the barrier tight junctions like that seen also in primary B-HAE, the absence of virus on the basolateral side implies that in HAE the secretion of HBoV1 is apically polarized. It is speculated that the milder damage of tight junctions in these cells might prevent virus release from the basolateral side of infected CuFi-HAE. Further studies will focus on understanding the permissiveness of CuFi-HAE to HBoV1 infection and on the reason for the ease of infection of an HAE with a cystic fibrosis phenotype.

It has been shown that HBoV1 remains detectable in the upper airways of patients for weeks and months, even up to half a year (Blessing et al., 2009; Martin et al., 2010; Brieu et al., 2008; Lehtoranta et al., 2010). However, the mechanism behind this persistence, i.e., whether it is due to persistent replication and shedding, passive persistence after primary infection, or recurrent mucosal surface contamination, has remained unknown. The present results in in vitro HAE cultures showed that HBoV1 is able to replicate and shed from both the apical and basolateral surfaces at least for three weeks, supporting the notion that shedding of the virus from the airways is a long-lasting process. This may further explain why a high rate of co-infection, or co-detection, between HBoV1 and other respiratory viruses has been reported. Since recombinant AAV persists as an episome in transduced tissues, which prolongs gene expression, it is possible that also the HBoV1 genome can be presented as an episome for long term expression and replication. Apparently, the mechanism underlying this feature of HBoV1 infection warrants further investigation. However, in contrast to the other human-pathogenic B19V, HBoV1 does not seem to persist in human tissues for many years (Norja et al., 2010).

In conclusion, the reverse genetics system for HBoV1 mimics natural HBoV1 infection of the in vivo human cartilaginous airway epithelia. The pathogenesis of HBoV1 in co-infection with other respiratory viruses and in conditions of lung diseases is a focus of future study.

Example 2

Progeny HBoV1 Virions in the Apical Washes of Infected HAE are Highly Infectious in Polarized Primary HAE.

In Example 1, HBoV1 virions were produced from HEK293 cells transfected with a HBoV1 infectious clone, which were further concentrated and purified through cesium chloride equilibrium ultracentrifugation. During this process, significant viral inactivation occurred (McClure et al., 2011), and the precise infectivity of the virus was difficult to determine. However, progeny virions were persistently secreted from the apical surface of infected HAE at a high titer (about $1.0\times10^7$ vgc/μL) (Huang et al., 2012). Hence, it was hypothesized that the progeny virions washed from the apical surface mimic naturally secreted virions from HBoV1-infected lung airway-tract and thus are highly contagious.

To test this hypothesis, polarized primary HAE cultures were obtained in Millicell™ inserts of 0.6 $cm^2$ (Millipore) from the Tissue and Cell Culture Core of the Center for Gene Therapy, University of Iowa. These cultures were made by growing isolated human airway (tracheobronchial) epithelial cells at an ALI, as described previously (Karp et al., 2002; Yan et al., 2004; Zabner et al., 1996). The inserts were kept in wells of a 6-well tissue culture plate with 1 mL of ALI media. Infection of the HBoV1 progeny virions, which were collected from apical washes of purified HBoV1-infected primary HAE culture (Huang et al., 2012), was analyzed in primary HAE culture at an MOI ranged from 100 to 0.001 vgc/cell from the apical surface. HBoV1 virions diluted in 150 μL of the ALI media (Huang et al., 2012) were applied to the apical chanter. The HAE cultures were incubated at 37° C. and 5% $CO_2$ for 2 hours. After the inoculum was removed and the apical surface was washed three times with 0.4 mL of phosphate buffered saline (PBS), the cultures were returned to the incubator. The production of progeny virions following apical infection was monitored daily by collecting samples from both the apical and basolateral chambers of the HAE culture. Notably, HBoV1 virions were released from all these inoculated HAE cultures. However, the time to peak virus secretion was longer at lower MOIs. These times were 6, 9, 12, 15, 23 and 24 days post-infection (p.i.) for MOIs of 100, 10, 1, 0.1, 0.01 and 0.001 vgc/cell, respectively. Although the yields of released virions at the peaks were slightly decreased along with the decreased MOIs, a yield of about $10^8$ vgc/μL was consistently detected in infections at MOIs from 100-0.1 vgc/cell, and a yield of about $10^7$ vgc/μL was detected at MOIs of 0.01 and 0.001 vgc/cell. Mock-infected HAE had no virus release (undetectable by quantitative PCR) from both surfaces. These results suggest that HBoV1 replicates in HAE slowly or persistently.

Next, the transepithelial electrical resistance (TEER) was monitored during the course of infection at various MOIs. All the TEER of the infected HAE cultures decreased drastically with an onset of decrease that correlated with the input MOIs (at 3, 5, 7, 7, 9, 11 days p.i. for MOIs from 100, 10, 1, 0.1, 0.01 and 0.001 vgc/cell, respectively). To some degree, the declining curve in TEER correlated with the increased tendency of the virus release. Nevertheless, the final TEER of all the inoculated HAE cultures by the end of the infection declined to a value less than 400 $\Omega\cdot cm^2$, an about 2-3-fold decrease compared to that of the mock-infected HAE. Destruction of the airway epithelium was also histologically observed. Compared with the mock-infected HAE, the degree of airway epithelial damage at the end of infection, shown as the thickness of the epithelium and the presence of cilia, correlated with MOI of input viruses. Notably, HAE inoculated with an MOI of 100 vgc/cell showed a progressive histological change. At 12 days p.i., the flattening of the HAE inoculated with an MOI of 100 vgc/cell resembled what was observed for HAE inoculated with MOIs of 0.1 to 0.001 vgc/cell at 26-28 days p.i. Furthermore, epithelial damage caused by HBoV1 infection was substantiated by the following assays: 1) the co-detection of HBoV1 NS1 with a significantly decreased β-tubulin IV (a marker of cilia (Matrosovich et al., 2004; Villenave et al., 2010)), which was absent in infected HAE at MOIs 100-0.1 vgc/cell and was extremely low at MOIs of 0.01 and 0.001 vgc/cell; 2) a disassociation of the tight junction protein Zona occludens-1 (ZO-1) (11); and 3) nucleus enlargement at late infection. Early following infection, NS1 expressing cells predominantly contained little or no β-tubulin IV and had dissociated ZO-1 staining (MOI=100 vgc/cell, 5 days p.i.), suggesting that virus either initially infects non-ciliated cells or that cilia are shed early in the course of viral replication.

Collectively, it was demonstrated that the secreted progeny HBoV1 virions washed from the ALI apical surface are highly infectious in polarized primary HAE and cause severe damage of the infected pseudostratified airway epithelia, even at an MOI as low as 0.001 vgc/cell.

HBoV1 is Capable of Infecting Polarized Primary HAE from the Basolateral Surface.

HBoV1 apical infection of primary HAE was persistent and that progeny virions were secreted from both the apical and basolateral surfaces (Example 1). However, whether HBoV1 infects primary HAE from the basolateral surface remains elusive. To address this question, naive primary HAE were inoculated basolaterally with apically washed HBoV1 virions, as used above at an MOI of 1 vgc/cell.

For basolateral infection, HBoV1 virions were diluted in 1 mL of the ALI media in the basolateral chamber of HAE cultures. The cultures were incubated at 37° C. and 5% $CO_2$ for 2 hours. Then the basolateral inoculums were removed and washed twice with 1 mL PBS. After addition of fresh media, the cultures were returned to the incubator. Production of progeny virions following basolateral inoculation was monitored daily by collecting samples from both the apical and basolateral chambers. Following basolateral inoculation, the apical viral secretion increased slowly, but to a peak of about $5\times10^7$ vgc/μL at 16 days p.i. Virion release was maintained at a level of over $10^6$ vgc/μL throughout the course of infection. Progeny virions were also released from the basolateral surface following the basolateral inoculation, but at a level of about 1 log less than that from the apical surface over the course of infection, which is similar to what was observed following apical infection. This result suggests that HBoV1 infection of HAE from the basolateral surface is also persistently productive, similar to what was observed following apical infection.

TEER was also monitored during basolateral infection. While the TEER of the mock-infected HAE cultures was consistently at a level of around 1000 $\Omega\cdot cm^2$ during the experiment period, the TEER of basolaterally-inoculated HAE dropped gradually and to a value of about 400 $\Omega\cdot cm^2$ at 15 days p.i., seen slightly earlier (13 days p.i.) in apically-inoculated HAE (MOI=1). This result is consistent with the viral release kinetics, indicating that HBoV1 infection disrupts the epithelial barrier. Basolaterally-inoculated HAE showed a clear dissociation of the tight junction, compared with that in the mock-infected HAE.

By the end of infection, at 22 days p.i., a histology analysis of basolaterally-inoculated HAE was performed. In contrast to the mock control, infected HAE showed an absence of cilia and an obviously thinner epithelium. This observation was further confirmed by the absence of β-tubulin IV expression. The infected HAE also showed nuclear enlargement at late-stage infection (DAPI).

Taken together, these results demonstrate that the HBoV1 is capable of infecting polarized primary HAE from the basolateral surface. They also show that the basolateral infection is persistently productive, causes loss of the cilia, and ultimately disrupts the tight junction barrier of the epithelium. However, in comparison to apical HBoV1 infection, basolateral infection is less efficient, suggesting that HBoV1 infection has a stronger apical tropism. The basolateral infection suggests that HBoV1 viremia (Kantola et al., 2008; Nascimento-Carvalho et al., 2012) may facilitate viral infection all over the lung airway tracts in patients.

Overall, this study demonstrates that HBoV1 productively infects polarized primary HAE at a low MOI both at the apical and basolateral surfaces. Mature and uninjured airway epithelia are mitotically quiescent (<1% of cells dividing) (Ayers et al., 1988; Lergh et al., 1995; Wang et al., 1999).

Example 3

Materials and Methods

Plasmids.

pIHBoV1 is the infectious clone plasmid containing the 5543 bp full-length HBoV1 genome (Huang et al., 2012). prHBoV1-CBAluc is a recombinant HBoV1 (rHBoV1) transfer plasmid derived from pIHBoV1 and was constructed by replacing the 2.64 kb HindIII/BglII fragment of the HBoV1 genome by a 2.74 kb fragment containing the CMV enhancer/chicken β-actin promoter driven Luciferase gene. The NP1 gene, which plays an essential role in HBoV1 DNA replication, was completely removed in the resulting prHBoV1-CBAluc plasmid. To reduce the probability of rescued wild type virus through recombination, the 5' remained NS gene coding region was further disrupted by elimination of a BspE1 site using blunt ligation, and the 3' VP partial coding region was further deleted by removal of a 145 bp PstI to EcoRI fragment. The helper plasmid pHBoV1KUm630 harbors the 5299 bp HBoV1 genome (99 to 5395-nt) without terminal repeats (Chen et al., 2010), with the P5 promoter and 3' polyA signal being retained for the expression of viral genes. pAV-Rep2 and pAD4.1 are the helper plasmids supporting rAAV2 genome rescue and replication from proviral plasmids in 293 cells as described previously. pAV2-F5tg83luc is a rAAV2 cis transfer plasmid, containing a 4.85 kb rAAV proviral genome with a 180 bp synthetic promoter driving firefly luciferase gene. pAV2-CF5tg83luc is a longer form of pAV2-F5tg83luc, and was derived by inserting 600 bp of stuffer sequence upstream the 180 bp synthetic promoter to generate a rAAV2 proviral genome 5.4 kb in length. pAV2-CBAhCFTR harbors an oversized 5.5 kb rAAV2 proviral genome containing a human CFTR expression cassette with a 580 bp CMV IE enhancer plus β-actin promoter (CBA promoter), a 50 bp synthetic polyA signal, and a 4443 bp human CFTR cDNA containing 56 bp 5'UTR and 45 bp 3'UTR.

Recombinant Virus Production.

rAAV vectors, rAAV2/2.F5tg83luc and AV2/1.F5tg83luc, were generated by triple plasmid co-transfection using an adenovirus-free system in HEK293 cells as described in Yan et al. (2006); this system uses the rAAV trans helper plasmid pAVRC2.3, adenovirus helper plasmid pAD Helper 4.1, and rAAV2 proviral plasmid pAV2-F5tg83luc, transfected at a ratio of 2:3:1, respectively. The rHBoV1 vector stock (HBc-.CBAluc) was generated by co-transfection of helper pHBoV1KUm630 and proviral plasmid prHBoV1-CBAluc into HEK293 cell at a ratio of 3:1, respectively. Chimeric rAAV2/HBoV1 vectors were generated by pseudotyping the rAAV genome within HBoV1 capsid following co-transfection of pAV-Rep2, pAd4.1, pHBoV1KUm630 together with the rAAV cis proviral plasmid into HEK293 cells at a ratio of 1.5:3:3:1, respectively. The rAAV proviral plasmids used for the chimeric vector production were pAV2-F5tg83luc (4.8 kb), pAV2-CF5tg83luc (5.4 kb) and pAV2-CBAhCFTR (5.5 kb). All viruses were recovered from the cell pellets at 72 hours post-transfection and the cell crude lysates were treated as for rAAV vector production as described in Yan et al. (2013). After DNase I digestion, all viruses were purified by two rounds of CsCl ultracentrifugation and dialyzed against PBS. The titers of viral preparations as DNase I-resistant particles (DRP) were determined by TaqMan real time quantification PCR and confirmed with slot blot assays using a $^{32}$P-labeled probe against the luciferase gene (Yan et al., 2013).

Western Blotting.

$5\times10^9$ DRP of rAAV2 and chimeric rAAV2/HBoV1 were resolved by 10% SDS-PAGE. Following transfer to nitrocellulose membranes, two-color Westerns were performed with mouse anti-MV capsid monoclonal antibody B1 (1:1000) and rat anti-HBoV1 VP2 antiserum (recognizing both VP1 and VP2 proteins) (Chen et al., 2010) (1:200). Infrared detection used 1:10,000 dilution of the secondary antibody goat anti-mouse-IRDye700 (red, for AAV) and goat anti-rat-IRDye800 (green, for HBoV1). Images were then scanned using an Odyssey Infrared Image System.

Cell Culture and Virus Infection Conditions.

HEK293 and IB3 cells were cultured as monolayers in Dulbecco's modified Eagle medium (DMEM), supplemented with 10% fetal bovine serum and penicillin-streptomycin, and maintained in a 37° C. incubator at 5% $CO_2$. Undifferentiated immortalized CF human airway cells (CuFi8) were cultured as monolayers in bronchial epithelial cell growth medium (BEGM, Lonza) (Zabner et al., 2003). Polarized primary human airway epithelia were generated as previously described from lung transplant airway tissue (Yan et al., 2004; Karp et al., 2002) and were obtained from the Tissue and Cell Culture Core of The Center for Gene Therapy at the University of Iowa. Epithelia were grown on 12 mm Millicell membrane inserts (Millipore) and differentiated with 2% USG medium at an air-liquid interface prior to use. Polarization of CuFi8 cells at an ALI was performed using similar conditions to primary HAE. To apically infect the polarized airway epithelia, $1\times10^{10}$ DRP of virus was diluted in USG medium to the final volume of 50 it and applied to the upper chamber of the Millicell insert. For basolateral infections, $1\times10^{10}$ DRP of virus was directly added to the culture medium in the bottom chamber. Viruses were typically exposed to epithelia for 16 hrs and then removed. At this time, the Millicell inserts were briefly washed with a small amount USG medium and fed with fresh USG medium in the bottom chamber only. Approximately 1-$2\times10^6$ cells are in each Millicell insert and thus the multiplicity of infection (MOI) is estimated about 5,000 to 10,000 DRP/cell. Transduction was assessed by luciferase reporter assays at various time points post-infection using cell lysates or IVIS biophotonic imaging.

Measurement of Luciferase Reporter Expression.

Luciferase enzyme activity in cell lysates was determined using the Luciferase Assay System (Promega) in a 20/20 luminometer equipped with an automatic injector (Turner Biosystems). Quantification of luciferase activity in live cells was performed using the IVIS Biophotonic Imaging system according to the manufacturer's instructions. Images were captured 15 minutes after adding the VivoGlo Luciferin substrate (Promega) to the basolateral culture medium only, and quantification of images were processed with the Living Image 2.51 software (Xenogen).

Analysis of Internalized Viral Genome.

Fully-differentiated human polarized airway epithelia were infected with $1\times10^{10}$ particles of rAAV or chimeric rAAV/HBoV1 vectors. After a 4 hr infection period, virus was removed, and epithelia were extensively washed with PBS. The Millicell inserts then were fed with fresh medium in the bottom chamber and placed in a 37° C. incubator for 18 hours. Prior to harvesting cells for all viral internalization assays, Millicell inserts were washed thoroughly with 40 mL PBS in a 50 mL conical tube three times. The cells were then detached from the support membrane of the Millicell inserts by trypsin digestion. The cell pellets were then washed three more times with 1 mL PBS prior to subcellular fractionation and viral genome quantification. Control experiments utilizing virus bound for 1 hour at 4° C. demonstrated >98% removal of virus from the cell surface using this washing and trypsin digestion method (data not shown). Nuclei were isolated with the Nuclei EZ pre kit (Sigma) as described in Chen et al. (2011). The cytoplasmic fractions were pooled during the nuclei preparation and 1/10 was dried in a SpeedVac. The nuclei pellet and dried cytoplasmic fraction were dissolved in 50 μL digestion buffer (50 mM KCl, 2.5 mM $MgCl_2$, 10 mM Tris pH 8.0, 0.5% NP40, 0.5% Tween-20 and 400 μg/ml proteinase K). After digestion at 56° C. for 45 minutes and heat-inactivation at 95° C. for 15 minutes, 0.1 μL of the nuclear and 1 μL of the cytoplasmic digestion were used for TaqMan PCR to quantify viral genomes. When total viral internalization assays were performed in CuFi ALI cultures, non-polarized CuFi and HEK293 cell monolayers, the same washing and trypsinization procedure was used to remove cell-surface bound virions. However, the washed cell pellets were directly lysed with the above digestion buffer and used for viral genome quantification.

Quantitative Analysis of rAAV Genomes by TaqMan PCR.

TaqMan real time PCR was used to quantify the physical titer of the viral stocks and copies of viral genomes in cell lysates from AAV infected cells as described in Yan et al. (2006). The PCR primers used were 5'-TTTTTGAAGCGAAGGTTGTGG-3' (SEQ ID NO:6) (forward) and 5'-CACACACAGTTCGCCTCTTTG-3' (SEQ ID NO:7) (reverse) and amplify a 73 bp fragment of the rAAV2.Luc genome. The Taqman probe (5'-ATCTGGATACCGGGAAAACGCTGGGCGTTAAT-3') (SEQ ID NO:8) was synthesized by IDT (Coralville, Iowa). This probe was tagged with 6-carboxy fluorescein (FAM) at the 5'-end as the reporter and Dark Hole Quencher 1 (BHQ1) at the 3'-end as the quencher. The PCR reaction was performed and analyzed using Bio-Rad MyIQ™ Real-time PCR detection system and software.

Short Circuit Current Measurements.

Transepithelial short circuit currents (Isc) were measured using an epithelial voltage clamp (Model EC-825) and a self-contained Ussing chamber system (both purchased from Warner Instruments, Inc., Hamden, Conn.) as described in Lin et al. (2007). Throughout the experiment the chamber was kept at 37° C., and the chamber solution was aerated. The basolateral side of the chamber was filled with buffered Ringer's solution containing 135 mM NaCl, 1.2 mM $CaCl_2$, 1.2 mM $MgCl_2$, 2.4 mM $KH_2PO_4$, 0.2 mM $K_2HPO_4$, and 5 mM Hepes, pH 7.4. The apical side of the chamber was filled with a low chloride Ringer's solution in which 135 mM Na-gluconate was substituted for NaCl. Transepithelial voltage was clamped at zero with current pulses every 5 seconds to record the short-circuit current using a VCC MC8 multichannel voltage/current clamp (Physiologic Instruments) with Quick DataAcq software. The following chemicals were sequentially added into the apical chamber: (1) amiloride (100 μM) for inhibition of epithelial sodium conductance by ENaC; (2) 4,4'-diisothiocyanato-stilbene-2,2'-disulfonic acid (DIDS) (100 μM) to inhibit non-CFTR chloride channels; (3) cAMP agonists forskolin (10 μM)/3-isobutyl-I-methylxanthine (IBMX) (100 μM) to activate CFTR chloride channels; and (4) 10 μM CFTRinh-GlyH-101 (N-(2-naphthalenyl)-[(3,5-dibromo-2,4-dihydroxyphenyl) methylene] glycine hydrazide) to block $Cl^-$ secretion through CFTR. ΔIsc calculations were made by taking the difference of the plateau measurements average over 45 seconds before and after each experiment conditions (chemical stimulus).

CFTR Immunostaining.

Following short circuit current measurements, the HAE on the support membrane was cut out from the Millicell insert and embedded in OCT medium. 10 μm cryosections were fixed in 4% paraformaldehyde followed by blocking and immunofluorescence staining using an anti-CFTR antibody cocktail consisting of equal amount (at a 1:200 dilution) of three mouse anti-CFTR antibodies (clone MM13-4 (Millipore), clone M3A7 (Millipore), and clone 131 (R&D system)) and finally incubation with donkey anti-mouse FITC-labeled secondary antibody.

Results

Production of a Recombination HBoV1 (rHBoV1) Vector and its Transduction Properties in HAE Model Systems.

The plasmid clone of the full length HBoV1 genome (pIHBoV1) can be used to produce infectious HBoV1 virions following transfection in HEK293 cells without the need for helper virus functions (Huang et al., 2012). It was first attempted to generate rHBoV1 by testing if HBoV1 viral proteins could trans-complement and rescue replication and packaging of a rHBoV1 genome in HEK293 cells. The structure of the wild type HBoV1 genome found in the infectious plasmid (pIHBoV1), the rHBoV1 proviral plasmid (prHBoV1-CBAluc), and the trans-helper plasmid (pHBoV1KUm630) are schematically shown in FIG. 1A. The prHBoV1-CBAluc contained a 5.5 kb rHBoV1 proviral genome encoding a CBA promoter-driven luciferase gene. The ability of pHBoV1KUm630 to support rHBoV1 genome rescue and replication from prHBoV1-CBAluc was confirmed by co-transfecting these plasmids into HEK293 cells. Hirt DNA extracted from transfected cells was evaluated by Southern blot following DpnI digestion to eliminate the methylated plasmid background signal. As shown in FIG. 1B, rHBoV1 replication intermediates were only observed in cells co-transfected with prHBoV1-CBALuc and pHBoV1KUm630, but not with prHBoV1-CBALuc alone. Although the detected replication intermediates from the co-transfection were lower than the level from the wild type HBoV1 proviral plasmid pIHBoV1, we conclude the pHBoV1KUm630 plasmid does provide the necessary helper functions in trans to support rHBoV1 genome replication (FIG. 1C). To generate recombinant virus, prHBoV1-CBAluc and pHBoV1KUm630 were co-transfected into HEK293 followed by purification from cell lysates with CsCl equilibrium ultracentrifugation. Fractions from this gradient were evaluated for viral genomes by TaqMan PCR and demonstrated a peak at a density of 1.45 to 1.40 g/mL (FIG. 1C), suggesting successful encapsidation of viral DNA. Viral yields from thirty 150-mm plates yielded a total of $1.25\times10^{11}$ rHBoV1 genome copies (vc) or DNase I resistant particles (DRP). This is roughly 20% of the yield of wild type HBoV1 obtained from the transfection of pIHBoV1 in HEK293 cells (about $2\times10^{11}$ DRP per ten 150 mm dishes) (Huang et al., 2012).

Twice-CsCl banded rHBoV1.CBAluc was then evaluated for its transduction properties following infection of HEK 293 cells, 163 cells (a CF human airway cell line), monolayers of CuFi8 cells (a conditional transformed CF airway cell line (Zabner et al., 2003)), and ALI cultures derived from CuFi cells and primary human airway epithelial cells (FIG. 1D). Results demonstrated that rHBoV1.CBAluc was only capable of transducing (i.e., expressing its encoded transgene) polarized and differentiated ALI cultures derived from either primary or CuFi airway cells. These findings are similar to conditions required for productive infection with wild type HBoV1 (Huang et al., 2012). Following apical infection of polarized HAE with rHBoV1.CBAluc, maximal transgene expression occurred at 3 days post-infection and gradually declined by 11 days post-infection (FIG. 1E).

Encapsidation of a Recombinant AAV2 Genome in HBoV1 Virions Through Cross-Genera Parvovirus Pseudotyping.

Figure 2:
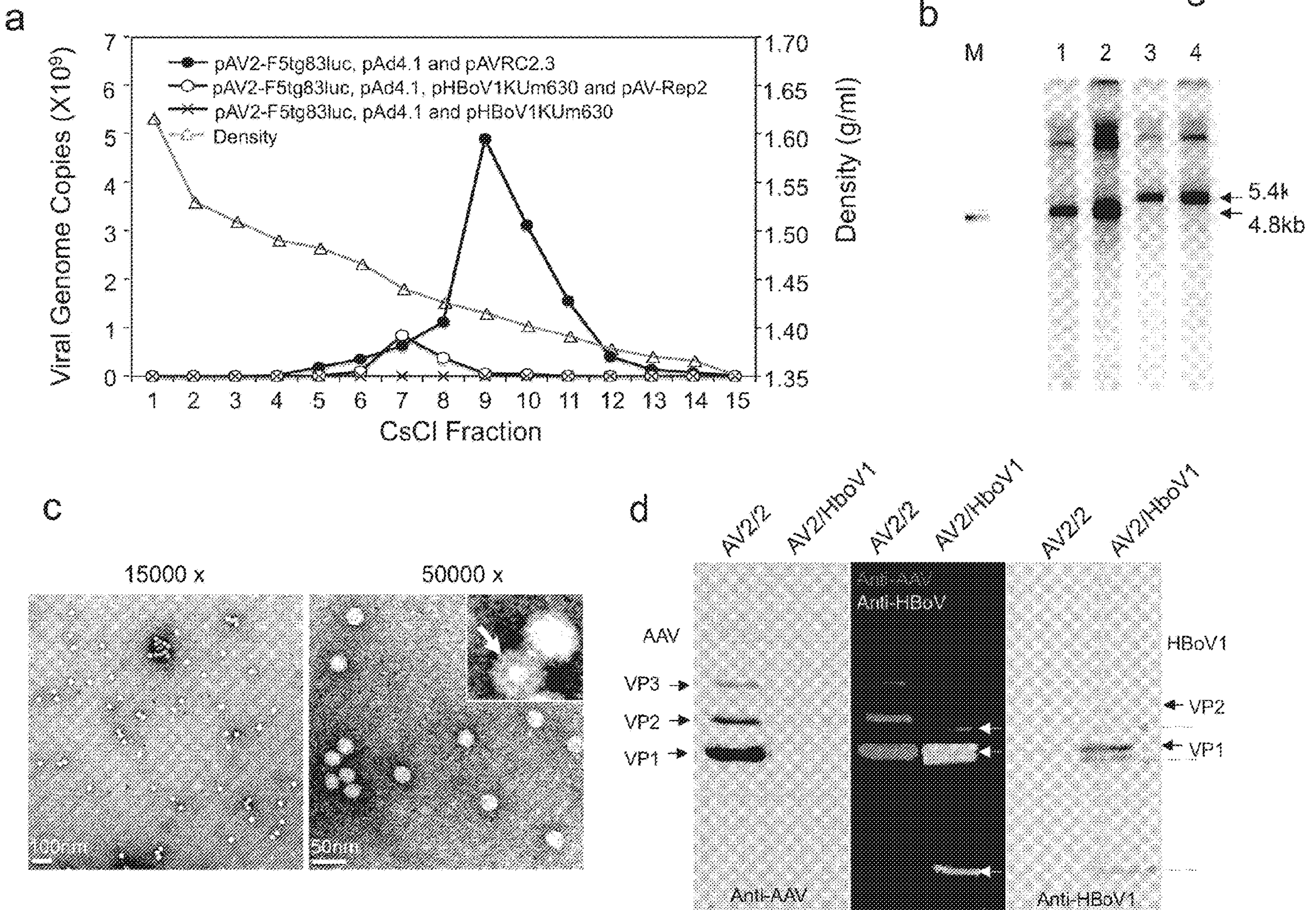
FIGS. 2A-D. Pseudopackaging rAAV2 genomes in HBoV1 capsid. (A) DNase I-digested cell lysates from the indicated HEK293 cell plasmid transfections were fractionated by CsCl equilibrium ultracentrifugation. The number of viral genomes in each fraction was determined by TaqMan PCR. (B) HEK293 cells were transfected with the indicated combinations of plasmids (M: Molecular weight marker.

Although wild type HBoV1 and rHBoV1 virions can be assembled in HEK293 cells following plasmid(s) transfection, the viral yields are relatively low. By contrast, rAAV vector replication is very efficient in HEK293 with the proper helper plasmids. We reasoned that HEK293 cell machinery supporting HBoV1 replication could be less efficient because the HEK293 cells are not a biologically permissive cell line for HBoV1 productive infection. Therefore, it was explored whether pseudotyping rAAV2 genomes with HBoV1 capsids would generate a rAAV2/HBoV1 chimeric vector with higher yields in these cells. Using this approach, the 4.85 kb rAAV genome from the cis rAAV proviral plasmid (pAV2-F5tg83luc) was successfully packaged into HBoV1 virions following co-transfection with pAD4.1 (encoding all the necessary helper function for AAV replication from adenovirus), pAV-Rep2 (encoding the AAV2 Rep genes), and pHBoV1KUm630 (encoding the HBoV1 capsids and NS genes). There were several reasons for using a helper plasmid that expressed all HBoV1 viral proteins to support encapsidation of the rAAV2 genome. First, the temporal regulation and transcriptional profiles of HBoV1 genes required to support packaging remain unknown. Second, the functional roles of HBoV1 NS and NP1 proteins in capsid assembly are unclear. Lastly, it is possible that NS proteins associate with AAV2 ITRs and this could potentially help to facilitate packaging of AAV2 genomes into HBoV1 capsids. Three days after co-transfection, substantial DNase I-resistant viral particles were recovered from crude lysates by CsCl banding (FIG. 2A). Omitting pAV-Rep2 from the transfection cocktail failed to produce DNase I resistant viral particles. Of note, the density of the chimeric rAAV2/HBoV1 virions was about 1.435 g/mL, similar to that of the rHBoV1 virions (FIG. 1A). This density was slightly heavier than the 1.414 g/ml density of the rAAV2/2 virions (FIG. 1A). The typical yields of the chimeric rAAV/HBoV1 vector were 10- to 20-fold less than rAAV2 vector, but 2- to 4-fold greater than rHBoV1 vector, when generated on a similar scale. By contrast, the pseudopackaging of a rAAV genome into human parvovirus B19 capsid is much less efficient than what we observed for rAAV2/HBoV1 (Ponnazhagan et al., 1998).

Examination of rAAV2 genome rescue and replication demonstrated that rAAV2 replication from DNA (RF DNA) in the rAAV2/HBoV1 production system was about 2 to 3-fold less abundant than that during rAAV2 production (FIG. 2B, compare lanes 2 and 4). This is consistent with previous reports describing that the parvovirus capsid plays a feedback role in virion formation (Cheng et al., 2010; Huang et al., 2012). Supporting this, it was observed that less rAAV2 RF DNA was present following co-transfection of the AAV2 proviral plasmids (pAV2.F5tg83luc and pAV2.CF5tg83luc) and the pAV2-Rep helper (missing intact AAV capsid genes) (FIG. 2B, lane 1 and lane 3), than following co-transfection of pAV2.F5tg83luc and the AAV2 Rep-Cap helper plasmid pAVRC2.3 (FIG. 2B, lane 2). Of note, the expression of the HBoV1 viral proteins appeared to not interfere with rAAV2 genome rescue and replication (FIG. 2B, compare lane 4 vs. lane 1 or 3). Transmission electron microscopy (EM) demonstrated that rAAV2/HBoV1 virions had a typical parvovirus icosahedral structure that was 26 nM in diameter (FIG. 2C), similar to wild type HBoV1 virions (Huang et al., 2012). The density of the interior of the virions by EM also suggested that >99% of virions were fully packaged with DNA. Examination of the chimeric rAAV2/HBoV1 virions by Western blot with anti-HBoV1 VP2 antiserum demonstrated the presence of HBoV1 VP1 and VP2 proteins, but no AAV2 VP proteins were detected in the rAAV/HBoV1 stock using an anti-AAV2 capsid monoclonal antibody B1 (FIG. 2D).

Characterization of Viral Genome Polarity and Capacity of rAAV2/HBoV1 Virions.

One significant difference between wild type AAV2 and HBoV1 virions is the polarity of packaged genomes—about 50% of AAV virions contain a plus DNA strand, while the other half contain a minus DNA strand, whereas HBoV1 selectively encapsidates the minus DNA strand more than 90% of the time (Schildgren et al., 2012). The two terminal palindromic sequences of HBoV1 are asymmetric (differing in size, primary sequence, and predicted structure (Huang et al., 2012)), while for MV, terminal palindromic sequences are identical inverted repeats. The terminal sequences in parvovirus genomes are critical to the formation of concatameric duplex replication intermediates and excision of single stranded progeny genomes for packaging (Cotmore et al., 1996). Given that the rAAV2/HBoV1 vector genome has identical inverted repeats at the ends of its genomes, it was hypothesized that rAAV2/1-1BoV1 would adopt unbiased packaging of both the plus and minus strands. This was indeed the case. Using sense and antisense probes against the luciferase transgene, rAAV2/HBoV1 virion DNA demonstrated approximately equal proportions of plus and minus strands, while rHBoV1 vector DNA demonstrated a preference (about 87%) for packaging the minus strand. These differences may, in part, account for the 2-3 fold higher yield in generation of rAAV2/HBoV1 over that of rHBoV1.

A second major difference between MV and HBoV1 genomes are their size—the AAV genome is 4679-nt in length, while the HBoV1 is 5543-nt in length. The packaging capacity of rAAV vectors has been extensively studied and has limits of 4.9 to 5.0 kb (Dong et al., 1996; Wa et al., 2010). This is a significant hurdle for delivery the CFTR gene by rAAV, and one that might be potentially overcome with rAAV2/HBoV1 vectors. Thus, it was hypothesized that the rAAV2/HBoV1 particle might offer a significant advantage for CFTR delivery by virtue of its ability to package oversized rAAV genomes up to 5.5 kb, as observed with rHBoV1 (FIG. 1D). To explore this possibility, two rAAV proviral genomes were generated with identical luciferase expression cassettes that differed in length by 600 bp (pAV2/HBc.F5tg83Luc at 4.8 kb and pAV2/HBc.CF5tg83Luc at 5.4 kb). Each of these proviral plasmids was used to generate rAAV2/2 (4.8 kb) and/or rAAV2/HBoV1 (4.8 and 5.4 kb) viruses, and the viral DNA was evaluated by alkaline-denatured agarose gel electrophoresis followed by Southern blot analysis. The viral yields of 5.4 kb rAAV2/HBoV1 was similar to 4.8 kb rAAV2/HBoV1. The Southern blot analysis of viral DNA revealed only genomes of the appropriate size with no obvious truncated forms (FIG. 3B). These findings demonstrate that HBoV1 pseudotyping accurately processes and packages both short and long rAAV genomes without altering genome integrity.

Viral genome recombination plays an important role in the evolution of many viruses, and strand recombination also occurs during the replication of single-stranded viruses (Martin et al., 2011). Enteric human bocavirus infections are also associated with a high level of viral genome recombination (Kapoor et al., 2010). It was evaluated whether recombination products between the helper and proviral plasmids were packaged into rHBoV1 and rAAV2/HBoV1 virions. Slot blot analyses of viral genomes from purified rAAV2/HBoV1 and rHBoV1 were conducted using a luciferase transgene probe and HBoV1 helper-specific viral probe (i.e., the HindIII/BglII 2.64 kb fragment replaced by the luciferase cassette in the rHBoV1 vector). Results from this analysis demonstrated that 17% of the viral genomes in purified rHBoV1 stocks contained HBoV1 sequences found only in the helper plasmid (FIG. 3C). The inclusion of 1.4 kb and 1.1 kb HBoV1 genome fragments flanking the luciferase cassette in the rHBoV1.CBAluc genome is the mostly likely cause of these recombination events. Although both the NS and VP protein coding domains were mutated in the rHBoV1.CBAluc genome (FIG. 1A), if recombination occurred outside these mutations in a double cross-over event, replication-competent rHBoV1 genomes would be expected in rHBoV1 viral stocks. The presence of replication-competent virus could be one of the reasons for the time-dependent decline in transgene expression of rHBoV1 infected HAE ALI cultures (FIG. 1E). In contrast to rHBoV1. HBoV1 helper genomes were not detected in purified rAAV2/HBoV1 virus, as would be expected, since there is no sequence homology between the proviral and helper plasmids. Thus, further development of packaging strategies for rHBoV1 are needed to eliminate the chance of generating replication competent HBoV1 (i.e, expression of NS and VP genes on separate helper plasmids and minimal cis-elements for packaging in the proviral genome). However, improved knowledge of the regulation of NS/VP viral genes and HBoV1 genome packaging will be needed before similar strategies that eliminate replication competent virus in the generation of rAAV can be applied.

Chimeric rAAV2/HBoV1 Vectors Mediate Highly Efficient Transduction from the Apical, but not Basolateral Membrane, of Human Polarized Airway Epithelia.

Figure 4:
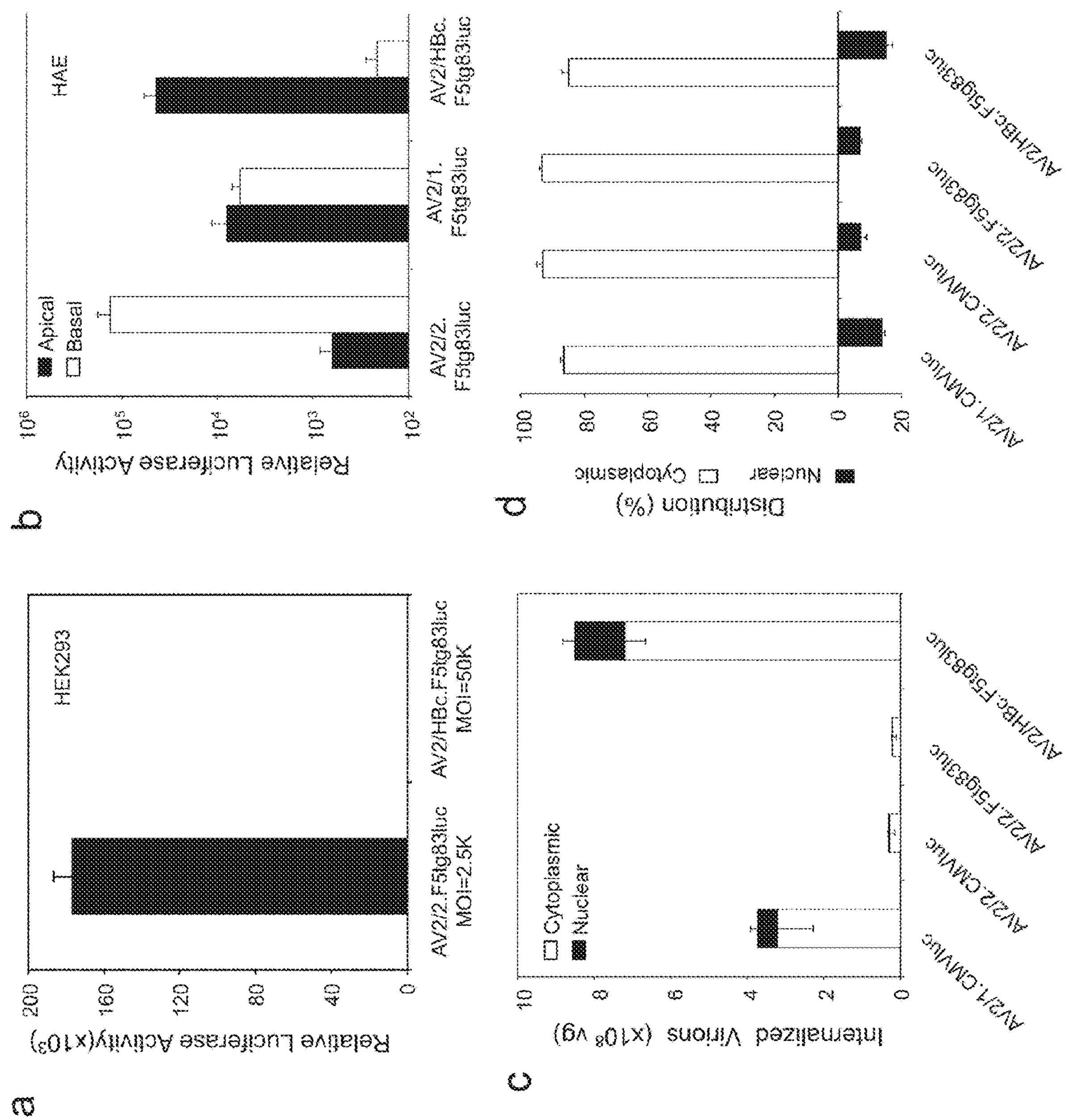

Next the transduction characteristics of the rAAV2/HBoV1 chimeric vectors was examined. A rAAV2/HBoV1 vector encoding the luciferase transgene failed to transduce HEK293 cells at even high MOIs (50,000 DRP/cell), while the analogous rAAV2/2 vector efficiently expressed luciferase at much lower MOIs (2,500 DRP/cell) (FIG. 4A). Experiments in primary HAE and CuFi ALI cultures confirmed that both AV2/HBc.F5tg83luc (4.8 kb genome) and AV2/HBc.CF5tg83luc (5.4 kb genome) gave rise to similar levels of luciferase expression following apical infection (data not shown), suggesting that vector size within this range did not impact transduction. Next the transduction of rAAV2/HBoV1 was compared to that of rAAV vectors under the same infection conditions. This direct comparison was only possible with AV2/HBc.F5tg83luc, AV2/1.F5tg83luc and AV2/2.F5tg83luc (with identical proviral genomes derived from pAV2-F5tg83luc), since the pAV2-CF5tg83luc genome (5.4 kb) was too large to be packaged into AAV capsids. The transduction patterns for primary HAE following apical and basolateral infection with AV2/HBc.F5tg83luc and AV2/2.F5tg83luc were strikingly different (FIG. 4B). As previously observed, rAAV2/2 transduced HAE with a strong basolateral preference (Yan et al., 2006: Yan et al., 2004) the luciferase expression following apical infection was 210-fold lower than that following basolateral infection (FIG. 4B). By contrast, rAAV2/HBoV1 demonstrated a 206-fold greater level of transduction following apical infection of primary HAE as compared to basolateral infection (FIG. 4B). Importantly, the level of transgene expression achieved following apical infection with AV2/HBc.F5tg83luc was 70-fold greater than that from AV2/2.F5tg83luc, and 5.6-fold greater than AV2/1.F5tg83luc. As previously demonstrated, rAAV2/1 lacked a polarity bias for transduction in polarized HAE, and had better apical transduction efficiency than rAAV2 (Yan et al., 2006).

Since HBoV1 is a recently discovered virus, little is known about HBoV1-cell interactions in HAE. Wild type HBoV1 can infect HAE at MOIs as low as 0.001 DRP/cell (Deng et al., 2013), suggesting that viral entry from the apical surface of HAE is quite efficient. However, with the added variable of viral replication, the efficiency of HBoV1 internalization and intracellular trafficking to the nucleus is difficult to directly evaluate. The creation of a replication defective rAAV2/HBoV1 chimeric virus provides the opportunity to directly evaluate these processes and furthermore compare the efficiency of these steps in transduction with rAAV vectors. To this end, virion uptake and viral genome distribution was compared in primary ALI cultures of HAE at 18 hours following apical infection. As controls, we included two rAAV pseudotyped vectors, rAAV2/1 (AV2/1.CMVluc) and rAAV2/2 (AV2/2.CMVluc), which are known to transduce HAE from the apical membrane with different efficiencies (Yan et al., 2006). rAAV1 has thus far been shown to be one of the most efficient AAV serotype for transduction of HAE, with greater virion uptake and faster nuclear translocation following apical infection (Yan et al., 2013; Yan et al., 2006). Additionally, both AV2/HBc.F5tg83luc and AV2/2.F5tg83luc viruses that contain the identical viral genome were evaluated. Results from these comparisons demonstrated that AV2/1.CMVluc and AV2/HBc.F5tg83luc showed about 14-fold and about 32-fold more viral uptake from the apical membrane of primary HAE than the rAAV2/2 vectors (AV2/2.CMVluc and AV2/2.F5tg83luc), respectively (FIG. 4C). AV2/HBc.F5tg83luc viral uptake was also 2.3-fold more efficient than AV2/1.CMVluc (P=0.026). Furthermore, the post-entry processing of rAAV2/HBoV1 to the nucleus appeared to be more rapid than for rAAV2/2, with about 15% of internalized AV2/HBc.F5tg83luc genomes detected in the nuclear fraction by 18 hours post-infection, as compared to about 7% for rAAV2/2 (FIGS. 4C and D). Interestingly, the cytoplasmic/nuclear distribution of viral genomes was similar for rAAV2/1 (86.4/13.6%) and rAAV2/HBoV1 (85.0/15.0%) (FIGS. 4C and D). In contrast to both rAAV serotypes tested, rAAV2/HBoV1 poorly transduced HAE from the basolateral membrane (FIG. 4B). Overall, these findings suggest that rAAV2/HBoV1 viral uptake and nuclear translocation is highly efficient following apical infection of primary differentiated HAE.

Modulating Proteasome Activity During the Infection Period Greatly Enhances Transduction Following Apical Infection with rAAV2/HBoV1.

Despite the fact that rAAV2/HBoV1 demonstrates a high transduction efficiency following apical infection in HAE ALI, the majority (85%) of internalized rAAV2/HBoV1 virions are retained in the cytoplasm at 18 hours post-infection. This suggested that intracellular barriers limiting effective nuclear transport of the virus, as observed for rAAV2 and rAAV1 transduction of HAE (Duan et al., 2000; Duan et al., 1998), may also exist for HBoV1. Thus, the transduction efficiency of rAAV2/HBoV1 could be further improved by overcoming these barriers. Impaired endosomal processing/intracellular trafficking is one of the major barriers that limit rAAV vector transduction of polarized HAE following apical infection. This barrier can be partially overcome by the application of proteasome inhibitors at the time of infection or within a certain period after infection (Duan et al., 2000; Zhang et al., 2008; Yan et al., 2004). These studies have demonstrated that both tripeptidyl aldehyde N-acetyl-1-leucyl-1-leucyl-1-norleucine (LLnL) and the anthracycline derivative doxorubicin (Dox) can enhance the rAAV2, rAAV5, and rAAV1 viral processing and translocation to the nucleus, leading to higher levels of transduction. Combined administration of these two distinct classes of proteasome activity modulating agents can induce transduction over 1000-fold following apical rAAV2/2 infection of primary HAE (Yan et al., 2006; Yan et al., 2004). Although there is a significant divergence between the HBoV1 and AAV2 capsid proteins at primary sequence level, these two viruses retain some conserved core capsid sequences and also share a similar surface icosahedral topology with other parvovirus particles (Gurda et al., 2010). Thus, it was hypothesized that treatment with proteasome inhibitors might also enhance transduction of HAE by rAAV2/HBoV1, and sought to study the kinetics of transduction between rAAV2/2 and rAAV2/HBoV1 in the presence and absence of LLnL and Dox. Results comparing rAAV2/2 to rAAV2/HBoV1 (FIGS. 5A and B) demonstrated a similar rise in transgene expression between 3-7 days post-infection, with a plateau at 7-11 days post-infection. For both vectors, treatment with proteasome inhibitors at the time of infection enhanced transduction at all time points greater than 1000-fold, and there was no decline in transgene expression at the 11 day period. These findings demonstrate that rAAV2/HBoV1 shares a similar proteasome-dependent barrier to transduction as observed with most other rAAV serotypes.

Polarization of Human Airway Epithelia is Required for HBoV1 Capsid-Mediated Gene Transfer.

The mechanism by which HBoV1 productively infects the apical membrane of polarized human airway epithelia remains unclear. In previous studies, we observed that infection of monolayers of CuFi cells with wild-type HBoV1 does not support viral replication and production of progeny virions (Huang et al., 2012), a finding similar to the lack of transduction of monolayer CuFi cells with luciferase expressing rHBoV1 (FIG. 1D). By contrast, when polarized, CuFi cells efficiently produce progeny virus following apical, but not basolateral, infection with wild-type HBoV1 (Huang et al., 2012). These findings suggest that polarization influences a cellular factor(s) required for productive infection, such as expression of a viral receptor/co-receptor or expression of factors involved in intracellular processing of the HBoV1 virion. Since viral replication does not occur within the chimeric rAAV2/HBoV1 vector, this was an opportunity to define the step(s) following HBoV1 infection that are influenced by polarization. To this end, experiments were performed with rAAV2/HBoV1 to address whether the polarization of airway epithelial cells influences HBoV1 capsid-mediated transduction through steps involving receptor binding/uptake or the post-entry intracellular processing of virions. Since the ubiquitin-proteasome pathway affects rAAV2/HBoV1 transduction in HAE ALI cultures, we also examined the influences of proteasome inhibitors on these two steps of infection.

Equivalent numbers of CuFi cells under monolayer (i.e., non-polarized) or polarized ALI culture conditions were incubated with equal amounts of AV2/HBc.F5tg83luc virus at 37° C. for 4 hours. After removal of the unbound vectors, the infected cells were either lysed for quantification of internalized vector genomes by TagMan PCR or cultured for an additional 20 hours prior to assessing transgene expression (FIG. 5C). Results from this analysis demonstrated that apical transduction of polarized CuFi ALI cultures with AV2/HBc.F5tg83luc was 72-fold more efficient than basolateral transduction, a finding consistent with AV2/HBc.F5tg83luc infection of primary HAE ALI cultures (FIG. 4B). Under these conditions, about 40-fold more virus was taken up by CuFi epithelia following a 4 hours apical infection as compared to basolateral infection (FIG. 5C), suggesting that polarization enhances the abundance of HBoV1 receptor/co-receptor on the apical membrane. Interestingly, AV2/HBc.F5tg83luc entered CuFi cell monolayers at an efficiency similar to that observed following apical infection of polarized CuFi epithelia (FIG. 5C), despite significantly reduced transduction of non-polarized CuFi cultures (FIG. 4B). Additionally, analysis of viral uptake and transduction of HEK293 cells infected with AV2/

HBc.F5tg83luc, which is not permissive to HBoV1 infection, revealed substantial viral uptake without transgene expression (FIG. 5C). These two observations in CuFi and HEK293 monolayer cultures suggest that post-entry barriers, rather than receptor-mediated uptake, also play a key role in rAAV2/HBoV1 transduction.

To further investigate post-entry barriers to rAAV2/HBoV1 transduction, the influences of proteasome inhibitors were evaluated. Overall, proteasome inhibitors had little effect on viral uptake following infection under all the conditions evaluated (apical or basolateral infection of polarized CuFi ALI or infection of non-polarized CuFi monolayers) (FIG. 5C). By contrast, proteasome inhibitor application during the 4 hour infection period enhanced transduction 45-fold following apical infection of polarized CuFi epithelia, while only marginally enhancing transduction following basolateral infection of polarized CuFi epithelia (5 fold) or infection of CuFi monolayers (4.3-fold) (FIG. 5C). These results suggest proteasome-dependent barriers to intracellular processing of HBoV1 virions are greater from the apical membrane of polarized CuFi epithelia. Furthermore, CuFi monolayers appear to have the greatest post-entry block to HBoV1 virion processing that is also less proteasome-dependent. Cumulatively, these results suggest that polarization/differentiation of airway epithelial cells alter both receptor-mediated uptake and intracellular processing of HBoV1 virions.

A rAAV2/HBoV1 Vector Harboring a 5.5 kb Genome with a Strong CBA-hCFTR Expression Cassette can Correct CFTR-Mediated Chloride Currents in CF HAE.

The application of rAAV vectors for CF gene therapy has been hindered by the relatively small packaging capacity of the virus and the large size of full-length CFTR cDNA (4443 bp of coding sequence). This has necessitated the use of very small synthetic weaker promoters and/or the deletion of CFTR domains not critical for chloride channel function (Zhang et al., 1998). Both of these approaches are suboptimal for CFTR-mediated gene therapy. A rAAV2/HBoV1 vector would have enough space to accommodate strong transcription regulatory elements for human CFTR gene expression. To provide the proof-of-concept for this approach, a rAAV2 proviral plasmid was constructed that harbored a 5.5 kb genome containing a 5.2 kb human CFTR expression cassette driven by the strong CBA promoter. When this proviral plasmid was packaged into HBoV1 virions, the resultant viral yield (AV2/HBc.CBAhCFTR) averaged $1.5\times10^{11}$ DRP from ten 150-mm dishes of transfected HEK293 cells, a similar level of production for rAAV2/HBoV1 vectors with luciferase reporters. The integrity of the 5.5 kb rAAV genome within AV2/HBc.CBAhCFTR was confirmed by alkaline agarose gel analysis (data not shown).

To validate the function of AV2/HBc.CBAhCFTR virus, primary differentiated CF HAE were infected with $10^{10}$ DPR (5,000-10,000 DRP/cell) from the apical surface in the presence of proteasome inhibitors and assessed CFTR function at 10 days following infection. CFTR function was evaluated as the change in cAMP-mediated short-circuit current (Isc) following stimulation with IBMX and forskolin and inhibition with GlyH101 (a CFTR inhibitor). DIDS and amiloride were used to block non-CFTR chloride channels and ENaC-mediated sodium currents prior to cAMP induction. Results comparing complementation of CFTR-mediate chloride currents following apical infection with AV2/HBc.CF5tg83Luc (control vector) and AV2/HBc.CBAhCFTR are shown in FIG. 6A. A significant change in cAMP-inducible Isc was observed following AV2/HBc.CBAhCFTR infection, as compared control AV2/HBc.CF5tg83Luc infected samples, and this current was blocked by the addition of the CFTR inhibitor GlyH101. FIG. 6B summarizes the $\Delta Isc_{(cAMP)}$ following cAMP agonist induction and the $\Delta Isc_{(glyH)}$ following GlyH101 inhibition for the two infections conditions and non-CF controls. The level of correction following AV2/HBc.CBAhCFTR infection ($\Delta Isc_{(cAMP)}$=2.60+1-0.96 μA/cm$^2$ and $\Delta Isc_{(glyH)}$=2.98+/−0.73 μA/cm$^2$) reflects about 30% of the $\Delta Isc_{(cAMP)}$ and $\Delta Isc_{(glyH)}$ observed in non-CF HAE. Expression of hCFTR protein on the apical surface of AV2/HBc.CBAhCFTR infected CF HAE was also confirmed by immunofluorescent staining (FIG. 6C). Little immunoreactivity was observed in the AV2/HBc.F5tg83Luc infected samples, as might be expected since ΔF508-CFTR is efficiently degraded in primary CF HAE (Flotte, 2001).

Discussion

The newly discovered and partially characterized HBoV1 provides several potential attractive advantages for the design of CF airway gene therapy vectors. First, wild-type HBoV1 efficiently infects HAE from the apical surface at extremely low MOIs, suggesting that its capsid proteins are highly adapted for airway infection. Second, wild-type HBoV1 has a genome of 5500-nt, suggesting that larger CFTR expression cassettes could be efficiently packaged into a recombinant HBoV1 virus. For these reasons, we successfully generated both replication-defective rHBoV1 and pseudotyped rAAV2/HBoV1 vectors and studied their transduction profiles in HAE. Our findings demonstrate that rAAV2/HBoV1 vectors may indeed be an attractive alternative to rAAV vectors for gene therapy of CF. Additionally, our studies evaluating these new recombinant HBoV1-based vectors have uncovered interesting biology regarding how polarization/differentiation influences HBoV1 capsid-mediated infection and transduction from the apical and basolateral membranes of HAE.

Although cross-genera parvovirus pseudopackaging has been known to be possible for some time, the efficiency appears much higher for HBoV1-based vectors. For example, the efficiency of the rAAV2 genome encapsidation in parvovirus B19 capsids yields viral titers of about $10^9$ DRP/ml (Ponnazhagan et al., 1995), while yields of rAAV2/HBoV1 vectors are about $2\times10^{11}$ DPR/ml. Yields of rAAV2/HBoV1 were slightly higher (about 2-4 fold) than that for rHBoV1, but similar to that of wild type HBoV1 production in HEK 293 cells following transfection of the infectious clone pIHBoV1 (Huang et al., 2012). However, it remains clear that improvements in viral packaging are still needed, as the yield of rAAV2/HBoV1 vectors remains about 10% of the level for rAAV2.

One unique aspect of the HBoV1 capsid is the fact it more efficiently transduces (>100-fold) polarized airway epithelia from the apical surface as compared to the basolateral surface. This membrane polarity of HAE transduction is distinct from all other rAAV serotypes studied to date. For example, rAAV2, rAAV5, and rAAV6 preferentially transduce HAE from basolateral membrane with about 100-fold preference (Yan et al., 2013; Yan et al., 2006; Duan et al., 1998), while rAAV1 demonstrates an equal preference for transduction from both apical and basolateral membranes (Yan et al., 2006). In the context of HBoV1 capsid, polarization appears to be key to induce viral receptors and/or co-receptors required for efficient transduction from the apical membrane. Indeed, enhanced viral genome uptake from the apical, as compared to basolateral, membranes of polarized CuFi epithelia suggests that the expression of an HBoV1 receptor(s) is likely regulated by polarization. The ability of proteasome inhibitors to effectively enhance rAAV2/HBoV1 transduction from the apical, but not basolateral, membrane also suggests that infection from these two membranes differs with respect to capsid processing biology of internalized HBoV1 virions.

Figure 7:
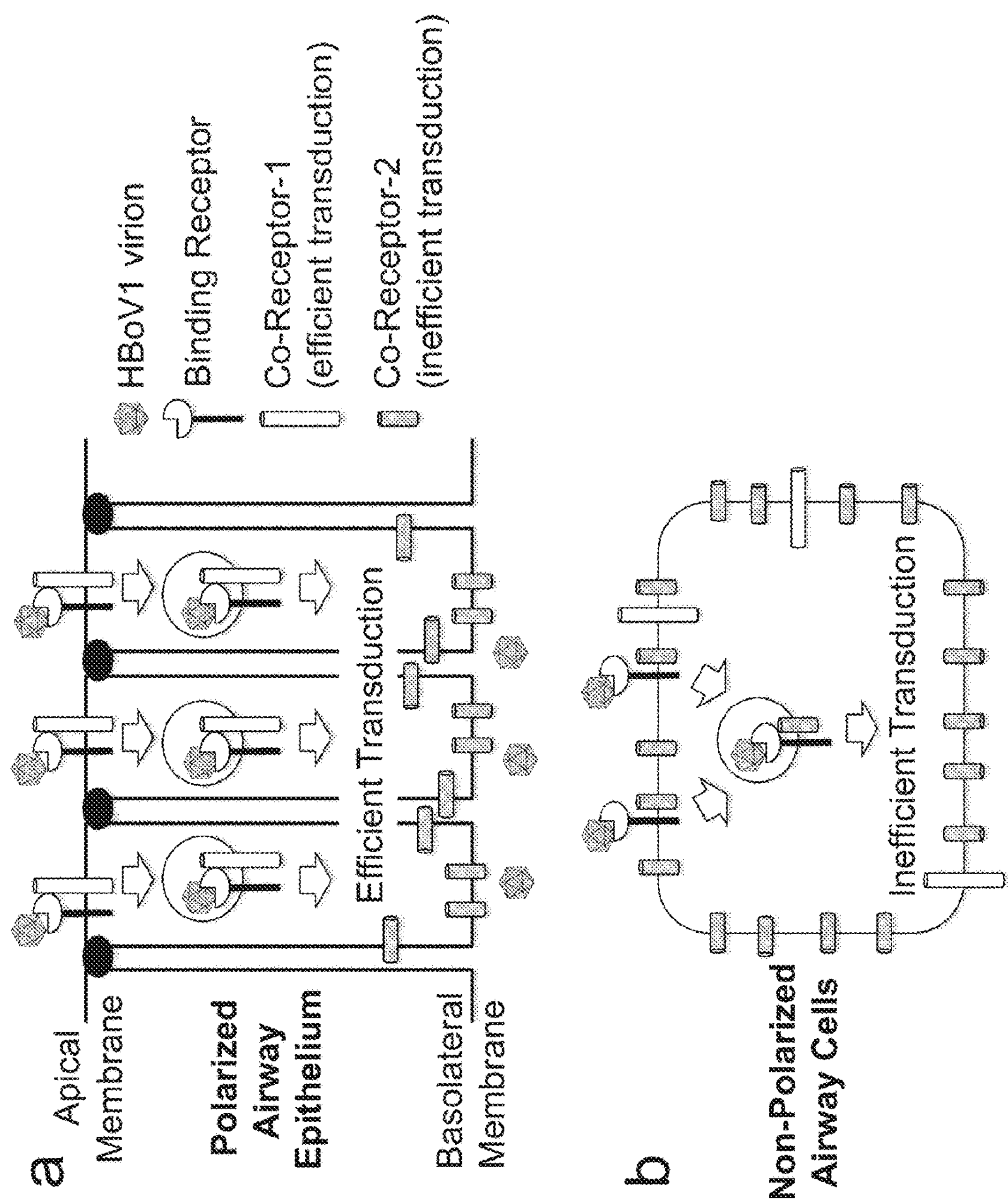

Interestingly, the process of HBoV1 infection of non-polarized CuFi cells represents a biologic process that is uniquely different from that of apical or basolateral infection of polarized cells. In this context, CuFi monolayers exhibit efficient uptake of rAAV2/HBoV1, as seen following apical infection of CuFi ALI cultures, but largely lack proteasome responsiveness as observed following basolateral infection of CuFi ALI cultures. One potential explanation for these findings might be the partitioning of certain binding receptor and co-receptor pairs at the apical membrane that route virus to be productively processed through a proteasome-interacting pathway (FIG. 7). For example, following polarization, a binding receptor/co-receptor that efficiently processes internalized virus may be shuttled to the apical membrane, resulting in low viral uptake from the basolateral membrane (FIG. 7A). In the case of CuFi monolayers, efficient binding receptors may remain on the surface and interact with a more abundant second co-receptor that shuffles virus to an intracellular compartment that is less efficient for transduction and non-responsive to proteasome inhibition (FIG. 7B). This second inefficient co-receptor may be sequestered in the basolateral membrane of polarized cells, thus preventing interference with apical infection (FIG. 7A). This is only one scenario of many, and assumes the expression of binding receptors and co-receptors do not change following polarization. Alternative explanations for the differences in transduction biology between the three CuFi models may involve uniquely expressed binding receptors and/or co-receptors that are influences by polarization and differentiation.

Like most rAAV serotypes, rAAV2/HBoV1 transduction of primary HAE from the apical membrane was significantly enhanced (>1000 fold) by the addition of proteasome inhibitors at the time of apical infection (FIG. 5B). Proteasome inhibitors have been shown to enhance trafficking of rAAV virions to the nucleus by promoting ubiquitination of the capsid (Yan et al., 2002) and our results demonstrating no change in rAAV2/HBoV1 viral uptake following proteasome inhibitor treatment are consistent with action at a post-entry point following infection. However, it remains unclear if the mechanism of the proteasome-sensitive post-entry barrier is similar for rAAV and HBoV1 virions. For example, although we observed similar patterns of cytoplasmic and nuclear distribution between the rAAV2/HBoV1 and rAAV2/1 following apical infection of primary HAE, rAAV2/HBoV1 was about 10-fold more sensitive to enhancement of transduction by proteasome inhibitors than previous observed for rAAV1 (Yan et al., 2006). Differences in the mechanism of virion processing and uncoating between rAAVs and HBoV1 may be responsible for these observations and warrants further investigation.

One of the most important differences between rAAV2/HBoV1 and rAAV vectors is the packaging capacity for a transgene cassette. rAAV2/HBoV1 vectors can carry genomes up to 5.5 kb as compared to 4.9 kb for rAAV vectors. Although the upper limit of genome packaging within HBoV1 capsids was not evaluated in this study, the 12% increase in genome size (600 bp) is very significant for delivery of CFTR expression cassettes. rAAV2/HBoV1 packaging enabled the use of a strong CBA promoter-driven CFTR expression cassette, and resulted in very reasonable correction of CFTR-dependent chloride currents in CF HAE. Based on the ability of rAAV to effectively package 5% more DNA than the wild type genome, it is reasonable to expect that HBoV1-based vectors may be capable of efficiently packaging genomes up to 5.8 kb in length. Additionally, it may be possible to encapsidate self-complementary (sc) double-stranded forms of rAAV genomes (2.7 to 2.8 kb in length) into HBoV1 capsids.

In conclusion, two new types of recombinant HBoV1-based vectors were developed for efficient gene therapy to the human airway. However, chimeric rAAV2/HBoV1 vectors have three clear advantages over the authentic rHBoV1 vectors for human gene therapy. First, rAAV2/HBoV1 vector yields were significantly greater in an HEK293 cell production system than that for rHBoV1. Second, the rAAV2 genome has already been used in clinical trials and avoids potential safety concerns that might accompany use of a new viral genome. Third, the application of rHBoV1 vectors could be hampered by the potential for contamination of replication-competent virus in the vector stocks, which could be generated through homologous recombination of helper plasmids. This later concern is likely theoretical as we did not observe cytopathology in HAE following infection with rHBoV1. Nonetheless, further vector development is required for the application of rHBoV1 to both minimize the potential for replication-competent virus and improve vector yields.

Despite the promise of this new rAAV2/HBoV1 vector system, several unknowns require further investigation prior to considering clinical applications. For example, is there pre-existing airway humoral immunity to HBoV1 caspids in most CF patients, and if so, does this impact rAAV2/HBoV1 infection? Studies have suggested that approximately 71% of humans ranging from birth to 41 years of age contain circulating antibodies against HBoVs (Schildgren et al., 2005), however, nothing is known concerning neutralizing antibodies to this virus in the airway. Given that HBoV1 infections primarily occur within the first year of life, it is assumed that such immunity is protective to secondary infections. However, the frequent detection of HBoVs in stool from both healthy children and adults, as well as seroepidemiology studies, suggests that viral shedding can occur for long periods and/or patients can have frequent recurrent infections (Kapoor et al., 2010). Secondary infections or anamnestic immune responses also appear to commonly occur, and while HBoV1 primary infections are strongly associated with respiratory illness, secondary immuno-activation by HBoV1 is not (Meriluoto et al., 2012). It remains unclear whether such humoral immunity can prevent infection from the airway surface or acts to limit replication and spread of HBoV1 (Korner et al., 2011). The fact that wild type HBoV1 shows long-term and low-level persistence in the respiratory tract following primary infection (Martin et al., 2010; Allander et al., 2005) suggests that this virus may have methods of evading immune detection. The development of rHBoV1 and rAAV2/HBoV1 vectors should enable such questions to be addressed using HAE reconstitution experiments combining recombinant reporter virus with serum or bronchioalveolar lavage samples from HBoV1 infected patients. Despite these unknowns, the development of HBoV1-based recombinant vectors may have unique utilities for CF gene therapy and/or vaccination of infants to protect from wild type HBoV1 infections.

Interestingly, the process of HBoV1 infection of non-polarized CuFi cells represents a biologic process that is uniquely different from that of apical or basolateral infection of polarized cells. In this context, CuFi monolayers exhibit efficient uptake of rAAV2/HBoV1, as seen following apical infection of CuFi ALI cultures, but largely lack proteasome responsiveness as observed following basolateral infection of CuFi ALI cultures. One potential explanation for these findings might be the partitioning of certain binding receptor and co-receptor pairs at the apical membrane that route virus to be productively processed through a proteasome-interacting pathway (FIG. 7). For example, following polarization, a binding receptor/co-receptor that efficiently processes internalized virus may be shuttled to the apical membrane, resulting in low viral uptake from the basolateral membrane (FIG. 7A). In the case of CuFi monolayers, efficient binding receptors may remain on the surface and interact with a more abundant second co-receptor that shuttles virus to an intracellular compartment that is less efficient for transduction and non-responsive to proteasome inhibition (FIG. 7B). This second inefficient co-receptor may be sequestered in the basolateral membrane of polarized cells, thus preventing interference with apical infection (FIG. 7A). This is only one scenario of many and assumes the expression of binding receptors and co-receptors do not change following polarization. Alternative explanations for the differences in transduction biology between the three CuFi models may involve uniquely expressed binding receptors and/or co-receptors that are influences by polarization and differentiation.

Like most rAAV serotypes. rAAV2/HBoV1 transduction of primary HAE from the apical membrane was significantly enhanced (>1000 fold) by the addition of proteasome inhibitors at the time of apical infection (FIG. 5B). Proteasome inhibitors have been shown to enhance trafficking of rAAV virions to the nucleus by promoting ubiquitination of the capsid (Yan et al., 2002) and our results demonstrating no change in rAAV2/HBoV1 viral uptake following proteasome inhibitor treatment are consistent with action at a post-entry point following infection. However, it remains unclear if the mechanism of the proteasome-sensitive post-entry barrier is similar for rAAV and HBoV1 virions. For example, although similar patterns of cytoplasmic and nuclear distribution were observed between the rAAV2/HBoV1 and rAAV2/1 following apical infection of primary HAE, rAAV2/HBoV1 was about 10-fold more sensitive to enhancement of transduction by proteasome inhibitors than previous observed for rAAV1 (Yan et al., 2006). Differences in the mechanism of virion processing and uncoating between rAAVs and HBoV1 may be responsible for these observations and warrants further investigation.

One of the most important differences between rAAV2/HBoV1 and rAAV vectors is the packaging capacity for a transgene cassette. rAAV2/HBoV1 vectors can carry genomes up to 5.5 kb as compared to 4.9 kb for rAAV vectors. Although the upper limit of genome packaging within HBoV1 capsids was not evaluated in this study, the 12% increase in genome size (600 bp) is very significant for delivery of CFTR expression cassettes. rAAV2/HBoV1 packaging enabled the use of a strong CBA promoter-driven CFTR expression cassette, and resulted in very reasonable correction of CFTR-dependent chloride currents in CF HAE. Based on the ability of rAAV to effectively package about 5% more DNA than the wild type genome, it is reasonable to expect that HBoV1-based vectors may be capable of efficiently packaging genomes up to 5.8 kb in length.

In conclusion, two new types of recombinant HBoV1-based vectors were developed for efficient gene therapy to the human airway. However, chimeric rAAV2/HBoV1 vectors have three clear advantages over the authentic rHBoV1 vectors for human gene therapy. First, rAAV2/HBoV1 vector yields were significantly greater in an HEK293 cell production system than that for rHBoV1. Second, the rAAV2 genome has already been used in clinical trials and avoids potential safety concerns that might accompany use of a new viral genome. Third, the application of rHBoV1 vectors could be hampered by the potential for contamination of replication-competent virus in the vector stocks, which could be generated through homologous recombination of helper plasmids. This later concern is likely theoretical as cytopathology in HAE was not observed following infection with rHBoV1.

Example 4

Figure 10A:
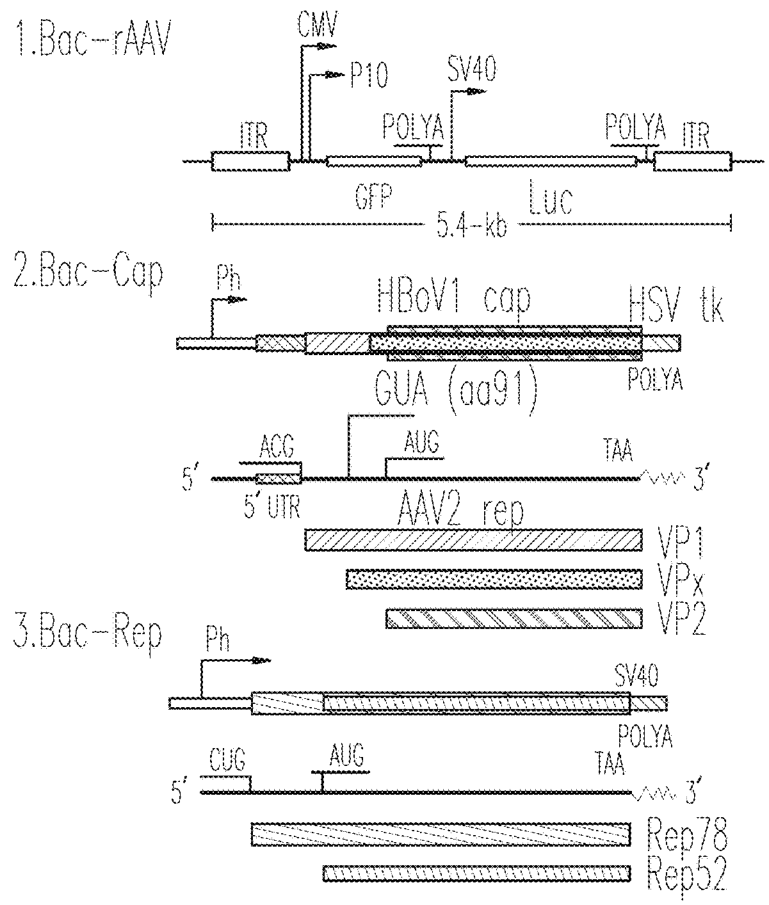
Figure 10B:
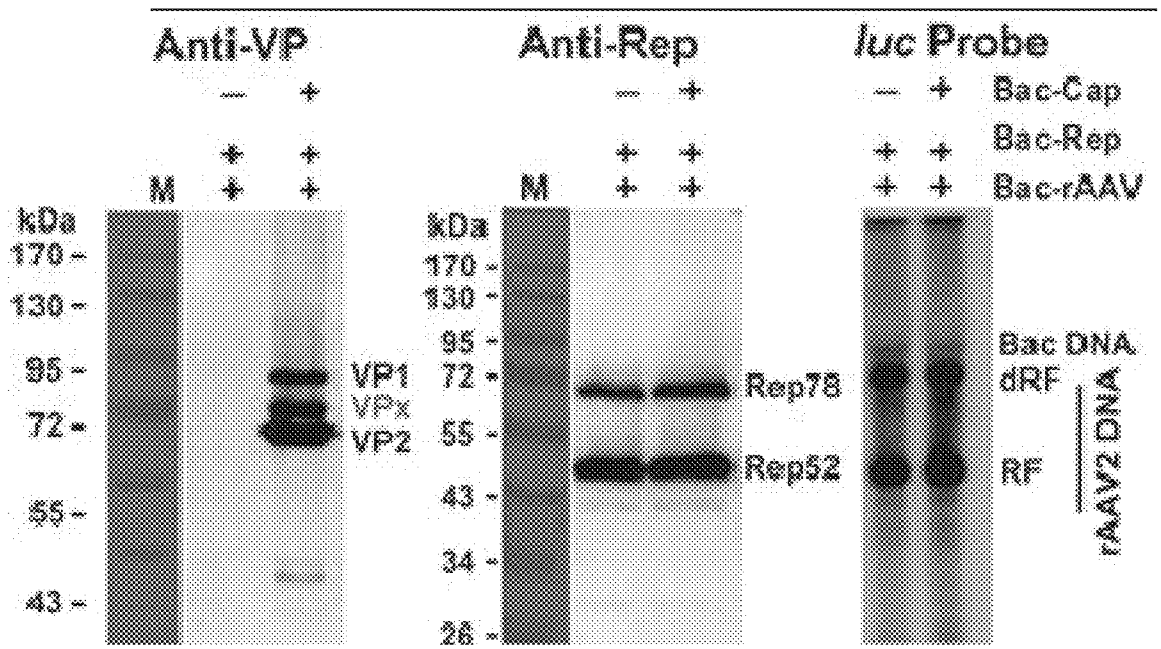
Figure 10C:
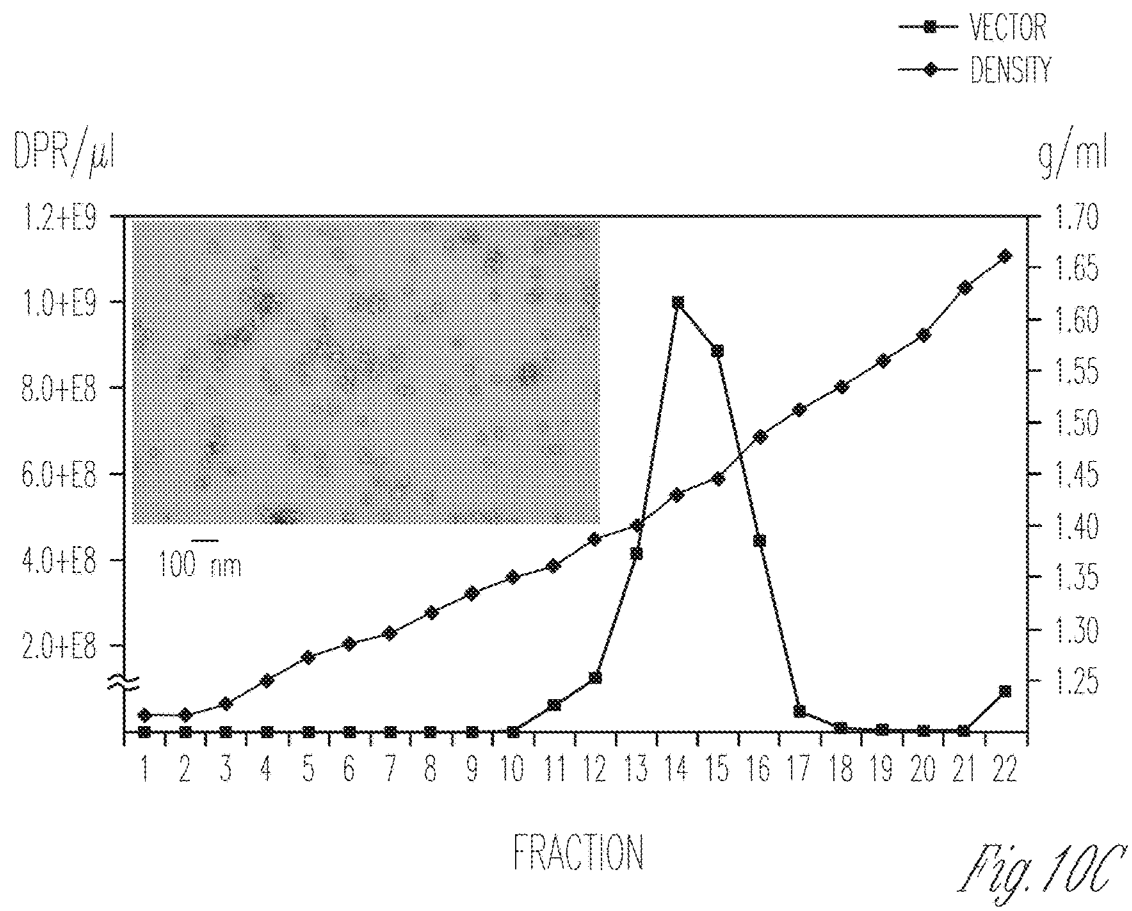
Figure 10D:
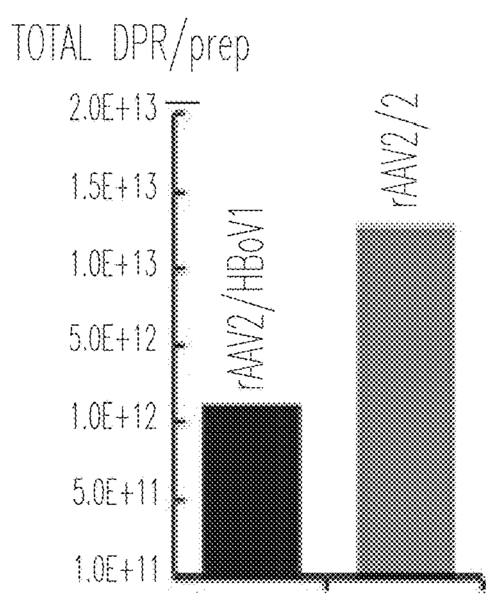
Figure 10E:
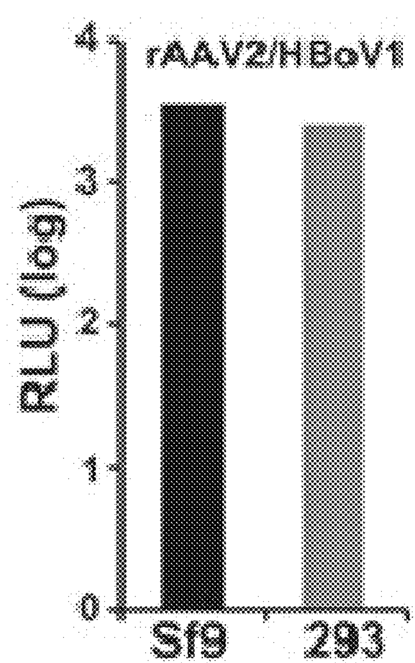

An optimized HBoV1 capsid helper, pCMVHBoV1 NS1 (−)Cap (FIG. 10A), in which a strong CMV promoter was used and the NS1 ORF was terminated early, yielded a significant increase in production (to about $1.5\times10^{12}$ DRP/20 145-mm plates of transfected HEK293 cells), a level comparable to that for rAAV2/2 (FIG. 9C). As rAAV vector production in Sf9 insect cells with baculovirus expression vector (BEV) is highly efficient and linearly scalable, a BEV-based rAAV2/HBoV1 vector production system was established to further increase yield. Specifically, the following BEV vectors were constructed (FIG. 10A): AAV2 Rep helper baculovirus (Bac-Rep), which expresses AAV2 Rep78/Rep52; HBoV1 Cap helper virus (Bac-Cap), which expresses HBoV1 capsid proteins VP1, VPx, and VP2; and transfer vector (Bac-rAAV), which contains an rAAV2 genome. The expression of these vectors and their ability to promote replication of the rAAV2 genome were confirmed (FIG. 10B). Co-infection of 200 mL of Sf9 cell culture ($2\times10^{6}$ cells/mL) with an equal MOI (5 pfu/cell) of each virus produced vector at a yield of $1\times10^{12}$ DRP (FIGS. 10C&D), and the vectors produced from Sf9 and 293 cells had a similar ability to transduce CuFi-ALI (FIG. 10E). These results demonstrate that infectious rAAV2/HBoV1 vector can be produced in the BEV-Sf9 cell system as efficiently as in the optimized 4-plasmid co-transfected-293 cell system (FIG. 9). Even before optimization, the production of rAAV2/HBoV1 vector from Sf9 cells achieved 10% of the yield of rAAV2/2 vector from Sf9 cells (FIG. 10D). As rAAV vector production in Sf9 cells can be scaled up using a bioreactor and further increased using a rep- and cap-expressing Sf9 cell line, it was hypothesized that rAAV2/HBoV1 production in a bioreactor can be increased a further ten fold, to a yield above $10^{14}$ DRP per liter of Sf9 cell culture.

Increased packaging capability is one of the key advantages of the rAAV2/HBoV1 vector, especially with respect to regulating expression of the CFTR gene in the HAE. Although an oversized rAAV2 genome (5.5 kb) can be encapsidated in the HBoV1 capsid to enable effective expression of FL-CFTR ORF under the control of a strong CBA promoter, expansion by a further 5% would make it possible to utilize the FOXJ1 promoter, which drives expression in the ciliated cells of the airway epithelium (Verdiev & Descoates, 1999), and to also incorporate most of the key sequences of the CFTR 3'UTR (microRNA-targeting sites) into the rAAV2 genome for appropriate regulation of CFTR expression.

The HBoV1 capsid packaged a larger rAAV2 genome of 5.9 kb without a significant loss vector production (FIG. 11). And as shown in FIG. 12, the rAAV2/HBoV1 vector efficiently transduced ciliated and K18-positive epithelial cells in HAE-ALI cultures.

Example 5 rAAV2/HBoV1 Vectors Encoding a Human Full-Length CFTR ORF.

Due to limitations of the packaging capacity of rAAV, an 83-bp synthetic promoter (tg83) was used to drive expression of the FL-CFTR ORF in AV2/2.tg83-CFTR (FIG. 13B). A screen of a synthetic oligonucleotide (about 100 bp) library of >50,000 unique sequences (Schalabach et al., 2010) for short enhancers revealed that the F5 enhancer raises tg83 promoter activity to a level as high as 60% of that of the strong CMV promoter in HAE-ALI (FIG. 13A). This promoter was engineered into the AV2/HBc.F5tg83luc and AV2.HBc.F5tg83luc-CMVmcherry (FIG. 12) vectors. Incorporation of the short (185-nt) but efficient F5tg83 promoter for CFTR expression in rAAV2/2 vectors necessitates the use of a shortened CFTR ORF, for example a partial deletion (159 bp) at the R-domain [CFTR(ΔR)] (Ostedgaard et al., 2002; Gillen et al., 2011), which might compromise CFTR function (FIG. 13B) besides the natural (albeit low) apical tropism of the AAV2/2 vector. However, the F5tg83 could serve as an ideal promoter for driving expression of the FL-CFTR ORF in the rAAV2/HBoV1 vector. The AV2/HBc.F5tg83hCFTR vector has at least 600 bp of space for further optimization of regulatory CFTR expression. By incorporating a short CFTR 3'UTR sequence that contains targeting sites for microRNAs that have been reported to regulate CFTR expression, e.g., miR101, miR-145 and miR-494 (Gillen et al., 2011; Megiorni et al., 2011), the (post-)transcriptional regulation strategy will enable autonomous regulation of CFTR expression, and thus bring about endogenous levels of CFTR expression and more physiologic complementation patterns To incorporate longer regulatory elements, such as a 1-kb ciliated cell-specific promoter, FOXJ1 (Ostrowski et al., 2003) for site-specific CFTR expression from the AV2/HBc.FOXJ1hCFTR vector of 5.8 kb (FIG. 13C), needs an expandable package capacity of HBoV1 capsid.

To generate new rAAV2 constructs to be pseudotyped in the HBoV1 capsid (AV2.F5tg83hCFTR, AV2.F5tg83hCFTR(plus) and AV2.FOXJ1hCFTR) (FIG. 13C) and to compare their effectiveness in correcting the CFTR-specific $Cl^-$ defect with AV2/HBc.CBAhCFTR, the functionalities of the new vectors in CuFi-ALI derived from the immortalized human CF airway cell line CuFi8 (genotype: ΔF508/ΔF508) are tested. The changes of short circuit current (Isc) for the complementation of cAMP-regulated $Cl^-$ channel activities are measured, and the levels of fully processed CFTR protein on the apical surface at 10 days p.i. examined. To test the hypothesis that the expression of CFTR at a more physiologic level will restore CFTR activity, side-by side comparative assessments of CFTR expression levels and function in CF xenografts infected using these vectors with four vector doses spanning a 50-fold range is conducted. Transepithelial potential differences (TEPDs) are measured to assess the level of CFTR complementation. Then airway fluid is harvested for in vitro bacterial killing assays, as well as in vivo bacterial challenge experiments assessing bacterial clearance (at termination of the experiment). Expression of CFTR on the surface epithelium will be quantified by IF staining at the apical membrane, using Metamorph software and/or immunoprecipitation kinase assays for the fully-processed B and C. Vector-derived CFTR mRNA and the number of intracellular vector genome copies (vgc) in graft samples will be quantified by qPCR, as described by our laboratory previously.

Most of the CFTR mutations that are associated with severe CF lung disease are located downstream of exon 10 (FIG. 14C). The SMaRT approach would repair CFTR malfunction at the mRNA level, and would affect only those cells that express CFTR endogenously. This repair technique relies on hybridization of intronic domains in the vector-derived pre-mRNA and the endogenous CFTR pre-mRNA to trigger a trans-splicing process that reconstitutes a mutation-free CFTR mRNA. Vector AV2.CMV-PTM24CF (FIG. 14A) encodes a pre-therapeutic RNA molecule (PTM), which consists of an optimized trans-spicing domain (FIG. 14B) and CFTR exons 10-26. The trans-spicing domain targets a PTM24-complementary/binding RNA sequence (binding domain=BD) near the 3' splice site (SS) of intron 9, resulting in trans-splicing from the 5'SS of intron 9 of the endogenous (defective) CFTR pre-mRNA to the 3'SS of the PTM RNA, and subsequently to production of a functional CFTR mRNA (FIG. 14C). The effectiveness of the PTM in AV2.CMV-PTM24CF has been validated in CF (ΔF508/ΔF508) HAE-ALI (Ostrowski et al., 2003). The high efficiency of apical transduction and the expanded genome capacity of the rAAV2/HBoV1 vector may overcome the problem of the inherent weakness of the rAAV vector with respect to correcting CFTR expression through the SMaRT approach, and that a fully-reconstituted CFTR mRNA with an intact 3'UTR (1,557 bp) (Ostrowski et al., 2003) provides precisely regulated CFTR protein expression at endogenous level through post-transcriptional regulation, e.g., regulation by miRNAs.

The effectiveness of a 5.55 kb rAAV2 PTM genome, AV2.CBA-PTM24CF-3UTR, in rescuing CFTR function is tested (FIG. 14D). While retaining the already optimized PTM trans-splicing domain from the first-generation vector (AV2.CMV-PTM24CF), this genome also includes a 1.5 kb 3'UTR of the CFTR cDNA and use the CBA promoter instead of the CMV promoter. AV2.CBA-PTM24CF, which does not transcribe the 3'UTR, will serve as a control. The rAAV2 genomes AV2.CBA-PTM24CF-3UTR and AV2.CBA-PTM24CF are pseudotyped, using the HBoV1 capsid for its high packaging capacity and efficient apical transduction. These rAAV2/HBoV1 PTM vectors are apically applied to CF HAE-ALI cultures at an MOI of 5 k, and the functional correction of CFTR expression will be assessed at 3 days and 1 week p.i. At 4 weeks p.i., the experiment will be terminated and in vivo bacterial challenge assays will be conducted to assess bacterial clearance in the grafts.

REFERENCES

Agbandje-McKenna et al., *Methods Mol. Biol.,* 807:47 (2011).

Aitken et al., *Hum. Gene Ther.* 12:1907 (2001).

Allander et al., *Clin. Infect. Dis.,* 44:904 (2007).

Allander et al., *Proc. Natl. Acad. Sci. USA,* 102:12891 (2005).

Allander, et al., *Clin. Infect. Dis.* 44:904 (2007).

Arthur et al., *PLoS Pathog.* 5:e1000391 (2009).

Ayers et al., *Eur. Respir. J.,* 1:58 (1988).

Berns, *Microbiol. Rev.* 54: 316 (1990).

Blessing et al., *Pediatr. Infect. Dis. J.* 28:1018 (2009).

Brieu et al., *Pediatr. Infect. Dis. J.,* 27:969 (2008).

Calvo et al., *Acta. Paediatr.* 99:883 (2010).

Carson et al., *N. Engl. J. Med.* 312:463 (1985).

Carter, *Human Gene Ther.* 16:541 (2005).

Chen et al. *Virology,* 403: 145 (2010).

Chen et al., *J. Virol.,* 60:1085 (1986).

Chen et al., *J. Virol.* 84:5615 (2010).
Chen et al., *PLoS Pathos.* 7:e1002088 (2011).
Chen et al., *Virology,* 403:145 (2010).
Cheng et al., *J. Virol.* 84:2687 (2010)
Christensen et al., *J. Clin. Virol.* 49:158 (2010).
Cotmore et al., *Adv. Virus Res.* 33:91 (1987).
Cotmore et al., in: DePamphilis, M (ed). DNA replication in eukaryotic cells. Cold Spring Harbor Laboratory Press: Cold Spring Harbor, N.Y. pp 799 (1996).
Cotmore et al., In: Kerr J, Cotmore S F, Bloom M E, Linden R M, Parrish C R, editors. Parvoviruses. London: Hoddler Arond. pp. 171 (2005).
Cozens et al., *Am. J. Respir. Cell Mol. Biol.,* 10:38 (1994).
Deng et al., *J. Virol.* 87:4097 (2013).
Deng et al., *PLoS One* 7:e34353 (2012).
Dijkman et al., *J. Virol.* 83:7739 (2009).
Ding et al., *Gene Ther.,* 12:873 (2005).
Ding et al., *Mol. Ther.* 13:671 (2006).
Don et al., *Pediatr. Pulmonol.* 45:120 (2010).
Dong et al., *Hum. Gene Ther.,* 7: 2101 (1996).
Driskell et al., *Annu. Rev. Physiol.* 65:585 (2003).
Duan et al., *Hum. Gene Ther.* 9:2761 (1998).
Duan et al., *J. Clin. Invest.* 105:1573 (2000).
Duan et al., *J. Virol.,* 72:8568 (1998).
Duan et al., *J. Virol.* 75:7662 (2001).
Edner et al., *J. Clin. Microbiol.* 50:531 (2011).
Excoffon et al., *Proc. Natl. Acad. Sci. U.S.A.* 106:3865 (2009).
Fisher et al., *J. Biol. Chem.,* 287:21673 (2012).
Flotte et al., *Mol. Ther.* 18:594 (2010).
Flotte et al., *Mol. Ther.* 18:594 (2010).
Flotte, *Curr. Opin. Mol. Ther.* 3:497 (2001).
Futcher et al., *Methods Mot Med.,* 107:183 (2005).
Garcia-Garcia et al., *Pediatr. Pulmonol.* 45:585 (2010).
Gillen et al., *Biochem. J.* 438:25 (2011).
Giorgi et al., *Pediatr. Pulmonol.,* 14:201 (1992).
Gonzalez-Mariscal et al., *Proci. Biophys. Mol. Biol.,* 81:1 (2003).
Griesenbach et al., *Virus Adaptation and Treatment* 2:159 (2010).
Guan et al., *J. Virol.,* 83:9541 (2009).
Gurda et al., *J. Virol.,* 84:5880 (2010).
Hao et al., *J. Virol.* 86:13524 (2012).
Holt et at, *Nat. Rev. Immunol.* 8:142 (2008).
Huang et at, *PLoS Pathos.,* 8:e1002899 (2012a).
Huang et at, *Virology,* 426:167 (2012b).
Jartti et al., *Rev. Med. Virol.,* 22:46 (2011).
Kahn, *Curr. Opin. Pediatr.* 20:62 (2008).
Kantola et at, *Clin. Infect. Dis.* 46:540 (2008).
Kantola et at, *J. Clin. Microbiol.,* 48:4044 (2010).
Kantola et at, *J. infect. Dis.,* 204:1403 (2011).
Kapoor et al., *J. Infect. Dis.* 199:196 (2009).
Kapoor et al., *J. Infect. Dis.* 201:1633 (2010).
Kapoor et at, *PLoS ONE,* 6:e21362 (2011).
Kapoor et at, *J Gen Virol.,* 93:341 (2012).
Kapranov et at, *Hum. Gene Ther.,* 23:46 (2012).
Karp et at, *Methods Mol. Biol.,* 188:115 (2002).
Korner et al., *Emerp. Infect. Dis.,* 17:2303 (2011).
Lau et al., *J. Gen. Virol.,* 93:1573 (2012).
Lehtoranta et al., *Int. J. Pediatr. Otorhinolaryngol.,* 76:206 (2012).
Leigh et al., *Am. J. Respir. Cell Mot Biol.,* 12:605 (1995).
Li et al., *Mol. Ther.,* 17:2067 (2009).
Li et al., *Virol. J.,* 10:54 (2013).
Limberis et al., *Mol. Ther.,* 17:294 (2009).
Lin et al., *Infect Agent Cancer,* 2:3 (2007).
Liu et al., *Am. J. Respir. Cell Mol. Biol.,* 36:313 (2007a).
Liu et al., *Gene Ther.,* 14:1543 (2007b).
Liu et al., *J. Virol.,* 78:12929 (2004).
Liu et al., *Mot Ther.,* 15:2114 (2007c).
Lopez et al., *Lancet,* 367:1747 (2006).
Luo et al., *J. Virol.,* 85:133 (2011).
Lusebrink et al., *PLoS ONE,* 6:e19457 (2011).
Malecki et al., *Future Virol.,* 6:1107 (2011).
Martin et al., *J. Infect. Dis.,* 201:1625 (2010).
Martin et al., *Viruses-Basel,* 3:1699 (2011).
Matrosovich et al., *Proc. Natl. Acad. Sci. USA,* 101:4620 (2004).
McCarty, *Mol. Ther.,* 16:1648 (2008).
McClure et al., *J. Vis. Exp.,* 27:e3348 (2011)
Megiorni et al., *PLoS One,* 6:e26601 (2011).
Mengmen et al., The Scientific World J., article ID 947084, http://dx.doi.org/10.1155/20114/947084 (2014).
Meriluoto et al., *Emerg. Infect. Dis.,* 18:264 (2012).
Mitchell et al., *J. Virol.,* 85:1125 (2011).
Moss et al. *Human Gene Ther.,* 18:726 (2007).
Mueller et al., *Clin. Rev. Allergy Immunol.,* 35:164 (2008).
Nakai et al., *J. Virol.,* 75:6969 (2001).
Nascimento-Carvalho et al., *J. Med. Virol.,* 84:253 (2012).
Norja et al., *J. Med. Virol.,* 84:1276 (2012).
Ostedgaard et al., *Proc. Natl. Acad. Sci. U.S.A.,* 102:2952 (2005).
Ostedgaard et at, *Proc. Natl. Acad. Sci. USA,* 99:3093 (2002).
Ostrowski et at, *Mol. Ther.,* 8:637 (2003).
Palermo et al., *J. Virol.,* 83:6900 (2009).
Plevka et at, *J. Viral.,* 85:4822 (2011).
Ponnazhagan et at, *J. Virol.,* 72:5224 (1998).
Pyrc et al., *J. Virol.,* 84:11255 (2010).
Qiu et at, *J. Virol.,* 80:654 (2006).
Qiu et al., *J. Virol.,* 81:12080 (2007).
Qiu et at, *Mol. Cell Biol.,* 22:3639(2002).
Reina et at, *J. Clin. Pathol.,* 54:924 (2001).
Rommens et at, *Science* 245:1059 (1989).
Rowe et at, *N. Engl. J. Med.* 352:1992 (2005).
Schildgen et at, *Clin. Microbiol. Rev.,* 21:291 (2008).
Schildgen et at, *Future Virol.,* 7:31 (2012).
Schlabach et al., *Proc. Natl. Acad. Sci. USA,* 107:2538 (2010).
Shay et at, *JAMA,* 282:1440 (1999).
Sims et at, *J. Virol.,* 79:15511 (2005).
Soderlund-Venermo et at, *Emerg. Infect. Dis.,* 15:1423 (2009).
Streiter et at, *Virol. J.,* 8:417 (2011).
Sun et al., *J. Virol.,* 83:3956 (2009).
Tijssen et al., In: King A M, Lefkowitz E, Adams M J, Carstens E B, editors. Virus Taxonomy: Ninth Report of the International Committee on Taxonomy of Viruses. London: Elsevier. pp. 405 (2012).
Tijssen et al., In: King, M, Adams, M J., Carstens, E. and Lefkowitz E J. (ed). Parvoviridae. Elsevier: San Diego (2010).
Tijssen et al., Parvoviridae, In: M. Q. King, M. J. Adams, E. Carstens, and E. J. Lefkowitz (eds.), Virus taxonomy: classification and nomenclature of viruses: Ninth Report of the International Committee on Taxonomy of Viruses. Elsevier, San Diego (2011).
Tristram et al., *Arch. Otolaryngol. Head Neck Sure.,* 124:777 (1998).
Ursic et al., *J. Clin. Microbiol.,* 49:1179 (2011).
Ursic et al., *J. Med. Virol.,* 84:99.
Verdier & Descotes, *Toxicol. Sci.,* 47:9 (1999).
Villenave et al., *Proc. Natl. Acad. Sci. U.S.A.,* 109:5040 (2012).

Wagner et al., *Human Gene Ther.,* 13:1349 (2002).
Wang et al., *J. Clin. Virol.,* 47:148 (2010).
Wang et al., *J. Gene Med.,* 1:22 (1999).
Wang et al., *J. Virol.,* 74:9234 (2000).
Widdicombe et al., *Respir. Phvsiol.,* 99:3 (1995).
Wobbe et al., *Proc. Natl. Acad. Sci. USA,* 82:5710 (1985).
Wu et al., *Mol. Ther.,* 18:80 (2010).
Yan et al., Gene Ther June 14: Epub ahead of print. doi: 10.1038/gt.2012.46. PMID:22695783.
Yan et at, *Gene Ther.,* 20:328 (2012).
Yan et al., *J. Biol. Chem.,* 281:29684 (2006).
Yan et at, *J. Virol.,* 76:2043 (2002).
Yan et al., *J. Virol.,* 78:2863 (2004).
Yan et at, *J. Virology,* 76:2043 (2002).
Zabner et at, *Am. J. Physiol. Lung Cell Mot Physiol.,* 284:L844 (2003).
Zabner et al., *J. Virol.,* 70:6994 (1996).
Zhang et at, *J. Virol.,* 76:5654 (2002).
Zhang et al., *Mol. Ther.,* 10:990 (2004).
Zhang et at, *Proc. Natl. Acad. Sci. USA,* 95:10158 (1998).
Zhang et at, *Virology,* 421:67 (2011).
Zhi et at, *Virology,* 318:142 (2004).
Zhong et at, *Mol. Ther.,* 15:1323 (2007).
Zhong et at, *Virology,* 381:194 (2008).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to express a heterologous gene product in mammalian cells comprising providing isolated chimeric virus comprising human bocavirus (BoV) capsid protein and a recombinant adeno-associated viral (AAV) genome comprising an expression cassette encoding the heterologous gene product; and infecting mammalian cells having the tropism of human bovavirus with the chimeric virus an amount effective to express the heterologous gene product.

2. The method of claim 1 wherein the gene product is a catalytic RNA, a microRNA, RNA pre-transplicing molecule (PTM-RNA), a neutralizing antibody or an antigen binding fragment thereof, a prophylactic gene product, or a polypeptide.

3. The method of claim 1 further comprising contacting the mammalian cells with at least one agent in an amount effective to additively or synergistically enhance rAAV transduction relative to corresponding mammalian cells contacted with the chimeric virus but not the agent.

4. The method of claim 3 wherein the mammalian cells are contacted with the agent before the mammalian cells are contacted with the virus.

5. The method of claim 3 wherein the mammalian cells are cell or contacted with the virus before the mammalian cells are contacted with the agent.

6. The method of claim 1 wherein the gene product encodes a therapeutic protein.

7. The method of claim 1 wherein the rAAV genome is a rAAV-1, rAAV-2, rAAV-3, rAAV-4, rAAV-5, rAAV-6, rAAV-7, rAAV-8 or rAAV-9 genome.

8. The method of claim 1 wherein the gene product is a viral antigen, bacterial antigen, tumor antigen, parasite antigen, or fungal antigen.

9. The method of claim 1 wherein the gene product is cystic fibrosis transmembrane conductance regulator, b-globin, g-globin, tyrosine hydroxylase, glucocerebrosidase, aryl sulfatase A, factor VIII, dystrophin, alpha 1-antitrypsin, surfactant protein SP-D, SP-A or SP-C, erythropoietin, HBoV protein, influenza virus protein, respiratory syncytial virus (RSV) protein, a bacterial protein, a neutralizing antibody or an antigen binding fragment thereof, severe acute respiratory syndrome (SARS) virus protein, interferon (IFN)-alpha, gamma, tumor necrosis factor (TNF), interleukin (IL)-1, IL-17, or IL-6.

10. The method of claim 1 wherein the HBoV is HBoV1.

11. The of claim 1 wherein the BoV is HBoV2.

12. The method of claim 1 wherein the BoV is HBoV3.

13. The method of claim 1 wherein the BoV is HBoV4.

14. The method of claim 1 wherein the heterologous gene product comprises a cystic fibrosis transmembrane conductance regulator.

15. The method of claim 1 wherein the gene product is a therapeutic gene product.

* * * * *

UNITED STATES PATENT AND TRADEMARK OFFICE

CERTIFICATE OF CORRECTION

PATENT NO. : 10,793,835 B2
APPLICATION NO. : 15/822956
DATED : October 6, 2020
INVENTOR(S) : Yan et al.

It is certified that error appears in the above-identified patent and that said Letters Patent is hereby corrected as shown below:

On the Title Page

On page 3, in Column 1, under "Other Publications", Line 32, delete "Pro?le" and insert --Profile-- therefor In the Specification In Column 3, Line 1, delete "vector." and insert --vector,-- therefor In Column 3, Line 55, delete "MV" and insert --AAV-- therefor In Column 4, Line 6, delete "MV" and insert --AAV-- therefor In Column 4, Line 8, delete "MV" and insert --AAV-- therefor In Column 6, Line 41, delete "MV" and insert --AAV-- therefor In Column 8, Line 11, delete "β globin," and insert --β-globin,-- therefor In Column 10, Line 34, delete "(+PI)." and insert --(+PI),-- therefor In Column 11, Line 30, delete "HoBV" and insert --HBoV-- therefor In Column 12, Line 60, delete "(isc)," and insert --(Isc),-- therefor In Column 12, Line 61, delete "Ussing" and insert --Using-- therefor In Column 13, Line 65, delete "MV-8." and insert --AAV-8.-- therefor In Column 13, Line 66, delete "MV" and insert --AAV-- therefor Signed and Sealed this
Sixth Day of September, 2022

Katherine Kelly Vidal

Katherine Kelly Vidal
*Director of the United States Patent and Trademark Office*

In Column 13, Line 67, delete "MV" and insert --AAV-- therefor

In Column 14, Line 19, delete "MV," and insert --AAV,-- therefor

In Column 14, Line 26, delete "MV." and insert --AAV.-- therefor

In Column 14, Line 45, delete "MV" and insert --AAV-- therefor

In Column 16, Line 2, delete "MV" and insert --AAV-- therefor

In Column 16, Line 10, delete "MV" and insert --AAV-- therefor

In Column 20, Line 8, after "See", insert --,--

In Column 20, Line 34, delete "HoBV1" and insert --HBoV1-- therefor

In Column 20, Line 45, delete "MV" and insert --AAV-- therefor

In Column 20, Line 60, delete "MV" and insert --AAV-- therefor

In Column 20, Lines 63-64, delete "(icoshedral" and insert --(icosahedral-- therefor In Column 21, Line 45, delete "MV" and insert --AAV-- therefor In Column 21, Line 64, delete "rAAV2/1-1BoV1-CFTR" and insert --rAAV2/HBoV1-CFTR-- therefor In Column 22, Line 36, delete "MV" and insert --AAV-- therefor In Column 22, Line 38, delete "MV:" and insert --AAV;-- therefor In Column 22, Line 42, delete "MV:" and insert --AAV;-- therefor In Column 22, Line 47, delete "MV" and insert --AAV-- therefor In Column 22, Line 50, delete "MV" and insert --AAV-- therefor In Column 22, Line 51, delete "MV;" and insert --AAV;-- therefor In Column 22, Line 56, delete "MV;" and insert --AAV;-- therefor In Column 22, Line 58, delete "MV;" and insert --AAV;-- therefor In Column 22, Line 61, delete "MV" and insert --AAV-- therefor In Column 22, Line 64, delete "MV." and insert --AAV.-- therefor In Column 23, Line 3, delete “MV;” and insert --AAV;-- therefor In Column 23, Line 14, delete “MV;” and insert --AAV;-- therefor In Column 23, Line 15, delete “MV” and insert --AAV-- therefor In Column 23, Line 33, delete “MV” and insert --AAV-- therefor In Column 23, Line 36, delete “MV.” and insert --AAV.-- therefor In Column 24, Line 54, delete “17” and insert --T7-- therefor In Column 24, Line 60, delete “EIA” and insert --E1A-- therefor In Column 25, Line 3, delete “MV” and insert --AAV-- therefor In Column 25, Line 25, delete “MV” and insert --AAV-- therefor In Column 25, Line 60, delete “MV,” and insert --AAV,-- therefor In Column 26, Line 1, delete “MV” and insert --AAV-- therefor In Column 26, Line 4, delete “MV” and insert --AAV-- therefor In Column 29, Line 15, delete “(immunoprecipitation,” and insert --(immunoprecipitations,-- therefor In Column 38, Line 33, after “IFN-alpha,”, insert --INFγ,--

In Column 39, Line 44, delete “(ATCC CCL-185).” and insert --(ATCC CCL-185),-- therefor In Column 39, Line 60, delete “cm2,” and insert --$cm^2$,-- therefor In Column 40, Line 1, delete “infectibility” and insert --infectability-- therefor In Column 40, Line 2, delete “1,000 V·cm2” and insert --1,000 V·$cm^2$-- therefor In Column 41, Line 22, delete “pi HBoV1NP1(2)” and insert --pIHBoV1NP1(2)-- therefor In Column 41, Line 26, delete “pIHBoV1 VP2(2)” and insert --pIHBoV1VP2(2)-- therefor In Column 41, Line 36, delete “Eta,” and insert --E2a,-- therefor In Column 43, Line 3, delete “GAG” and insert --GAC-- therefor In Column 44, Lines 62-63, delete “pi HBoV1-transfected” and insert --pIHBoV1-transfected-- therefor In Column 45, Line 24, delete "2×10[1]a gc." and insert --$2 \times 10^{10}$ gc.-- therefor In Column 45, Line 50, after "days", insert --p.i.,--

In Column 45, Line 66, delete "b-tubulin" and insert --β-tubulin-- therefor

In Column 46, Line 23, delete "(Reins" and insert --(Reina-- therefor

In Column 47, Line 17, delete "GO" and insert --G0-- therefor

In Column 48, Line 52, delete "Cl2" and insert --$Cl_2$-- therefor

In Column 49, Line 64, delete "chanter." and insert --chamber.-- therefor

In Column 50, Line 40, after "p.i.", insert --.--

In Column 52, Line 58, delete "anti-MV" and insert --anti-AAV-- therefor

In Column 53, Line 17, delete "it" and insert --μl-- therefor

In Column 54, Line 65, delete "131" and insert --13-1-- therefor

In Column 55, Line 46, delete "163" and insert --IB3-- therefor

In Column 57, Line 7, delete "MV," and insert --AAV,-- therefor

In Column 57, Line 14, delete "rAAV2/1-1BoV1" and insert --rAAV2/HBoV1-- therefor In Column 57, Line 23, delete "MV" and insert --AAV-- therefor In Column 58, Line 46, delete "2006:" and insert --2006;-- therefor In Column 59, Line 56, delete "N-acetyl-1-leucyl-1-leucyl-1-norleucine" and insert --*N*-acetyl-l-leucyl-l-leucyl-l-norleucine-- therefor In Column 60, Line 50, delete "TagMan" and insert --TaqMan-- therefor In Column 61, Line 18, delete "(5 fold)" and insert --(5-fold)-- therefor In Column 63, Line 23, delete "shuffles" and insert --shuttles-- therefor In Column 64, Line 1, delete "5%" and insert --~5%-- therefor In Column 65, Line 24, delete "serotypes." and insert --serotypes,-- therefor In Column 68, Line 44, delete "p.i." and insert --p.i..-- therefor In Column 69, Line 33, delete "Futcher" and insert --Fulcher-- therefor In the Claims In Column 185, Line 25, in Claim 1, delete "bovavirus" and insert --bocavirus-- therefor In Column 185, Line 25, in Claim 1, before "an", insert --in--

In Column 185, Line 42, in Claim 5, after "are", delete "cell or"

In Column 186, Line 33, in Claim 9, delete "gamma," and insert --IFN-gamma,-- therefor In Column 186, Line 36, in Claim 11, before "of", insert --method--

SEQUENCE LISTING

```
<160> NUMBER OF SEQ ID NOS: 46

<210> SEQ ID NO 1
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 1

gcacagccac gtgacgaa                                                   18


<210> SEQ ID NO 2
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 2

tggactccct tttcttttgt agga                                            24


<210> SEQ ID NO 3
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 3

tgagctcagg gaatatgaaa gacaagcatc g                                    31


<210> SEQ ID NO 4
<211> LENGTH: 22
<212> TYPE: DNA
<213> ORGANISM: Human bocavirus

<400> SEQUENCE: 4

gcgccttagt tatatataac at                                              22


<210> SEQ ID NO 5

<400> SEQUENCE: 5

000


<210> SEQ ID NO 6
```

```
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 6

tttttgaagc gaaggttgtg g                                            21


<210> SEQ ID NO 7
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 7

cacacacagt tcgcctcttt g                                            21


<210> SEQ ID NO 8
<211> LENGTH: 32
<212> TYPE: DNA
<213> ORGANISM: Artificial Sequence
<220> FEATURE:
<223> OTHER INFORMATION: A synthetic oligonucleotide

<400> SEQUENCE: 8

atctggatac cgggaaaacg ctgggcgtta at                                32


<210> SEQ ID NO 9
<211> LENGTH: 5543
<212> TYPE: DNA
<213> ORGANISM: Human bocavirus

<400> SEQUENCE: 9

gtggttgtac agacgccatc ttggaatcca atatgtctgc cggctcagtc atgcctgcgc     60

tgcgcgcagc gcgctgcgcg cgcgcatgat ctaatcgccg gcagacatat tggattccaa    120

gatggcgtct gtacaaccac gtcacatata aaataataaa tattcacaag gaggagtggt    180

tatatgatgt aatccataac cactcccagg aaatgacgta tgatagccaa tcagaattga    240

gtattaaacc tatataagct gctgcacttc ctgattcaat cagactgcat ccggtctccg    300

gcgagtgaac atctctggaa aaagctccac gcttgtggtg agtctactat ggctttcaat    360

cctcctgtga ttagagcttt ttctcaacct gcttttactt atgtcttcaa atttccatat    420

ccacaatgga aagaaaaaga atggctgctt catgcacttt tagctcatgg aactgaacaa    480

tctatgatac aattaagaaa ctgcgctcct catccggatg aagacataat ccgtgatgac    540

ttgcttattt ctttagaaga tcgccatttt ggggctgttc tctgcaaggc tgtttacatg    600

gcaacaacta ctctcatgtc acacaaacaa aggaatatgt ttcctcgttg tgacatcata    660

gttcagtctg agctaggaga gaaaaactta cactgccata ttatagttgg gggagaagga    720

ctaagcaaga ggaatgctaa atcatcctgt gctcagttct atggtttaat actagctgaa    780

ataattcaac gctgcaaatc tcttctggct acacgtcctt ttgaacctga agaggctgac    840

atatttcaca ctttaaaaaa ggctgagcga gaggcatggg gtggagttac tggcggcaac    900

atgcaaatcc ttcaatatag agatcgcaga ggagaccttc atgcacaaac agtggatcct    960

cttcgcttct tcaaaaacta ccttttacct aaaaatagat gtatttcatc ttacagcaaa   1020

cctgatgttt gtacttctcc tgacaactgg ttcattttag ctgaaaaaac ttactctcac   1080

actcttatta acgggctgcc gcttccagaa cattacagaa aaaactacca cgcaacccta   1140
```

```
gataacgaag tcattccagg gcctcaaaca atggcctatg gaggacgtgg tccgtgggaa   1200
catcttcctg aggtaggaga tcagcgccta gctgcgtctt ctgttagcac tacttataaa   1260
cctaacaaaa aagaaaaact tatgctaaac ttgctagaca aatgtaaaga gctaaatcta   1320
ttagtttatg aagacttagt agctaattgt cctgaactac tccttatgct tgaaggtcaa   1380
ccaggagggg cacgccttat agaacaagtc ttgggcatgc accatattaa tgtttgttct   1440
aactttacag ctctcacata tctttttcat ctacatcctg ttacttcgct tgactcagac   1500
aataaagctt tacagctttt gttgattcaa ggctataatc ctctagccgt tggtcacgcc   1560
ctatgctgtg tcctgaacaa acaattcggg aaacaaaaca ctgtttgctt ttacgggcct   1620
gcctcaacag gtaaaacaaa tatggccaag gcaatcgtcc aagggattag actttatggg   1680
tgtgttaatc atttgaacaa aggatttgta tttaatgact gcagacaacg cctagttgtt   1740
tggtgggagg agtgcttaat gcaccaggat tgggtggaac ctgcaaagtg tatcttgggc   1800
gggacagaat gcagaattga cgtcaagcat agagacagtg tacttttaac tcaaacacct   1860
gtaattatat ccactaacca cgatatctac gcggttgttg gtggcaattc tgtttctcat   1920
gttcacgcgg ctccattaaa agaaagagtg attcagctaa attttatgaa acaacttcct   1980
caaacatttg gagaaatcac tgctactgag attgcagctc ttctacagtg gtgtttcaat   2040
gagtacgact gtactctgac aggatttaaa caaaaatgga atttagataa aattccaaac   2100
tcatttcctc ttggggtcct ttgtcctact cattcacagg actttacact tcacgaaaac   2160
ggatactgca ctgattgcgg tggttacctt cctcatagtg ctgacaattc tatgtacact   2220
gatcgcgcaa gcgaaactag cacaggagac atcacaccaa gtaagtaaat acgcatgcgc   2280
aagtaattct tttactttca cttcgctatt tttaccaatt tttactttta ggtgacttgg   2340
gggattcgga cggagaagac accaagcctg agacatcgca agtggactat tgtccaccca   2400
agaaacgtcg tctaactgct ccagcaagtc ctccaaactc acctgcgagc tctgtaagta   2460
ctattacttt ctttaacact tggcacgcac agccacgtga cgaagatgag ctcagggaat   2520
atgaaagaca agcatcgctc ctacaaaaga aaagggagtc cagaaagagg ggagaggaag   2580
agacactggc agacaactca tcacaggagc aggagccgca gcccgatccg acacagtggg   2640
gagagaggct cgggctcata tcatcaggaa cacccaatca gccacctatc gtcttgcact   2700
gcttcgaaga cctcagacca agtgatgaag acgagggaga gtacatcggg gaaaaaagac   2760
aatagaacaa atccatacac tgtattcagt caacacagag cttccaatcc tgaagctcca   2820
gggtggtgtg ggttctactg gcactctact cgcattgcta gagatggtac taattcaatc   2880
tttaatgaaa tgaaacaaca gtttcaacag ctacaaattg ataataaaat aggatgggat   2940
aacactagag aactattgtt taatcaaaag aaaacactag atcaaaaata cagaaatatg   3000
ttctggcact ttagaaataa ctctgattgt gaaagatgta attactggga tgatgtgtac   3060
cgtagacact tagctaatgt ttcctcacag acagaagcag acgagataac tgacgaggaa   3120
atgctttctg ctgctgaaag catggaagca gatgcctcca attaagagac agcctagagg   3180
gtgggtgctg cctggataca gatatcttgg gccatttaat ccacttgata acggtgaacc   3240
tgtaaataac gctgatcgcg ctgctcaatt acatgatcac gcctactctg aactaataaa   3300
gagtggtaaa aatccatacc tgtatttcaa taaagctgat gaaaaattca ttgatgatct   3360
aaaagacgat tggtcaattg gtggaattat tggatccagt ttttttaaaa taaagcgcgc   3420
cgtggctcct gctctgggaa ataaagagag agcccaaaaa agacactttt actttgctaa   3480
```

```
ctcaaataaa ggtgcaaaaa aaacaaaaaa aagtgaacct aaaccaggaa cctcaaaaat   3540

gtctgacact gacattcaag accaacaacc tgatactgta gacgcaccac agaacacctc   3600

agggggagga acaggaagta ttggaggagg aaaaggatct ggtgtgggga tttccactgg   3660

agggtgggtc ggaggttctc acttttcaga caaatatgtg gttactaaaa acacaagaca   3720

atttataacc acaattcaga atggtcacct ctacaaaaca gaggccattg aaacaacaaa   3780

ccaaagtgga aaatcacagc gctgcgtcac aactccatgg acatacttta actttaatca   3840

atacagctgt cacttctcac cacaggattg gcagcgcctt acaaatgaat ataagcgctt   3900

cagacctaaa gcaatgcaag taaagattta caacttgcaa ataaaacaaa tactttcaaa   3960

tggtgctgac acaacataca acaatgacct cacagctggc gttcacatct tttgtgatgg   4020

agagcatgct tacccaaatg catctcatcc atgggatgag gacgtcatgc ctgatcttcc   4080

atacaagacc tggaaacttt ttcaatatgg atatattcct attgaaaatg aactcgcaga   4140

tcttgatgga aatgcagctg gaggcaatgc tacagaaaaa gcacttctgt atcagatgcc   4200

ttttttttcta cttgaaaaca gtgaccacca agtacttaga actggtgaga gcactgaatt   4260

tacttttaac tttgactgtg aatgggttaa caatgaaaga gcatacattc ctcctggact   4320

aatgtttaat ccaaaagttc caacaagaag agttcagtac ataagacaaa acggaagcac   4380

agcagccagc acaggcagaa ttcagccata ctcaaaacca acaagctgga tgacaggacc   4440

tggcctgctc agtgcacaga gagtaggacc acagtcatca gacactgctc cattcatggt   4500

ttgcactaac ccagaaggaa cacacataaa cacaggtgct gcaggatttg gatctggctt   4560

tgatcctcca agcggatgtc tggcaccaac taacctagaa tacaaacttc agtggtacca   4620

gacaccagaa ggaacaggaa ataatggaaa cataattgca aacccatcac tctcaatgct   4680

tagagaccaa ctcctataca aaggaaacca gaccacatac aatctagtgg gggacatatg   4740

gatgtttcca aatcaagtct gggacagatt tcctatcacc agagaaaatc caatctggtg   4800

caaaaaacca agagctgaca aacacacaat catggatcca tttgatggat caattgcaat   4860

ggatcatcct ccaggcacta tttttataaa aatggcaaaa attccagttc caactgcctc   4920

aaatgcagac tcatacctaa acatatactg tactggacaa gtcagctgtg agattgtatg   4980

ggaagtaaaa agatacgcaa caaagaactg gcgtccagaa agaagacata ctgcactcgg   5040

gatgtcactg ggaggagaaa gcaactacac gcctacatac cacgtggatc caacaggagc   5100

atacatccag cccacgtcat atgatcaatg tatgccagta aaaacaaaca tcaataaagt   5160

gttgtaatct tataagcctc ttttttgctt ctgcttacaa gttcctcctc aatggacaag   5220

cggaaagtga agggtgactg tagtcctgag ctcatgggtt caagaccaca gcccgatggt   5280

agtggtgtta ccgtctcgaa cctagccgac agcccttgta cattgtgggg ggagctgttt   5340

tgtttgctta tgcaatcgcg aaactctata tcttttaatg tgttgttgtt gtacatgcgc   5400

catcttagtt ttatatcagc tggcgcctta gttatataac atgcatgtta tataactaag   5460

gcgccagctg atataaaact aagatggcgc atgtacaaca acaacacatt aaaagatata   5520

gagtttcgcg attgcataag caa                                           5543
```

<210> SEQ ID NO 10
<211> LENGTH: 781
<212> TYPE: PRT
<213> ORGANISM: Human bocavirus

<400> SEQUENCE: 10

Met Ala Phe Asn Pro Pro Val Ile Arg Ala Phe Ser Gln Pro Ala Phe

```
1               5                   10                  15

Thr Tyr Val Phe Lys Phe Pro Tyr Pro Gln Trp Lys Glu Lys Glu Trp
            20                  25                  30

Leu Leu His Ala Leu Leu Ala His Gly Thr Glu Gln Ser Met Ile Gln
        35                  40                  45

Leu Arg Asn Cys Ala Pro His Pro Asp Glu Asp Ile Ile Arg Asp Asp
    50                  55                  60

Leu Leu Ile Ser Leu Glu Asp Arg His Phe Gly Ala Val Leu Cys Lys
65                  70                  75                  80

Ala Val Tyr Met Ala Thr Thr Thr Leu Met Ser His Lys Gln Arg Asn
                85                  90                  95

Met Phe Pro Arg Cys Asp Ile Ile Val Gln Ser Glu Leu Gly Glu Lys
            100                 105                 110

Asn Leu His Cys His Ile Ile Val Gly Gly Glu Gly Leu Ser Lys Arg
        115                 120                 125

Asn Ala Lys Ser Ser Cys Ala Gln Phe Tyr Gly Leu Ile Leu Ala Glu
    130                 135                 140

Ile Ile Gln Arg Cys Lys Ser Leu Leu Ala Thr Arg Pro Phe Glu Pro
145                 150                 155                 160

Glu Glu Ala Asp Ile Phe His Thr Leu Lys Lys Ala Glu Arg Glu Ala
                165                 170                 175

Trp Gly Gly Val Thr Gly Gly Asn Met Gln Ile Leu Gln Tyr Arg Asp
            180                 185                 190

Arg Arg Gly Asp Leu His Ala Gln Thr Val Asp Pro Leu Arg Phe Phe
        195                 200                 205

Lys Asn Tyr Leu Leu Pro Lys Asn Arg Cys Ile Ser Ser Tyr Ser Lys
    210                 215                 220

Pro Asp Val Cys Thr Ser Pro Asp Asn Trp Phe Ile Leu Ala Glu Lys
225                 230                 235                 240

Thr Tyr Ser His Thr Leu Ile Asn Gly Leu Pro Leu Pro Glu His Tyr
                245                 250                 255

Arg Lys Asn Tyr His Ala Thr Leu Asp Asn Glu Val Ile Pro Gly Pro
            260                 265                 270

Gln Thr Met Ala Tyr Gly Gly Arg Gly Pro Trp Glu His Leu Pro Glu
        275                 280                 285

Val Gly Asp Gln Arg Leu Ala Ala Ser Ser Val Ser Thr Thr Tyr Lys
    290                 295                 300

Pro Asn Lys Lys Glu Lys Leu Met Leu Asn Leu Leu Asp Lys Cys Lys
305                 310                 315                 320

Glu Leu Asn Leu Leu Val Tyr Glu Asp Leu Val Ala Asn Cys Pro Glu
                325                 330                 335

Leu Leu Leu Met Leu Glu Gly Gln Pro Gly Gly Ala Arg Leu Ile Glu
            340                 345                 350

Gln Val Leu Gly Met His His Ile Asn Val Cys Ser Asn Phe Thr Ala
        355                 360                 365

Leu Thr Tyr Leu Phe His Leu His Pro Val Thr Ser Leu Asp Ser Asp
    370                 375                 380

Asn Lys Ala Leu Gln Leu Leu Leu Ile Gln Gly Tyr Asn Pro Leu Ala
385                 390                 395                 400

Val Gly His Ala Leu Cys Cys Val Leu Asn Lys Gln Phe Gly Lys Gln
                405                 410                 415

Asn Thr Val Cys Phe Tyr Gly Pro Ala Ser Thr Gly Lys Thr Asn Met
            420                 425                 430
```

```
Ala Lys Ala Ile Val Gln Gly Ile Arg Leu Tyr Gly Cys Val Asn His
        435                 440                 445

Leu Asn Lys Gly Phe Val Phe Asn Asp Cys Arg Gln Arg Leu Val Val
    450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Arg Asp
                485                 490                 495

Ser Val Leu Leu Thr Gln Thr Pro Val Ile Ile Ser Thr Asn His Asp
            500                 505                 510

Ile Tyr Ala Val Val Gly Gly Asn Ser Val Ser His Val His Ala Ala
        515                 520                 525

Pro Leu Lys Glu Arg Val Ile Gln Leu Asn Phe Met Lys Gln Leu Pro
    530                 535                 540

Gln Thr Phe Gly Glu Ile Thr Ala Thr Glu Ile Ala Ala Leu Leu Gln
545                 550                 555                 560

Trp Cys Phe Asn Glu Tyr Asp Cys Thr Leu Thr Gly Phe Lys Gln Lys
                565                 570                 575

Trp Asn Leu Asp Lys Ile Pro Asn Ser Phe Pro Leu Gly Val Leu Cys
            580                 585                 590

Pro Thr His Ser Gln Asp Phe Thr Leu His Glu Asn Gly Tyr Cys Thr
        595                 600                 605

Asp Cys Gly Gly Tyr Leu Pro His Ser Ala Asp Asn Ser Met Tyr Thr
    610                 615                 620

Asp Arg Ala Ser Glu Thr Ser Thr Gly Asp Ile Thr Pro Ser Asp Leu
625                 630                 635                 640

Gly Asp Ser Asp Gly Glu Asp Thr Lys Pro Glu Thr Ser Gln Val Asp
                645                 650                 655

Tyr Cys Pro Pro Lys Lys Arg Arg Leu Thr Ala Pro Ala Ser Pro Pro
            660                 665                 670

Asn Ser Pro Ala Ser Ser Val Ser Thr Ile Thr Phe Phe Asn Thr Trp
        675                 680                 685

His Ala Gln Pro Arg Asp Glu Asp Glu Leu Arg Glu Tyr Glu Arg Gln
    690                 695                 700

Ala Ser Leu Leu Gln Lys Lys Arg Glu Ser Arg Lys Arg Gly Glu Glu
705                 710                 715                 720

Glu Thr Leu Ala Asp Asn Ser Ser Gln Glu Gln Glu Pro Gln Pro Asp
                725                 730                 735

Pro Thr Gln Trp Gly Glu Arg Leu Gly Leu Ile Ser Ser Gly Thr Pro
            740                 745                 750

Asn Gln Pro Pro Ile Val Leu His Cys Phe Glu Asp Leu Arg Pro Ser
        755                 760                 765

Asp Glu Asp Glu Gly Glu Tyr Ile Gly Glu Lys Arg Gln
    770                 775                 780


<210> SEQ ID NO 11
<211> LENGTH: 639
<212> TYPE: PRT
<213> ORGANISM: Human bocavirus

<400> SEQUENCE: 11

Met Ala Phe Asn Pro Pro Val Ile Arg Ala Phe Ser Gln Pro Ala Phe
1               5                   10                  15

Thr Tyr Val Phe Lys Phe Pro Tyr Pro Gln Trp Lys Glu Lys Glu Trp
```

```
                20                  25                  30

Leu Leu His Ala Leu Leu Ala His Gly Thr Glu Gln Ser Met Ile Gln
            35                  40                  45

Leu Arg Asn Cys Ala Pro His Pro Asp Glu Asp Ile Ile Arg Asp Asp
    50                  55                  60

Leu Leu Ile Ser Leu Glu Asp Arg His Phe Gly Ala Val Leu Cys Lys
65                  70                  75                  80

Ala Val Tyr Met Ala Thr Thr Thr Leu Met Ser His Lys Gln Arg Asn
                85                  90                  95

Met Phe Pro Arg Cys Asp Ile Ile Val Gln Ser Glu Leu Gly Glu Lys
            100                 105                 110

Asn Leu His Cys His Ile Ile Val Gly Gly Glu Gly Leu Ser Lys Arg
        115                 120                 125

Asn Ala Lys Ser Ser Cys Ala Gln Phe Tyr Gly Leu Ile Leu Ala Glu
    130                 135                 140

Ile Ile Gln Arg Cys Lys Ser Leu Leu Ala Thr Arg Pro Phe Glu Pro
145                 150                 155                 160

Glu Glu Ala Asp Ile Phe His Thr Leu Lys Lys Ala Glu Arg Glu Ala
                165                 170                 175

Trp Gly Gly Val Thr Gly Gly Asn Met Gln Ile Leu Gln Tyr Arg Asp
            180                 185                 190

Arg Arg Gly Asp Leu His Ala Gln Thr Val Asp Pro Leu Arg Phe Phe
        195                 200                 205

Lys Asn Tyr Leu Leu Pro Lys Asn Arg Cys Ile Ser Ser Tyr Ser Lys
    210                 215                 220

Pro Asp Val Cys Thr Ser Pro Asp Asn Trp Phe Ile Leu Ala Glu Lys
225                 230                 235                 240

Thr Tyr Ser His Thr Leu Ile Asn Gly Leu Pro Leu Pro Glu His Tyr
                245                 250                 255

Arg Lys Asn Tyr His Ala Thr Leu Asp Asn Glu Val Ile Pro Gly Pro
            260                 265                 270

Gln Thr Met Ala Tyr Gly Gly Arg Gly Pro Trp Glu His Leu Pro Glu
        275                 280                 285

Val Gly Asp Gln Arg Leu Ala Ala Ser Ser Val Ser Thr Thr Tyr Lys
    290                 295                 300

Pro Asn Lys Lys Glu Lys Leu Met Leu Asn Leu Leu Asp Lys Cys Lys
305                 310                 315                 320

Glu Leu Asn Leu Leu Val Tyr Glu Asp Leu Val Ala Asn Cys Pro Glu
                325                 330                 335

Leu Leu Leu Met Leu Glu Gly Gln Pro Gly Gly Ala Arg Leu Ile Glu
            340                 345                 350

Gln Val Leu Gly Met His His Ile Asn Val Cys Ser Asn Phe Thr Ala
        355                 360                 365

Leu Thr Tyr Leu Phe His Leu His Pro Val Thr Ser Leu Asp Ser Asp
    370                 375                 380

Asn Lys Ala Leu Gln Leu Leu Leu Ile Gln Gly Tyr Asn Pro Leu Ala
385                 390                 395                 400

Val Gly His Ala Leu Cys Cys Val Leu Asn Lys Gln Phe Gly Lys Gln
                405                 410                 415

Asn Thr Val Cys Phe Tyr Gly Pro Ala Ser Thr Gly Lys Thr Asn Met
            420                 425                 430

Ala Lys Ala Ile Val Gln Gly Ile Arg Leu Tyr Gly Cys Val Asn His
        435                 440                 445
```

```
Leu Asn Lys Gly Phe Val Phe Asn Asp Cys Arg Gln Arg Leu Val Val
    450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Arg Asp
                485                 490                 495

Ser Val Leu Leu Thr Gln Thr Pro Val Ile Ile Ser Thr Asn His Asp
            500                 505                 510

Ile Tyr Ala Val Val Gly Gly Asn Ser Val Ser His Val His Ala Ala
        515                 520                 525

Pro Leu Lys Glu Arg Val Ile Gln Leu Asn Phe Met Lys Gln Leu Pro
    530                 535                 540

Gln Thr Phe Gly Glu Ile Thr Ala Thr Glu Ile Ala Ala Leu Leu Gln
545                 550                 555                 560

Trp Cys Phe Asn Glu Tyr Asp Cys Thr Leu Thr Gly Phe Lys Gln Lys
                565                 570                 575

Trp Asn Leu Asp Lys Ile Pro Asn Ser Phe Pro Leu Gly Val Leu Cys
            580                 585                 590

Pro Thr His Ser Gln Asp Phe Thr Leu His Glu Asn Gly Tyr Cys Thr
        595                 600                 605

Asp Cys Gly Gly Tyr Leu Pro His Ser Ala Asp Asn Ser Met Tyr Thr
    610                 615                 620

Asp Arg Ala Ser Glu Thr Ser Thr Gly Asp Ile Thr Pro Ser Lys
625                 630                 635


<210> SEQ ID NO 12
<211> LENGTH: 160
<212> TYPE: PRT
<213> ORGANISM: Human bocavirus

<400> SEQUENCE: 12

Met Tyr Thr Asp Arg Ala Ser Glu Thr Ser Thr Gly Asp Ile Thr Pro
1               5                   10                  15

Ser Asp Leu Gly Asp Ser Asp Gly Glu Asp Thr Lys Pro Glu Thr Ser
            20                  25                  30

Gln Val Asp Tyr Cys Pro Pro Lys Lys Arg Arg Leu Thr Ala Pro Ala
        35                  40                  45

Ser Pro Pro Asn Ser Pro Ala Ser Ser Val Ser Thr Ile Thr Phe Phe
    50                  55                  60

Asn Thr Trp His Ala Gln Pro Arg Asp Glu Asp Glu Leu Arg Glu Tyr
65                  70                  75                  80

Glu Arg Gln Ala Ser Leu Leu Gln Lys Lys Arg Glu Ser Arg Lys Arg
                85                  90                  95

Gly Glu Glu Glu Thr Leu Ala Asp Asn Ser Ser Gln Glu Gln Glu Pro
            100                 105                 110

Gln Pro Asp Pro Thr Gln Trp Gly Glu Arg Leu Gly Leu Ile Ser Ser
        115                 120                 125

Gly Thr Pro Asn Gln Pro Pro Ile Val Leu His Cys Phe Glu Asp Leu
    130                 135                 140

Arg Pro Ser Asp Glu Asp Glu Gly Glu Tyr Ile Gly Glu Lys Arg Gln
145                 150                 155                 160


<210> SEQ ID NO 13
<211> LENGTH: 219
<212> TYPE: PRT
```

```
<213> ORGANISM: Human bocavirus

<400> SEQUENCE: 13

Met Ser Ser Gly Asn Met Lys Asp Lys His Arg Ser Tyr Lys Arg Lys
1               5                   10                  15

Gly Ser Pro Glu Arg Gly Glu Arg Lys Arg His Trp Gln Thr Thr His
            20                  25                  30

His Arg Ser Arg Ser Arg Ser Pro Ile Arg His Ser Gly Glu Arg Gly
        35                  40                  45

Ser Gly Ser Tyr His Gln Glu His Pro Ile Ser His Leu Ser Ser Cys
    50                  55                  60

Thr Ala Ser Lys Thr Ser Asp Gln Val Met Lys Thr Arg Glu Ser Thr
65                  70                  75                  80

Ser Gly Lys Lys Asp Asn Arg Thr Asn Pro Tyr Thr Val Phe Ser Gln
                85                  90                  95

His Arg Ala Ser Asn Pro Glu Ala Pro Gly Trp Cys Gly Phe Tyr Trp
            100                 105                 110

His Ser Thr Arg Ile Ala Arg Asp Gly Thr Asn Ser Ile Phe Asn Glu
        115                 120                 125

Met Lys Gln Gln Phe Gln Gln Leu Gln Ile Asp Asn Lys Ile Gly Trp
    130                 135                 140

Asp Asn Thr Arg Glu Leu Leu Phe Asn Gln Lys Lys Thr Leu Asp Gln
145                 150                 155                 160

Lys Tyr Arg Asn Met Phe Trp His Phe Arg Asn Asn Ser Asp Cys Glu
                165                 170                 175

Arg Cys Asn Tyr Trp Asp Asp Val Tyr Arg Arg His Leu Ala Asn Val
            180                 185                 190

Ser Ser Gln Thr Glu Ala Asp Glu Ile Thr Asp Glu Glu Met Leu Ser
        195                 200                 205

Ala Ala Glu Ser Met Glu Ala Asp Ala Ser Asn
    210                 215


<210> SEQ ID NO 14
<211> LENGTH: 671
<212> TYPE: PRT
<213> ORGANISM: Human bocavirus

<400> SEQUENCE: 14

Met Pro Pro Ile Lys Arg Gln Pro Arg Gly Trp Val Leu Pro Gly Tyr
1               5                   10                  15

Arg Tyr Leu Gly Pro Phe Asn Pro Leu Asp Asn Gly Glu Pro Val Asn
            20                  25                  30

Asn Ala Asp Arg Ala Ala Gln Leu His Asp His Ala Tyr Ser Glu Leu
        35                  40                  45

Ile Lys Ser Gly Lys Asn Pro Tyr Leu Tyr Phe Asn Lys Ala Asp Glu
    50                  55                  60

Lys Phe Ile Asp Asp Leu Lys Asp Asp Trp Ser Ile Gly Gly Ile Ile
65                  70                  75                  80

Gly Ser Ser Phe Phe Lys Ile Lys Arg Ala Val Ala Pro Ala Leu Gly
                85                  90                  95

Asn Lys Glu Arg Ala Gln Lys Arg His Phe Tyr Phe Ala Asn Ser Asn
            100                 105                 110

Lys Gly Ala Lys Lys Thr Lys Lys Ser Glu Pro Lys Pro Gly Thr Ser
        115                 120                 125

Lys Met Ser Asp Thr Asp Ile Gln Asp Gln Gln Pro Asp Thr Val Asp
```

```
    130                 135                 140

Ala Pro Gln Asn Thr Ser Gly Gly Gly Thr Gly Ser Ile Gly Gly Gly
145                 150                 155                 160

Lys Gly Ser Gly Val Gly Ile Ser Thr Gly Gly Trp Val Gly Gly Ser
                165                 170                 175

His Phe Ser Asp Lys Tyr Val Val Thr Lys Asn Thr Arg Gln Phe Ile
            180                 185                 190

Thr Thr Ile Gln Asn Gly His Leu Tyr Lys Thr Glu Ala Ile Glu Thr
        195                 200                 205

Thr Asn Gln Ser Gly Lys Ser Gln Arg Cys Val Thr Thr Pro Trp Thr
    210                 215                 220

Tyr Phe Asn Phe Asn Gln Tyr Ser Cys His Phe Ser Pro Gln Asp Trp
225                 230                 235                 240

Gln Arg Leu Thr Asn Glu Tyr Lys Arg Phe Arg Pro Lys Ala Met Gln
                245                 250                 255

Val Lys Ile Tyr Asn Leu Gln Ile Lys Gln Ile Leu Ser Asn Gly Ala
            260                 265                 270

Asp Thr Thr Tyr Asn Asn Asp Leu Thr Ala Gly Val His Ile Phe Cys
        275                 280                 285

Asp Gly Glu His Ala Tyr Pro Asn Ala Ser His Pro Trp Asp Glu Asp
    290                 295                 300

Val Met Pro Asp Leu Pro Tyr Lys Thr Trp Lys Leu Phe Gln Tyr Gly
305                 310                 315                 320

Tyr Ile Pro Ile Glu Asn Glu Leu Ala Asp Leu Asp Gly Asn Ala Ala
                325                 330                 335

Gly Gly Asn Ala Thr Glu Lys Ala Leu Leu Tyr Gln Met Pro Phe Phe
            340                 345                 350

Leu Leu Glu Asn Ser Asp His Gln Val Leu Arg Thr Gly Glu Ser Thr
        355                 360                 365

Glu Phe Thr Phe Asn Phe Asp Cys Glu Trp Val Asn Asn Glu Arg Ala
    370                 375                 380

Tyr Ile Pro Pro Gly Leu Met Phe Asn Pro Lys Val Pro Thr Arg Arg
385                 390                 395                 400

Val Gln Tyr Ile Arg Gln Asn Gly Ser Thr Ala Ala Ser Thr Gly Arg
                405                 410                 415

Ile Gln Pro Tyr Ser Lys Pro Thr Ser Trp Met Thr Gly Pro Gly Leu
            420                 425                 430

Leu Ser Ala Gln Arg Val Gly Pro Gln Ser Ser Asp Thr Ala Pro Phe
        435                 440                 445

Met Val Cys Thr Asn Pro Glu Gly Thr His Ile Asn Thr Gly Ala Ala
    450                 455                 460

Gly Phe Gly Ser Gly Phe Asp Pro Pro Ser Gly Cys Leu Ala Pro Thr
465                 470                 475                 480

Asn Leu Glu Tyr Lys Leu Gln Trp Tyr Gln Thr Pro Glu Gly Thr Gly
                485                 490                 495

Asn Asn Gly Asn Ile Ile Ala Asn Pro Ser Leu Ser Met Leu Arg Asp
            500                 505                 510

Gln Leu Leu Tyr Lys Gly Asn Gln Thr Thr Tyr Asn Leu Val Gly Asp
        515                 520                 525

Ile Trp Met Phe Pro Asn Gln Val Trp Asp Arg Phe Pro Ile Thr Arg
    530                 535                 540

Glu Asn Pro Ile Trp Cys Lys Lys Pro Arg Ala Asp Lys His Thr Ile
545                 550                 555                 560
```

```
Met Asp Pro Phe Asp Gly Ser Ile Ala Met Asp His Pro Pro Gly Thr
                565                 570                 575

Ile Phe Ile Lys Met Ala Lys Ile Pro Val Pro Thr Ala Ser Asn Ala
            580                 585                 590

Asp Ser Tyr Leu Asn Ile Tyr Cys Thr Gly Gln Val Ser Cys Glu Ile
        595                 600                 605

Val Trp Glu Val Lys Arg Tyr Ala Thr Lys Asn Trp Arg Pro Glu Arg
    610                 615                 620

Arg His Thr Ala Leu Gly Met Ser Leu Gly Gly Glu Ser Asn Tyr Thr
625                 630                 635                 640

Pro Thr Tyr His Val Asp Pro Thr Gly Ala Tyr Ile Gln Pro Thr Ser
                645                 650                 655

Tyr Asp Gln Cys Met Pro Val Lys Thr Asn Ile Asn Lys Val Leu
            660                 665                 670


<210> SEQ ID NO 15
<211> LENGTH: 542
<212> TYPE: PRT
<213> ORGANISM: Human bocavirus

<400> SEQUENCE: 15

Met Ser Asp Thr Asp Ile Gln Asp Gln Gln Pro Asp Thr Val Asp Ala
1               5                   10                  15

Pro Gln Asn Thr Ser Gly Gly Gly Thr Gly Ser Ile Gly Gly Gly Lys
            20                  25                  30

Gly Ser Gly Val Gly Ile Ser Thr Gly Gly Trp Val Gly Gly Ser His
        35                  40                  45

Phe Ser Asp Lys Tyr Val Val Thr Lys Asn Thr Arg Gln Phe Ile Thr
    50                  55                  60

Thr Ile Gln Asn Gly His Leu Tyr Lys Thr Glu Ala Ile Glu Thr Thr
65                  70                  75                  80

Asn Gln Ser Gly Lys Ser Gln Arg Cys Val Thr Thr Pro Trp Thr Tyr
                85                  90                  95

Phe Asn Phe Asn Gln Tyr Ser Cys His Phe Ser Pro Gln Asp Trp Gln
            100                 105                 110

Arg Leu Thr Asn Glu Tyr Lys Arg Phe Arg Pro Lys Ala Met Gln Val
        115                 120                 125

Lys Ile Tyr Asn Leu Gln Ile Lys Gln Ile Leu Ser Asn Gly Ala Asp
    130                 135                 140

Thr Thr Tyr Asn Asn Asp Leu Thr Ala Gly Val His Ile Phe Cys Asp
145                 150                 155                 160

Gly Glu His Ala Tyr Pro Asn Ala Ser His Pro Trp Asp Glu Asp Val
                165                 170                 175

Met Pro Asp Leu Pro Tyr Lys Thr Trp Lys Leu Phe Gln Tyr Gly Tyr
            180                 185                 190

Ile Pro Ile Glu Asn Glu Leu Ala Asp Leu Asp Gly Asn Ala Ala Gly
        195                 200                 205

Gly Asn Ala Thr Glu Lys Ala Leu Leu Tyr Gln Met Pro Phe Phe Leu
    210                 215                 220

Leu Glu Asn Ser Asp His Gln Val Leu Arg Thr Gly Glu Ser Thr Glu
225                 230                 235                 240

Phe Thr Phe Asn Phe Asp Cys Glu Trp Val Asn Asn Glu Arg Ala Tyr
                245                 250                 255

Ile Pro Pro Gly Leu Met Phe Asn Pro Lys Val Pro Thr Arg Arg Val
```

```
            260                 265                 270

Gln Tyr Ile Arg Gln Asn Gly Ser Thr Ala Ala Ser Thr Gly Arg Ile
        275                 280                 285

Gln Pro Tyr Ser Lys Pro Thr Ser Trp Met Thr Gly Pro Gly Leu Leu
    290                 295                 300

Ser Ala Gln Arg Val Gly Pro Gln Ser Ser Asp Thr Ala Pro Phe Met
305                 310                 315                 320

Val Cys Thr Asn Pro Glu Gly Thr His Ile Asn Thr Gly Ala Ala Gly
                325                 330                 335

Phe Gly Ser Gly Phe Asp Pro Pro Ser Gly Cys Leu Ala Pro Thr Asn
                340                 345                 350

Leu Glu Tyr Lys Leu Gln Trp Tyr Gln Thr Pro Glu Gly Thr Gly Asn
        355                 360                 365

Asn Gly Asn Ile Ile Ala Asn Pro Ser Leu Ser Met Leu Arg Asp Gln
    370                 375                 380

Leu Leu Tyr Lys Gly Asn Gln Thr Thr Tyr Asn Leu Val Gly Asp Ile
385                 390                 395                 400

Trp Met Phe Pro Asn Gln Val Trp Asp Arg Phe Pro Ile Thr Arg Glu
                405                 410                 415

Asn Pro Ile Trp Cys Lys Lys Pro Arg Ala Asp Lys His Thr Ile Met
            420                 425                 430

Asp Pro Phe Asp Gly Ser Ile Ala Met Asp His Pro Pro Gly Thr Ile
        435                 440                 445

Phe Ile Lys Met Ala Lys Ile Pro Val Pro Thr Ala Ser Asn Ala Asp
    450                 455                 460

Ser Tyr Leu Asn Ile Tyr Cys Thr Gly Gln Val Ser Cys Glu Ile Val
465                 470                 475                 480

Trp Glu Val Lys Arg Tyr Ala Thr Lys Asn Trp Arg Pro Glu Arg Arg
                485                 490                 495

His Thr Ala Leu Gly Met Ser Leu Gly Gly Glu Ser Asn Tyr Thr Pro
            500                 505                 510

Thr Tyr His Val Asp Pro Thr Gly Ala Tyr Ile Gln Pro Thr Ser Tyr
        515                 520                 525

Asp Gln Cys Met Pro Val Lys Thr Asn Ile Asn Lys Val Leu
    530                 535                 540


<210> SEQ ID NO 16
<211> LENGTH: 120
<212> TYPE: PRT
<213> ORGANISM: Human bocavirus

<400> SEQUENCE: 16

Met Val Leu Thr Gln His Thr Thr Met Thr Ser Gln Leu Ala Phe Thr
1               5                   10                  15

Ser Phe Val Met Glu Ser Met Leu Thr Gln Met His Leu Ile His Gly
            20                  25                  30

Met Arg Thr Ser Cys Leu Ile Phe His Thr Arg Pro Gly Asn Phe Phe
        35                  40                  45

Asn Met Asp Ile Phe Leu Leu Lys Met Asn Ser Gln Ile Leu Met Glu
    50                  55                  60

Met Gln Leu Glu Ala Met Leu Gln Lys Lys His Phe Cys Ile Arg Cys
65                  70                  75                  80

Leu Phe Phe Tyr Leu Lys Thr Val Thr Thr Lys Tyr Leu Glu Leu Val
                85                  90                  95
```

```
Arg Ala Leu Asn Leu Leu Leu Thr Leu Thr Val Asn Gly Leu Thr Met
            100                 105                 110

Lys Glu His Thr Phe Leu Leu Asp
        115                 120


<210> SEQ ID NO 17
<211> LENGTH: 5217
<212> TYPE: DNA
<213> ORGANISM: Human bocavirus

<400> SEQUENCE: 17

caaggaggag tggttatatg atgtaatcca taaccactcc caggaaatga cgtatgatag      60

ccaatcagaa ttgagtattg aacctatata agctgctgca cttcctgatt caatcagact     120

gcatccggtc tccggcgagt gaacatctct ggaaaaagct ccacgcttgt ggtgagtcta     180

ctatggcttt caatcctcct gtgattagag ctttttctca acctgctttt acttatgtct     240

tcaaatttcc atatccacaa tggaaagaaa aagaatggct gcttcatgca cttttagctc     300

atggaactga acaatctatg atacaattaa gaaactgcgc tcctcatccg gatgaagaca     360

taatccgtga tgacttgctt atttctttag aagatcgcca ttttggggct gttctctgca     420

aggctgttta catggcaaca actactctca tgtcacacaa acaaaggaat atgtttcctc     480

gttgtgacat catagttcag tctgagctag gagagaaaaa cttacactgc catattatag     540

ttgggggaga aggactaagc aagaggaatg ctaaatcatc ctgtgctcag ttctatggtt     600

taatactagc tgaaataatt caacgctgca aatctcttct ggctacacgt ccttttgaac     660

ctgaagaggc tgacatattt cacactttaa aaaaggctga gcgagaggca tggggtggag     720

ttactggcgg caacatgcaa atccttcaat atagagatcg cagaggagac cttcatgcac     780

aaacagtgga tcctcttcgc ttcttcaaaa actacctttt acctaaaaat agatgtattt     840

catcttacag caaacctgat gtttgtactt ctcctgacaa ctggttcatt ttagctgaaa     900

aaacttactc tcacactctt attaacgggc tgccgcttcc agaacattac agaaaaaact     960

accacgcaac cctagataac gaagtcattc cagggcctca aacaatggcc tatggaggac    1020

gtggtccgtg ggaacatctt cctgaggtag gagatcagcg cctagctgcg tcttctgtta    1080

gcactactta taaacctaac aaaaaagaaa aacttatgct aaacttgcta gacaaatgta    1140

aagagctaaa tctattagtt tatgaagact tagtagctaa ttgtcctgaa ctactcctta    1200

tgcttgaagg tcaaccagga ggggcacgcc ttatagaaca agtcttgggc atgcaccata    1260

ttaatgtttg ttctaacttt acagctctca catatctttt tcatctacat cctgttactt    1320

cgcttgactc agacaataaa gctttacagc ttttgttgat tcaaggctat aatcctctag    1380

ccgttggtca cgccctgtgc tgtgtcctga acaaacaatt cgggaaacaa aacactgttt    1440

gcttttacgg gcctgcctca acaggtaaaa caaatatggc caaggcaatc gtccaaggga    1500

ttagacttta tgggtgtgtt aatcatttga acaaaggatt tgtatttaat gactgcagac    1560

aacgcttagt tgtttggtgg gaggagtgct taatgcacca ggattgggtg gaacctgcaa    1620

agtgtatctt gggcgggaca gaatgcagaa ttgacgtcaa gcatagagac agtgtacttt    1680

taactcaaac acctgtaatt atatccacta accacgatat ctacgcggtt gttggtggca    1740

attctgtttc tcatgttcac gcggctccat taaaagaaag agtgattcag ctaaatttta    1800

tgaaacaact tcctcaaaca tttggagaaa tcactgctac tgagattgca gctcttctac    1860

agtggtgttt caatgagtac gactgtactc tgacaggatt taaacaaaaa tggaatttag    1920

ataaaattcc aaactcattt cctcttgggg tcctttgtcc tactcattca caggacttta    1980
```

```
cacttcacga aaacggatac tgcactgatt gcggtggtta ccttcctcat agtgctgaca   2040
attctatgta cactgatcgc gcaagcgaaa ctagcacagg agacatcaca ccaagtaagt   2100
aaatacgcat gcgcaagtaa ttcttttact ttcacttcgc tatttttacc aatttttact   2160
tttaggtgac ttgggggatt cggacggaga agacaccgag cctgagacat cgcaagtgga   2220
ctattgtcca cccaagaaac gtcgtctaac tgctccagca agtcctccaa actcacctgc   2280
gagctctgta agtactatta ctttctttaa cacttggcac gcacagccac gtgacgaaga   2340
tgagctcagg gaatatgaaa gacaagcatc gctcctacaa aagaaaaggg agtccagaaa   2400
gaggggagag gaagagacac tggcagacaa ctcatcacag gagcaggagc cgcagcccga   2460
tccgacacag tggggagaga ggctcgggct catatcatca ggaacaccca atcagccacc   2520
tatcgtcttg cactgcttcg aagacctcag accaagtgat gaagacgagg gagagtacat   2580
cggggaaaaa agacaataga acaaatccat acactgtatt cagtcaacac agagcttcca   2640
atcctgaagc tccagggtgg tgtgggttct actggcactc tactcgcatt gctagagatg   2700
gtactaattc aatctttaat gaaatgaaac aacagtttca acagctacaa attgataata   2760
aaataggatg ggataacact agagaactat tgtttaatca aaagaaaaca ctagatcaaa   2820
aatacagaaa tatgttctgg cactttagaa ataactctga ttgtgaaaga tgtaattact   2880
gggatgatgt gtaccgtagg cacttagcta atgtttcctc acagacagaa gcagacgaga   2940
taactgacga ggaaatgctt tctgctgctg aaagcatgga agcagatgcc tccaattaag   3000
agacagccta gagggtgggt gctgcctgga tacagatatc ttgggccatt taatccactt   3060
gataacggtg aacctgtaaa taacgctgat cgcgctgctc aattacatga tcacgcctac   3120
tctgaactaa taaagagtgg taaaaatcca tacctgtatt tcaataaagc tgatgaaaaa   3180
ttcattgatg atctaaaaga cgattggtca attggtggaa ttattggatc cagttttttt   3240
aaaataaagc gcgccgtggc tcctgctctg ggaaataaag agagagccca aaaaagacac   3300
ttttactttg ctaactcaaa taaaggtgca aaaaaaacaa aaaaaagtga acctaaacca   3360
ggaacctcaa aaatgtctga cactgacatt caagaccaac aacctgatac tgtggacgca   3420
ccacagaacg cctcaggggg aggaacagga agtattggag gaggaaaagg atctggtgtg   3480
gggatttcca ctggagggtg ggtcggaggt tctcactttt cagacaaata tgtggttact   3540
aaaaacacaa gacaatttat aaccacaatt cagaatggtc acctctacaa aacagaggcc   3600
attgaaacaa caaaccaaag tggaaaatca cagcgctgcg tcacaactcc atggacatac   3660
tttaacttta atcaatacag ctgtcacttc tcaccacaag attggcagcg ccttacaaat   3720
gaatataagc gcttcagacc taaagcaatg caagtaaaga tttacaactt gcaaataaaa   3780
caaatacttt caaatggtgc tgacacaaca tacaacaatg acctcacagc tggcgttcac   3840
atcttttgtg atggagagca tgcttaccca aatgcatctc atccatggga tgaggacgtc   3900
atgcctgatc ttccatacaa gacctggaaa ctttttcaat atggatatat tcctattgaa   3960
aatgaactag cagatcttga tggaaatgca gctggaggca atgctacaga aaaagcactt   4020
ctgtatcaga tgcctttttt tctacttgaa aacagtgacc accaagtact tagaactggt   4080
gagagcactg aatttacttt taactttgac tgtgaatggg ttaataatga aagagcatac   4140
attcctcctg gattgatgtt caatccaaaa gttccaacaa gaagagttca gtacataaga   4200
caaaacggaa gcacagcagc cagcacaggc agaattcagc catactcaaa accaacaagc   4260
tggatgacag gacctggcct gctcagtgca cagagagtag gaccacagtc atcagacact   4320
```

```
gctccattca tggtttgcac taacccagaa ggaacacaca taaacacagg tgctgcagga   4380

tttggatctg gctttgatcc tccaagcgga tgtctggcac caactaacct agaatacaaa   4440

cttcagtggt accagacacc agaaggaaca ggaaataatg gaaacataat tgcaaaccca   4500

tcactctcaa tgcttagaga ccaactccta tacaaaggaa accagaccac atacaatcta   4560

gtgggggaca tatggatgtt tccaaatcaa gtctgggaca gatttcctat caccagagaa   4620

aatccaatct ggtgcaaaaa accaagggct gacaaacaca caatcatgga tccatttgat   4680

ggatccattg caatggatca tcctccaggc actattttta taaaaatggc aaaaattcca   4740

gtaccaactg caacaaatgc agactcatat ctaaacatat actgtactgg acaagtcagc   4800

tgtgaaattg tatgggaagt agaaagatac gcaacaaaga actggcgtcc agaaagaaga   4860

catactgcac tcgggatgtc actgggagga gagagcaact acacgcctac ataccacgtg   4920

gatccaacag gagcatacat ccagcccacg tcatatgatc agtgtatgcc agtaaaaaca   4980

aacatcaata aagtgttgta atcttataag cctctttttt gcttctgctt acaagttcct   5040

cctcaatgga caagcggaaa gtgaagggtg actgtagtcc tgagctcatg ggttcaagac   5100

cacagcccga tggtagtggt gttaccgtct cgaacctagc cgacagccct tgtacattgt   5160

ggggggagct gttttgtttg cttatgcaat cgcgaaactc tatatctttt aatgtgt      5217
```

<210> SEQ ID NO 18
<211> LENGTH: 5299
<212> TYPE: DNA
<213> ORGANISM: Human bocavirus

<400> SEQUENCE: 18

```
gccggcagac atattggatt ccaagatggc gtctgtacaa ccacgtcaca tataaaataa     60

taaatattca caaggaggag tggttatatg atgtaatcca taaccactcc caggaaatga    120

cgtatgatag ccaatcagaa ttgagtatta aacctatata agctgctgca cttcctgatt    180

caatcagact gcatccggtc tccggcgagt gaacatctct ggaaaaagct ccacgcttgt    240

ggtgagtcta ctatggcttt caatcctcct gtgattagag ctttttctca acctgctttt    300

acttatgtct tcaaatttcc atatccacaa tggaaagaaa aagaatggct gcttcatgca    360

cttttagctc atggaactga acaatctatg atacaattaa gaaactgcgc tcctcatccg    420

gatgaagaca taatccgtga tgacttgctt atttctttag aagatcgcca ttttggggct    480

gttctctgca aggctgttta catggcaaca actactctca tgtcacacaa acaaaggaat    540

atgtttcctc gttgtgacat catagttcag tctgagctag gagagaaaaa cttacactgc    600

catattatag ttgggggaga aggactaagc aagaggaatg ctaaatcatc ctgtgctcag    660

ttctatggtt taatactagc tgagataatt caacgctgca aatctcttct ggctacacgt    720

ccttttgaac ctgaggaggc tgacatattt cacactctaa aaaaggctga gcgagaggca    780

tggggtggag ttactggcgg caacatgcag atccttcaat atagagatcg cagaggagac    840

cttcatgcac aaacagtgga tcctcttcgc ttcttcaaaa actacctttt acctaaaaat    900

agatgtattt catcttacag caaacctgat gtttgtactt ctcctgacaa ctggttcatt    960

ttagctgaaa aaacttactc tcacactctt attaacgggc tgccgcttcc agaacattac   1020

agaaaaaact accacgcaac cctagataac gaagtcattc cagggcctca aacaatggcc   1080

tatggaggac gtggtccgtg ggaacatctt cctgaggtag gagatcagcg cctagctgcg   1140

tcttctgtta gcactactta taaacctaac aaaaaagaaa aacttatgct aaacttgcta   1200

gacaaatgta aagagctaaa tctattagtt tatgaagact tagtagctaa ttgtcctgaa   1260
```

```
ctactcctta tgcttgaagg tcaaccagga ggggcacgcc ttatagaaca agtcttgggc   1320
atgcaccata ttaatgtttg ttctaacttt acagctctca catatctttt tcatctacat   1380
cctgttactt cgcttgactc agacaataaa gctttacagc ttttgttgat tcaaggctat   1440
aatcctctag ccgttggtca cgccctgtgc tgtgtcctga acaaacaatt cgggaaacaa   1500
aacactgttt gcttttacgg gcctgcctca acaggtaaaa caaatatggc caaggcaatc   1560
gtccaaggga ttagacttta tgggtgtgtt aatcatttga acaaaggatt tgtatttaat   1620
gactgcagac aacgcctagt tgtttggtgg gaggagtgct taatgcacca ggattgggtg   1680
gaacctgcaa agtgtatctt gggcgggaca gaatgcagaa ttgacgtcaa gcatagagac   1740
agtgtacttt taactcaaac acctgtaatt atatccacta accacgatat ctacgcggtt   1800
gttggtggca attctgtttc tcatgttcac gcggctccat taaaagaaag agtgattcag   1860
ctaaatttta tgaaacaact tcctcaaaca tttggagaaa tcactgctac tgagattgca   1920
gctcttctac agtggtgttt caatgagtac gactgtactc tgacaggatt taaacaaaaa   1980
tggaatttag ataaaattcc aaactcattt cctcttgggg tcctttgtcc tactcattca   2040
caggacttta cacttcacga aaacggatac tgcactgatt gcggtggtta ccttcctcat   2100
agtgctgaca attctatgta cactgatcgc gcaagcgaaa ctagcacagg agacatcaca   2160
ccaagtaagt aaatacgcat gcgcaagtaa ttcttttact ttcacttcgc tatttttacc   2220
aatttttact tttaggtgac ttggggggatt cggacggaga agacaccgag cctgagacat   2280
cgcaagtgga ctattgtcca cccaagaaac gtcgtctaac tgctccagca agtcctccaa   2340
actcacctgc gagctctgta agtactatta ctttctttaa cacttggcac gcacagccac   2400
gtgacgaaga tgagctcagg gaatatgaaa gacaagcatc gctcctacaa aagaaaaggg   2460
agtccagaaa gaggggagag gaagagacac tggcagacaa ctcatcacag gagcaggagc   2520
cgcagcccga tccgacacag tggggagaga ggctcgggct catatcatca ggaacaccca   2580
atcagccacc tatcgtcttg cactgcttcg aagacctcag accaagtgat gaagacgagg   2640
gagagtacat cggggaaaaa agacaataga acaaatccat acactgtatt cagtcaacac   2700
agagcttcca atcctgaagc tccagggtgg tgtgggttct actggcactc tactcgcatt   2760
gctagagatg gtactaattc aatctttaat gaaatgaaac aacagtttca acaactacaa   2820
attgataata aaataggatg ggataacact agagaactat tgtttaatca aaagaaaaca   2880
ctagatcaaa aatacagaaa tatgttctgg cactttagaa ataactctga ttgtgaaaga   2940
tgtaattact gggatgatgt gtaccgtaga cacttagcta atgtttcctc acagacagaa   3000
gcagacgaga taactgacga ggaaatgctt tctgctgctg aaagcatgga agcagatgcc   3060
tccaattaag agacagccta gagggtgggt gctgcctgga tacagatatc ttgggccatt   3120
taatccactt gataacggtg aacctgtaaa taacgctgat cgcgctgctc aattacatga   3180
tcacgcctac tctgaactaa taaagagtgg taaaaatcca tacctgtatt tcaataaagc   3240
tgatgaaaaa ttcattgatg atctaaaaga cgattggtca attggtggaa ttattggatc   3300
cagttttttt aaaataaagc gcgccgtggc tcctgctctg ggaaataaag agagagccca   3360
aaaaagacac ttttactttg ctaactcaaa taaaggtgca aaaaaaacaa aaaaaagtga   3420
acctaaacca ggaacctcaa aaatgtctga cactgacatt caagaccaac aacctgatac   3480
tgtggacgca ccacaaaaca cctcaggggg aggaacagga agtattggag gaggaaaagg   3540
atctggtgtg gggatttcca ctggagggtg ggtcggaggt tctcactttt cagacaaata   3600
```

```
tgtggttact aaaaacacaa gacaatttat aaccacaatt cagaatggtc acctctacaa   3660

aacagaggcc attgaaacaa caaaccaaag tggaaaatca cagcgctgcg tcacaactcc   3720

atggacatac tttaacttta atcaatacag ctgtcacttc tcaccacagg attggcagcg   3780

ccttacaaat gaatataagc gcttcagacc taaagcaatg caagtaaaga tttacaactt   3840

gcaaataaaa caaatacttt caaatggtgc tgacacaaca tacaacaatg acctcacagc   3900

tggcgttcac atcttttgtg atggagagca tgcttaccca aatgcatctc atccatggga   3960

tgaggacgtc atgcctgatc ttccatacaa gacctggaaa ctttttcaat atggatatat   4020

tcctattgaa aatgaactcg cagatcttga tggaaatgca gctggaggca atgctacaga   4080

aaaagcactt ctgtatcaga tgcctttttt tctacttgaa aacagtgacc accaagtact   4140

tagaactggt gagagcactg aatttacttt taactttgac tgtgaatggg ttaacaatga   4200

aagagcatac attcctcctg gactaatgtt taatccaaaa gtcccaacaa gaagagttca   4260

gtacataaga caaaacggaa gcacagcagc cagcacaggc agaattcagc catactcaaa   4320

accaacaagc tggatgacag gacctggcct gctcagtgca caaagagtag gaccacagtc   4380

atcagacact gctccattca tggtttgcac taacccagaa ggaacacaca taaacacagg   4440

tgctgcagga tttggatctg gctttgatcc tccaaacgga tgtctggcac caactaacct   4500

agaatacaaa cttcagtggt accagacacc agaaggaaca ggaaataatg gaaacataat   4560

tgcaaaccca tcactctcaa tgcttagaga ccaactccta tacaaaggaa accaaaccac   4620

atacaatcta gtgggggaca tatggatgtt tccaaatcaa gtctgggaca gatttcctat   4680

caccagagaa aatccaatct ggtgcaaaaa accaagggct gacaaacaca caatcatgga   4740

tccatttgat ggatcaattg caatggatca tcctccaggc actattttta taaaaatggc   4800

aaaaattcca gttccaactg cctcaaatgc agactcatac ctaaacatat actgtactgg   4860

acaagtcagc tgtgaaattg tatgggaggt agaaagatac gcaacaaaga actggcgtcc   4920

agaaagaaga catactgcac tcgggatgtc actgggagga gagagcaact acacgcctac   4980

ataccacgtg gatccaacag gagcatacat ccagcccacg tcatatgatc agtgtatgcc   5040

agtaaaaaca aacatcaata aagtgttgta atcttataag cctctttttt gcttctgctt   5100

acaagttcct cctcaatgga caagcggaaa gtgaagggtg actgtagtcc tgagctcatg   5160

ggttcaagac cacagcccga tggtagtggt gttaccgtct cgaacctagc cgacagccct   5220

tgtacattgt ggggggagct gttttgtttg cttatgcaat cgcgaaactc tatatctttt   5280

aatgtgttgt tgttgtaca                                                 5299
```

<210> SEQ ID NO 19
<211> LENGTH: 639
<212> TYPE: PRT
<213> ORGANISM: Human bocavirus

<400> SEQUENCE: 19

```
Met Ala Phe Asn Pro Pro Val Ile Arg Ala Phe Ser Gln Pro Ala Phe
1               5                   10                  15

Thr Tyr Val Phe Lys Phe Pro Tyr Pro Gln Trp Lys Glu Lys Glu Trp
            20                  25                  30

Leu Leu His Ala Leu Leu Ala His Gly Thr Glu Gln Ser Met Ile Gln
        35                  40                  45

Leu Arg Asn Cys Ala Pro His Pro Asp Glu Asp Ile Ile Arg Asp Asp
    50                  55                  60

Leu Leu Ile Ser Leu Glu Asp Arg His Phe Gly Ala Val Leu Cys Lys
```

-continued

```
65                  70                  75                  80

Ala Val Tyr Met Ala Thr Thr Thr Leu Met Ser His Lys Gln Arg Asn
                85                  90                  95

Met Phe Pro Ala Cys Asp Ile Ile Val Gln Ser Glu Leu Gly Glu Lys
            100                 105                 110

Asn Leu His Cys His Ile Ile Val Gly Gly Glu Gly Leu Ser Lys Arg
        115                 120                 125

Asn Ala Lys Ser Ser Cys Ala Gln Phe Tyr Gly Leu Ile Leu Ala Glu
    130                 135                 140

Ile Ile Gln Arg Cys Lys Ser Leu Leu Ala Thr Arg Pro Phe Glu Pro
145                 150                 155                 160

Glu Glu Ala Asp Ile Phe His Thr Leu Lys Lys Ala Glu Arg Glu Ala
                165                 170                 175

Trp Gly Gly Val Thr Gly Gly Asn Met Gln Ile Leu Gln Tyr Arg Asp
            180                 185                 190

Arg Arg Gly Asp Leu His Ala Gln Thr Val Asp Pro Leu Arg Phe Phe
        195                 200                 205

Lys Asn Tyr Leu Leu Pro Lys Asn Arg Cys Ile Ser Ser Tyr Ser Lys
    210                 215                 220

Pro Asp Val Cys Thr Ser Pro Asp Asn Trp Phe Ile Leu Ala Glu Lys
225                 230                 235                 240

Thr Tyr Ser His Thr Leu Ile Asn Gly Leu Pro Leu Pro Glu His Tyr
                245                 250                 255

Arg Lys Asn Tyr His Ala Thr Leu Asp Asn Glu Val Ile Pro Gly Pro
            260                 265                 270

Gln Thr Met Ala Tyr Gly Gly Arg Gly Pro Trp Glu His Leu Pro Glu
        275                 280                 285

Val Gly Asp Gln Arg Leu Ala Ala Ser Ser Val Ser Thr Thr Tyr Lys
    290                 295                 300

Pro Asn Lys Lys Glu Lys Leu Met Leu Asn Leu Leu Asp Lys Cys Lys
305                 310                 315                 320

Glu Leu Asn Leu Leu Val Tyr Glu Asp Leu Val Ala Asn Cys Pro Glu
                325                 330                 335

Leu Leu Leu Met Leu Glu Gly Gln Pro Gly Gly Ala Arg Leu Ile Glu
            340                 345                 350

Gln Val Leu Gly Met His His Ile Asn Val Cys Ser Asn Phe Thr Ala
        355                 360                 365

Leu Thr Tyr Leu Phe His Leu His Pro Val Thr Ser Leu Asp Ser Asp
    370                 375                 380

Asn Lys Ala Leu Gln Leu Leu Leu Ile Gln Gly Tyr Asn Pro Leu Ala
385                 390                 395                 400

Val Gly His Ala Leu Cys Cys Val Leu Asn Lys Gln Phe Gly Lys Gln
                405                 410                 415

Asn Thr Val Cys Phe Tyr Gly Pro Ala Ser Thr Gly Lys Thr Asn Met
            420                 425                 430

Ala Lys Ala Ile Val Gln Gly Ile Arg Leu Tyr Gly Cys Val Asn His
        435                 440                 445

Leu Asn Lys Gly Phe Val Phe Asn Asp Cys Arg Gln Arg Leu Val Val
    450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Arg Asp
                485                 490                 495
```

```
Ser Val Leu Leu Thr Gln Thr Pro Val Ile Ile Ser Thr Asn His Asp
            500                 505                 510

Ile Tyr Ala Val Val Gly Gly Asn Ser Val Ser His Val His Ala Ala
        515                 520                 525

Pro Leu Lys Glu Arg Val Ile Gln Leu Asn Phe Met Lys Gln Leu Pro
    530                 535                 540

Gln Thr Phe Gly Glu Ile Thr Ala Thr Glu Ile Ala Ala Leu Leu Gln
545                 550                 555                 560

Trp Cys Phe Asn Glu Tyr Asp Cys Thr Leu Thr Gly Phe Lys Gln Lys
                565                 570                 575

Trp Asn Leu Asp Lys Ile Pro Asn Ser Phe Pro Leu Gly Val Leu Cys
            580                 585                 590

Pro Thr His Ser Gln Asp Phe Thr Leu His Glu Asn Gly Tyr Cys Thr
        595                 600                 605

Asp Cys Gly Gly Tyr Leu Pro His Ser Ala Asp Asn Ser Met Tyr Thr
    610                 615                 620

Asp Arg Ala Ser Glu Thr Ser Thr Gly Asp Ile Thr Pro Ser Lys
625                 630                 635


<210> SEQ ID NO 20
<211> LENGTH: 219
<212> TYPE: PRT
<213> ORGANISM: Human bocavirus

<400> SEQUENCE: 20

Met Ser Ser Gly Asn Met Lys Asp Lys His Arg Ser Tyr Lys Arg Lys
1               5                   10                  15

Gly Ser Pro Glu Arg Gly Glu Arg Lys Arg His Trp Gln Thr Thr His
            20                  25                  30

His Arg Ser Arg Ser Arg Ser Pro Ile Arg His Ser Gly Glu Arg Gly
        35                  40                  45

Ser Gly Ser Tyr His Gln Glu His Pro Ile Ser His Leu Ser Ser Cys
    50                  55                  60

Thr Ala Ser Lys Thr Ser Asp Gln Val Met Lys Thr Arg Glu Ser Thr
65                  70                  75                  80

Ser Gly Lys Lys Asp Asn Arg Thr Asn Pro Tyr Thr Val Phe Ser Gln
                85                  90                  95

His Arg Ala Ser Asn Pro Glu Ala Pro Gly Trp Cys Gly Phe Tyr Trp
            100                 105                 110

His Ser Thr Arg Ile Ala Arg Asp Gly Thr Asn Ser Ile Phe Asn Glu
        115                 120                 125

Met Lys Gln Gln Phe Gln Gln Leu Gln Ile Asp Asn Lys Ile Gly Trp
    130                 135                 140

Asp Asn Thr Arg Glu Leu Leu Phe Asn Gln Lys Lys Thr Leu Asp Gln
145                 150                 155                 160

Lys Tyr Arg Asn Met Phe Trp His Phe Arg Asn Asn Ser Asp Cys Glu
                165                 170                 175

Arg Cys Asn Tyr Trp Asp Asp Val Tyr Arg Arg His Leu Ala Asn Val
            180                 185                 190

Ser Ser Gln Thr Glu Ala Asp Glu Ile Thr Asp Glu Glu Met Leu Ser
        195                 200                 205

Ala Ala Glu Ser Met Glu Ala Asp Ala Ser Asn
    210                 215
```

<210> SEQ ID NO 21
<211> LENGTH: 528
<212> TYPE: PRT
<213> ORGANISM: Human bocavirus

<400> SEQUENCE: 21

```
Met Pro Pro Ile Lys Arg Gln Pro Arg Gly Trp Val Leu Pro Gly Tyr
1               5                   10                  15

Arg Tyr Leu Gly Pro Phe Asn Pro Leu Asp Asn Gly Glu Pro Val Asn
            20                  25                  30

Asn Ala Asp Arg Ala Ala Gln Leu His Asp His Ala Tyr Ser Glu Leu
        35                  40                  45

Ile Lys Ser Gly Lys Asn Pro Tyr Leu Tyr Phe Asn Lys Ala Asp Glu
    50                  55                  60

Lys Phe Ile Asp Asp Leu Lys Asp Asp Trp Ser Ile Gly Gly Ile Ile
65                  70                  75                  80

Gly Ser Ser Phe Phe Lys Ile Lys Arg Ala Val Ala Pro Ala Leu Gly
                85                  90                  95

Asn Lys Glu Arg Ala Gln Lys Arg His Phe Tyr Phe Ala Asn Ser Asn
            100                 105                 110

Lys Gly Ala Lys Lys Thr Lys Lys Ser Glu Pro Lys Pro Gly Thr Ser
        115                 120                 125

Lys Met Ser Asp Thr Asp Ile Gln Asp Gln Gln Pro Asp Thr Val Asp
    130                 135                 140

Ala Pro Gln Asn Ala Ser Gly Gly Gly Thr Gly Ser Ile Gly Gly Gly
145                 150                 155                 160

Lys Gly Ser Gly Val Gly Ile Ser Thr Gly Gly Trp Val Gly Gly Ser
                165                 170                 175

His Phe Ser Asp Lys Tyr Val Val Thr Lys Asn Thr Arg Gln Phe Ile
            180                 185                 190

Thr Thr Ile Gln Asn Gly His Leu Tyr Lys Thr Glu Ala Ile Glu Thr
        195                 200                 205

Thr Asn Gln Ser Gly Lys Ser Gln Arg Cys Val Thr Thr Pro Trp Thr
    210                 215                 220

Tyr Phe Asn Phe Asn Gln Tyr Ser Cys His Phe Ser Pro Gln Asp Trp
225                 230                 235                 240

Gln Arg Leu Thr Asn Glu Tyr Lys Arg Phe Arg Pro Lys Ala Met Gln
                245                 250                 255

Val Lys Ile Tyr Asn Leu Gln Ile Lys Gln Ile Leu Ser Asn Gly Ala
            260                 265                 270

Asp Thr Thr Tyr Asn Asn Asp Leu Thr Ala Gly Val His Ile Phe Cys
        275                 280                 285

Asp Gly Glu His Ala Tyr Pro Asn Ala Ser His Pro Trp Asp Glu Asp
    290                 295                 300

Val Met Pro Asp Leu Pro Tyr Lys Thr Trp Lys Leu Phe Gln Tyr Gly
305                 310                 315                 320

Tyr Ile Pro Ile Glu Asn Glu Leu Ala Asp Leu Asp Gly Asn Ala Ala
                325                 330                 335

Gly Gly Asn Ala Thr Glu Lys Ala Leu Leu Tyr Gln Met Pro Phe Phe
            340                 345                 350

Leu Leu Glu Asn Ser Asp His Gln Val Leu Arg Thr Gly Glu Ser Thr
        355                 360                 365

Glu Phe Thr Phe Asn Phe Asp Cys Glu Trp Val Asn Asn Glu Arg Ala
    370                 375                 380
```

```
Tyr Ile Pro Pro Gly Leu Met Phe Asn Pro Lys Val Pro Thr Arg Arg
385                 390                 395                 400

Val Gln Tyr Ile Arg Gln Asn Gly Ser Thr Ala Ala Ser Thr Gly Arg
                405                 410                 415

Ile Gln Pro Tyr Ser Lys Pro Thr Ser Trp Met Thr Gly Pro Gly Leu
            420                 425                 430

Leu Ser Ala Gln Arg Val Gly Pro Gln Ser Ser Asp Thr Ala Pro Phe
        435                 440                 445

Met Val Cys Thr Asn Pro Glu Gly Thr His Ile Asn Thr Gly Ala Ala
    450                 455                 460

Gly Phe Gly Ser Gly Phe Asp Pro Pro Ser Gly Cys Leu Ala Pro Thr
465                 470                 475                 480

Asn Leu Glu Tyr Lys Leu Gln Trp Tyr Gln Thr Pro Glu Gly Thr Gly
                485                 490                 495

Asn Asn Gly Asn Ile Ile Ala Asn Pro Ser Leu Ser Met Leu Arg Asp
            500                 505                 510

Gln Leu Leu Tyr Lys Gly Asn Gln Thr Thr Tyr Asn Leu Val Gly Asp
        515                 520                 525


<210> SEQ ID NO 22
<211> LENGTH: 542
<212> TYPE: PRT
<213> ORGANISM: Human bocavirus

<400> SEQUENCE: 22

Met Ser Asp Thr Asp Ile Gln Asp Gln Gln Pro Asp Thr Val Asp Ala
1               5                   10                  15

Pro Gln Asn Ala Ser Gly Gly Gly Thr Gly Ser Ile Gly Gly Gly Lys
            20                  25                  30

Gly Ser Gly Val Gly Ile Ser Thr Gly Gly Trp Val Gly Gly Ser His
        35                  40                  45

Phe Ser Asp Lys Tyr Val Val Thr Lys Asn Thr Arg Gln Phe Ile Thr
    50                  55                  60

Thr Ile Gln Asn Gly His Leu Tyr Lys Thr Glu Ala Ile Glu Thr Thr
65                  70                  75                  80

Asn Gln Ser Gly Lys Ser Gln Arg Cys Val Thr Thr Pro Trp Thr Tyr
                85                  90                  95

Phe Asn Phe Asn Gln Tyr Ser Cys His Phe Ser Pro Gln Asp Trp Gln
            100                 105                 110

Arg Leu Thr Asn Glu Tyr Lys Arg Phe Arg Pro Lys Ala Met Gln Val
        115                 120                 125

Lys Ile Tyr Asn Leu Gln Ile Lys Gln Ile Leu Ser Asn Gly Ala Asp
    130                 135                 140

Thr Thr Tyr Asn Asn Asp Leu Thr Ala Gly Val His Ile Phe Cys Asp
145                 150                 155                 160

Gly Glu His Ala Tyr Pro Asn Ala Ser His Pro Trp Asp Glu Asp Val
                165                 170                 175

Met Pro Asp Leu Pro Tyr Lys Thr Trp Lys Leu Phe Gln Tyr Gly Tyr
            180                 185                 190

Ile Pro Ile Glu Asn Glu Leu Ala Asp Leu Asp Gly Asn Ala Ala Gly
        195                 200                 205

Gly Asn Ala Thr Glu Lys Ala Leu Leu Tyr Gln Met Pro Phe Phe Leu
    210                 215                 220

Leu Glu Asn Ser Asp His Gln Val Leu Arg Thr Gly Glu Ser Thr Glu
225                 230                 235                 240
```

```
Phe Thr Phe Asn Phe Asp Cys Glu Trp Val Asn Asn Glu Arg Ala Tyr
                245                 250                 255

Ile Pro Pro Gly Leu Met Phe Asn Pro Lys Val Pro Thr Arg Arg Val
            260                 265                 270

Gln Tyr Ile Arg Gln Asn Gly Ser Thr Ala Ala Ser Thr Gly Arg Ile
        275                 280                 285

Gln Pro Tyr Ser Lys Pro Thr Ser Trp Met Thr Gly Pro Gly Leu Leu
    290                 295                 300

Ser Ala Gln Arg Val Gly Pro Gln Ser Ser Asp Thr Ala Pro Phe Met
305                 310                 315                 320

Val Cys Thr Asn Pro Glu Gly Thr His Ile Asn Thr Gly Ala Ala Gly
                325                 330                 335

Phe Gly Ser Gly Phe Asp Pro Pro Ser Gly Cys Leu Ala Pro Thr Asn
            340                 345                 350

Leu Glu Tyr Lys Leu Gln Trp Tyr Gln Thr Pro Glu Gly Thr Gly Asn
        355                 360                 365

Asn Gly Asn Ile Ile Ala Asn Pro Ser Leu Ser Met Leu Arg Asp Gln
    370                 375                 380

Leu Leu Tyr Lys Gly Asn Gln Thr Thr Tyr Asn Leu Val Gly Asp Ile
385                 390                 395                 400

Trp Met Phe Pro Asn Gln Val Trp Asp Arg Phe Pro Ile Thr Arg Glu
                405                 410                 415

Asn Pro Ile Trp Cys Lys Lys Pro Arg Ala Asp Lys His Thr Ile Met
            420                 425                 430

Asp Pro Phe Asp Gly Ser Ile Ala Met Asp His Pro Pro Gly Thr Ile
        435                 440                 445

Phe Ile Lys Met Ala Lys Ile Pro Val Pro Thr Ala Thr Asn Ala Asp
    450                 455                 460

Ser Tyr Leu Asn Ile Tyr Cys Thr Gly Gln Val Ser Cys Glu Ile Val
465                 470                 475                 480

Trp Glu Val Glu Arg Tyr Ala Thr Lys Asn Trp Arg Pro Glu Arg Arg
                485                 490                 495

His Thr Ala Leu Gly Met Ser Leu Gly Gly Glu Ser Asn Tyr Thr Pro
            500                 505                 510

Thr Tyr His Val Asp Pro Thr Gly Ala Tyr Ile Gln Pro Thr Ser Tyr
        515                 520                 525

Asp Gln Cys Met Pro Val Lys Thr Asn Ile Asn Lys Val Leu
    530                 535                 540


<210> SEQ ID NO 23
<211> LENGTH: 671
<212> TYPE: PRT
<213> ORGANISM: Human bocavirus

<400> SEQUENCE: 23

Met Pro Pro Ile Lys Arg Gln Pro Arg Gly Trp Val Leu Pro Gly Tyr
1               5                   10                  15

Arg Tyr Leu Gly Pro Phe Asn Pro Leu Asp Asn Gly Glu Pro Val Asn
            20                  25                  30

Asn Ala Asp Arg Ala Ala Gln Leu His Asp His Ala Tyr Ser Glu Leu
        35                  40                  45

Ile Lys Ser Gly Lys Asn Pro Tyr Leu Tyr Phe Asn Lys Ala Asp Glu
    50                  55                  60

Lys Phe Ile Asp Asp Leu Lys Asp Asp Trp Ser Ile Gly Gly Ile Ile
```

```
65                  70                  75                  80

Gly Ser Ser Phe Phe Lys Ile Lys Arg Ala Val Ala Pro Ala Leu Gly
                85                  90                  95

Asn Lys Glu Arg Ala Gln Lys Arg His Phe Tyr Phe Ala Asn Ser Asn
            100                 105                 110

Lys Gly Ala Lys Lys Thr Lys Lys Ser Glu Pro Lys Pro Gly Thr Ser
        115                 120                 125

Lys Met Ser Asp Thr Asp Ile Gln Asp Gln Gln Pro Asp Thr Val Asp
    130                 135                 140

Ala Pro Gln Asn Thr Ser Gly Gly Gly Thr Gly Ser Ile Gly Gly Gly
145                 150                 155                 160

Lys Gly Ser Gly Val Gly Ile Ser Thr Gly Gly Trp Val Gly Gly Ser
                165                 170                 175

His Phe Ser Asp Lys Tyr Val Val Thr Lys Asn Thr Arg Gln Phe Ile
            180                 185                 190

Thr Thr Ile Gln Asn Gly His Leu Tyr Lys Thr Glu Ala Ile Glu Thr
        195                 200                 205

Thr Asn Gln Ser Gly Lys Ser Gln Arg Cys Val Thr Thr Pro Trp Thr
    210                 215                 220

Tyr Phe Asn Phe Asn Gln Tyr Ser Cys His Phe Ser Pro Gln Asp Trp
225                 230                 235                 240

Gln Arg Leu Thr Asn Glu Tyr Lys Arg Phe Arg Pro Lys Ala Met Gln
                245                 250                 255

Val Lys Ile Tyr Asn Leu Gln Ile Lys Gln Ile Leu Ser Asn Gly Ala
            260                 265                 270

Asp Thr Thr Tyr Asn Asn Asp Leu Thr Ala Gly Val His Ile Phe Cys
        275                 280                 285

Asp Gly Glu His Ala Tyr Pro Asn Ala Ser His Pro Trp Asp Glu Asp
    290                 295                 300

Val Met Pro Asp Leu Pro Tyr Lys Thr Trp Lys Leu Phe Gln Tyr Gly
305                 310                 315                 320

Tyr Ile Pro Ile Glu Asn Glu Leu Ala Asp Leu Asp Gly Asn Ala Ala
                325                 330                 335

Gly Gly Asn Ala Thr Glu Lys Ala Leu Leu Tyr Gln Met Pro Phe Phe
            340                 345                 350

Leu Leu Glu Asn Ser Asp His Gln Val Leu Arg Thr Gly Glu Ser Thr
        355                 360                 365

Glu Phe Thr Phe Asn Phe Asp Cys Glu Trp Val Asn Asn Glu Arg Ala
    370                 375                 380

Tyr Ile Pro Pro Gly Leu Met Phe Asn Pro Lys Val Pro Thr Arg Arg
385                 390                 395                 400

Val Gln Tyr Ile Arg Gln Asn Gly Ser Thr Ala Ala Ser Thr Gly Arg
                405                 410                 415

Ile Gln Pro Tyr Ser Lys Pro Thr Ser Trp Met Thr Gly Pro Gly Leu
            420                 425                 430

Leu Ser Ala Gln Arg Val Gly Pro Gln Ser Ser Asp Thr Ala Pro Phe
        435                 440                 445

Met Val Cys Thr Asn Pro Glu Gly Thr His Ile Asn Thr Gly Ala Ala
    450                 455                 460

Gly Phe Gly Ser Gly Phe Asp Pro Pro Asn Gly Cys Leu Ala Pro Thr
465                 470                 475                 480

Asn Leu Glu Tyr Lys Leu Gln Trp Tyr Gln Thr Pro Glu Gly Thr Gly
                485                 490                 495
```

```
Asn Asn Gly Asn Ile Ile Ala Asn Pro Ser Leu Ser Met Leu Arg Asp
            500                 505                 510

Gln Leu Leu Tyr Lys Gly Asn Gln Thr Thr Tyr Asn Leu Val Gly Asp
        515                 520                 525

Ile Trp Met Phe Pro Asn Gln Val Trp Asp Arg Phe Pro Ile Thr Arg
    530                 535                 540

Glu Asn Pro Ile Trp Cys Lys Lys Pro Arg Ala Asp Lys His Thr Ile
545                 550                 555                 560

Met Asp Pro Phe Asp Gly Ser Ile Ala Met Asp His Pro Pro Gly Thr
                565                 570                 575

Ile Phe Ile Lys Met Ala Lys Ile Pro Val Pro Thr Ala Ser Asn Ala
            580                 585                 590

Asp Ser Tyr Leu Asn Ile Tyr Cys Thr Gly Gln Val Ser Cys Glu Ile
        595                 600                 605

Val Trp Glu Val Glu Arg Tyr Ala Thr Lys Asn Trp Arg Pro Glu Arg
    610                 615                 620

Arg His Thr Ala Leu Gly Met Ser Leu Gly Gly Glu Ser Asn Tyr Thr
625                 630                 635                 640

Pro Thr Tyr His Val Asp Pro Thr Gly Ala Tyr Ile Gln Pro Thr Ser
                645                 650                 655

Tyr Asp Gln Cys Met Pro Val Lys Thr Asn Ile Asn Lys Val Leu
            660                 665                 670


<210> SEQ ID NO 24
<211> LENGTH: 542
<212> TYPE: PRT
<213> ORGANISM: Human bocavirus

<400> SEQUENCE: 24

Met Ser Asp Thr Asp Ile Gln Asp Gln Gln Pro Asp Thr Val Asp Ala
1               5                   10                  15

Pro Gln Asn Thr Ser Gly Gly Gly Thr Gly Ser Ile Gly Gly Gly Lys
            20                  25                  30

Gly Ser Gly Val Gly Ile Ser Thr Gly Gly Trp Val Gly Gly Ser His
        35                  40                  45

Phe Ser Asp Lys Tyr Val Val Thr Lys Asn Thr Arg Gln Phe Ile Thr
    50                  55                  60

Thr Ile Gln Asn Gly His Leu Tyr Lys Thr Glu Ala Ile Glu Thr Thr
65                  70                  75                  80

Asn Gln Ser Gly Lys Ser Gln Arg Cys Val Thr Thr Pro Trp Thr Tyr
                85                  90                  95

Phe Asn Phe Asn Gln Tyr Ser Cys His Phe Ser Pro Gln Asp Trp Gln
            100                 105                 110

Arg Leu Thr Asn Glu Tyr Lys Arg Phe Arg Pro Lys Ala Met Gln Val
        115                 120                 125

Lys Ile Tyr Asn Leu Gln Ile Lys Gln Ile Leu Ser Asn Gly Ala Asp
    130                 135                 140

Thr Thr Tyr Asn Asn Asp Leu Thr Ala Gly Val His Ile Phe Cys Asp
145                 150                 155                 160

Gly Glu His Ala Tyr Pro Asn Ala Ser His Pro Trp Asp Glu Asp Val
                165                 170                 175

Met Pro Asp Leu Pro Tyr Lys Thr Trp Lys Leu Phe Gln Tyr Gly Tyr
            180                 185                 190

Ile Pro Ile Glu Asn Glu Leu Ala Asp Leu Asp Gly Asn Ala Ala Gly
```

```
        195                 200                 205

Gly Asn Ala Thr Glu Lys Ala Leu Leu Tyr Gln Met Pro Phe Phe Leu
    210                 215                 220

Leu Glu Asn Ser Asp His Gln Val Leu Arg Thr Gly Glu Ser Thr Glu
225                 230                 235                 240

Phe Thr Phe Asn Phe Asp Cys Glu Trp Val Asn Asn Glu Arg Ala Tyr
                245                 250                 255

Ile Pro Pro Gly Leu Met Phe Asn Pro Lys Val Pro Thr Arg Arg Val
            260                 265                 270

Gln Tyr Ile Arg Gln Asn Gly Ser Thr Ala Ala Ser Thr Gly Arg Ile
        275                 280                 285

Gln Pro Tyr Ser Lys Pro Thr Ser Trp Met Thr Gly Pro Gly Leu Leu
    290                 295                 300

Ser Ala Gln Arg Val Gly Pro Gln Ser Ser Asp Thr Ala Pro Phe Met
305                 310                 315                 320

Val Cys Thr Asn Pro Glu Gly Thr His Ile Asn Thr Gly Ala Ala Gly
                325                 330                 335

Phe Gly Ser Gly Phe Asp Pro Pro Asn Gly Cys Leu Ala Pro Thr Asn
            340                 345                 350

Leu Glu Tyr Lys Leu Gln Trp Tyr Gln Thr Pro Glu Gly Thr Gly Asn
        355                 360                 365

Asn Gly Asn Ile Ile Ala Asn Pro Ser Leu Ser Met Leu Arg Asp Gln
    370                 375                 380

Leu Leu Tyr Lys Gly Asn Gln Thr Thr Tyr Asn Leu Val Gly Asp Ile
385                 390                 395                 400

Trp Met Phe Pro Asn Gln Val Trp Asp Arg Phe Pro Ile Thr Arg Glu
                405                 410                 415

Asn Pro Ile Trp Cys Lys Lys Pro Arg Ala Asp Lys His Thr Ile Met
            420                 425                 430

Asp Pro Phe Asp Gly Ser Ile Ala Met Asp His Pro Pro Gly Thr Ile
        435                 440                 445

Phe Ile Lys Met Ala Lys Ile Pro Val Pro Thr Ala Ser Asn Ala Asp
    450                 455                 460

Ser Tyr Leu Asn Ile Tyr Cys Thr Gly Gln Val Ser Cys Glu Ile Val
465                 470                 475                 480

Trp Glu Val Glu Arg Tyr Ala Thr Lys Asn Trp Arg Pro Glu Arg Arg
                485                 490                 495

His Thr Ala Leu Gly Met Ser Leu Gly Gly Glu Ser Asn Tyr Thr Pro
            500                 505                 510

Thr Tyr His Val Asp Pro Thr Gly Ala Tyr Ile Gln Pro Thr Ser Tyr
        515                 520                 525

Asp Gln Cys Met Pro Val Lys Thr Asn Ile Asn Lys Val Leu
    530                 535                 540


<210> SEQ ID NO 25
<211> LENGTH: 781
<212> TYPE: PRT
<213> ORGANISM: Human bocavirus

<400> SEQUENCE: 25

Met Ala Phe Asn Pro Pro Val Ile Arg Ala Phe Ser Gln Pro Ala Phe
1               5                   10                  15

Thr Tyr Val Phe Lys Phe Pro Tyr Pro Gln Trp Lys Glu Lys Glu Trp
            20                  25                  30
```

```
Leu Leu His Ala Leu Leu Ala His Gly Thr Glu Gln Ser Met Ile Gln
        35                  40                  45

Leu Arg Asn Cys Ala Pro His Pro Asp Glu Asp Ile Ile Arg Asp Asp
    50                  55                  60

Leu Leu Ile Ser Leu Glu Asp Arg His Phe Gly Ala Val Leu Cys Lys
65                  70                  75                  80

Ala Val Tyr Met Ala Thr Thr Thr Leu Met Ser His Lys Gln Arg Asn
                85                  90                  95

Met Phe Pro Arg Cys Asp Ile Ile Val Gln Ser Glu Leu Gly Glu Lys
            100                 105                 110

Asn Leu His Cys His Ile Ile Val Gly Gly Glu Gly Leu Ser Lys Arg
        115                 120                 125

Asn Ala Lys Ser Ser Cys Ala Gln Phe Tyr Gly Leu Ile Leu Ala Glu
    130                 135                 140

Ile Ile Gln Arg Cys Lys Ser Leu Leu Ala Thr Arg Pro Phe Glu Pro
145                 150                 155                 160

Glu Glu Ala Asp Ile Phe His Thr Leu Lys Lys Ala Glu Arg Glu Ala
                165                 170                 175

Trp Gly Gly Val Thr Gly Gly Asn Met Gln Ile Leu Gln Tyr Arg Asp
            180                 185                 190

Arg Arg Gly Asp Leu His Ala Gln Thr Val Asp Pro Leu Arg Phe Phe
        195                 200                 205

Lys Asn Tyr Leu Leu Pro Lys Asn Arg Cys Ile Ser Ser Tyr Ser Lys
    210                 215                 220

Pro Asp Val Cys Thr Ser Pro Asp Asn Trp Phe Ile Leu Ala Glu Lys
225                 230                 235                 240

Thr Tyr Ser His Thr Leu Ile Asn Gly Leu Pro Leu Pro Glu His Tyr
                245                 250                 255

Arg Lys Asn Tyr His Ala Thr Leu Asp Asn Glu Val Ile Pro Gly Pro
            260                 265                 270

Gln Thr Met Ala Tyr Gly Gly Arg Gly Pro Trp Glu His Leu Pro Glu
        275                 280                 285

Val Gly Asp Gln Arg Leu Ala Ala Ser Ser Val Ser Thr Thr Tyr Lys
    290                 295                 300

Pro Asn Lys Lys Glu Lys Leu Met Leu Asn Leu Leu Asp Lys Cys Lys
305                 310                 315                 320

Glu Leu Asn Leu Leu Val Tyr Glu Asp Leu Val Ala Asn Cys Pro Glu
                325                 330                 335

Leu Leu Leu Met Leu Glu Gly Gln Pro Gly Gly Ala Arg Leu Ile Glu
            340                 345                 350

Gln Val Leu Gly Met His His Ile Asn Val Cys Ser Asn Phe Thr Ala
        355                 360                 365

Leu Thr Tyr Leu Phe His Leu His Pro Val Thr Ser Leu Asp Ser Asp
    370                 375                 380

Asn Lys Ala Leu Gln Leu Leu Leu Ile Gln Gly Tyr Asn Pro Leu Ala
385                 390                 395                 400

Val Gly His Ala Leu Cys Cys Val Leu Asn Lys Gln Phe Gly Lys Gln
                405                 410                 415

Asn Thr Val Cys Phe Tyr Gly Pro Ala Ser Thr Gly Lys Thr Asn Met
            420                 425                 430

Ala Lys Ala Ile Val Gln Gly Ile Arg Leu Tyr Gly Cys Val Asn His
        435                 440                 445

Leu Asn Lys Gly Phe Val Phe Asn Asp Cys Arg Gln Arg Leu Val Val
```

```
    450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Arg Asp
                485                 490                 495

Ser Val Leu Leu Thr Gln Thr Pro Val Ile Ile Ser Thr Asn His Asp
            500                 505                 510

Ile Tyr Ala Val Val Gly Gly Asn Ser Val Ser His Val His Ala Ala
        515                 520                 525

Pro Leu Lys Glu Arg Val Ile Gln Leu Asn Phe Met Lys Gln Leu Pro
    530                 535                 540

Gln Thr Phe Gly Glu Ile Thr Ala Thr Glu Ile Ala Ala Leu Leu Gln
545                 550                 555                 560

Trp Cys Phe Asn Glu Tyr Asp Cys Thr Leu Thr Gly Phe Lys Gln Lys
                565                 570                 575

Trp Asn Leu Asp Lys Ile Pro Asn Ser Phe Pro Leu Gly Val Leu Cys
            580                 585                 590

Pro Thr His Ser Gln Asp Phe Thr Leu His Glu Asn Gly Tyr Cys Thr
        595                 600                 605

Asp Cys Gly Gly Tyr Leu Pro His Ser Ala Asp Asn Ser Met Tyr Thr
    610                 615                 620

Asp Arg Ala Ser Glu Thr Ser Thr Gly Asp Ile Thr Pro Ser Asp Leu
625                 630                 635                 640

Gly Asp Ser Asp Gly Glu Asp Thr Lys Pro Glu Thr Ser Gln Val Asp
                645                 650                 655

Tyr Cys Pro Pro Lys Lys Arg Arg Leu Thr Ala Pro Ala Ser Pro Pro
            660                 665                 670

Asn Ser Pro Ala Ser Ser Val Ser Thr Ile Thr Phe Phe Asn Thr Trp
        675                 680                 685

His Ala Gln Pro Arg Asp Glu Asp Glu Leu Arg Glu Tyr Glu Arg Gln
    690                 695                 700

Ala Ser Leu Leu Gln Lys Lys Arg Glu Ser Arg Lys Arg Gly Glu Glu
705                 710                 715                 720

Glu Thr Leu Ala Asp Asn Ser Ser Gln Glu Gln Glu Pro Gln Pro Asp
                725                 730                 735

Pro Thr Gln Trp Gly Glu Arg Leu Gly Leu Ile Ser Ser Gly Thr Pro
            740                 745                 750

Asn Gln Pro Pro Ile Val Leu His Cys Phe Glu Asp Leu Arg Pro Ser
        755                 760                 765

Asp Glu Asp Glu Gly Glu Tyr Ile Gly Glu Lys Arg Gln
    770                 775                 780


<210> SEQ ID NO 26
<211> LENGTH: 639
<212> TYPE: PRT
<213> ORGANISM: Human bocavirus

<400> SEQUENCE: 26

Met Ala Phe Asn Pro Pro Val Ile Arg Ala Phe Ser Gln Pro Ala Phe
1               5                   10                  15

Thr Tyr Val Phe Lys Phe Pro Tyr Pro Gln Trp Lys Glu Lys Glu Trp
            20                  25                  30

Leu Leu His Ala Leu Leu Ala His Gly Thr Glu Gln Ser Met Ile Gln
        35                  40                  45
```

```
Leu Arg Asn Cys Ala Pro His Pro Asp Glu Asp Ile Ile Arg Asp Asp
    50                  55                  60

Leu Leu Ile Ser Leu Glu Asp Arg His Phe Gly Ala Val Leu Cys Lys
65                  70                  75                  80

Ala Val Tyr Met Ala Thr Thr Thr Leu Met Ser His Lys Gln Arg Asn
                85                  90                  95

Met Phe Pro Arg Cys Asp Ile Ile Val Gln Ser Glu Leu Gly Glu Lys
            100                 105                 110

Asn Leu His Cys His Ile Ile Val Gly Gly Glu Gly Leu Ser Lys Arg
        115                 120                 125

Asn Ala Lys Ser Ser Cys Ala Gln Phe Tyr Gly Leu Ile Leu Ala Glu
    130                 135                 140

Ile Ile Gln Arg Cys Lys Ser Leu Leu Ala Thr Arg Pro Phe Glu Pro
145                 150                 155                 160

Glu Glu Ala Asp Ile Phe His Thr Leu Lys Lys Ala Glu Arg Glu Ala
                165                 170                 175

Trp Gly Gly Val Thr Gly Gly Asn Met Gln Ile Leu Gln Tyr Arg Asp
            180                 185                 190

Arg Arg Gly Asp Leu His Ala Gln Thr Val Asp Pro Leu Arg Phe Phe
        195                 200                 205

Lys Asn Tyr Leu Leu Pro Lys Asn Arg Cys Ile Ser Ser Tyr Ser Lys
    210                 215                 220

Pro Asp Val Cys Thr Ser Pro Asp Asn Trp Phe Ile Leu Ala Glu Lys
225                 230                 235                 240

Thr Tyr Ser His Thr Leu Ile Asn Gly Leu Pro Leu Pro Glu His Tyr
                245                 250                 255

Arg Lys Asn Tyr His Ala Thr Leu Asp Asn Glu Val Ile Pro Gly Pro
            260                 265                 270

Gln Thr Met Ala Tyr Gly Gly Arg Gly Pro Trp Glu His Leu Pro Glu
        275                 280                 285

Val Gly Asp Gln Arg Leu Ala Ala Ser Ser Val Ser Thr Thr Tyr Lys
    290                 295                 300

Pro Asn Lys Lys Glu Lys Leu Met Leu Asn Leu Leu Asp Lys Cys Lys
305                 310                 315                 320

Glu Leu Asn Leu Leu Val Tyr Glu Asp Leu Val Ala Asn Cys Pro Glu
                325                 330                 335

Leu Leu Leu Met Leu Glu Gly Gln Pro Gly Gly Ala Arg Leu Ile Glu
            340                 345                 350

Gln Val Leu Gly Met His His Ile Asn Val Cys Ser Asn Phe Thr Ala
        355                 360                 365

Leu Thr Tyr Leu Phe His Leu His Pro Val Thr Ser Leu Asp Ser Asp
    370                 375                 380

Asn Lys Ala Leu Gln Leu Leu Leu Ile Gln Gly Tyr Asn Pro Leu Ala
385                 390                 395                 400

Val Gly His Ala Leu Cys Cys Val Leu Asn Lys Gln Phe Gly Lys Gln
                405                 410                 415

Asn Thr Val Cys Phe Tyr Gly Pro Ala Ser Thr Gly Lys Thr Asn Met
            420                 425                 430

Ala Lys Ala Ile Val Gln Gly Ile Arg Leu Tyr Gly Cys Val Asn His
        435                 440                 445

Leu Asn Lys Gly Phe Val Phe Asn Asp Cys Arg Gln Arg Leu Val Val
    450                 455                 460

Trp Trp Glu Glu Cys Leu Met His Gln Asp Trp Val Glu Pro Ala Lys
```

```
465                 470                 475                 480

Cys Ile Leu Gly Gly Thr Glu Cys Arg Ile Asp Val Lys His Arg Asp
                485                 490                 495

Ser Val Leu Leu Thr Gln Thr Pro Val Ile Ile Ser Thr Asn His Asp
            500                 505                 510

Ile Tyr Ala Val Val Gly Gly Asn Ser Val Ser His Val His Ala Ala
        515                 520                 525

Pro Leu Lys Glu Arg Val Ile Gln Leu Asn Phe Met Lys Gln Leu Pro
    530                 535                 540

Gln Thr Phe Gly Glu Ile Thr Ala Thr Glu Ile Ala Ala Leu Leu Gln
545                 550                 555                 560

Trp Cys Phe Asn Glu Tyr Asp Cys Thr Leu Thr Gly Phe Lys Gln Lys
                565                 570                 575

Trp Asn Leu Asp Lys Ile Pro Asn Ser Phe Pro Leu Gly Val Leu Cys
            580                 585                 590

Pro Thr His Ser Gln Asp Phe Thr Leu His Glu Asn Gly Tyr Cys Thr
        595                 600                 605

Asp Cys Gly Gly Tyr Leu Pro His Ser Ala Asp Asn Ser Met Tyr Thr
    610                 615                 620

Asp Arg Ala Ser Glu Thr Ser Thr Gly Asp Ile Thr Pro Ser Lys
625                 630                 635


<210> SEQ ID NO 27
<211> LENGTH: 219
<212> TYPE: PRT
<213> ORGANISM: Human bocavirus

<400> SEQUENCE: 27

Met Ser Ser Gly Asn Met Lys Asp Lys His Arg Ser Tyr Lys Arg Lys
1               5                   10                  15

Gly Ser Pro Glu Arg Gly Glu Arg Lys Arg His Trp Gln Thr Thr His
            20                  25                  30

His Arg Ser Arg Ser Arg Ser Pro Ile Arg His Ser Gly Glu Arg Gly
        35                  40                  45

Ser Gly Ser Tyr His Gln Glu His Pro Ile Ser His Leu Ser Ser Cys
    50                  55                  60

Thr Ala Ser Lys Thr Ser Asp Gln Val Met Lys Thr Arg Glu Ser Thr
65                  70                  75                  80

Ser Gly Lys Lys Asp Asn Arg Thr Asn Pro Tyr Thr Val Phe Ser Gln
                85                  90                  95

His Arg Ala Ser Asn Pro Glu Ala Pro Gly Trp Cys Gly Phe Tyr Trp
            100                 105                 110

His Ser Thr Arg Ile Ala Arg Asp Gly Thr Asn Ser Ile Phe Asn Glu
        115                 120                 125

Met Lys Gln Gln Phe Gln Gln Leu Gln Ile Asp Asn Lys Ile Gly Trp
    130                 135                 140

Asp Asn Thr Arg Glu Leu Leu Phe Asn Gln Lys Lys Thr Leu Asp Gln
145                 150                 155                 160

Lys Tyr Arg Asn Met Phe Trp His Phe Arg Asn Asn Ser Asp Cys Glu
                165                 170                 175

Arg Cys Asn Tyr Trp Asp Asp Val Tyr Arg Arg His Leu Ala Asn Val
            180                 185                 190

Ser Ser Gln Thr Glu Ala Asp Glu Ile Thr Asp Glu Glu Met Leu Ser
        195                 200                 205
```

```
Ala Ala Glu Ser Met Glu Ala Asp Ala Ser Asn
    210                 215


<210> SEQ ID NO 28
<211> LENGTH: 671
<212> TYPE: PRT
<213> ORGANISM: Human bocavirus

<400> SEQUENCE: 28

Met Pro Pro Ile Lys Arg Gln Pro Arg Gly Trp Val Leu Pro Gly Tyr
1               5                   10                  15

Arg Tyr Leu Gly Pro Phe Asn Pro Leu Asp Asn Gly Glu Pro Val Asn
            20                  25                  30

Asn Ala Asp Arg Ala Ala Gln Leu His Asp His Ala Tyr Ser Glu Leu
        35                  40                  45

Ile Lys Ser Gly Lys Asn Pro Tyr Leu Tyr Phe Asn Lys Ala Asp Glu
    50                  55                  60

Lys Phe Ile Asp Asp Leu Lys Asp Asp Trp Ser Ile Gly Gly Ile Ile
65                  70                  75                  80

Gly Ser Ser Phe Phe Lys Ile Lys Arg Ala Val Ala Pro Ala Leu Gly
                85                  90                  95

Asn Lys Glu Arg Ala Gln Lys Arg His Phe Tyr Phe Ala Asn Ser Asn
            100                 105                 110

Lys Gly Ala Lys Lys Thr Lys Lys Ser Glu Pro Lys Pro Gly Thr Ser
        115                 120                 125

Lys Met Ser Asp Thr Asp Ile Gln Asp Gln Gln Pro Asp Thr Val Asp
    130                 135                 140

Ala Pro Gln Asn Thr Ser Gly Gly Gly Thr Gly Ser Ile Gly Gly Gly
145                 150                 155                 160

Lys Gly Ser Gly Val Gly Ile Ser Thr Gly Gly Trp Val Gly Gly Ser
                165                 170                 175

His Phe Ser Asp Lys Tyr Val Val Thr Lys Asn Thr Arg Gln Phe Ile
            180                 185                 190

Thr Thr Ile Gln Asn Gly His Leu Tyr Lys Thr Glu Ala Ile Glu Thr
        195                 200                 205

Thr Asn Gln Ser Gly Lys Ser Gln Arg Cys Val Thr Thr Pro Trp Thr
    210                 215                 220

Tyr Phe Asn Phe Asn Gln Tyr Ser Cys His Phe Ser Pro Gln Asp Trp
225                 230                 235                 240

Gln Arg Leu Thr Asn Glu Tyr Lys Arg Phe Arg Pro Lys Ala Met Gln
                245                 250                 255

Val Lys Ile Tyr Asn Leu Gln Ile Lys Gln Ile Leu Ser Asn Gly Ala
            260                 265                 270

Asp Thr Thr Tyr Asn Asn Asp Leu Thr Ala Gly Val His Ile Phe Cys
        275                 280                 285

Asp Gly Glu His Ala Tyr Pro Asn Ala Ser His Pro Trp Asp Glu Asp
    290                 295                 300

Val Met Pro Asp Leu Pro Tyr Lys Thr Trp Lys Leu Phe Gln Tyr Gly
305                 310                 315                 320

Tyr Ile Pro Ile Glu Asn Glu Leu Ala Asp Leu Asp Gly Asn Ala Ala
                325                 330                 335

Gly Gly Asn Ala Thr Glu Lys Ala Leu Leu Tyr Gln Met Pro Phe Phe
            340                 345                 350

Leu Leu Glu Asn Ser Asp His Gln Val Leu Arg Thr Gly Glu Ser Thr
        355                 360                 365
```

```
Glu Phe Thr Phe Asn Phe Asp Cys Glu Trp Val Asn Asn Glu Arg Ala
    370                 375                 380

Tyr Ile Pro Pro Gly Leu Met Phe Asn Pro Lys Val Pro Thr Arg Arg
385                 390                 395                 400

Val Gln Tyr Ile Arg Gln Asn Gly Ser Thr Ala Ala Ser Thr Gly Arg
                405                 410                 415

Ile Gln Pro Tyr Ser Lys Pro Thr Ser Trp Met Thr Gly Pro Gly Leu
            420                 425                 430

Leu Ser Ala Gln Arg Val Gly Pro Gln Ser Ser Asp Thr Ala Pro Phe
        435                 440                 445

Met Val Cys Thr Asn Pro Glu Gly Thr His Ile Asn Thr Gly Ala Ala
    450                 455                 460

Gly Phe Gly Ser Gly Phe Asp Pro Pro Ser Gly Cys Leu Ala Pro Thr
465                 470                 475                 480

Asn Leu Glu Tyr Lys Leu Gln Trp Tyr Gln Thr Pro Glu Gly Thr Gly
                485                 490                 495

Asn Asn Gly Asn Ile Ile Ala Asn Pro Ser Leu Ser Met Leu Arg Asp
            500                 505                 510

Gln Leu Leu Tyr Lys Gly Asn Gln Thr Thr Tyr Asn Leu Val Gly Asp
        515                 520                 525

Ile Trp Met Phe Pro Asn Gln Val Trp Asp Arg Phe Pro Ile Thr Arg
    530                 535                 540

Glu Asn Pro Ile Trp Cys Lys Lys Pro Arg Ala Asp Lys His Thr Ile
545                 550                 555                 560

Met Asp Pro Phe Asp Gly Ser Ile Ala Met Asp His Pro Pro Gly Thr
                565                 570                 575

Ile Phe Ile Lys Met Ala Lys Ile Pro Val Pro Thr Ala Ser Asn Ala
            580                 585                 590

Asp Ser Tyr Leu Asn Ile Tyr Cys Thr Gly Gln Val Ser Cys Glu Ile
        595                 600                 605

Val Trp Glu Val Lys Arg Tyr Ala Thr Lys Asn Trp Arg Pro Glu Arg
    610                 615                 620

Arg His Thr Ala Leu Gly Met Ser Leu Gly Gly Glu Ser Asn Tyr Thr
625                 630                 635                 640

Pro Thr Tyr His Val Asp Pro Thr Gly Ala Tyr Ile Gln Pro Thr Ser
                645                 650                 655

Tyr Asp Gln Cys Met Pro Val Lys Thr Asn Ile Asn Lys Val Leu
            660                 665                 670


<210> SEQ ID NO 29
<211> LENGTH: 542
<212> TYPE: PRT
<213> ORGANISM: Human bocavirus

<400> SEQUENCE: 29

Met Ser Asp Thr Asp Ile Gln Asp Gln Gln Pro Asp Thr Val Asp Ala
1               5                   10                  15

Pro Gln Asn Thr Ser Gly Gly Gly Thr Gly Ser Ile Gly Gly Gly Lys
            20                  25                  30

Gly Ser Gly Val Gly Ile Ser Thr Gly Gly Trp Val Gly Gly Ser His
        35                  40                  45

Phe Ser Asp Lys Tyr Val Val Thr Lys Asn Thr Arg Gln Phe Ile Thr
    50                  55                  60

Thr Ile Gln Asn Gly His Leu Tyr Lys Thr Glu Ala Ile Glu Thr Thr
```

```
65                  70                  75                  80

Asn Gln Ser Gly Lys Ser Gln Arg Cys Val Thr Thr Pro Trp Thr Tyr
                85                  90                  95

Phe Asn Phe Asn Gln Tyr Ser Cys His Phe Ser Pro Gln Asp Trp Gln
            100                 105                 110

Arg Leu Thr Asn Glu Tyr Lys Arg Phe Arg Pro Lys Ala Met Gln Val
        115                 120                 125

Lys Ile Tyr Asn Leu Gln Ile Lys Gln Ile Leu Ser Asn Gly Ala Asp
    130                 135                 140

Thr Thr Tyr Asn Asn Asp Leu Thr Ala Gly Val His Ile Phe Cys Asp
145                 150                 155                 160

Gly Glu His Ala Tyr Pro Asn Ala Ser His Pro Trp Asp Glu Asp Val
                165                 170                 175

Met Pro Asp Leu Pro Tyr Lys Thr Trp Lys Leu Phe Gln Tyr Gly Tyr
            180                 185                 190

Ile Pro Ile Glu Asn Glu Leu Ala Asp Leu Asp Gly Asn Ala Ala Gly
        195                 200                 205

Gly Asn Ala Thr Glu Lys Ala Leu Leu Tyr Gln Met Pro Phe Phe Leu
    210                 215                 220

Leu Glu Asn Ser Asp His Gln Val Leu Arg Thr Gly Glu Ser Thr Glu
225                 230                 235                 240

Phe Thr Phe Asn Phe Asp Cys Glu Trp Val Asn Asn Glu Arg Ala Tyr
                245                 250                 255

Ile Pro Pro Gly Leu Met Phe Asn Pro Lys Val Pro Thr Arg Arg Val
            260                 265                 270

Gln Tyr Ile Arg Gln Asn Gly Ser Thr Ala Ala Ser Thr Gly Arg Ile
        275                 280                 285

Gln Pro Tyr Ser Lys Pro Thr Ser Trp Met Thr Gly Pro Gly Leu Leu
    290                 295                 300

Ser Ala Gln Arg Val Gly Pro Gln Ser Ser Asp Thr Ala Pro Phe Met
305                 310                 315                 320

Val Cys Thr Asn Pro Glu Gly Thr His Ile Asn Thr Gly Ala Ala Gly
                325                 330                 335

Phe Gly Ser Gly Phe Asp Pro Pro Ser Gly Cys Leu Ala Pro Thr Asn
            340                 345                 350

Leu Glu Tyr Lys Leu Gln Trp Tyr Gln Thr Pro Glu Gly Thr Gly Asn
        355                 360                 365

Asn Gly Asn Ile Ile Ala Asn Pro Ser Leu Ser Met Leu Arg Asp Gln
    370                 375                 380

Leu Leu Tyr Lys Gly Asn Gln Thr Thr Tyr Asn Leu Val Gly Asp Ile
385                 390                 395                 400

Trp Met Phe Pro Asn Gln Val Trp Asp Arg Phe Pro Ile Thr Arg Glu
                405                 410                 415

Asn Pro Ile Trp Cys Lys Lys Pro Arg Ala Asp Lys His Thr Ile Met
            420                 425                 430

Asp Pro Phe Asp Gly Ser Ile Ala Met Asp His Pro Pro Gly Thr Ile
        435                 440                 445

Phe Ile Lys Met Ala Lys Ile Pro Val Pro Thr Ala Ser Asn Ala Asp
    450                 455                 460

Ser Tyr Leu Asn Ile Tyr Cys Thr Gly Gln Val Ser Cys Glu Ile Val
465                 470                 475                 480

Trp Glu Val Lys Arg Tyr Ala Thr Lys Asn Trp Arg Pro Glu Arg Arg
                485                 490                 495
```

```
His Thr Ala Leu Gly Met Ser Leu Gly Gly Glu Ser Asn Tyr Thr Pro
            500                 505                 510

Thr Tyr His Val Asp Pro Thr Gly Ala Tyr Ile Gln Pro Thr Ser Tyr
        515                 520                 525

Asp Gln Cys Met Pro Val Lys Thr Asn Ile Asn Lys Val Leu
    530                 535                 540


<210> SEQ ID NO 30
<211> LENGTH: 781
<212> TYPE: PRT
<213> ORGANISM: Human bocavirus

<400> SEQUENCE: 30

Met Ala Phe Asn Pro Pro Val Ile Arg Ala Phe Ser Gln Pro Ala Phe
1               5                   10                  15

Thr Tyr Val Phe Lys Phe Pro Tyr Pro Gln Trp Lys Glu Lys Glu Trp
            20                  25                  30

Leu Leu His Ala Leu Leu Ala His Gly Thr Glu Gln Ser Met Ile Gln
        35                  40                  45

Leu Arg Asn Cys Ala Pro His Pro Asp Glu Asp Ile Ile Arg Asp Asp
    50                  55                  60

Leu Leu Ile Ser Leu Glu Asp Arg His Phe Gly Ala Val Leu Cys Lys
65                  70                  75                  80

Ala Val Tyr Met Ala Thr Thr Thr Leu Met Ser His Lys Gln Arg Asn
                85                  90                  95

Met Phe Pro Arg Cys Asp Ile Ile Val Gln Ser Glu Leu Gly Glu Lys
            100                 105                 110

Asn Leu His Cys His Ile Ile Val Gly Gly Glu Gly Leu Ser Lys Arg
        115                 120                 125

Asn Ala Lys Ser Ser Cys Ala Gln Phe Tyr Gly Leu Ile Leu Ala Glu
    130                 135                 140

Ile Ile Gln Arg Cys Lys Ser Leu Leu Ala Thr Arg Pro Phe Glu Pro
145                 150                 155                 160

Glu Glu Ala Asp Ile Phe His Thr Leu Lys Lys Ala Glu Arg Glu Ala
                165                 170                 175

Trp Gly Gly Val Thr Gly Gly Asn Met Gln Ile Leu Gln Tyr Arg Asp
            180                 185                 190

Arg Arg Gly Asp Leu His Ala Gln Thr Val Asp Pro Leu Arg Phe Phe
        195                 200                 205

Lys Asn Tyr Leu Leu Pro Lys Asn Arg Cys Ile Ser Ser Tyr Ser Lys
    210                 215                 220

Pro Asp Val Cys Thr Ser Pro Asp Asn Trp Phe Ile Leu Ala Glu Lys
225                 230                 235                 240

Thr Tyr Ser His Thr Leu Ile Asn Gly Leu Pro Leu Pro Glu His Tyr
                245                 250                 255

Arg Lys Asn Tyr His Ala Thr Leu Asp Asn Glu Val Ile Pro Gly Pro
            260                 265                 270

Gln Thr Met Ala Tyr Gly Gly Arg Gly Pro Trp Glu His Leu Pro Glu
        275                 280                 285

Val Gly Asp Gln Arg Leu Ala Ala Ser Ser Val Ser Thr Thr Tyr Lys
    290                 295                 300

Pro Asn Lys Lys Glu Lys Leu Met Leu Asn Leu Leu Asp Lys Cys Lys
305                 310                 315                 320

Glu Leu Asn Leu Leu Val Tyr Glu Asp Leu Val Ala Asn Cys Pro Glu
```

```
                325                 330                 335

Leu Leu Leu Met Leu Glu Gly Gln Pro Gly Gly Ala Arg Leu Ile Glu
            340                 345                 350

Gln Val Leu Gly Met His His Ile Asn Val Cys Ser Asn Phe Thr Ala
        355                 360                 365

Leu Thr Tyr Leu Phe His Leu His Pro Val Thr Ser Leu Asp Ser Asp
    370                 375                 380

Asn Lys Ala Leu Gln Leu Leu Leu Ile Gln Gly Tyr Asn Pro Leu Ala
385                 390                 395                 400

Val Gly His Ala Leu Cys Cys Val Leu Asn Lys Gln Phe Gly Lys Gln
                405                 410                 415

Asn Thr Val Cys Phe Tyr Gly Pro Ala Ser Thr Gly Lys Thr Asn Met
            420                 425                 430

Ala Lys Ala Ile Val Gln Gly Ile Arg Leu Tyr Gly Cys Val Asn His
        435                 440                 445

Leu Asn Lys Gly Phe Val Phe Asn Asp Cys Arg Gln Arg Leu Val Val
    450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Arg Asp
                485                 490                 495

Ser Val Leu Leu Thr Gln Thr Pro Val Ile Ile Ser Thr Asn His Asp
            500                 505                 510

Ile Tyr Ala Val Val Gly Gly Asn Ser Val Ser His Val His Ala Ala
        515                 520                 525

Pro Leu Lys Glu Arg Val Ile Gln Leu Asn Phe Met Lys Gln Leu Pro
    530                 535                 540

Gln Thr Phe Gly Glu Ile Thr Ala Thr Glu Ile Ala Ala Leu Leu Gln
545                 550                 555                 560

Trp Cys Phe Asn Glu Tyr Asp Cys Thr Leu Thr Gly Phe Lys Gln Lys
                565                 570                 575

Trp Asn Leu Asp Lys Ile Pro Asn Ser Phe Pro Leu Gly Val Leu Cys
            580                 585                 590

Pro Thr His Ser Gln Asp Phe Thr Leu His Glu Asn Gly Tyr Cys Thr
        595                 600                 605

Asp Cys Gly Gly Tyr Leu Pro His Ser Ala Asp Asn Ser Met Tyr Thr
    610                 615                 620

Asp Arg Ala Ser Glu Thr Ser Thr Gly Asp Ile Thr Pro Ser Asp Leu
625                 630                 635                 640

Gly Asp Ser Asp Gly Glu Asp Thr Lys Pro Glu Thr Ser Gln Val Asp
                645                 650                 655

Tyr Cys Pro Pro Lys Lys Arg Arg Leu Thr Ala Pro Ala Ser Pro Pro
            660                 665                 670

Asn Ser Pro Ala Ser Ser Val Ser Thr Ile Thr Phe Phe Asn Thr Trp
        675                 680                 685

His Ala Gln Pro Arg Asp Glu Asp Glu Leu Arg Glu Tyr Glu Arg Gln
    690                 695                 700

Ala Ser Leu Leu Gln Lys Lys Arg Glu Ser Arg Lys Arg Gly Glu Glu
705                 710                 715                 720

Glu Thr Leu Ala Asp Asn Ser Ser Gln Glu Gln Glu Pro Gln Pro Asp
                725                 730                 735

Pro Thr Gln Trp Gly Glu Arg Leu Gly Leu Ile Ser Ser Gly Thr Pro
            740                 745                 750
```

```
Asn Gln Pro Pro Ile Val Leu His Cys Phe Glu Asp Leu Arg Pro Ser
        755                 760                 765

Asp Glu Asp Glu Gly Glu Tyr Ile Gly Glu Lys Arg Gln
    770                 775                 780


<210> SEQ ID NO 31
<211> LENGTH: 639
<212> TYPE: PRT
<213> ORGANISM: Human bocavirus

<400> SEQUENCE: 31

Met Ala Phe Asn Pro Pro Val Ile Arg Ala Phe Ser Gln Pro Ala Phe
1               5                   10                  15

Thr Tyr Val Phe Lys Phe Pro Tyr Pro Gln Trp Lys Glu Lys Glu Trp
            20                  25                  30

Leu Leu His Ala Leu Leu Ala His Gly Thr Glu Gln Ser Met Ile Gln
        35                  40                  45

Leu Arg Asn Cys Ala Pro His Pro Asp Glu Asp Ile Ile Arg Asp Asp
    50                  55                  60

Leu Leu Ile Ser Leu Glu Asp Arg His Phe Gly Ala Val Leu Cys Lys
65                  70                  75                  80

Ala Val Tyr Met Ala Thr Thr Thr Leu Met Ser His Lys Gln Arg Asn
                85                  90                  95

Met Phe Pro Arg Cys Asp Ile Ile Val Gln Ser Glu Leu Gly Glu Lys
            100                 105                 110

Asn Leu His Cys His Ile Ile Val Gly Gly Glu Gly Leu Ser Lys Arg
        115                 120                 125

Asn Ala Lys Ser Ser Cys Ala Gln Phe Tyr Gly Leu Ile Leu Ala Glu
    130                 135                 140

Ile Ile Gln Arg Cys Lys Ser Leu Leu Ala Thr Arg Pro Phe Glu Pro
145                 150                 155                 160

Glu Glu Ala Asp Ile Phe His Thr Leu Lys Lys Ala Glu Arg Glu Ala
                165                 170                 175

Trp Gly Gly Val Thr Gly Gly Asn Met Gln Ile Leu Gln Tyr Arg Asp
            180                 185                 190

Arg Arg Gly Asp Leu His Ala Gln Thr Val Asp Pro Leu Arg Phe Phe
        195                 200                 205

Lys Asn Tyr Leu Leu Pro Lys Asn Arg Cys Ile Ser Ser Tyr Ser Lys
    210                 215                 220

Pro Asp Val Cys Thr Ser Pro Asp Asn Trp Phe Ile Leu Ala Glu Lys
225                 230                 235                 240

Thr Tyr Ser His Thr Leu Ile Asn Gly Leu Pro Leu Pro Glu His Tyr
                245                 250                 255

Arg Lys Asn Tyr His Ala Thr Leu Asp Asn Glu Val Ile Pro Gly Pro
            260                 265                 270

Gln Thr Met Ala Tyr Gly Gly Arg Gly Pro Trp Glu His Leu Pro Glu
        275                 280                 285

Val Gly Asp Gln Arg Leu Ala Ala Ser Ser Val Ser Thr Thr Tyr Lys
    290                 295                 300

Pro Asn Lys Lys Glu Lys Leu Met Leu Asn Leu Leu Asp Lys Cys Lys
305                 310                 315                 320

Glu Leu Asn Leu Leu Val Tyr Glu Asp Leu Val Ala Asn Cys Pro Glu
                325                 330                 335

Leu Leu Leu Met Leu Glu Gly Gln Pro Gly Gly Ala Arg Leu Ile Glu
```

```
            340                 345                 350

Gln Val Leu Gly Met His His Ile Asn Val Cys Ser Asn Phe Thr Ala
        355                 360                 365

Leu Thr Tyr Leu Phe His Leu His Pro Val Thr Ser Leu Asp Ser Asp
    370                 375                 380

Asn Lys Ala Leu Gln Leu Leu Leu Ile Gln Gly Tyr Asn Pro Leu Ala
385                 390                 395                 400

Val Gly His Ala Leu Cys Cys Val Leu Asn Lys Gln Phe Gly Lys Gln
                405                 410                 415

Asn Thr Val Cys Phe Tyr Gly Pro Ala Ser Thr Gly Lys Thr Asn Met
            420                 425                 430

Ala Lys Ala Ile Val Gln Gly Ile Arg Leu Tyr Gly Cys Val Asn His
        435                 440                 445

Leu Asn Lys Gly Phe Val Phe Asn Asp Cys Arg Gln Arg Leu Val Val
    450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Arg Asp
                485                 490                 495

Ser Val Leu Leu Thr Gln Thr Pro Val Ile Ile Ser Thr Asn His Asp
            500                 505                 510

Ile Tyr Ala Val Val Gly Gly Asn Ser Val Ser His Val His Ala Ala
        515                 520                 525

Pro Leu Lys Glu Arg Val Ile Gln Leu Asn Phe Met Lys Gln Leu Pro
    530                 535                 540

Gln Thr Phe Gly Glu Ile Thr Ala Thr Glu Ile Ala Ala Leu Leu Gln
545                 550                 555                 560

Trp Cys Phe Asn Glu Tyr Asp Cys Thr Leu Thr Gly Phe Lys Gln Lys
                565                 570                 575

Trp Asn Leu Asp Lys Ile Pro Asn Ser Phe Pro Leu Gly Val Leu Cys
            580                 585                 590

Pro Thr His Ser Gln Asp Phe Thr Leu His Glu Asn Gly Tyr Cys Thr
        595                 600                 605

Asp Cys Gly Gly Tyr Leu Pro His Ser Ala Asp Asn Ser Met Tyr Thr
    610                 615                 620

Asp Arg Ala Ser Glu Thr Ser Thr Gly Asp Ile Thr Pro Ser Lys
625                 630                 635


<210> SEQ ID NO 32
<211> LENGTH: 160
<212> TYPE: PRT
<213> ORGANISM: Human bocavirus

<400> SEQUENCE: 32

Met Tyr Thr Asp Arg Ala Ser Glu Thr Ser Thr Gly Asp Ile Thr Pro
1               5                   10                  15

Ser Asp Leu Gly Asp Ser Asp Gly Glu Asp Thr Lys Pro Glu Thr Ser
            20                  25                  30

Gln Val Asp Tyr Cys Pro Pro Lys Lys Arg Arg Leu Thr Ala Pro Ala
        35                  40                  45

Ser Pro Pro Asn Ser Pro Ala Ser Ser Val Ser Thr Ile Thr Phe Phe
    50                  55                  60

Asn Thr Trp His Ala Gln Pro Arg Asp Glu Asp Glu Leu Arg Glu Tyr
65                  70                  75                  80
```

```
Glu Arg Gln Ala Ser Leu Leu Gln Lys Lys Arg Glu Ser Arg Lys Arg
                85                  90                  95

Gly Glu Glu Glu Thr Leu Ala Asp Asn Ser Ser Gln Glu Gln Glu Pro
            100                 105                 110

Gln Pro Asp Pro Thr Gln Trp Gly Glu Arg Leu Gly Leu Ile Ser Ser
        115                 120                 125

Gly Thr Pro Asn Gln Pro Pro Ile Val Leu His Cys Phe Glu Asp Leu
    130                 135                 140

Arg Pro Ser Asp Glu Asp Glu Gly Glu Tyr Ile Gly Glu Lys Arg Gln
145                 150                 155                 160


<210> SEQ ID NO 33
<211> LENGTH: 219
<212> TYPE: PRT
<213> ORGANISM: Human bocavirus

<400> SEQUENCE: 33

Met Ser Ser Gly Asn Met Lys Asp Lys His Arg Ser Tyr Lys Arg Lys
1               5                   10                  15

Gly Ser Pro Glu Arg Gly Glu Arg Lys Arg His Trp Gln Thr Thr His
            20                  25                  30

His Arg Ser Arg Ser Arg Ser Pro Ile Arg His Ser Gly Glu Arg Gly
        35                  40                  45

Ser Gly Ser Tyr His Gln Glu His Pro Ile Ser His Leu Ser Ser Cys
    50                  55                  60

Thr Ala Ser Lys Thr Ser Asp Gln Val Met Lys Thr Arg Glu Ser Thr
65                  70                  75                  80

Ser Gly Lys Lys Asp Asn Arg Thr Asn Pro Tyr Thr Val Phe Ser Gln
                85                  90                  95

His Arg Ala Ser Asn Pro Glu Ala Pro Gly Trp Cys Gly Phe Tyr Trp
            100                 105                 110

His Ser Thr Arg Ile Ala Arg Asp Gly Thr Asn Ser Ile Phe Asn Glu
        115                 120                 125

Met Lys Gln Gln Phe Gln Gln Leu Gln Ile Asp Asn Lys Ile Gly Trp
    130                 135                 140

Asp Asn Thr Arg Glu Leu Leu Phe Asn Gln Lys Lys Thr Leu Asp Gln
145                 150                 155                 160

Lys Tyr Arg Asn Met Phe Trp His Phe Arg Asn Asn Ser Asp Cys Glu
                165                 170                 175

Arg Cys Asn Tyr Trp Asp Asp Val Tyr Arg Arg His Leu Ala Asn Val
            180                 185                 190

Ser Ser Gln Thr Glu Ala Asp Glu Ile Thr Asp Glu Glu Met Leu Ser
        195                 200                 205

Ala Ala Glu Ser Met Glu Ala Asp Ala Ser Asn
    210                 215


<210> SEQ ID NO 34
<211> LENGTH: 671
<212> TYPE: PRT
<213> ORGANISM: Human bocavirus

<400> SEQUENCE: 34

Met Pro Pro Ile Lys Arg Gln Pro Arg Gly Trp Val Leu Pro Gly Tyr
1               5                   10                  15

Arg Tyr Leu Gly Pro Phe Asn Pro Leu Asp Asn Gly Glu Pro Val Asn
            20                  25                  30
```

```
Asn Ala Asp Arg Ala Ala Gln Leu His Asp His Ala Tyr Ser Glu Leu
        35                  40                  45

Ile Lys Ser Gly Lys Asn Pro Tyr Leu Tyr Phe Asn Lys Ala Asp Glu
    50                  55                  60

Lys Phe Ile Asp Asp Leu Lys Asp Asp Trp Ser Ile Gly Gly Ile Ile
65                  70                  75                  80

Gly Ser Ser Phe Phe Lys Ile Lys Arg Ala Val Ala Pro Ala Leu Gly
                85                  90                  95

Asn Lys Glu Arg Ala Gln Lys Arg His Phe Tyr Phe Ala Asn Ser Asn
            100                 105                 110

Lys Gly Ala Lys Lys Thr Lys Lys Ser Glu Pro Lys Pro Gly Thr Ser
        115                 120                 125

Lys Met Ser Asp Thr Asp Ile Gln Asp Gln Gln Pro Asp Thr Val Asp
    130                 135                 140

Ala Pro Gln Asn Thr Ser Gly Gly Gly Thr Gly Ser Ile Gly Gly Gly
145                 150                 155                 160

Lys Gly Ser Gly Val Gly Ile Ser Thr Gly Gly Trp Val Gly Gly Ser
                165                 170                 175

His Phe Ser Asp Lys Tyr Val Val Thr Lys Asn Thr Arg Gln Phe Ile
            180                 185                 190

Thr Thr Ile Gln Asn Gly His Leu Tyr Lys Thr Glu Ala Ile Glu Thr
        195                 200                 205

Thr Asn Gln Ser Gly Lys Ser Gln Arg Cys Val Thr Thr Pro Trp Thr
    210                 215                 220

Tyr Phe Asn Phe Asn Gln Tyr Ser Cys His Phe Ser Pro Gln Asp Trp
225                 230                 235                 240

Gln Arg Leu Thr Asn Glu Tyr Lys Arg Phe Arg Pro Lys Ala Met Gln
                245                 250                 255

Val Lys Ile Tyr Asn Leu Gln Ile Lys Gln Ile Leu Ser Asn Gly Ala
            260                 265                 270

Asp Thr Thr Tyr Asn Asn Asp Leu Thr Ala Gly Val His Ile Phe Cys
        275                 280                 285

Asp Gly Glu His Ala Tyr Pro Asn Ala Ser His Pro Trp Asp Glu Asp
    290                 295                 300

Val Met Pro Asp Leu Pro Tyr Lys Thr Trp Lys Leu Phe Gln Tyr Gly
305                 310                 315                 320

Tyr Ile Pro Ile Glu Asn Glu Leu Ala Asp Leu Asp Gly Asn Ala Ala
                325                 330                 335

Gly Gly Asn Ala Thr Glu Lys Ala Leu Leu Tyr Gln Met Pro Phe Phe
            340                 345                 350

Leu Leu Glu Asn Ser Asp His Gln Val Leu Arg Thr Gly Glu Ser Thr
        355                 360                 365

Glu Phe Thr Phe Asn Phe Asp Cys Glu Trp Val Asn Asn Glu Arg Ala
    370                 375                 380

Tyr Ile Pro Pro Gly Leu Met Phe Asn Pro Lys Val Pro Thr Arg Arg
385                 390                 395                 400

Val Gln Tyr Ile Arg Gln Asn Gly Ser Thr Ala Ala Ser Thr Gly Arg
                405                 410                 415

Ile Gln Pro Tyr Ser Lys Pro Thr Ser Trp Met Thr Gly Pro Gly Leu
            420                 425                 430

Leu Ser Ala Gln Arg Val Gly Pro Gln Ser Ser Asp Thr Ala Pro Phe
        435                 440                 445

Met Val Cys Thr Asn Pro Glu Gly Thr His Ile Asn Thr Gly Ala Ala
```

```
    450                 455                 460

Gly Phe Gly Ser Gly Phe Asp Pro Pro Ser Gly Cys Leu Ala Pro Thr
465                 470                 475                 480

Asn Leu Glu Tyr Lys Leu Gln Trp Tyr Gln Thr Pro Glu Gly Thr Gly
                485                 490                 495

Asn Asn Gly Asn Ile Ile Ala Asn Pro Ser Leu Ser Met Leu Arg Asp
            500                 505                 510

Gln Leu Leu Tyr Lys Gly Asn Gln Thr Thr Tyr Asn Leu Val Gly Asp
        515                 520                 525

Ile Trp Met Phe Pro Asn Gln Val Trp Asp Arg Phe Pro Ile Thr Arg
    530                 535                 540

Glu Asn Pro Ile Trp Cys Lys Lys Pro Arg Ala Asp Lys His Thr Ile
545                 550                 555                 560

Met Asp Pro Phe Asp Gly Ser Ile Ala Met Asp His Pro Pro Gly Thr
                565                 570                 575

Ile Phe Ile Lys Met Ala Lys Ile Pro Val Pro Thr Ala Ser Asn Ala
            580                 585                 590

Asp Ser Tyr Leu Asn Ile Tyr Cys Thr Gly Gln Val Ser Cys Glu Ile
        595                 600                 605

Val Trp Glu Val Lys Arg Tyr Ala Thr Lys Asn Trp Arg Pro Glu Arg
    610                 615                 620

Arg His Thr Ala Leu Gly Met Ser Leu Gly Gly Glu Ser Asn Tyr Thr
625                 630                 635                 640

Pro Thr Tyr His Val Asp Pro Thr Gly Ala Tyr Ile Gln Pro Thr Ser
                645                 650                 655

Tyr Asp Gln Cys Met Pro Val Lys Thr Asn Ile Asn Lys Val Leu
            660                 665                 670


<210> SEQ ID NO 35
<211> LENGTH: 542
<212> TYPE: PRT
<213> ORGANISM: Human bocavirus

<400> SEQUENCE: 35

Met Ser Asp Thr Asp Ile Gln Asp Gln Gln Pro Asp Thr Val Asp Ala
1               5                   10                  15

Pro Gln Asn Thr Ser Gly Gly Gly Thr Gly Ser Ile Gly Gly Gly Lys
            20                  25                  30

Gly Ser Gly Val Gly Ile Ser Thr Gly Gly Trp Val Gly Gly Ser His
        35                  40                  45

Phe Ser Asp Lys Tyr Val Val Thr Lys Asn Thr Arg Gln Phe Ile Thr
    50                  55                  60

Thr Ile Gln Asn Gly His Leu Tyr Lys Thr Glu Ala Ile Glu Thr Thr
65                  70                  75                  80

Asn Gln Ser Gly Lys Ser Gln Arg Cys Val Thr Thr Pro Trp Thr Tyr
                85                  90                  95

Phe Asn Phe Asn Gln Tyr Ser Cys His Phe Ser Pro Gln Asp Trp Gln
            100                 105                 110

Arg Leu Thr Asn Glu Tyr Lys Arg Phe Arg Pro Lys Ala Met Gln Val
        115                 120                 125

Lys Ile Tyr Asn Leu Gln Ile Lys Gln Ile Leu Ser Asn Gly Ala Asp
    130                 135                 140

Thr Thr Tyr Asn Asn Asp Leu Thr Ala Gly Val His Ile Phe Cys Asp
145                 150                 155                 160
```

```
Gly Glu His Ala Tyr Pro Asn Ala Ser His Pro Trp Asp Glu Asp Val
                165                 170                 175

Met Pro Asp Leu Pro Tyr Lys Thr Trp Lys Leu Phe Gln Tyr Gly Tyr
            180                 185                 190

Ile Pro Ile Glu Asn Glu Leu Ala Asp Leu Asp Gly Asn Ala Ala Gly
        195                 200                 205

Gly Asn Ala Thr Glu Lys Ala Leu Leu Tyr Gln Met Pro Phe Phe Leu
    210                 215                 220

Leu Glu Asn Ser Asp His Gln Val Leu Arg Thr Gly Glu Ser Thr Glu
225                 230                 235                 240

Phe Thr Phe Asn Phe Asp Cys Glu Trp Val Asn Asn Glu Arg Ala Tyr
                245                 250                 255

Ile Pro Pro Gly Leu Met Phe Asn Pro Lys Val Pro Thr Arg Arg Val
            260                 265                 270

Gln Tyr Ile Arg Gln Asn Gly Ser Thr Ala Ala Ser Thr Gly Arg Ile
        275                 280                 285

Gln Pro Tyr Ser Lys Pro Thr Ser Trp Met Thr Gly Pro Gly Leu Leu
    290                 295                 300

Ser Ala Gln Arg Val Gly Pro Gln Ser Ser Asp Thr Ala Pro Phe Met
305                 310                 315                 320

Val Cys Thr Asn Pro Glu Gly Thr His Ile Asn Thr Gly Ala Ala Gly
                325                 330                 335

Phe Gly Ser Gly Phe Asp Pro Pro Ser Gly Cys Leu Ala Pro Thr Asn
            340                 345                 350

Leu Glu Tyr Lys Leu Gln Trp Tyr Gln Thr Pro Glu Gly Thr Gly Asn
        355                 360                 365

Asn Gly Asn Ile Ile Ala Asn Pro Ser Leu Ser Met Leu Arg Asp Gln
    370                 375                 380

Leu Leu Tyr Lys Gly Asn Gln Thr Thr Tyr Asn Leu Val Gly Asp Ile
385                 390                 395                 400

Trp Met Phe Pro Asn Gln Val Trp Asp Arg Phe Pro Ile Thr Arg Glu
                405                 410                 415

Asn Pro Ile Trp Cys Lys Lys Pro Arg Ala Asp Lys His Thr Ile Met
            420                 425                 430

Asp Pro Phe Asp Gly Ser Ile Ala Met Asp His Pro Pro Gly Thr Ile
        435                 440                 445

Phe Ile Lys Met Ala Lys Ile Pro Val Pro Thr Ala Ser Asn Ala Asp
    450                 455                 460

Ser Tyr Leu Asn Ile Tyr Cys Thr Gly Gln Val Ser Cys Glu Ile Val
465                 470                 475                 480

Trp Glu Val Lys Arg Tyr Ala Thr Lys Asn Trp Arg Pro Glu Arg Arg
                485                 490                 495

His Thr Ala Leu Gly Met Ser Leu Gly Gly Glu Ser Asn Tyr Thr Pro
            500                 505                 510

Thr Tyr His Val Asp Pro Thr Gly Ala Tyr Ile Gln Pro Thr Ser Tyr
        515                 520                 525

Asp Gln Cys Met Pro Val Lys Thr Asn Ile Asn Lys Val Leu
    530                 535                 540
```

<210> SEQ ID NO 36
<211> LENGTH: 120
<212> TYPE: PRT
<213> ORGANISM: Human bocavirus

<400> SEQUENCE: 36

```
Met Val Leu Thr Gln His Thr Thr Met Thr Ser Gln Leu Ala Phe Thr
1               5                   10                  15

Ser Phe Val Met Glu Ser Met Leu Thr Gln Met His Leu Ile His Gly
            20                  25                  30

Met Arg Thr Ser Cys Leu Ile Phe His Thr Arg Pro Gly Asn Phe Phe
        35                  40                  45

Asn Met Asp Ile Phe Leu Leu Lys Met Asn Ser Gln Ile Leu Met Glu
    50                  55                  60

Met Gln Leu Glu Ala Met Leu Gln Lys Lys His Phe Cys Ile Arg Cys
65                  70                  75                  80

Leu Phe Phe Tyr Leu Lys Thr Val Thr Thr Lys Tyr Leu Glu Leu Val
                85                  90                  95

Arg Ala Leu Asn Leu Leu Leu Thr Leu Thr Val Asn Gly Leu Thr Met
            100                 105                 110

Lys Glu His Thr Phe Leu Leu Asp
        115                 120


<210> SEQ ID NO 37
<211> LENGTH: 5267
<212> TYPE: DNA
<213> ORGANISM: Swine bocavirus

<400> SEQUENCE: 37

aaccagacat tgggagagca gatgtttttc tcgtcaagag tgtgtaatct ggaggatatt     60

cttgcagaac aaggatacag gcagtgtttt atgatcggat cggatgtgac attcggcgga    120

cgaaaagctt attttaacag ccatggaaat tgtgagatct gggactatta taccgctgtc    180

gaagaaggaa gaattccgga agattattac agatggtggg gatatgagga cgagaagctc    240

tttacatatg ccagggaaaa actgacagag ctgagttcag gatcagaacc attcaatctt    300

acacttctta cagtagacac acattttgaa gacggatatg tctgtgattt gtgtcaggat    360

gaattcggag atgaccagta cgcgaatgtt atggcatgct caagtagaca gattgcagca    420

tttattgaat ggatacagca gcaggatttc tatgagaata cgacgatcat actttgtggt    480

gagtaaccat gcctctgaac aactttcaag ccgcatttga aagcttcggg ggaattgcat    540

atacttatat tctgagactt cctaaatttc ctacgaataa ttatcataat atgctgcagc    600

gatgtttggg ggatagcgag catatctact tgcatgaaag agaggaatgc ggaaagcact    660

atccagactt tccaaatggt tgctccgact tagcagatta ccagaaaaaa tcatacgaac    720

acaacattgc tatatttgct gaaaccgccg taaaaaaggt gtttgaaaat cagcaaatga    780

caagaacacc atcttatgct tgctttgttc aagttgagca cggaaaaaat ctccatgttc    840

atttagtatt atcaggagac ggactcacaa aatatacagc aaaaaacttt agatcaaaat    900

tagctgtata tttttacgca caacttgaac aaaaacaaaa agaagaatta caagagctgt    960

atggaaaccc aaattgggaa gcatatacaa aaccaatttc agaagctcta actaaatcac   1020

aagatggaag cacagaattc tgcacagtac tacagtacaa aagcagaaac ggagaaatgt   1080

actcttgccg cgtggacgca agaagcttca tagctaatta tatgctacca aagaacttag   1140

aaatcaacga taaaatatgg tcaaatacct acaagattcc gggaccacta gcagacacgt   1200

ttcttttaaa tgggaaaact tatacataca gcagcatcaa ctcaatgcaa atcttaccgc   1260

acattagaag agatctaaaa gagtggctgg aagatttgca tggaataaac actgacgaac   1320

caattttttc tggagatccg ctttctgatc tgcctaaggt aagaaaggca caatgggaaa   1380
```

-continued

```
aaacaactca gccgggagga aaaatgtcta aaagagaagg acttgtacta gactgtatga   1440
atagagccat tgaatctgac tgtttaacgt atgaacaact agtagacaaa catccagaaa   1500
taataataat gatggaaagc caagcaggag gaagcaaatt aatagagcag actttgaaca   1560
tggtgcatat aaaacttacg caaaagtata cagccatgtc atatatgatg aaacggtttc   1620
caacctttaa cctgcaatca aacaataaag caataagact gttaaattat caaggatata   1680
attactggca ggttggacat tggctatgca ctgttttaga taagaagagc ggaaagcaga   1740
acacaataag tttttatggt cctgccagta caggaaagac aaaccttgcc aaggccatag   1800
tgaattgtgt taatctattt ggcaatgtta atcatttaaa caagaacttt gtattcaatg   1860
attgctcaaa caaacttgtt gtatggtggg aagaagcact gatgcatacg gactgggtag   1920
aacctgctaa atgtgttttg ggaggaacaa ccgtacgaat tgacagaaaa cacaaagact   1980
cacaattact gccacagaca ccatgcatca tatccacaaa taacaatata tacgagtgtg   2040
ttggtggtaa tcatgtgtct catgtacatt gcaaaccgct aaaagacaga gtggttcaac   2100
taaattttat gaagacactg ccgcaacact ttggtgaaat ttcaacagaa gaggtggcag   2160
catggctcct aacttgcaag aacaaatttc agtgcacatt agaaggttac tgcaatcaat   2220
ggaaagtgaa gcacgtaata aacgacatgc cgcttgccaa agtgtgtgcc tctcattcac   2280
aggattttac cttacatgaa caaggaacgt gcacccattg tggtgcttac ctgcctctta   2340
ctattgatat tgaatcttgc ggcggtgata atcctgggga cgacggacgt aagtaacatt   2400
ttttacaaaa gggacaggga aataaatctt taaaagatac taaatatcta tttcttcata   2460
ggtgtccctg attcagcaat catcggaact aatagctcga gtgctcgagg tcaaggcgga   2520
gaacctgaca gaaagaaggt gaaataccag gtacttacta aagaacagga agaattccta   2580
gatgagtggg catcacaacc acaggatgaa tcagagatcg agctatacaa ccgaagaaga   2640
gagcagctct tcgaatcgcc gctctcctct ggcagcaagg acatctccga aacagagccg   2700
acatcggagt tggagtcgga gtcggagtcg gagtccaaga agaaaaaggg aggagagccc   2760
atacaggggg aggaaagaga tgagcagatc tccccagaaa caggggaaag agaggattga   2820
gcagcctaga aaacaattta aagaaaaaaa gaatagcatt gttgatgctt ttgtaaaata   2880
taaagctaag cataatactg atcaatcttt ttgcgggttt cactggcatt catggagatt   2940
agctaaaaag ggcacagaca gggtatttga tgaaatgaaa gctgaatttc aaattcgctg   3000
cagggatggg aaaattgagt ggcctgatgc aagagaaatg ttgtttaaat ttaaaaaagc   3060
tatagataaa gattacagaa gcatgctgtg gcacttcaga tttactgaat gtactaaatg   3120
tgatttttgg gatgatgtgt acaaaaaaca tatggctaat gtgcatcatg aacctccaca   3180
ggaattaaca gacgaagagc tacttgcagc attgcaagaa gctgaagctg gaaaataaaa   3240
ctgatgatca ttgtgctcat gtttattata agcttaataa aatttgacat atgaatcaat   3300
tgtttcctgt ggtacgctcc aaaaaaaacg acggcaaaag aggacacggg aaaaaagctg   3360
aaaaacgacc aagtgaacta aaagatcctg aaaaacctac aggtgaactc gaactagttg   3420
gagaaagatc caactgttcc aaaactcaaa gacattttta ctttgcgcgc caaaaccaag   3480
gtgcaaaaag agcaaaaatg tccgcacagg ggggcgagaa cattgaagag gttgaagtgg   3540
atacaggtgc gggaagtggg cggtcaggcg gtggcggagg aggtggagga ggaggaggct   3600
ctacaaatgg aggaattgga atggcaacag gaggttgggt tggaggaaca tactttggaa   3660
aaaacaaaat agtaacaaac ataacacgtc aatggtacgt gccgatatat aacggccaca   3720
aatacacaaa acagacagaa acagataata ctaacttttg gaacggaata agaacaccat   3780
```

```
ggggctacat taacatgaac tcatacagct gtcatttttc tccaaatgac tggcaaagac   3840

ttttaaacaa ctacaaaagg tggaaaccaa aaaaaatgag gctgcagtta tacaacttac   3900

aaataaagca agtagtccaa ctaggcacag atacactata caacaatgat ctgacagcag   3960

gggtgcacat tatgtatgac gggtcacacc aatacccata ctcacaaagt ggatgggaca   4020

gtgagctaat ccctgaactg ccagggatga tttataaact accaaactat tgctacttcc   4080

aggaactagg tgacataggt gatacaggct cagacttaag agaatcatgg ctagggacag   4140

catgtccctt attctttctt gaaagctcct cacatgaggt actaagaaca ggagaagaaa   4200

caggatttga atttgatttt gattgtggat gggtacataa tgacagagca ttttgtccac   4260

cacaatgcga ctttaatccc ctaatcaaaa ccaggcgaag cagaataata atgggttctt   4320

caggaaacac atcagaacca tactatgact acaaaaaacc tagcaattgg atgccaggac   4380

caggaactcg actaaacgga caccaatcag gaagcaatct aaaaacatct tctgggccct   4440

ttaacacatc atgggcacca ccaggggtaa cacagggaag tgacacaacc tacctaaact   4500

caccagcaat gaatcaatca caatgggcct caaaatcaat gccaacagca ccagcaaatg   4560

ctgcatgcag tcaagtagac ccaaactcac tagcattcaa cgaaccaaca caattaggac   4620

agcaaggtga cactaacata agatacaaca acataagcaa tgatctaact agatggggaa   4680

cagtatggag tcagtcacaa caagtataca catcacaacc aacacgaact cgactagaca   4740

cagtatggca atacccaatg caagcatgga acggacagga agtaacacgc tacgctccaa   4800

tttgggacaa acaaccaaac acagattacc atacaacatt atcatcatca gacggaacac   4860

ttccaatgaa acatcctcca ggaaacatat tcattaaagt agcaaaaatt ccaataccaa   4920

cggaaacaaa cacagattca tatctaaaca tatactgcac aggacaaatt tccattgaaa   4980

ttgaatggga cgctgaagaa tatgaaacaa agaactggag accagaacta agaataacat   5040

cctcaaacat tggcagaggg gtgtacaaca taaatgccgc aggagaatac aacacaacag   5100

gaagccaact cagcaacatg ccaacaagat ttggaatgaa cagaatcaac taaacaagga   5160

tttgatattt ctttacaaga ccaccaccag gacgccatat ttgttttggg aaattatttt   5220

tcccaaaact aactttgtga tctatcctcc tgtttcttct cctgttc                  5267
```

<210> SEQ ID NO 38
<211> LENGTH: 620
<212> TYPE: PRT
<213> ORGANISM: Swine bocavirus

<400> SEQUENCE: 38

```
Met Asn Gln Leu Phe Pro Val Val Arg Ser Lys Lys Asn Asp Gly Lys
1               5                   10                  15

Arg Gly His Gly Lys Lys Ala Glu Lys Arg Pro Ser Glu Leu Lys Asp
            20                  25                  30

Pro Glu Lys Pro Thr Gly Glu Leu Glu Leu Val Gly Glu Arg Ser Asn
        35                  40                  45

Cys Ser Lys Thr Gln Arg His Phe Tyr Phe Ala Arg Gln Asn Gln Gly
    50                  55                  60

Ala Lys Arg Ala Lys Met Ser Ala Gln Gly Gly Glu Asn Ile Glu Glu
65                  70                  75                  80

Val Glu Val Asp Thr Gly Ala Gly Ser Gly Arg Ser Gly Gly Gly Gly
                85                  90                  95

Gly Gly Gly Gly Gly Gly Gly Ser Thr Asn Gly Gly Ile Gly Met Ala
            100                 105                 110
```

```
Thr Gly Gly Trp Val Gly Gly Thr Tyr Phe Gly Lys Asn Lys Ile Val
        115                 120                 125

Thr Asn Ile Thr Arg Gln Trp Tyr Val Pro Ile Tyr Asn Gly His Lys
    130                 135                 140

Tyr Thr Lys Gln Thr Glu Thr Asp Asn Thr Asn Phe Trp Asn Gly Ile
145                 150                 155                 160

Arg Thr Pro Trp Gly Tyr Ile Asn Met Asn Ser Tyr Ser Cys His Phe
                165                 170                 175

Ser Pro Asn Asp Trp Gln Arg Leu Leu Asn Asn Tyr Lys Arg Trp Lys
            180                 185                 190

Pro Lys Lys Met Arg Leu Gln Leu Tyr Asn Leu Gln Ile Lys Gln Val
        195                 200                 205

Val Gln Leu Gly Thr Asp Thr Leu Tyr Asn Asn Asp Leu Thr Ala Gly
    210                 215                 220

Val His Ile Met Tyr Asp Gly Ser His Gln Tyr Pro Tyr Ser Gln Ser
225                 230                 235                 240

Gly Trp Asp Ser Glu Leu Ile Pro Glu Leu Pro Gly Met Ile Tyr Lys
                245                 250                 255

Leu Pro Asn Tyr Cys Tyr Phe Gln Glu Leu Gly Asp Ile Gly Asp Thr
            260                 265                 270

Gly Ser Asp Leu Arg Glu Ser Trp Leu Gly Thr Ala Cys Pro Leu Phe
        275                 280                 285

Phe Leu Glu Ser Ser Ser His Glu Val Leu Arg Thr Gly Glu Glu Thr
    290                 295                 300

Gly Phe Glu Phe Asp Phe Asp Cys Gly Trp Val His Asn Asp Arg Ala
305                 310                 315                 320

Phe Cys Pro Pro Gln Cys Asp Phe Asn Pro Leu Ile Lys Thr Arg Arg
                325                 330                 335

Ser Arg Ile Ile Met Gly Ser Ser Gly Asn Thr Ser Glu Pro Tyr Tyr
            340                 345                 350

Asp Tyr Lys Lys Pro Ser Asn Trp Met Pro Gly Pro Gly Thr Arg Leu
        355                 360                 365

Asn Gly His Gln Ser Gly Ser Asn Leu Lys Thr Ser Ser Gly Pro Phe
    370                 375                 380

Asn Thr Ser Trp Ala Pro Pro Gly Val Thr Gln Gly Ser Asp Thr Thr
385                 390                 395                 400

Tyr Leu Asn Ser Pro Ala Met Asn Gln Ser Gln Trp Ala Ser Lys Ser
                405                 410                 415

Met Pro Thr Ala Pro Ala Asn Ala Ala Cys Ser Gln Val Asp Pro Asn
            420                 425                 430

Ser Leu Ala Phe Asn Glu Pro Thr Gln Leu Gly Gln Gln Gly Asp Thr
        435                 440                 445

Asn Ile Arg Tyr Asn Asn Ile Ser Asn Asp Leu Thr Arg Trp Gly Thr
    450                 455                 460

Val Trp Ser Gln Ser Gln Gln Val Tyr Thr Ser Gln Pro Thr Arg Thr
465                 470                 475                 480

Arg Leu Asp Thr Val Trp Gln Tyr Pro Met Gln Ala Trp Asn Gly Gln
                485                 490                 495

Glu Val Thr Arg Tyr Ala Pro Ile Trp Asp Lys Gln Pro Asn Thr Asp
            500                 505                 510

Tyr His Thr Thr Leu Ser Ser Ser Asp Gly Thr Leu Pro Met Lys His
        515                 520                 525
```

```
Pro Pro Gly Asn Ile Phe Ile Lys Val Ala Lys Ile Pro Ile Pro Thr
    530                 535                 540

Glu Thr Asn Thr Asp Ser Tyr Leu Asn Ile Tyr Cys Thr Gly Gln Ile
545                 550                 555                 560

Ser Ile Glu Ile Glu Trp Asp Ala Glu Glu Tyr Glu Thr Lys Asn Trp
                565                 570                 575

Arg Pro Glu Leu Arg Ile Thr Ser Ser Asn Ile Gly Arg Gly Val Tyr
            580                 585                 590

Asn Ile Asn Ala Ala Gly Glu Tyr Asn Thr Thr Gly Ser Gln Leu Ser
        595                 600                 605

Asn Met Pro Thr Arg Phe Gly Met Asn Arg Ile Asn
    610                 615                 620


<210> SEQ ID NO 39
<211> LENGTH: 551
<212> TYPE: PRT
<213> ORGANISM: Swine bocavirus

<400> SEQUENCE: 39

Met Ser Ala Gln Gly Gly Glu Asn Ile Glu Glu Val Glu Val Asp Thr
1               5                   10                  15

Gly Ala Gly Ser Gly Arg Ser Gly Gly Gly Gly Gly Gly Gly Gly Gly
            20                  25                  30

Gly Gly Ser Thr Asn Gly Gly Ile Gly Met Ala Thr Gly Gly Trp Val
        35                  40                  45

Gly Gly Thr Tyr Phe Gly Lys Asn Lys Ile Val Thr Asn Ile Thr Arg
    50                  55                  60

Gln Trp Tyr Val Pro Ile Tyr Asn Gly His Lys Tyr Thr Lys Gln Thr
65                  70                  75                  80

Glu Thr Asp Asn Thr Asn Phe Trp Asn Gly Ile Arg Thr Pro Trp Gly
                85                  90                  95

Tyr Ile Asn Met Asn Ser Tyr Ser Cys His Phe Ser Pro Asn Asp Trp
            100                 105                 110

Gln Arg Leu Leu Asn Asn Tyr Lys Arg Trp Lys Pro Lys Lys Met Arg
        115                 120                 125

Leu Gln Leu Tyr Asn Leu Gln Ile Lys Gln Val Val Gln Leu Gly Thr
    130                 135                 140

Asp Thr Leu Tyr Asn Asn Asp Leu Thr Ala Gly Val His Ile Met Tyr
145                 150                 155                 160

Asp Gly Ser His Gln Tyr Pro Tyr Ser Gln Ser Gly Trp Asp Ser Glu
                165                 170                 175

Leu Ile Pro Glu Leu Pro Gly Met Ile Tyr Lys Leu Pro Asn Tyr Cys
            180                 185                 190

Tyr Phe Gln Glu Leu Gly Asp Ile Gly Asp Thr Gly Ser Asp Leu Arg
        195                 200                 205

Glu Ser Trp Leu Gly Thr Ala Cys Pro Leu Phe Phe Leu Glu Ser Ser
    210                 215                 220

Ser His Glu Val Leu Arg Thr Gly Glu Glu Thr Gly Phe Glu Phe Asp
225                 230                 235                 240

Phe Asp Cys Gly Trp Val His Asn Asp Arg Ala Phe Cys Pro Pro Gln
                245                 250                 255

Cys Asp Phe Asn Pro Leu Ile Lys Thr Arg Arg Ser Arg Ile Ile Met
            260                 265                 270

Gly Ser Ser Gly Asn Thr Ser Glu Pro Tyr Tyr Asp Tyr Lys Lys Pro
        275                 280                 285
```

```
Ser Asn Trp Met Pro Gly Pro Gly Thr Arg Leu Asn Gly His Gln Ser
    290                 295                 300

Gly Ser Asn Leu Lys Thr Ser Ser Gly Pro Phe Asn Thr Ser Trp Ala
305                 310                 315                 320

Pro Pro Gly Val Thr Gln Gly Ser Asp Thr Thr Tyr Leu Asn Ser Pro
                325                 330                 335

Ala Met Asn Gln Ser Gln Trp Ala Ser Lys Ser Met Pro Thr Ala Pro
            340                 345                 350

Ala Asn Ala Ala Cys Ser Gln Val Asp Pro Asn Ser Leu Ala Phe Asn
        355                 360                 365

Glu Pro Thr Gln Leu Gly Gln Gln Gly Asp Thr Asn Ile Arg Tyr Asn
    370                 375                 380

Asn Ile Ser Asn Asp Leu Thr Arg Trp Gly Thr Val Trp Ser Gln Ser
385                 390                 395                 400

Gln Gln Val Tyr Thr Ser Gln Pro Thr Arg Thr Arg Leu Asp Thr Val
                405                 410                 415

Trp Gln Tyr Pro Met Gln Ala Trp Asn Gly Gln Glu Val Thr Arg Tyr
            420                 425                 430

Ala Pro Ile Trp Asp Lys Gln Pro Asn Thr Asp Tyr His Thr Thr Leu
        435                 440                 445

Ser Ser Ser Asp Gly Thr Leu Pro Met Lys His Pro Pro Gly Asn Ile
    450                 455                 460

Phe Ile Lys Val Ala Lys Ile Pro Ile Pro Thr Glu Thr Asn Thr Asp
465                 470                 475                 480

Ser Tyr Leu Asn Ile Tyr Cys Thr Gly Gln Ile Ser Ile Glu Ile Glu
                485                 490                 495

Trp Asp Ala Glu Glu Tyr Glu Thr Lys Asn Trp Arg Pro Glu Leu Arg
            500                 505                 510

Ile Thr Ser Ser Asn Ile Gly Arg Gly Val Tyr Asn Ile Asn Ala Ala
        515                 520                 525

Gly Glu Tyr Asn Thr Thr Gly Ser Gln Leu Ser Asn Met Pro Thr Arg
    530                 535                 540

Phe Gly Met Asn Arg Ile Asn
545                 550


<210> SEQ ID NO 40
<211> LENGTH: 708
<212> TYPE: PRT
<213> ORGANISM: Swine bocavirus

<400> SEQUENCE: 40

Met Ala Pro Thr Asn Arg Lys Pro Gly Gly Trp Val Leu Pro Gly His
1               5                   10                  15

Arg Tyr Leu Gly Pro Phe Asn Pro Ile Glu Asn Gly Glu Pro Val Asn
            20                  25                  30

Ala Ala Asp Ala Ala Ala Arg Arg His Asp Leu Lys Tyr Asp Gln Tyr
        35                  40                  45

Leu Lys Glu Gly Lys Asn Pro Tyr Leu Tyr Phe Asn Lys Ala Asp Ser
    50                  55                  60

Asp Phe Leu Glu Asp Leu Glu Ser Asp Arg Ser Phe Gly Gly Trp Ile
65                  70                  75                  80

Gly Lys Gly Val Phe Gly Leu Lys Arg Ala Ile Ala Pro Thr Leu Asp
                85                  90                  95

Glu Ser Ser Gly Lys Gln Asn Thr Gly Gly Pro Ser Ala Ala Lys Lys
```

```
            100                 105                 110

Pro Arg Val Asp Pro Gln Arg Ala Gln Lys Arg Lys Leu Tyr Phe Ala
        115                 120                 125

Arg Gln Ala Lys Glu Ala Lys Lys Gln Lys Met Ser Ser Gly Gly Asp
    130                 135                 140

Pro Ser Glu Asp Thr Gly Ala Gly Asp Gly Glu Gln Gly Gly Glu Ser
145                 150                 155                 160

Ser Ala Met Thr Gly Arg Ser Gly Gly Gly Ala Gly Gly Gly Gly Gly
                165                 170                 175

Gly Gly Ser Val Gly Phe Ser Thr Gly Gly Trp Glu Gly Gly Thr Tyr
            180                 185                 190

Phe Ser Asp His Thr Val Thr Thr Thr Asn Thr Arg Gln Trp Tyr Thr
        195                 200                 205

Gly Ile Leu Asn Gly His Arg Tyr Ser Lys Leu Ala Gln Thr Thr Gly
    210                 215                 220

Ser Asn Leu Gln Ala Ala Lys Pro Trp Val Gly Ile Gln Thr Pro Trp
225                 230                 235                 240

Ala Tyr Leu Asn Leu Asn Cys Tyr His Cys Leu Phe Ser Pro Gln Asp
                245                 250                 255

Trp Gln Arg Leu Leu Asn Glu Tyr Lys Ala Trp Arg Pro Lys Arg Met
            260                 265                 270

His Val Arg Ile Tyr Asn Leu Gln Ile Lys Gln Ile Thr Thr Val Gly
        275                 280                 285

Ala Asp Thr Leu Tyr Gln Asn Asp Leu Thr Ala Gly Val His Ile Phe
    290                 295                 300

Cys Asp Gly Ser His Gln Tyr Pro Tyr Ala Gln His Pro Trp Asp Glu
305                 310                 315                 320

Gly Ala Ser Pro Glu Leu Pro Asn Glu Ile Trp Lys Leu Pro Gln Tyr
                325                 330                 335

Ala Tyr Phe Gln Tyr Gln Gly Asp Leu Thr Asp His Ala Thr Ala Asn
            340                 345                 350

Thr Pro Gln Asn Val Glu Ser Met Leu Lys Ser Asn Ile Pro Leu Phe
        355                 360                 365

Leu Leu Glu Asn Ser Asn His Glu Val Leu Arg Thr Gly Glu Met Thr
    370                 375                 380

Glu Phe Ser Phe Thr Phe Gln Ser Gly Trp Val Thr Asn Asp Arg Ala
385                 390                 395                 400

Tyr Cys Cys Pro Gln Ser Asp Phe Asn Pro Leu Val Gln Thr Arg Arg
                405                 410                 415

Tyr Tyr Pro Thr Trp Asn Gly Ser Ser Asn Ser Tyr Ser Tyr Asn Arg
            420                 425                 430

Tyr Gly Pro Tyr Lys Lys Pro Ser Asn Trp Met Pro Gly Pro Gly Leu
        435                 440                 445

Ala Tyr Lys Gly Ala Thr His Thr Asn Gln Asn Pro Asp Asp Ala Arg
    450                 455                 460

Gly Pro Ile Ile Thr Thr Ile Ala Pro Arg Gly Thr Ile Ser Val Gly
465                 470                 475                 480

Ser Thr Pro Ser Asn Glu Ala Pro Asn Asp Gly Asp Asn Thr Ile Ser
                485                 490                 495

Ser Asp Gly Val Lys Gln Gly Gly Trp Gln Thr Ala Pro Val Asn Gly
            500                 505                 510

Ala Cys Ser Arg Thr Asp Tyr Pro Thr Leu Ala Phe Asp Pro Ser Asp
        515                 520                 525
```

```
Arg Ser Ser Asn Gln Asn Ile Pro Thr Arg Asn Leu Asp Ile Asp Met
    530                 535                 540

Thr Arg Trp Tyr Arg Val His Glu Ala Val Arg Gly Ala Ser Gly Ser
545                 550                 555                 560

Thr Tyr Tyr Asn Val Asp Asp Ile Trp Met Tyr Pro Asn Gln Ala Trp
                565                 570                 575

Asn Ser Thr Pro Ile Cys Arg Asp Asn Pro Ile Trp Asp Lys Val Pro
            580                 585                 590

Arg Thr Asp Lys His Thr Leu Leu Asp Ser Ser Asp Gly Thr Leu Pro
        595                 600                 605

Met Lys His Pro Pro Gly Asn Ile Phe Ile Lys Cys Ala Lys Ile Pro
    610                 615                 620

Val Pro Thr Ser Asn Asn Thr Asp Ser Tyr Leu Asn Ile Tyr Val Thr
625                 630                 635                 640

Gly Gln Val Thr Tyr Thr Val Glu Trp Glu Val Gln Arg Tyr Gln Thr
                645                 650                 655

Lys Asn Trp Arg Pro Glu Leu Arg Thr Ser Ala Gly Ser Tyr Asn Gln
            660                 665                 670

His Glu Ile Tyr Asn Ile Gly Glu Asn Gly Val Tyr Asn Arg Ala Asn
        675                 680                 685

Thr Phe Asn Glu Cys Met Pro Thr Lys Cys Gly Ile Asn Arg Val Leu
    690                 695                 700

Lys Asn Trp Arg
705


<210> SEQ ID NO 41
<211> LENGTH: 566
<212> TYPE: PRT
<213> ORGANISM: Swine bocavirus

<400> SEQUENCE: 41

Met Ser Ser Gly Gly Asp Pro Ser Glu Asp Thr Gly Ala Gly Asp Gly
1               5                   10                  15

Glu Gln Gly Gly Glu Ser Ser Ala Met Thr Gly Arg Ser Gly Gly Gly
            20                  25                  30

Ala Gly Gly Gly Gly Gly Gly Gly Ser Val Gly Phe Ser Thr Gly Gly
        35                  40                  45

Trp Glu Gly Gly Thr Tyr Phe Ser Asp His Thr Val Thr Thr Thr Asn
    50                  55                  60

Thr Arg Gln Trp Tyr Thr Gly Ile Leu Asn Gly His Arg Tyr Ser Lys
65                  70                  75                  80

Leu Ala Gln Thr Thr Gly Ser Asn Leu Gln Ala Ala Lys Pro Trp Val
                85                  90                  95

Gly Ile Gln Thr Pro Trp Ala Tyr Leu Asn Leu Asn Cys Tyr His Cys
            100                 105                 110

Leu Phe Ser Pro Gln Asp Trp Gln Arg Leu Leu Asn Glu Tyr Lys Ala
        115                 120                 125

Trp Arg Pro Lys Arg Met His Val Arg Ile Tyr Asn Leu Gln Ile Lys
    130                 135                 140

Gln Ile Thr Thr Val Gly Ala Asp Thr Leu Tyr Gln Asn Asp Leu Thr
145                 150                 155                 160

Ala Gly Val His Ile Phe Cys Asp Gly Ser His Gln Tyr Pro Tyr Ala
                165                 170                 175

Gln His Pro Trp Asp Glu Gly Ala Ser Pro Glu Leu Pro Asn Glu Ile
```

```
            180                 185                 190

Trp Lys Leu Pro Gln Tyr Ala Tyr Phe Gln Tyr Gln Gly Asp Leu Thr
        195                 200                 205

Asp His Ala Thr Ala Asn Thr Pro Gln Asn Val Glu Ser Met Leu Lys
    210                 215                 220

Ser Asn Ile Pro Leu Phe Leu Leu Glu Asn Ser Asn His Glu Val Leu
225                 230                 235                 240

Arg Thr Gly Glu Met Thr Glu Phe Ser Phe Thr Phe Gln Ser Gly Trp
                245                 250                 255

Val Thr Asn Asp Arg Ala Tyr Cys Cys Pro Gln Ser Asp Phe Asn Pro
            260                 265                 270

Leu Val Gln Thr Arg Arg Tyr Tyr Pro Thr Trp Asn Gly Ser Ser Asn
        275                 280                 285

Ser Tyr Ser Tyr Asn Arg Tyr Gly Pro Tyr Lys Lys Pro Ser Asn Trp
    290                 295                 300

Met Pro Gly Pro Gly Leu Ala Tyr Lys Gly Ala Thr His Thr Asn Gln
305                 310                 315                 320

Asn Pro Asp Asp Ala Arg Gly Pro Ile Ile Thr Thr Ile Ala Pro Arg
                325                 330                 335

Gly Thr Ile Ser Val Gly Ser Thr Pro Ser Asn Glu Ala Pro Asn Asp
            340                 345                 350

Gly Asp Asn Thr Ile Ser Ser Asp Gly Val Lys Gln Gly Gly Trp Gln
        355                 360                 365

Thr Ala Pro Val Asn Gly Ala Cys Ser Arg Thr Asp Tyr Pro Thr Leu
    370                 375                 380

Ala Phe Asp Pro Ser Asp Arg Ser Ser Asn Gln Asn Ile Pro Thr Arg
385                 390                 395                 400

Asn Leu Asp Ile Asp Met Thr Arg Trp Tyr Arg Val His Glu Ala Val
                405                 410                 415

Arg Gly Ala Ser Gly Ser Thr Tyr Tyr Asn Val Asp Asp Ile Trp Met
            420                 425                 430

Tyr Pro Asn Gln Ala Trp Asn Ser Thr Pro Ile Cys Arg Asp Asn Pro
        435                 440                 445

Ile Trp Asp Lys Val Pro Arg Thr Asp Lys His Thr Leu Leu Asp Ser
    450                 455                 460

Ser Asp Gly Thr Leu Pro Met Lys His Pro Pro Gly Asn Ile Phe Ile
465                 470                 475                 480

Lys Cys Ala Lys Ile Pro Val Pro Thr Ser Asn Asn Thr Asp Ser Tyr
                485                 490                 495

Leu Asn Ile Tyr Val Thr Gly Gln Val Thr Tyr Thr Val Glu Trp Glu
            500                 505                 510

Val Gln Arg Tyr Gln Thr Lys Asn Trp Arg Pro Glu Leu Arg Thr Ser
        515                 520                 525

Ala Gly Ser Tyr Asn Gln His Glu Ile Tyr Asn Ile Gly Glu Asn Gly
    530                 535                 540

Val Tyr Asn Arg Ala Asn Thr Phe Asn Glu Cys Met Pro Thr Lys Cys
545                 550                 555                 560

Gly Ile Asn Arg Val Leu
                565
```

<210> SEQ ID NO 42
<211> LENGTH: 5331
<212> TYPE: DNA
<213> ORGANISM: Feline bocavirus

<400> SEQUENCE: 42

```
cctggcgcga tgacgtgtca gtgagggtgt tgtctaaaga ctatagggat caatgatagg     60
ttcagccatg taatgattaa ctgacccttta acgtgattgg ttgggagtta atgattaaca    120
tgtgaccttt acagtgattg gttctctgaa cctataaaaa gagctgcatt tccgtgtctg    180
tgtcattctg cttccggcgc tcgacgagat cggacctgga gaagaacaag ttccgtcaat    240
tggtgagtcg ccatcaatgg ctgaattcga tacagcaagt ctcgacgact tcatccaatt    300
tgcagaccca gcatatacat acgtgctgcg tcttccatta cctacagggg aaaattatga    360
gagccagcta cagaatgtat tatgcgctcg ataccccgat ttattatccg atccggcatt    420
gttcgcaaca atgcctggac ctgaatctcc aggcgctcag actgattttt tggagcgttt    480
tggtcctagc cgctgctttg ggctgaagt ctgctatgcg gcgcatatgg cagcctttaa    540
ctwctttagt aggaaacagg gaaargcgcc rcctatygcc agcatctaca cacaatgcga    600
attaggccag agaaacattc awtgtcatct agtcatggcc ggcgacggtc tgtctcgttt    660
ctcggctaar agcgctgcct acatactagg ccaaaaattt gcagacaatc tgatttctat    720
catcgaaaat aatctaagaa arggcgacgt magyaatcca gcttttgcta ccgcttttat    780
caragaaata caagargctc aaagaaaatg cgaaccaggc aacgctggcg acctttgtac    840
tgtgwtgcaa tataaaagta gaggaggcgg catgtacgcg tgccgaatcg atggccgcga    900
gtacatctgt aactacctat tatgcaagaa cctgaaatgg gtatcttgcg tggaaccaga    960
caaggcgact cctcttaaag ccttctttcc aatcgcttca aaaacatatg catttactct   1020
aattaatgga aagattgttc cgtatcacgt acgtcgtgaa tggtggaatc aactacgaga   1080
caaggtccta gtcagggacg aaccaatctt taagggagac gtgtttggag atcttccaaa   1140
ggtaaatgct gcgtcatgga aattaactgg taatatgggt caaggtacat ctcagccgca   1200
tgtgaatgcc agaatgagta aaaaagaatc attaatacta gactgtctta aacgttgcga   1260
ggataatcta tggctaacct atgaagatct ggtcggtggt tgtgccgatt taattttaat   1320
gttggaatcg atgccaggtg gaagtaaatt aattgagtct gtacttaaca tgttgcatgt   1380
tagaatcact caaactcata gtgcgttgtc ctatttgcat gtgagatatg acatgaaaga   1440
actggcgact cacgcagact cgctccacgc taataaagca tggagattac tactaaaaca   1500
aggatataat cctctacaag tgggacattg gatctgctgt gtcctacata aaaaagcagg   1560
aaaacaaaat acattaaatt tctttggacc ggctagcacc ggtaaaacaa atctggcaaa   1620
agcaatcgtg aatgcaatca agctctatgg ttgcgtcaat caccaaaaca aaaattttat   1680
ctttaacgat tgtgccgcaa aactagttgt ctggtgggaa gaatgtctca tgcattcaga   1740
ctgggtcgag caagctaaat gtatcttggg cggcacggag tttagaattg acagaaaaca   1800
cagagaatcg catctattgc cacaaactcc tgtaatcatc tcaacgaata acaatatata   1860
tcaaacactg ggtggcaact cggtctcaca tgtacatgaa gctcctctaa gagaaagagt   1920
cgtccagttt aatttcatga cacgtctaga aagcaccttt ggagagattg aaccaagaga   1980
agtagccgaa tggctatcca tctgtctctc tcggtttgac atctctctgg ttggctttca   2040
tactcaatgg aagctaaata aaactccaaa tgactttcca ttggctaaat tctgcggtgg   2100
tcactcacag gatctcgtgt tacatgagac cggaacgtgt atgagctgtg gcggatacta   2160
tcctctagaa ctacacgatc gaggcgacat cgaggacgct acaccaggta cgagctactc   2220
aactctatta caattaacac ctaaatctga aaaatacata caagaattta acttggatct   2280
```

-continued

```
cttgaaatct ccaatagcgg ccacgagcac tcctgtgact cgacaggatc cacctgagct   2340
tcctccaaaa aagaaggtac gcaaagaaaa acactgcgca cgcgctctct ttactgacga   2400
ctggtgctct caacctcgag acgatgtcga gtggcgcgtc gtccaagaac gagcagaagc   2460
ggcggcggcc gaggtctctg gatcgagatc cgagtccgat tccggacaag cgagctcgat   2520
ggagctcgac ctctcaccag aacaatgggg agagatgctc ggactcatct ccggggacat   2580
cgaagcggga gaaccgccga tcacactcca ctgctttgaa tccatcaccg aagctgactt   2640
actttgtcaa acggactcag aaaccgaata aacaaacacc tcttgatgtc tttatgaaac   2700
atagagccaa agagggggga gatgtacctc cattttgtgg gttttactgg catagtacta   2760
gattagcaag atttggaaca gatgcaatct ttaatttgta taaacctaaa tttcaagaaa   2820
tgtcaaaaaa caatgtaatt acgtgggatc aatgtcgtga tttgttgttt gattttaaaa   2880
agaacctaga ctataaatac agatctatga tgtggcattt tagcatgggt gaacaatgtc   2940
ataaatgtaa ttactgggat aaaatgtacg ctgggcatct ggctaatgta tctctatcta   3000
cacaggaaga ggactctgac cctgtaactg acgctgaaat gctggcggtt gccatggagg   3060
ttgatggcac cgaccaatag gcgtcctggc ggttggactc tgcccggttt cagatatctt   3120
ggtccattta atccattgaa taacggtaaa ccagtaaacg aagtagataa agttgctcaa   3180
aagcacgata aagcttacga ttcttatatc aaggctggcg tcaatccata tttgcacttt   3240
aataaagctg actctgattt cattgattcg ctgtctactg attcgtctgt tgccgggtgg   3300
ctgggaaaat cggcgtttaa actcaagaga cttttggcgc cacatctttc aaaagaaaaa   3360
gaagcagcgg gtaataaagg aggaactggt ggaaaacgcg ccaagcttga tccggtacgg   3420
gctcaaaaaa gaaaatatta ttttgcccgt caaaaccagg gaaaaaatcc taaacaacaa   3480
aaaatggaaa atgaagttga gacggctggg gatggacaag agggggcgcc agctggcact   3540
gctcgtgctg gtggtggtgg taacggtgct ggtatgggtg gtggtggcca tggtgtcggt   3600
gtaagcacgg gagggtggag agctggaact atcttttctg ataatgttat aattacaaca   3660
tcaactagac aatggtatgt tccaatatat aatggtcatc tgtacaaaga aatattcgca   3720
aatgggagcg taagagaatg ggtaggaata agtacccctt ggggatactt taatttcaat   3780
gaatacgatg ctcactttac accaaacgat tggcaacgac tcacaaacga gtatgccaaa   3840
tggagaccaa aaagaatgca tgtcaagata tacaatctcc aaattaaaca aaaggtgaca   3900
ctgggggtgg acaccctata taacaacgac cttacggcgg gtgtacacat tttttgtgac   3960
ggttctcatc aattcccata ctcacaaaaa ccttgggatt ttggaacaat gccagaattg   4020
ccatatgatg tatggaagct tccacaatac gggtattttc aatttcaaaa tgatctctca   4080
gatcaatcat caaactcgct tgcagcagat aatgtagaaa aaaatattgt gagaaatgct   4140
ccattttttg tattagaatc tgcatctcac gaggtcctca gaacaggaga agaaacagaa   4200
ttcaactttg aatttgaatg tgggtgggtc acaaatacac gtgcatatgc tccgcctcag   4260
gcagacttca atccattagt tgaaactaga cgttattatc caacatacga caactcatct   4320
agcactaaat ttgtatacgc tagatattca ccatataaca aacctagtaa ctggatgccc   4380
ggtccgagta ttggatatat aggaaacaca acaaccggct caaactacca aacaagaggg   4440
ccaatcacag tatgcccaca tccatatttt actacacctg gaaatttaga aacagacagg   4500
gcatatgacc cacaaagtgg aacaaataca ttaaccgaag ctggcatgag aaaatcggga   4560
tacgatgtaa cacctgtaaa tggtgcctgc tcccgactgg actctgttga cttggcatat   4620
gattcgtctg aatatagctt aaatcaaaca aaattaattt caagaaacat agatagtgac   4680
```

```
atggctagat ggggttcagt gtgggcacag gatggattga ataaagaaat aggagacaat   4740
ggacaaccaa acaacacaga cagaaaaaat atcagccagc taaaaaacat atggatgtat   4800
ccaaaccagg catgggacac aacaccaata gcaagaaaca cacccatatg ggacaaagtt   4860
ccagacacag acagaaacac tatgctagat tcggctgatg gcacactacc gatgccacat   4920
ccacctggta ctatctttgt aaaagttgca aaaataccaa taccaaccga aaacaatgca   4980
gatgcatatt tagatctata tgtaacagga caagtaacat gtacaataga atgggaagta   5040
gcaagattca agaccaaaaa ctggagaccg gaaatcagaa catctgcaac aatgttttca   5100
gacccaaaaa tatactctgt caatgccagt ggtgtataca atacaccaga aaccttcaca   5160
gaatctatgc caacaaaatg ggaatcaac aaagttctgt aaaaataaaa ttacatcatt    5220
catcaaactg tacgtgtcac gtgagttttc ttttgcgcgc caaaaaatct ttcgttgatc   5280
tctatactct tatacaacac cctccacact gctacgtcag tgtgtatgag a            5331
```

<210> SEQ ID NO 43
<211> LENGTH: 5413
<212> TYPE: DNA
<213> ORGANISM: Canine bocavirus

<400> SEQUENCE: 43

```
tacaccgagc ggcttcgccg ctgcgccctg cgggcgcgct gtatatgttc ctcggcgaac     60
gtgacgtaat gtagtagtgg tgtctataaa gattatatca attgcgctgt cttgtggttg    120
gttaatgagt gactcgctgt gtcagctgtt tgcgattggc tgttgtttta tggccttgtt    180
atgttattgg ttactgattg atgaattttg ggcgggccga gtgactatat atataagtgt    240
gcttcctgct tcgtgtcatt ctgcttccgg ctttcgtcgc gttgagatct ctctgagggt    300
gagtgatggc tcttgctctg gccggggtcg acgatattat tcactttgct cgtcctgcct    360
atacctatgt tctcaagttt ccttacgctg agtggcggcg ggatgaggct cgtcttcaga    420
gcgctctggg gtacccgcat catgatttac tcaaggactc gactccgttc cttactatgc    480
cggggcaaga ttctccggcc gagcaggctt cctttctgga gtctaagggt cctcagtacg    540
gatatgcctt attactggca cgcacggctc acgctgctgc atattctata ttctcgcaga    600
agcagggcaa atatcctcct gctgctagca tatatgttca gtgcgagctt ggccttaagt    660
atcttcacgt acacgtcgtg atgggcggtg acggcttgaa ccggtacaac gccaaggcca    720
cttgctctaa cctggcctat aagtggctgg acaacattca gtctcagctc gagattaacg    780
tcaagaccgg tcacaacacc gaccttgaca tgtgcaattc tctcatcggc tgcgtctacc    840
aggccaagag agagtgcttt gacatgagga ccgagatttg taccatcctg cagtacaagt    900
gccggaacgg cgagatgtac gcctgccggg tcgatcctat agagtttatc tgtaactacc    960
tgttgtgcaa aaacttgaaa ttctttacta tggtcgaccc tgacagagca actccgtttg   1020
tctctcactt tgcctgttct ggtaaaacgt acgcggctac atttgtcaat gggaagtggg   1080
tcttgcctca ggttaggaag cagtggctaa attatcttcg agactctgtc tgtcagaagg   1140
ccgatccagt cttttccggc gacatgtttg aaaacttacc caaggtacct cgcgcgacct   1200
ggtcggtcga agtttcctcc aataaatcta aaatcactaa aaaggaaact ctgatgattg   1260
actgtatcga tcgctgcgaa aagaatcact tgcttaccta tgaagatttg gtcaatgagt   1320
gttctgatct tgtaatcatg ctcggctcac agccgggcgg aactaaattg attgagacct   1380
tgcttcagat ggttcacatt aagatttgtc agaaatatac ggccttgtct tatgtcttgt   1440
```

```
cgcggtactc ggcgattgag ctgctgcctg agaacaaggc tatacagctc ttgatctttc   1500
agggatacaa tccctggcag gtcggccact ggctgtgctg cgtgctgcac aagacggccg   1560
gtaaacagaa taccgtgtgc tttttcggtc cggccagcac cggcaagacc aactttgcca   1620
aggctatagt gaatgccgtt aagctgtacg gatgtgtgaa ccatcagaat aagaattttg   1680
tgtttaacga ctgcgcgtcc aagctggtca attggtggga agagtgcctc atgcacaatg   1740
attgggtaga gcaggccaag tgcctgctgg gaggaacgga gtttagaatc gaccgtaagc   1800
ataaagactc tcagctgctg ccgcagactc ctgttgtgat cagtaccaat cacgacgtgt   1860
acaccgtggt cggtggaaac accactacta tggttcacgc taagccgctt cgggaaagga   1920
tcgttcagtt taatttcatg aaacagctgt cttccacctt tggggagatt gatcctatgg   1980
atgtggtggc tctgttgcaa gcctgctctt ctcgattcga tgcgtcgctc gactcgtttt   2040
atgctcagtg gcagcttcag tgcactccta acgattttcc tctcgcttcg ttctgtgacg   2100
ggcattcgca ggactttgtc cttcacgagg tcggcttctg cgacacgtgc ggtggctacg   2160
ctcctctgga gactacggac cgcagtcagc cgctgccggc tcgacctgct tcgtccggtg   2220
agtctttgat tttgcctgt acgctgcctt gactgtttta ttttctgtat gctatactca    2280
gctttgtgct ctttttcag cgtcgggtgt gaagcgtcgc ctggactttg acccggatcc    2340
tgctccttcc acgtcgacgg ctcctccggc gaagcgccac tccaaggtga ggcgtcccgt   2400
gttccacgac gactggtgta gtcagccggt agatcgccta gaccgcatcc gctatgaaaa   2460
gttcgtcgag agcgtcgtcg gcgcgtcaga cgagtcacca tcggagccgg agtcggagtc   2520
cacgggactc acgccttcag agtggggaga gatgctcgga gtcgtctgca agtcgctgga   2580
ggaggaaccg atcgtcttac actgcttcga agacatcacc tctctctcgg aaaccgaaga   2640
cgactccgat ggaggtcttc aatcaacacc gcgccaagac aaagactgac atttcaatgt   2700
gtggctttta ctggcacagt actcgcctcg cgcggtcggg taccgactgg atctttaaca   2760
gtggaaagcc tctgtttcaa tctaaatgtt ctaataatct tgtatcttgg gatgtggttc   2820
gtgagattct gtttgaattt aaaaaaacta tagatcagaa atatagaaat atgctgtggc   2880
actttggtcg ggtgggtac tgcaataaat gtgaatactg ggataatgtg taccttgaac    2940
acctagctaa tgtagattcc tctaatgatg ttgttatgca ggagataagt gacgctgaga   3000
tgttggaggc tgccatggag attgatggcg ccagcgaata gaaagcccgg tggttgggtc   3060
gtgcctggct atagatattt gggtcccttt aaccctgctg acaacgggga acctgtaaat   3120
tctgctgacg aggccgctcg gtctcatgat ctcgcctatc agtcctatct cgatgctggt   3180
gtaaacccgt actttagcta caataaagct gattctgatt tcattgagtc attggctcac   3240
gactcttcat tcggcggctg gctggggcgc tcggcctttg gcctcaagaa attgcttgcg   3300
ccgcatctcg cggatacaaa gggcaatcct gacgctccgt ccacctcgcg gggaggttcc   3360
tctgtatcca agtcagagag agcacaaaag agaaaactct attttgccag atcaaacaaa   3420
caggccaaac aacaaaagat gtcagctcca gaagctccga ccgaagatgt ggcagaaccg   3480
ggtccatctg gctccgatcc gcgggcggga ggaaatggag gtggtggagg catgggagga   3540
ggtggaggac atggagtggg agtgagcacc ggcggatgga aggccgggac cgtgtttggg   3600
aatgactttg tcatcaccac aaacaccaga cagtggttcg ctcccatctt taacggccac   3660
gagtacaaac gcatggcgcc gaacgagaac agcgaaccgg ccaccaacag acactgggtg   3720
ggaatcagta ctccgtgggg atactttaac tttaacgagt acagttcaca tttctcacca   3780
caagactggc agcgcctcac caacgaatat aaaagatgga gacccaaggc catgagggtc   3840
```

```
aaagtataca acctgcaaat aaaacaggtg gtcactctgg ggtcagacac tttatacaac   3900

aatgacctga cggccggcgt tcacatcttt tgtgacggga gccatcagtt tccgtactct   3960

cagcatccgt gggacaccgg gaccatgccc gagctgcctc atcgcatctg gaggatctcg   4020

cagtacgggt actttcagct acaggctgac ctgacgaacg ggggcgtatc atccgagacg   4080

cccgacgtcg ggaaccaaga aaagcagctg ctaaagagtg cgccgctata catgctcgag   4140

acggcgtcgc accaagtgtt gaggacgggg gaggaatcca gcttctcttt ctcgtttgac   4200

agcgggtggg ttatcaacga caaggcatac gccattccac aggcagattt taaccctctg   4260

attcacacca gacgatactt tcctacacga aacaataaca ccacatcaac aggggggctc   4320

atgttttacc atagatataa tccatacaac aaaccgagca actggatgcc ggggccgagc   4380

ttgggctacc tgggggcgac acagacatca accaatccac agtacgcgcg tggtccggtt   4440

actgttgtca cgcagccgcc gggaacgacg gcagatagcg ccaatataga cgagcaatca   4500

accacacacg tcccgtcaaa ggcgaccatg caaaattcag ggtacgacgt gaaccctgtc   4560

aactgcggta gcagcagatt agacgcgcac tcgcttgcat atgattcagg gccagagagt   4620

cgaggacaga acatcattac cgtaaggggg atagacttag acatggcctt gggtctccat   4680

caaatggtgc aggacggaac agaaacagaa gttggtaccc aaactcccag aactaatttt   4740

actgaactca aaaacgtatg gatgtaccca aatcaggcgt gggacaccac tccggtatcc   4800

agggacactc ctatttgggt caagattcca aaaacagaca ggcacaccat gcaagacacc   4860

tcggacggaa cgctgccgat ggcgcatccg ccgggaacca tctttgtcag ggtcgcaaag   4920

gtgcccattc cgggggagtc agactcttac ctaaacctat acgtgacagg acagataacg   4980

tgtgaaatac tctgggaaac agagaggttc cagaccaaaa attggagacc ggaaatcaaa   5040

aacgatccat ccgtattcag cgacccttta ctatacactt tcgacagaca gggggtctac   5100

aatacaccgg aaacattcat agagggcatg cccacaaaac ggggaataaa cagggtcctg   5160

taactttaag aacaaataaa gccataaaac gaaaagtttt gcgcatttgt tatttcttta   5220

aaaggaccat cagtactgta cgtcactata gatcatctga tacggtcagg tattgcttaa   5280

ttatatggcg cagcttagtt atatatcagg tatatgctcg tcacataact aagctaccat   5340

ataattaagc aatacctgac gtatcagatg atctatagtg acgtacagta ctgatggtcc   5400

ttttaaagaa tac                                                      5413
```

<210> SEQ ID NO 44
<211> LENGTH: 712
<212> TYPE: PRT
<213> ORGANISM: Canine bocavirus

<400> SEQUENCE: 44

```
Met Ala Pro Ala Asn Arg Lys Pro Gly Gly Trp Val Val Pro Gly Tyr
1               5                   10                  15

Arg Tyr Leu Gly Pro Phe Asn Pro Ala Asp Asn Gly Glu Pro Val Asn
            20                  25                  30

Ser Ala Asp Glu Ala Ala Arg Ser His Asp Leu Ala Tyr Gln Ser Tyr
        35                  40                  45

Leu Asp Ala Gly Val Asn Pro Tyr Phe Ser Tyr Asn Lys Ala Asp Ser
    50                  55                  60

Asp Phe Ile Glu Ser Leu Ala His Asp Ser Ser Phe Gly Gly Trp Leu
65                  70                  75                  80

Gly Arg Ser Ala Phe Gly Leu Lys Lys Leu Leu Ala Pro His Leu Ala
```

```
                85                  90                  95

Asp Thr Lys Gly Asn Pro Asp Ala Pro Ser Thr Ser Arg Gly Gly Ser
            100                 105                 110

Ser Val Ser Lys Ser Glu Arg Ala Gln Lys Arg Lys Leu Tyr Phe Ala
        115                 120                 125

Arg Ser Asn Lys Gln Ala Lys Gln Gln Lys Met Ser Ala Pro Glu Ala
    130                 135                 140

Pro Thr Glu Asp Val Ala Glu Pro Gly Pro Ser Gly Ser Asp Pro Arg
145                 150                 155                 160

Ala Gly Gly Asn Gly Gly Gly Gly Gly Met Gly Gly Gly Gly Gly His
                165                 170                 175

Gly Val Gly Val Ser Thr Gly Gly Trp Lys Ala Gly Thr Val Phe Gly
            180                 185                 190

Asn Asp Phe Val Ile Thr Thr Asn Thr Arg Gln Trp Phe Ala Pro Ile
        195                 200                 205

Phe Asn Gly His Glu Tyr Lys Arg Met Ala Pro Asn Glu Asn Ser Glu
    210                 215                 220

Pro Ala Thr Asn Arg His Trp Val Gly Ile Ser Thr Pro Trp Gly Tyr
225                 230                 235                 240

Phe Asn Phe Asn Glu Tyr Ser Ser His Phe Ser Pro Gln Asp Trp Gln
                245                 250                 255

Arg Leu Thr Asn Glu Tyr Lys Arg Trp Arg Pro Lys Ala Met Arg Val
            260                 265                 270

Lys Val Tyr Asn Leu Gln Ile Lys Gln Val Val Thr Leu Gly Ser Asp
        275                 280                 285

Thr Leu Tyr Asn Asn Asp Leu Thr Ala Gly Val His Ile Phe Cys Asp
    290                 295                 300

Gly Ser His Gln Phe Pro Tyr Ser Gln His Pro Trp Asp Thr Gly Thr
305                 310                 315                 320

Met Pro Glu Leu Pro His Arg Ile Trp Arg Ile Ser Gln Tyr Gly Tyr
                325                 330                 335

Phe Gln Leu Gln Ala Asp Leu Thr Asn Gly Gly Val Ser Ser Glu Thr
            340                 345                 350

Pro Asp Val Gly Asn Gln Glu Lys Gln Leu Leu Lys Ser Ala Pro Leu
        355                 360                 365

Tyr Met Leu Glu Thr Ala Ser His Gln Val Leu Arg Thr Gly Glu Glu
    370                 375                 380

Ser Ser Phe Ser Phe Ser Phe Asp Ser Gly Trp Val Ile Asn Asp Lys
385                 390                 395                 400

Ala Tyr Ala Ile Pro Gln Ala Asp Phe Asn Pro Leu Ile His Thr Arg
                405                 410                 415

Arg Tyr Phe Pro Thr Arg Asn Asn Asn Thr Thr Ser Thr Gly Gly Leu
            420                 425                 430

Met Phe Tyr His Arg Tyr Asn Pro Tyr Asn Lys Pro Ser Asn Trp Met
        435                 440                 445

Pro Gly Pro Ser Leu Gly Tyr Leu Gly Ala Thr Gln Thr Ser Thr Asn
    450                 455                 460

Pro Gln Tyr Ala Arg Gly Pro Val Thr Val Val Thr Gln Pro Pro Gly
465                 470                 475                 480

Thr Thr Ala Asp Ser Ala Asn Ile Asp Glu Gln Ser Thr Thr His Val
                485                 490                 495

Pro Ser Lys Ala Thr Met Gln Asn Ser Gly Tyr Asp Val Asn Pro Val
            500                 505                 510
```

```
Asn Cys Gly Ser Ser Arg Leu Asp Ala His Ser Leu Ala Tyr Asp Ser
        515                 520                 525

Gly Pro Glu Ser Arg Gly Gln Asn Ile Ile Thr Val Arg Gly Ile Asp
    530                 535                 540

Leu Asp Met Ala Leu Gly Leu His Gln Met Val Gln Asp Gly Thr Glu
545                 550                 555                 560

Thr Glu Val Gly Thr Gln Thr Pro Arg Thr Asn Phe Thr Glu Leu Lys
                565                 570                 575

Asn Val Trp Met Tyr Pro Asn Gln Ala Trp Asp Thr Thr Pro Val Ser
            580                 585                 590

Arg Asp Thr Pro Ile Trp Val Lys Ile Pro Lys Thr Asp Arg His Thr
        595                 600                 605

Met Gln Asp Thr Ser Asp Gly Thr Leu Pro Met Ala His Pro Pro Gly
    610                 615                 620

Thr Ile Phe Val Arg Val Ala Lys Val Pro Ile Pro Gly Glu Ser Asp
625                 630                 635                 640

Ser Tyr Leu Asn Leu Tyr Val Thr Gly Gln Ile Thr Cys Glu Ile Leu
                645                 650                 655

Trp Glu Thr Glu Arg Phe Gln Thr Lys Asn Trp Arg Pro Glu Ile Lys
            660                 665                 670

Asn Asp Pro Ser Val Phe Ser Asp Pro Leu Leu Tyr Thr Phe Asp Arg
        675                 680                 685

Gln Gly Val Tyr Asn Thr Pro Glu Thr Phe Ile Glu Gly Met Pro Thr
    690                 695                 700

Lys Arg Gly Ile Asn Arg Val Leu
705                 710


<210> SEQ ID NO 45
<211> LENGTH: 570
<212> TYPE: PRT
<213> ORGANISM: Canine bocavirus

<400> SEQUENCE: 45

Met Ser Ala Pro Glu Ala Pro Thr Glu Asp Val Ala Glu Pro Gly Pro
1               5                   10                  15

Ser Gly Ser Asp Pro Arg Ala Gly Gly Asn Gly Gly Gly Gly Gly Met
            20                  25                  30

Gly Gly Gly Gly Gly His Gly Val Gly Val Ser Thr Gly Gly Trp Lys
        35                  40                  45

Ala Gly Thr Val Phe Gly Asn Asp Phe Val Ile Thr Thr Asn Thr Arg
    50                  55                  60

Gln Trp Phe Ala Pro Ile Phe Asn Gly His Glu Tyr Lys Arg Met Ala
65                  70                  75                  80

Pro Asn Glu Asn Ser Glu Pro Ala Thr Asn Arg His Trp Val Gly Ile
                85                  90                  95

Ser Thr Pro Trp Gly Tyr Phe Asn Phe Asn Glu Tyr Ser Ser His Phe
            100                 105                 110

Ser Pro Gln Asp Trp Gln Arg Leu Thr Asn Glu Tyr Lys Arg Trp Arg
        115                 120                 125

Pro Lys Ala Met Arg Val Lys Val Tyr Asn Leu Gln Ile Lys Gln Val
    130                 135                 140

Val Thr Leu Gly Ser Asp Thr Leu Tyr Asn Asn Asp Leu Thr Ala Gly
145                 150                 155                 160

Val His Ile Phe Cys Asp Gly Ser His Gln Phe Pro Tyr Ser Gln His
```

```
                165                 170                 175

Pro Trp Asp Thr Gly Thr Met Pro Glu Leu Pro His Arg Ile Trp Arg
            180                 185                 190

Ile Ser Gln Tyr Gly Tyr Phe Gln Leu Gln Ala Asp Leu Thr Asn Gly
        195                 200                 205

Gly Val Ser Ser Glu Thr Pro Asp Val Gly Asn Gln Glu Lys Gln Leu
    210                 215                 220

Leu Lys Ser Ala Pro Leu Tyr Met Leu Glu Thr Ala Ser His Gln Val
225                 230                 235                 240

Leu Arg Thr Gly Glu Glu Ser Ser Phe Ser Phe Ser Phe Asp Ser Gly
                245                 250                 255

Trp Val Ile Asn Asp Lys Ala Tyr Ala Ile Pro Gln Ala Asp Phe Asn
            260                 265                 270

Pro Leu Ile His Thr Arg Arg Tyr Phe Pro Thr Arg Asn Asn Asn Thr
        275                 280                 285

Thr Ser Thr Gly Gly Leu Met Phe Tyr His Arg Tyr Asn Pro Tyr Asn
    290                 295                 300

Lys Pro Ser Asn Trp Met Pro Gly Pro Ser Leu Gly Tyr Leu Gly Ala
305                 310                 315                 320

Thr Gln Thr Ser Thr Asn Pro Gln Tyr Ala Arg Gly Pro Val Thr Val
                325                 330                 335

Val Thr Gln Pro Pro Gly Thr Thr Ala Asp Ser Ala Asn Ile Asp Glu
            340                 345                 350

Gln Ser Thr Thr His Val Pro Ser Lys Ala Thr Met Gln Asn Ser Gly
        355                 360                 365

Tyr Asp Val Asn Pro Val Asn Cys Gly Ser Ser Arg Leu Asp Ala His
    370                 375                 380

Ser Leu Ala Tyr Asp Ser Gly Pro Glu Ser Arg Gly Gln Asn Ile Ile
385                 390                 395                 400

Thr Val Arg Gly Ile Asp Leu Asp Met Ala Leu Gly Leu His Gln Met
                405                 410                 415

Val Gln Asp Gly Thr Glu Thr Glu Val Gly Thr Gln Thr Pro Arg Thr
            420                 425                 430

Asn Phe Thr Glu Leu Lys Asn Val Trp Met Tyr Pro Asn Gln Ala Trp
        435                 440                 445

Asp Thr Thr Pro Val Ser Arg Asp Thr Pro Ile Trp Val Lys Ile Pro
    450                 455                 460

Lys Thr Asp Arg His Thr Met Gln Asp Thr Ser Asp Gly Thr Leu Pro
465                 470                 475                 480

Met Ala His Pro Pro Gly Thr Ile Phe Val Arg Val Ala Lys Val Pro
                485                 490                 495

Ile Pro Gly Glu Ser Asp Ser Tyr Leu Asn Leu Tyr Val Thr Gly Gln
            500                 505                 510

Ile Thr Cys Glu Ile Leu Trp Glu Thr Glu Arg Phe Gln Thr Lys Asn
        515                 520                 525

Trp Arg Pro Glu Ile Lys Asn Asp Pro Ser Val Phe Ser Asp Pro Leu
    530                 535                 540

Leu Tyr Thr Phe Asp Arg Gln Gly Val Tyr Asn Thr Pro Glu Thr Phe
545                 550                 555                 560

Ile Glu Gly Met Pro Thr Lys Arg Gly Ile
                565                 570
```

<210> SEQ ID NO 46

-continued

```
<211> LENGTH: 204
<212> TYPE: DNA
<213> ORGANISM: Artificial Sequence
<220> FEATURE:
<223> OTHER INFORMATION: A synthetic oligonucleotide

<400> SEQUENCE: 46

tcacgctcag gattcacttg cctccaatta tcatcctaag cagaagtgta tattcttatt     60

tgtaaagatt ctattaactc atttgattca aaatatttaa aatacttcct gtttcaggta    120

ctctgctatg caccccccga acattattat aacgttgctc gaatactaac tggtacctct    180

tctttttttt ttgatatcct gcag                                           204
```